United States Patent
Isobe et al.

(10) Patent No.: US 7,157,465 B2
(45) Date of Patent: Jan. 2, 2007

(54) ADENINE DERIVATIVES

(75) Inventors: Yoshiaki Isobe, Osaka (JP); Haruhisa Ogita, Osaka (JP); Masanori Tobe, Osaka (JP); Haruo Takaku, Osaka (JP); Tetsuhiro Ogino, Osaka (JP); Ayumu Kurimoto, Hyogo (JP); Hajime Kawakami, Hyogo (JP)

(73) Assignee: Dainippon Simitomo Pharma Co., Ltd., Osaka (JP)

( * ) Notice: Subject to any disclaimer, the term of this patent is extended or adjusted under 35 U.S.C. 154(b) by 238 days.

(21) Appl. No.: 10/474,199

(22) PCT Filed: Apr. 15, 2002

(86) PCT No.: PCT/JP02/03727

§ 371 (c)(1),
(2), (4) Date: Oct. 17, 2003

(87) PCT Pub. No.: WO02/085905

PCT Pub. Date: Oct. 31, 2002

(65) Prior Publication Data

US 2004/0132748 A1    Jul. 8, 2004

(30) Foreign Application Priority Data

Apr. 17, 2001   (JP) ............................. 2001-118232

(51) Int. Cl.
- *C07D 473/16* (2006.01)
- *C07D 473/18* (2006.01)
- *C07D 473/24* (2006.01)
- *A61K 31/52* (2006.01)
- *A61K 31/522* (2006.01)

(52) U.S. Cl. .............. 514/263.2; 514/263.21; 514/263.22; 514/263.37; 544/276

(58) Field of Classification Search ............ 514/263.2, 514/263.21, 263.22, 263.37; 544/276
See application file for complete search history.

(56) References Cited

U.S. PATENT DOCUMENTS

| | | | |
|---|---|---|---|
| 2,705,715 A * | 4/1955 | Baker et al. ................. | 544/276 |
| 4,689,338 A | 8/1987 | Gerster | |
| 4,698,348 A | 10/1987 | Gerster | |
| 4,714,701 A | 12/1987 | Beauchamp | |
| 4,772,606 A * | 9/1988 | Sircar et al. ............ | 514/263.22 |
| 6,028,076 A | 2/2000 | Hirota et al. | |
| 6,329,381 B1 | 12/2001 | Kurimoto et al. | |
| 2003/0149060 A1* | 8/2003 | Cristalli ................. | 514/263.23 |
| 2003/0191086 A1 | 10/2003 | Hanus et al. | |
| 2006/0052403 A1* | 3/2006 | Isobe et al. .............. | 514/263.2 |

OTHER PUBLICATIONS

Patent Abstracts of Japan Abstract of JP 11-193282.
Partial Translation of JP 48-16519.
G. D. Mayer, et al., Science, vol. 169, pp. 1214-1215 1970.
F. R. Nichol, et al., "Stimulation of Murine Interferon by a Substituted Pyrimidine", Antimicrobial Agents and Chemotherapy, vol. 9, No. 3, pp. 433-439 1976.
D. A. Stringfellow, et al., "Antiviral and Interferon-Inducing Properties of 1,5-Diamino Anthraquinones", Antimicrobial Agents and Chemotherapy, vol. 15, No. 1, pp. 111-118.
Michael J. Reiter, et al., "Cytokine induction in mice by the immunomodulator imiquimod", Journal of Leukocyte Biology, vol. 55, pp. 234-240 1994.

* cited by examiner

*Primary Examiner*—Mark L. Berch

(57) ABSTRACT

This invention relates to an adenine derivative, a tautomer thereof, or a pharmaceutically acceptable salt thereof represented by general formula (I):

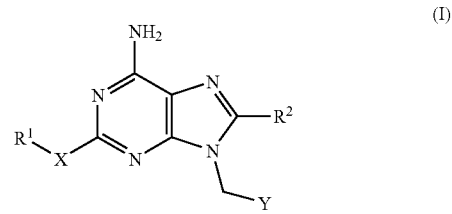

wherein X represents $NR^3$ (wherein $R^3$ represents a hydrogen atom or $C_{1-3}$ alkyl) or the like; $R^1$ represents substituted or unsubstituted alkyl or the like; $R^2$ represents hydroxyl or the like; and Y represents a substituted or unsubstituted aromatic hetero ring or the like. Also, the present invention relates to pharmaceuticals such as an interferon inducer, antiviral agent, anticancer agent, type 2 helper T cell selective immune response inhibitor, antiallergic agent, and immune response modulator comprising the above derivative as an active ingredient.

12 Claims, 4 Drawing Sheets

ADENINE DERIVATIVES

TECHNICAL FIELD

The present invention relates to an adenine derivative that is useful for preventing or treating viral diseases such as hepatitis B, hepatitis C, or AIDS, cancerous diseases, or the like. Also, the present invention relates to a pharmaceutical preparation such as an interferon inducer, antiviral agent, anticancer agent, type 2 helper T cell-selective immune response inhibitor, antiallergic agent, or immune response modulator comprising the above derivative as an active ingredient.

BACKGROUND ART

Interferon is one of the most important factors that are in charge of phylaxis or immune modulation. It has been already put to practical use as a therapeutic agent for hepatitis B and C and an immunotherapeutic agent for cancer. In particular, interferon is practically the only therapeutic agent available for hepatitis C. Interferon is a polypeptide having a molecular weight of about 20,000. It is produced by gene recombination or cell culture, and it can be administered only in the form of injection. What is desired is, accordingly, the development of an interferon inducer that can be orally administered.

Examples of known substances having interferon-inducing activity include double-stranded nucleic acids derived from viruses or other living organisms and high molecular weight polymers such as Poly(I)/Poly(C) or polycarboxylate. Double-stranded nucleic acids or high molecular weight polymers, however, are problematic in, for example, antigenicity, contamination by pathogenic microorganisms or biological stability. In addition, since they has a high molecular weight, development of oral preparations therefrom is difficult. Several substances, such as fluorenones, pyrimidinones, or anthraquinones have been examined as low molecular weight interferon-inducing substances (Mayer, G. D., et al.: Science, 1970, 169, 1214, Nichol, F. R. et al.: Antimicrob. Agents Chemother., 1976, 9, 433, Stringfellow, D. A., et al.: Antimicrob. Agents Chemother., 1991, 15, 111). Because of their low therapeutic effect or toxicity, however, development of pharmaceutical preparations therefrom was relinquished (Reiter, M. A., et al.: J. Leukocyte Biol. 1994, 55, 234). An imidazoquinoline derivative, R-837 (Imiquimod), is known as another low molecular weight interferon-inducing substance (EP 145,340). R-837, however, has low interferon-inducing activity, and the development thereof in the field of oral preparations was no longer performed due to its side effects. The present inventors also found that a specific purine derivative had interferon-inducing activity (WO 99-28321). Since these compounds had low water-solubility, they were not sufficient in terms of gastrointestinal absorption.

In contrast, helper T cells play major roles in immune responses. There are two types of helper T cells, i.e., Th1 cells and Th2 cells. Examples of cytokines produced upon the activation of Th1 cells are interleukin-2 (IL-2) and interferon-γ (IFN-γ). Examples of cytokines produced from Th2 cells are interleukin-4 (IL-4) and interleukin-5 (IL-5). Th1 cytokines activate macrophages, natural killer cells, or the like, and they are known to be mainly involved with cellular immunity such as phylaxis against viruses or bacteria. Th2 cytokines are involved with humoral immunity such as antibody production from B cells. In particular, IL-4 induces B cells to produce IgE antibodies and has actions of Th2 cell differentiation or proliferation. IL-5 is capable of activating eosinocytes, accelerating differentiation or proliferation, life lengthening, or the like. Accordingly, it often plays a major role in allergic inflammation. In fact, these Th2 cytokines are increased in lesions of patients having allergic inflammation such as asthma or atopic dermatitis with which Th2 cells are mainly involved. Steroid drugs are often used to treat these diseases. However, chronic administration of steroid drugs disadvantageously generates a variety of side effects such as diabetes, osteoporosis, adrenal disorder, or moon face. Since steroid drugs inhibitorily act against both T cells, i.e., Th1 cells and Th2 cells, they may cause infectious diseases as a result of inhibiting Th1 cells. Accordingly, pharmaceuticals that can selectively inhibit Th2 immune responses can be safe therapeutic agents for allergic diseases without causing infectious diseases.

DISCLOSURE OF THE INVENTION

An object of the present invention is to provide a low molecular weight compound with improved physical properties (such as solubility or pharmacokinetics) that are effective for preventing or treating viral diseases such as hepatitis B, hepatitis C, or AIDS, cancerous diseases, and diseases resulting from type 2 helper-T cells and that can be orally administered.

Under the above circumstances, the present inventors have conducted concentrated studies. As a result, they found that an adenine derivative with a specific structure had excellent interferon-inducing activity, type 2 helper T-cell-selective immune response inhibitory activity, and excellent physical properties. This has led to the completion of the present invention.

More specifically, the present invention includes the following.

(1) An adenine derivative, a tautomer thereof, or a pharmaceutically acceptable salt thereof represented by general formula (I):

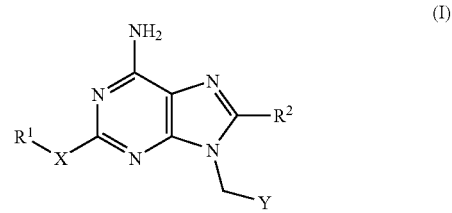

wherein X represents $NR^3$ (wherein $R^3$ represents a hydrogen atom or $C_{1-3}$ alkyl), an oxygen atom, or a sulfur atom; $R^1$ represents substituted or unsubstituted alkyl, substituted or unsubstituted alkenyl, substituted or unsubstituted alkynyl, substituted or unsubstituted aryl, or substituted or unsubstituted heteroaryl; $R^2$ represents hydroxyl, mercapto, $C_{1-8}$ acyloxy, or $C_{2-8}$ alkoxycarbonyloxy; and Y represents a substituted or unsubstituted naphthalene ring, a substituted or unsubstituted 5- or 6-membered monocyclic aromatic hetero ring containing 1 or 2 hetero atoms selected from the group consisting of nitrogen, oxygen, and sulfur atoms, or a substituted or unsubstituted fused bicyclic aromatic hetero ring containing 1 or 2 hetero atoms selected from the group consisting of nitrogen, oxygen, and sulfur atoms.

(2) The compound according to (1) above, wherein, in general formula (I), $R^1$ represents $C_{1-8}$ alkyl, $C_{2-8}$ alkenyl, $C_{2-8}$ alkynyl, $C_{2-8}$ alkoxyalkyl, $C_{1-8}$ hydroxyalkyl, aryl, heteroaryl, aralkyl, or heteroarylalkyl.

(3) The compound according to (1) or (2) above, wherein, in general formula (I), $R^1$ represents $C_{1-6}$ alkyl.

(4) The compound according to any of (1) to (3) above, wherein, in general formula (I), X represents NH.

(5) The compound according to any of (1) to (3) above, wherein, in general formula (I), X represents an oxygen atom.

(6) The compound according to any of (1) to (5) above, wherein, in general formula (I), Y represents a unsubstituted or substituted pyridine ring or a substituted or unsubstituted pyrazine ring.

(7) The compound according to any of (1) to (5) above, wherein, in general formula (I), Y represents a unsubstituted or substituted naphthalene ring or a substituted or unsubstituted thiophene ring.

(8) The compound according to any of (1) to (6) above, wherein, in general formula (I), Y has 1 to 4 substituents when Y is a pyridine ring, and 1 to 3 substituents when Y is a pyrazine ring at any positions, wherein the substituent is selected from the group consisting of $C_{1-4}$ alkyl, $C_{1-4}$ alkoxy, hydroxyl, mercapto, $C_{1-4}$ alkylthio, a halogen atom, amino, $C_{2-8}$ dialkylamino, $C_{1-4}$ monoalkylamino, pyrrolidinyl, piperidino, and morpholino.

(9) The compound according to any of (1) to (6) and (8) above, wherein, in general formula (I), Y represents a pyridine ring which may have a substituent selected from the group consisting of $C_{1-4}$ alkyl, $C_{1-4}$ alkoxy, hydroxyl, mercapto, $C_{1-4}$ alkylthio, a halogen atom, amino, $C_{2-8}$ dialkylamino, $C_{1-4}$ monoalkylamino, pyrrolidinyl, piperidino, and morpholino; $R^1$ represents $C_{1-6}$ alkyl; and $R^2$ represents hydroxyl.

(10) The compound according to (9) above, wherein X represents NH or an oxygen atom.

(11) A pharmaceutical comprising, as an active ingredient, the compound according to any of (1) to (10) above.

(12) An interferon inducer comprising, as an active ingredient, the compound according to any of (1) to (10) above.

(13) An antiviral agent comprising, as an active ingredient, the compound according to any of (1) to (10) above.

(14) An anticancer agent comprising, as an active ingredient, the compound according to any of (1) to (10) above.

(15) A type 2 helper T cell selective immune response inhibitor comprising, as an active ingredient, the compound according to any of (1) to (10) above.

(16) An antiallergic agent comprising, as an active ingredient, the compound according to any of (1) to (10) above.

(17) An immune response modulator comprising, as an active ingredient, the compound according to any of (1) to (10) above.

The compounds according to the present invention are hereafter described in detail.

In general formula (I), alkyl, alkenyl, or alkynyl represented by $R^1$ is preferably $C_{1-8}$ alkyl, $C_{2-8}$ alkenyl, or $C_{2-8}$ alkynyl. Further, examples of substituents of alkyl, alkenyl, or alkynyl represented by $R^1$ include hydroxyl, $C_{1-8}$ alkoxy, aryl, heteroaryl, and a halogen atom (e.g., chlorine, fluorine, bromine, or iodine). Particularly preferable examples of substituted alkyl, alkenyl, or alkynyl represented by $R^1$ include $C_{2-8}$ alkoxyalkyl, $C_{1-8}$ hydroxyalkyl, aralkyl, and heteroarylalkyl.

Examples of the aforementioned $C_{1-8}$ alkyl include methyl, ethyl, 1-propyl, 2-propyl, 1-butyl, 2-butyl, 1-pentyl, 2-pentyl, 1-hexyl, 2-hexyl, 1-heptyl, 2-heptyl, 3-heptyl, octyl, 2-methylpropyl, 2-methylbutyl, 3-methylbutyl, 2-methylpentyl, 3-methylpentyl, 4-methylpentyl, methylhexyl, methylheptyl, 1,1-dimethylethyl, 1,1-dimethylpropyl, 2-ethylhexyl, cyclopentylmethyl, cyclohexylmethyl, cyclopropyl, cyclobutyl, cyclopentyl, methylcyclopentyl, cyclohexyl, methylcyclohexyl, cycloheptyl, and cyclooctyl.

Examples of the aforementioned $C_{2-8}$ alkenyl include vinyl, allyl, crotyl, 1-propenyl, cyclopentenyl, cyclopentadienyl, and cyclohexenyl.

Examples of the aforementioned $C_{2-8}$ alkynyl include ethynyl, propynyl, and butynyl.

Examples of the aforementioned $C_{1-8}$ hydroxyalkyl include 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, and 4-hydroxybutyl.

Examples of the aforementioned aralkyl include benzyl, 1-phenethyl, 2-phenethyl, phenylpropyl, and phenylbutyl.

Examples of the aforementioned heteroarylalkyl include 4-pyridylmethyl and 3-pyridylmethyl.

Examples of the aforementioned $C_{2-8}$ alkoxyalkyl include methoxymethyl, 2-methoxyethyl, 3-methoxypropyl, 4-methoxybutyl, ethoxymethyl, 2-ethoxyethyl, and 3-ethoxypropyl.

Each of the aforementioned substituents represented by $R^1$ may have a substituent such as alkyl, hydroxyl, mercapto, a halogen atom, amino, or alkoxy.

In general formula (I), examples of aryl or heteroaryl represented by $R^1$ include phenyl, 1-naphthyl, 2-naphthyl, 2-pyridyl, 3-pyridyl, 4-pyridyl, 2-pyrazinyl, 3-pyrazinyl, 2-pyrimidinyl, 4-pyrimidinyl, 5-pyrimidinyl, 2-furyl, 3-furyl, 2-thienyl, and 3-thienyl. The aforementioned aryl or heteroaryl may or may not have a substituent. Examples of substituents include $C_{1-4}$ alkyl, $C_{1-4}$ alkoxy, hydroxyl, mercapto, $C_{1-4}$ alkylthio, a halogen atom, amino, $C_{2-8}$ dialkylamino, $C_{1-4}$ monoalkylamino, and methylenedioxy. Examples of the aforementioned $C_{1-4}$ alkyl include methyl, ethyl, 1-propyl, 2-propyl, 1-butyl, and 2-butyl. Examples of $C_{1-4}$ alkoxy include methoxy, ethoxy, 1-propoxy, 2-propoxy, 1-butoxy, and 2-butoxy. Examples of the aforementioned $C_{2-8}$ dialkylamino include dimethylamino, diethylamino, dipropylamino, dibutylamino, ethylmethylamino, and methylpropylamino. Examples of the aforementioned $C_{1-4}$ monoalkylamino include methylamino, ethylamino, propylamino, and butylamino. Examples of the aforementioned $C_{1-4}$ alkylthio include methylthio, ethylthio, 1-propylthio, 2-propylthio, 1-butylthio, 2-butylthio, and t-butylthio. Examples of the aforementioned halogen atom include fluorine, chlorine, and bromine.

Examples of aryl or heteroaryl represented by $R^1$ having a substituent include 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-butylphenyl, 3-butylphenyl, 4-butylphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-ethoxyphenyl, 3-ethoxyphenyl, 4-ethoxyphenyl, 2-propoxyphenyl, 3-propoxyphenyl, 4-propoxyphenyl, 2-isopropoxyphenyl, 3-isopropoxyphenyl, 4-isopropoxyphenyl, 2-butoxyphenyl, 3-butoxyphenyl, 4-butoxyphenyl, 2-methylaminophenyl, 3-methylaminophenyl, 4-methylaminophenyl, 2-ethylaminophenyl, 3-ethylaminophenyl, 4-ethylaminophenyl, 2-propylaminophenyl, 3-propylaminophenyl, 4-propylaminophenyl, 2-isopropylaminophenyl, 3-isopropylaminophenyl, 4-isopropylaminophenyl, 2-butylaminophenyl, 3-butylaminophenyl, 4-butylaminophenyl, 2-dimethylaminophenyl, 3-dimethylaminophenyl, 4-dimethylaminophenyl, 2-diethylaminophenyl, 3-diethylaminophenyl, 4-diethylaminophenyl, 2-dipropylaminophenyl, 3-dipropylaminophenyl, 4-dipropylaminophenyl, 2-dibutylaminophenyl, 3-dibutylaminophenyl, 4-dibutylaminophenyl, 2-ethylmethylaminophenyl, 3-ethylmethylaminophenyl, 4-ethylmethylaminophenyl, 2-methylthiophenyl, 3-methylthiophenyl, 4-methylthiophenyl, 2-ethylthiophenyl, 3-ethylthiophenyl, 4-ethylthiophenyl, 2-propylthiophenyl, 3-propylthiophenyl, 4-propylthiophenyl, 2-isopropylthiophenyl, 3-isopropylthiophenyl, 4-isopropylthiophenyl, 2-butylthiophenyl, 3-butylthiophenyl, 4-butylthiophenyl, 2-methyl-1-naphthyl, 3-methyl-1-naphthyl, 4-methyl-1-naphthyl, 5-methyl-1-naphthyl, 6-methyl-1-naphthyl, 7-methyl-1-naphthyl, 8-methyl-1-naphthyl, 1-methyl-2-naphthyl, 3-methyl-2-naphthyl, 4-methyl-2-naphthyl, 5-methyl-2-naphthyl, 6-methyl-2-naphthyl, 7-methyl-2-naphthyl, 8-methyl-2-naphthyl, 2-methoxy-1-naphthyl, 3-methoxy-1-naphthyl, 4-methoxy-1-naphthyl, 5-methoxy-1-naphthyl, 6-methoxy-1-naphthyl, 7-methoxy-1-naphthyl, 8-methoxy-1-naphthyl, 1-methoxy-2-naphthyl, 3-methoxy-2-naphthyl, 4-methoxy-2-naphthyl, 5-methoxy-2-naphthyl, 6-methoxy-2-naphthyl, 7-methoxy-2-naphthyl, 8-methoxy-2-naphthyl, 2-ethoxy-1-naphthyl, 3-ethoxy-1-naphthyl, 4-ethoxy-1-naphthyl, 5-ethoxy-1-naphthyl, 6-ethoxy-1-naphthyl, 7-ethoxy-1-naphthyl, 8-ethoxy-1-naphthyl, 1-ethoxy-2-naphthyl, 3-ethoxy-2-naphthyl, 4-ethoxy-2-naphthyl, 5-ethoxy-2-naphthyl, 6-ethoxy-2-naphthyl, 7-ethoxy-2-naphthyl, 8-ethoxy-2-naphthyl, 2-hydroxy-1-naphthyl, 3-hydroxy-1-naphthyl, 4-hydroxy-1-naphthyl, 5-hydroxy-1-naphthyl, 6-hydroxy-1-naphthyl, 7-hydroxy-1-naphthyl, 8-hydroxy-1-naphthyl, 1-hydroxy-2-naphthyl, 3-hydroxy-2-naphthyl, 4-hydroxy-2-naphthyl, 5-hydroxy-2-naphthyl, 6-hydroxy-2-naphthyl, 7-hydroxy-2-naphthyl, 8-hydroxy-2-naphthyl, 2-chloro-1-naphthyl, 3-chloro-1-naphthyl, 4-chloro-1-naphthyl, 5-chloro-1-naphthyl, 6-chloro-1-naphthyl, 7-chloro-1-naphthyl, 8-chloro-1-naphthyl, 1-chloro-2-naphthyl, 3-chloro-2-naphthyl, 4-chloro-2-naphthyl, 5-chloro-2-naphthyl, 6-chloro-2-naphthyl, 7-chloro-2-naphthyl, 8-chloro-2-naphthyl, 2-fluoro-1-naphthyl, 3-fluoro-1-naphthyl, 4-fluoro-1-naphthyl, 5-fluoro-1-naphthyl, 6-fluoro-1-naphthyl, 7-fluoro-1-naphthyl, 8-fluoro-1-naphthyl, 1-fluoro-2-naphthyl, 3-fluoro-2-naphthyl, 4-fluoro-2-naphthyl, 5-fluoro-2-naphthyl, 6-fluoro-2-naphthyl, 7-fluoro-2-naphthyl, 8-fluoro-2-naphthyl, 2-amino-1-naphthyl, 3-amino-1-naphthyl, 4-amino-1-naphthyl, 5-amino-1-naphthyl, 6-amino-1-naphthyl, 7-amino-1-naphthyl, 8-amino-1-naphthyl, 1-amino-2-naphthyl, 3-amino-2-naphthyl, 4-amino-2-naphthyl, 5-amino-2-naphthyl, 6-amino-2-naphthyl, 7-amino-2-naphthyl, 8-amino-2-naphthyl, 2-methylamino-1-naphthyl, 3-methylamino-1-naphthyl, 4-methylamino-1-naphthyl, 5-methylamino-1-naphthyl, 6-methylamino-1-naphthyl, 7-methylamino-1-naphthyl, 8-methylamino-1-naphthyl, 1-methylamino-2-naphthyl, 3-methylamino-2-naphthyl, 4-methylamino-2-naphthyl, 5-methylamino-2-naphthyl, 6-methylamino-2-naphthyl, 7-methylamino-2-naphthyl, 8-methylamino-2-naphthyl, 2-dimethylamino-1-naphthyl, 3-dimethylamino-1-naphthyl, 4-dimethylamino-1-naphthyl, 5-dimethylamino-1-naphthyl, 6-dimethylamino-1-naphthyl, 7-dimethylamino-1-naphthyl, 8-dimethylamino-1-naphthyl, 1-dimethylamino-2-naphthyl, 3-dimethylamino-2-naphthyl, 4-dimethylamino-2-naphthyl, 5-dimethylamino-2-naphthyl, 6-dimethylamino-2-naphthyl, 7-dimethylamino-2-naphthyl, 8-dimethylamino-2-naphthyl, 2-methyl-3-pyridyl, 4-methyl-3-pyridyl, 5-methyl-3-pyridyl, 6-methyl-3-pyridyl, 3-methyl-2-pyridyl, 4-methyl-2-pyridyl, 5-methyl-2-pyridyl, 6-methyl-2-pyridyl, 2-methyl-4-pyridyl, 3-methyl-4-pyridyl, 5-methyl-4-pyridyl, 6-methyl-4-pyridyl, 2-ethyl-3-pyridyl, 4-ethyl-3-pyridyl, 5-ethyl-3-pyridyl, 6-ethyl-3-pyridyl, 3-methyl-2-pyridyl, 4-methyl-2-pyridyl, 5-methyl-2-pyridyl, 6-methyl-2-pyridyl, 2-ethyl-4-pyridyl, 3-ethyl-4-pyridyl, 5-ethyl-4-pyridyl, 6-ethyl-4-pyridyl, 2-methoxy-3-pyridyl, 4-methoxy-3-pyridyl, 5-methoxy-3-pyridyl, 6-methoxy-3-pyridyl, 3-methoxy-2-pyridyl, 4-methoxy-2-pyridyl, 5-methoxy-2-pyridyl, 6-methoxy-2-pyridyl, 2-methoxy-4-pyridyl, 3-methoxy-4-pyridyl, 5-methoxy-4-pyridyl, 6-methoxy-4-pyridyl, 2-ethoxy-3-pyridyl, 4-ethoxy-3-pyridyl, 5-ethoxy-3-pyridyl, 6-ethoxy-3-pyridyl, 3-ethoxy-2-pyridyl, 4-ethoxy-2-pyridyl, 5-ethoxy-2-pyridyl, 6-ethoxy-2-pyridyl, 2-ethoxy-4-pyridyl, 3-ethoxy-4-pyridyl, 5-ethoxy-4-pyridyl, 6-ethoxy-4-pyridyl, 2-hydroxy-3-pyridyl, 4-hydroxy-3-pyridyl, 5-hydroxy-3-pyridyl, 6-hydroxy-3-pyridyl, 3-hydroxy-2-pyridyl, 4-hydroxy-2-pyridyl, 5-hydroxy-2-pyridyl, 6-hydroxy-2-pyridyl, 2-hydroxy-4-pyridyl, 3-hydroxy-4-pyridyl, 5-hydroxy-4-pyridyl, 6-hydroxy-4-pyridyl, 2-mercapto-3-pyridyl, 4-mercapto-3-pyridyl, 5-mercapto-3-pyridyl, 6-mercapto-3-pyridyl, 3-mercapto-2-pyridyl, 4-mercapto-2-pyridyl, 5-mercapto-2-pyridyl, 6-mercapto-2-pyridyl, 2-mercapto-4-pyridyl, 3-mercapto-4-pyridyl, 5-mercapto-4-pyridyl, 6-mercapto-4-pyridyl, 2-methylthio-3-pyridyl, 4-methylthio-3-pyridyl, 5-methylthio-3-pyridyl, 6-methylthio-3-pyridyl, 3-methylthio-2-pyridyl, 4-methylthio-2-pyridyl, 5-methylthio-2-pyridyl, 6-methylthio-2-pyridyl, 2-methylthio-4-pyridyl, 3-methylthio-4-pyridyl, 5-methylthio-4-pyridyl, 6-methylthio-4-pyridyl, 2-chloro-3-pyridyl, 4-chloro-3-pyridyl, 5-chloro-3-pyridyl, 6-chloro-3-pyridyl, 3-chloro-2-pyridyl, 4-chloro-2-pyridyl, 5-chloro-2-pyridyl, 6-chloro-2-pyridyl, 2-chloro-4-pyridyl, 3-chloro-4-pyridyl, 5-chloro-4-pyridyl, 6-chloro-4-pyridyl, 2-amino-3-pyridyl, 4-amino-3-pyridyl, 5-amino-3-pyridyl, 6-amino-3-pyridyl, 3-amino-2-pyridyl, 4-amino-2-pyridyl, 5-amino-2-pyridyl, 6-amino-2-pyridyl, 2-amino-4-pyridyl, 3-amino-4-pyridyl, 5-amino-4-pyridyl, 6-amino-4-pyridyl, 2-monomethylamino-3-pyridyl, 4-monomethylamino-3-pyridyl, 5-monomethylamino-3-pyridyl, 6-monomethylamino-3-pyridyl, 3-monomethylamino-2-pyridyl, 4-monomethylamino-2-pyridyl, 5-monomethylamino-2-pyridyl, 6-monomethylamino-2-pyridyl, 2-monomethylamino-4-pyridyl, 3-monomethylamino-4-pyridyl, 5-monomethylamino-4-pyridyl, 6-monomethylamino-4-pyridyl, 2-dimethylamino-3-pyridyl, 4-dimethylamino-3-pyridyl, 5-dimethylamino-3-pyridyl, 6-dimethylamino-3-pyridyl, 3-dimethylamino-2-pyridyl, 4-dimethylamino-2-pyridyl, 5-dimethylamino-2-pyridyl, 6-dimethylamino-2-pyridyl, 2-dimethylamino-4-pyridyl, 3-dimethylamino-4-pyridyl, 5-dimethylamino-4-pyridyl, 6-dimethylamino-4-pyridyl, 2-fluoro-3-pyridyl, 4-fluoro-3-pyridyl, 5-fluoro-3-pyridyl, 6-fluoro-3-pyridyl, 3-fluoro-2-pyridyl, 4-fluoro-2-pyridyl, 5-fluoro-2-pyridyl, 6-fluoro-2-pyridyl, 2-fluoro-4-pyridyl, 3-fluoro-4-pyridyl, 5-fluoro-4-pyridyl, 6-fluoro-4-pyridyl, 2,4-dimethyl-3-pyridyl, 2,6-dimethyl-3-pyridyl, 5,6-dimethyl-3-pyridyl, 4,6-dimethyl-3-pyridyl, 4,5-dimethyl-2-pyridyl, 5,6-dimethyl-2-pyridyl, 2,3-dimethyl-4-pyridyl, 2,6-dimethyl-4-pyridyl, 2,4-dimethoxy-3-pyridyl, 2,6-dimethoxy-3-pyridyl, 5,6-dimethoxy-3-pyridyl, 4,6-dimethoxy-3-pyridyl, 4,5-dimethoxy-2-pyridyl, 5,6-dimethoxy-2-pyridyl, 2,3-dimethoxy-4-pyridyl, 2,6-dimethoxy-4-pyridyl, 2-chloro-6-methyl-3-pyridyl, 6-chloro-2-methyl-3-pyridyl, 2-chloro-6-methoxy-3-pyridyl, 6-chloro-2-methoxy-3-pyridyl, 5-methyl-6-chloro-3-pyridyl, 5-methoxy-6-chloro-3-pyridyl, 5-ethoxy-6-chloro-3-pyridyl, 5-chloro-6-methyl-3-pyridyl, 5-methoxy-6-methyl-3-pyridyl, 5-ethoxy-6-methyl-3-pyridyl, 5-chloro-6-methoxy-3-pyridyl, 5-chloro-6-ethoxy-3-pyridyl, 2,5,6- trimethyl-3-pyridyl, 2-pyrazinyl, 5-methyl-2-pyrazinyl, 6-methyl-2-pyrazinyl, 5-methoxy-2-pyrazinyl, 6-methoxy-2-pyrazinyl, 5-ethoxy-2-pyrazinyl, 6-ethoxy-2-pyrazinyl, 5-chloro-2-pyrazinyl, 6-chloro-2-pyrazinyl, 3-methyl-2-furyl, 4-methyl-2-furyl, 5-methyl-2-furyl, 2-methyl-3-furyl, 4-methyl-3-furyl, 5-methyl-3-furyl, 3-methoxy-2-furyl, 4-methoxy-2-furyl, 5-methoxy-2-furyl, 2-methoxy-3-furyl, 4-methoxy-3-furyl, 5-methoxy-3-furyl, 3-chloro-2-furyl, 4-chloro-2-furyl, 5-chloro-2-furyl, 2-chloro-3-furyl, 4-chloro-3-furyl, 5-chloro-3-furyl, 3-fluoro-2-furyl, 4-fluoro-2-furyl, 5-fluoro-2-furyl, 2-fluoro-3-furyl, 4-fluoro-3-furyl, 5-fluoro-3-furyl, 3-methyl-2-thienyl, 4-methyl-2-thienyl, 5-methyl-2-thienyl, 2-methyl-3-thienyl, 4-methyl-3-thienyl, 5-methyl-3-thienyl, 3-methoxy-2-thienyl, 4-methoxy-2-thienyl, 5-methoxy-2-thienyl, 2-methoxy-3-thienyl, 4-methoxy-3-thienyl, 5-methoxy-3-thienyl, 3-chloro-2-thienyl, 4-chloro-2-thienyl, 5-chloro-2-thienyl, 2-chloro-3-thienyl, 4-chloro-3-thienyl, 5-chloro-3-thienyl, 3-fluoro-2-thienyl, 4-fluoro-2-thienyl, 5-fluoro-2-thienyl, 2-fluoro-3-thienyl, 4-fluoro-3-thienyl, and 5-fluoro-3-thienyl.

In general formula (I), examples of substituents represented by $R^2$ include hydroxyl, mercapto, $C_{1-8}$ acyloxy, and $C_{2-8}$ alkoxycarbonyloxy.

Examples of the aforementioned $C_{1-8}$ acyloxy include formyloxy, acetyloxy, propionyloxy, butanoyloxy, pentanoyloxy, hexanoyloxy, heptanoyloxy, octanoyloxy, and benzoyloxy.

Examples of the aforementioned $C_{2-8}$ alkoxycarbonyloxy include methoxycarbonyloxy, ethoxycarbonyloxy, propoxycarbonyloxy, butoxycarbonyloxy, pentyloxycarbonyloxy, hexyloxycarbonyloxy, heptyloxycarbonyloxy, isopropyloxycarbonyloxy, isobutyloxycarbonyloxy, t-butyloxycarbonyloxy, isopentyloxycarbonyloxy, and benzyloxycarbonyloxy.

In general formula (I), X represents any of $NR^3$, an oxygen atom, or a sulfur atom, wherein the aforementioned $R^3$ represents a hydrogen atom or $C_{1-3}$ alkyl, and examples of the alkyl include methyl, ethyl, n-propyl, and isopropyl.

In general formula (I), examples of 5- or 6-membered monocyclic aromatic hetero rings containing 1 or 2 hetero atoms selected from a nitrogen atom, an oxygen atom, or a sulfur atom represented by Y include thiophene ring, furan ring, pyrrole ring, thiazole ring, isoxazole ring, oxazole ring, pyrazole ring, imidazole ring, pyridine ring, pyrazine ring, pyrimidine ring, and pyridazine ring. Examples of fused bicyclic aromatic hetero rings containing 1 or 2 hetero atoms selected from a nitrogen atom, an oxygen atom, or a sulfur atom include benzothiophene ring, benzofuran ring, indole ring, benzothiazole ring, benzoxazole ring, benzoimidazole ring, quinoline ring, and isoquinoline ring. The aforementioned Y may be unsubstituted or partially substituted by a substituent. Examples of preferable Y include naphthalene ring, thiophene ring, pyridine ring, and pyrazine ring, and these rings may be unsubstituted or partially substituted by a substituent. For example, when Y is a pyridine ring, one to four substituents may substitute at any position on a pyridine ring. When Y is a pyrazine ring, one to three substituents may substitute at any position on a pyrazine ring. When Y is substituted with two or more substituents, they may be the same or different.

Examples of the substituents for Y include $C_{1-4}$ alkyl, $C_{1-4}$ alkoxy, hydroxyl, mercapto, $C_{1-4}$ alkylthio, a halogen atom, amino, $C_{2-8}$ dialkylamino, $C_{1-4}$ monoalkylamino, 1-pyrrolidinyl, 2-pyrrolidinyl, 3-pyrrolidinyl, piperidino, morpholino, and 3-morpholinyl. Alkyl in the aforementioned $C_{1-4}$ alkyl and $C_{1-4}$ alkoxy, further in the aforementioned $C_{2-8}$ dialkylamino and $C_{1-4}$ monoalkylamino is the same as that in the aforementioned case of $R^1$. Examples of the aforementioned $C_{1-4}$ alkylthio include methylthio, ethylthio, 1-propylthio, 2-propylthio, 1-butylthio, 2-butylthio, and t-butylthio. Examples of the aforementioned halogen atom include fluorine, chlorine, and bromine.

Examples of Y having a substituent include 2-methyl-1-naphthyl, 3-methyl-1-naphthyl, 4-methyl-1-naphthyl, 5-methyl-1-naphthyl, 6-methyl-1-naphthyl, 7-methyl-1-naphthyl, 8-methyl-1-naphthyl, 1-methyl-2-naphthyl, 3-methyl-2-naphthyl, 4-methyl-2-naphthyl, 5-methyl-2-naphthyl, 6-methyl-2-naphthyl, 7-methyl-2-naphthyl, 8-methyl-2-naphthyl, 2-methoxy-1-naphthyl, 3-methoxy-1-naphthyl, 4-methoxy-1-naphthyl, 5-methoxy-1-naphthyl, 6-methoxy-1-naphthyl, 7-methoxy-1-naphthyl, 8-methoxy-1-naphthyl, 1-methoxy-2-naphthyl, 3-methoxy-2-naphthyl, 4-methoxy-2-naphthyl, 5-methoxy-2-naphthyl, 6-methoxy-2-naphthyl, 7-methoxy-2-naphthyl, 8-methoxy-2-naphthyl, 2-ethoxy-1-naphthyl, 3-ethoxy-1-naphthyl, 4-ethoxy-1-naphthyl, 5-ethoxy-1-naphthyl, 6-ethoxy-1-naphthyl, 7-ethoxy-1-naphthyl, 8-ethoxy-1-naphthyl, 1-ethoxy-2-naphthyl, 3-ethoxy-2-naphthyl, 4-ethoxy-2-naphthyl, 5-ethoxy-2-naphthyl, 6-ethoxy-2-naphthyl, 7-ethoxy-2-naphthyl, 8-ethoxy-2-naphthyl, 2-hydroxy-1-naphthyl, 3-hydroxy-1-naphthyl, 4-hydroxy-1-naphthyl; 5-hydroxy-1-naphthyl, 6-hydroxy-1-naphthyl, 7-hydroxy-1-naphthyl, 8-hydroxy-1-naphthyl, 1-hydroxy-2-naphthyl, 3-hydroxy-2-naphthyl, 4-hydroxy-2-naphthyl, 5-hydroxy-2-naphthyl, 6-hydroxy-2-naphthyl, 7-hydroxy-2-naphthyl, 8-hydroxy-2-naphthyl, 2-chloro-1-naphthyl, 3-chloro-1-naphthyl, 4-chloro-1-naphthyl, 5-chloro-1-naphthyl, 6-chloro-1-naphthyl, 7-chloro-1-naphthyl, 8-chloro-1-naphthyl, 1-chloro-2-naphthyl, 3-chloro-2-naphthyl, 4-chloro-2-naphthyl, 5-chloro-2-naphthyl, 6-chloro-2-naphthyl, 7-chloro-2-naphthyl, 8-chloro-2-naphthyl, 2-fluoro-1-naphthyl, 3-fluoro-1-naphthyl, 4-fluoro-1-naphthyl, 5-fluoro-1-naphthyl, 6-fluoro-1-naphthyl, 7-fluoro-1-naphthyl, 8-fluoro-1-naphthyl, 1-fluoro-2-naphthyl, 3-fluoro-2-naphthyl, 4-fluoro-2-naphthyl, 5-fluoro-2-naphthyl, 6-fluoro-2-naphthyl, 7-fluoro-2-naphthyl, 8-fluoro-2-naphthyl, 2-amino-1-naphthyl, 3-amino-1-naphthyl, 4-amino-1-naphthyl, 5-amino-1-naphthyl, 6-amino-1-naphthyl, 7-amino-1-naphthyl, 8-amino-1-naphthyl, 1-amino-2-naphthyl, 3-amino-2-naphthyl, 4-amino-2-naphthyl, 5-amino-2-naphthyl, 6-amino-2-naphthyl, 7-amino-2-naphthyl, 8-amino-2-naphthyl, 2-methylamino-1-naphthyl, 3-methylamino-1-naphthyl, 4-methylamino-1-naphthyl, 5-methylamino-1-naphthyl, 6-methylamino-1-naphthyl, 7-methylamino-1-naphthyl, 8-methylamino-1-naphthyl, 1-methylamino-2-naphthyl, 3-methylamino-2-naphthyl, 4-methylamino-2-naphthyl, 5-methylamino-2-naphthyl, 6-methylamino-2-naphthyl, 7-methylamino-2-naphthyl, 8-methylamino-2-naphthyl, 2-dimethylamino-1-naphthyl, 3-dimethylamino-1-naphthyl, 4-dimethylamino-1-naphthyl, 5-dimethylamino-1-naphthyl, 6-dimethylamino-1-naphthyl, 7-dimethylamino-1-naphthyl, 8-dimethylamino-1-naphthyl, 1-dimethylamino-2-naphthyl, 3-dimethylamino-2-naphthyl, 4-dimethylamino-2-naphthyl, 5-dimethylamino-2-naphthyl, 6-dimethylamino-2-naphthyl, 7-dimethylamino-2-naphthyl, 8-dimethylamino-2-naphthyl, 3-methyl-2-thienyl, 4-methyl-2-thienyl, 5-methyl-2-thienyl, 2-methyl-3-thienyl, 4-methyl-3-thienyl, 5-methyl-3-thienyl, 3-methoxy-2-thienyl, 4-methoxy-2-thienyl, 5-methoxy-2-thienyl, 2-methoxy-3-thienyl, 4-methoxy-3-thienyl, 5-methoxy-3-thienyl, 3-chloro-2-thienyl, 4-chloro-2-thienyl, 5-chloro-2-thienyl, 2-chloro-3-thienyl, 4-chloro-3-thienyl, 5-chloro-3-thienyl, 3-fluoro-2-thienyl, 4-fluoro-2-thienyl, 5-fluoro-2-thienyl, 2-fluoro-3-thienyl, 4-fluoro-3-thienyl, 5-fluoro-3-thienyl, 3-methyl-2-furyl, 4-methyl-2-furyl, 5-methyl-2-furyl, 2-methyl-3-furyl, 4-methyl-3-furyl, 5-methyl-3-furyl, 3-methoxy-2-furyl, 4-methoxy-2-furyl, 5-methoxy-2-furyl, 2-methoxy-3-furyl, 4-methoxy-3-furyl, 5-methoxy-3-furyl, 3-chloro-2-furyl, 4-chloro-2-furyl, 5-chloro-2-furyl, 2-chloro-3-furyl, 4-chloro-3-furyl, 5-chloro-3-furyl, 3-fluoro-2-furyl, 4-fluoro-2-furyl, 5-fluoro-2-furyl, 2-fluoro-3-furyl, 4-fluoro-3-furyl, 5-fluoro-3-furyl, 3-methyl-2-pyrrolyl, 4-methyl-2-pyrrolyl, 5-methyl-2-pyrrolyl, 2-methyl-3-pyrrolyl, 4-methyl-3-pyrrolyl, 5-methyl-3-pyrrolyl, 3-methoxy-2-pyrrolyl, 4-methoxy-2-pyrrolyl, 5-methoxy-2-pyrrolyl, 2-methoxy-3-pyrrolyl, 4-methoxy-3-pyrrolyl, 5-methoxy-3-pyrrolyl, 3-chloro-2-pyrrolyl, 4-chloro-2-pyrrolyl, 5-chloro-2-pyrrolyl, 2-chloro-3-pyrrolyl, 4-chloro-3-pyrrolyl, 5-chloro-3-pyrrolyl, 3-fluoro-2-pyrrolyl, 4-fluoro-2-pyrrolyl, 5-fluoro-2-pyrrolyl, 2-fluoro-3-pyrrolyl, 4-fluoro-3-pyrrolyl, 5-fluoro-3-pyrrolyl, 1-methyl-2-imidazolyl, 4-methyl-2-imidazolyl, 1-methyl-4-imidazolyl, 2-methyl-4-imidazolyl, 5-methyl-4-imidazolyl, 1-methyl-5-imidazolyl, 4-methoxy-2-imidazolyl, 2-methoxy-4-imidazolyl, 5-methoxy-4-imidazolyl, 4-chloro-2-imidazolyl, 2-chloro-4-imidazolyl, 5-chloro-4-imidazolyl, 4-fluoro-2-imidazolyl, 2-fluoro-4-imidazolyl, 5-fluoro-4-imidazolyl, 2-methyl-3-pyridyl, 4-methyl-3-pyridyl, 5-methyl-3-pyridyl, 6-methyl-3-pyridyl, 3-methyl-2-pyridyl, 4-methyl-2-pyridyl, 5-methyl-2-pyridyl, 6-methyl-2-pyridyl, 2-methyl-4-pyridyl, 3-methyl-4-pyridyl, 5-methyl-4-pyridyl, 6-methyl-4-pyridyl, 2-ethyl-3-pyridyl, 4-ethyl-3-pyridyl, 5-ethyl-3-pyridyl, 6-ethyl-3-pyridyl, 3-methyl-2-pyridyl, 4-methyl-2-pyridyl, 5-methyl-2-pyridyl, 6-ethyl-2-pyridyl, 2-ethyl-4-pyridyl, 3-ethyl-4-pyridyl, 5-ethyl-4-pyridyl, 6-ethyl-4-pyridyl, 2-methoxy-3-pyridyl, 4-methoxy-3-pyridyl, 5-methoxy-3-pyridyl, 6-methoxy-3-pyridyl, 3-methoxy-2-pyridyl, 4-methoxy-2-pyridyl, 5-methoxy-2-pyridyl, 6-methoxy-2-pyridyl, 2-methoxy-4-pyridyl, 3-methoxy-4-pyridyl, 5-methoxy-4-pyridyl, 6-methoxy-4-pyridyl, 2-ethoxy-3-pyridyl, 4-ethoxy-3-pyridyl, 5-ethoxy-3-pyridyl, 6-ethoxy-3-pyridyl, 3-ethoxy-2-pyridyl, 4-ethoxy-2-pyridyl, 5-ethoxy-2-pyridyl, 6-ethoxy-2-pyridyl, 2-ethoxy-4-pyridyl, 3-ethoxy-4-pyridyl, 5-ethoxy-4-pyridyl, 6-ethoxy-4-pyridyl, 2-hydroxy-3-pyridyl, 4-hydroxy-3-pyridyl, 5-hydroxy-3-pyridyl, 6-hydroxy-3-pyridyl, 3-hydroxy-2-pyridyl, 4-hydroxy-2-pyridyl, 5-hydroxy-2-pyridyl, 6-hydroxy-2-pyridyl, 2-hydroxy-4-pyridyl, 3-hydroxy-4-pyridyl, 5-hydroxy-4-pyridyl, 6-hydroxy-4-pyridyl, 2-mercapto-3-pyridyl, 4-mercapto-3-pyridyl, 5-mercapto-3-pyridyl, 6-mercapto-3-pyridyl, 3-mercapto-2-pyridyl, 4-mercapto-2-pyridyl, 5-mercapto-2-pyridyl, 6-mercapto-2-pyridyl, 2-mercapto-4-pyridyl, 3-mercapto-4-pyridyl, 5-mercapto-4-pyridyl, 6-mercapto-4-pyridyl, 2-methylthio-3-pyridyl, 4-methylthio-3-pyridyl, 5-methylthio-3-pyridyl, 6-methylthio-3-pyridyl, 3-methylthio-2-pyridyl, 4-methylthio-2-pyridyl, 5-methylthio-2-pyridyl, 6-methylthio-2-pyridyl, 2-methylthio-4-pyridyl, 3-methylthio-4-pyridyl, 5-methylthio-4-pyridyl, 6-methylthio-4-pyridyl, 2-chloro-3-pyridyl, 4-chloro-3-pyridyl, 5-chloro-3-pyridyl, 6-chloro-3-pyridyl, 3-chloro-2-pyridyl, 4-chloro-2-pyridyl, 5-chloro-2-pyridyl, 6-chloro-2-pyridyl, 2-chloro-4-pyridyl, 3-chloro-4-pyridyl, 5-chloro-4-pyridyl, 6-chloro-4-pyridyl, 2-amino-3-pyridyl, 4-amino-3-pyridyl, 5-amino-3-pyridyl, 6-amino-3-pyridyl, 3-amino-2-pyridyl, 4-amino-2-pyridyl, 5-amino-2-pyridyl, 6-amino-2-pyridyl, 2-amino-4-pyridyl, 3-amino-4-pyridyl, 5-amino-4-pyridyl, 6-amino-4-pyridyl, 2-monomethylamino-3-pyridyl, 4-monomethylamino-3-pyridyl, 5-monomethylamino-3-pyridyl, 6-monomethylamino-3-pyridyl, 3-monomethylamino-2-pyridyl, 4-monomethylamino-2-pyridyl, 5-monomethylamino-2-pyridyl, 6-monomethylamino-2-pyridyl, 2-monomethylamino-4-pyridyl, 3-monomethylamino-4-pyridyl, 5-monomethylamino-4-pyridyl, 6-monomethylamino-4-pyridyl, 2-dimethylamino-3-pyridyl, 4-dimethylamino-3-pyridyl, 5-dimethylamino-3-pyridyl, 6-dimethylamino-3-pyridyl, 3-dimethylamino-2-pyridyl, 4-dimethylamino-2-pyridyl, 5-dimethylamino-2-pyridyl, 6-dimethylamino-2-pyridyl, 2-dimethylamino-4-pyridyl, 3-dimethylamino-4-pyridyl, 5-dimethylamino-4-pyridyl, 6-dimethylamino-4-pyridyl, 2-(1-pyrrolidinyl)-3-pyridyl, 4-(1-pyrrolidinyl)-3-pyridyl, 5-(1-pyrrolidinyl)-3-pyridyl, 6-(1-pyrrolidinyl)-3-pyridyl, 3-(1-pyrrolidinyl)-2-pyridyl, 4-(1-pyrrolidinyl)-2-pyridyl, 5-(1-pyrrolidinyl)-2-pyridyl, 6-(1-pyrrolidinyl)-2-pyridyl, 2-(1-pyrrolidinyl)-4-pyridyl, 3-(1-pyrrolidinyl)-4-pyridyl, 5-(1-pyrrolidinyl)-4-pyridyl, 6-(1-pyrrolidinyl)-4-pyridyl, 2-piperidino-3-pyridyl, 4-piperidino-3-pyridyl, 5-piperidino-3-pyridyl, 6-piperidino-3-pyridyl, 3-piperidino-2-pyridyl, 4-piperidino-2-pyridyl, 5-piperidino-2-pyridyl, 6-piperidino-2-pyridyl, 2-piperidino-4-pyridyl, 3-piperidino-4-pyridyl, 5-piperidino-4-pyridyl, 6-piperidino-4-pyridyl, 2-morpholino-3-pyridyl, 4-morpholino-3-pyridyl, 5-morpholino-3-pyridyl, 6-morpholino-3-pyridyl, 3-morpholino-2-pyridyl, 4-morpholino-2-pyridyl, 5-morpholino-2-pyridyl, 6-morpholino-2-pyridyl, 2-morpholino-4-pyridyl, 3-morpholino-4-pyridyl, 5-morpholino-4-pyridyl, 6-morpholino-4-pyridyl, 2-fluoro-3-pyridyl, 4-fluoro-3-pyridyl, 5-fluoro-3-pyridyl, 6-fluoro-3-pyridyl, 3-fluoro-2-pyridyl, 4-fluoro-2-pyridyl, 5-fluoro-2-pyridyl, 6-fluoro-2-pyridyl, 2-fluoro-4-pyridyl, 3-fluoro-4-pyridyl, 5-fluoro-4-pyridyl, 6-fluoro-4-pyridyl, 2,4-dimethyl-3-pyridyl, 2,6-dimethyl-3-pyridyl, 5,6-dimethyl-3-pyridyl, 4,6-dimethyl-3-pyridyl, 4,5-dimethyl-2-pyridyl, 5,6-dimethyl-2-pyridyl, 2,3-dimethyl-4-pyridyl, 2,6-dimethyl-4-pyridyl, 2,4-dimethoxy-3-pyridyl, 2,6-dimethoxy-3-pyridyl, 5,6-dimethoxy-3-pyridyl, 4,6-dimethoxy-3-pyridyl, 4,5-dimethoxy-2-pyridyl, 5,6-dimethoxy-2-pyridyl, 2,3-dimethoxy-4-pyridyl, 2,6-dimethoxy-4-pyridyl, 2-chloro-6-methyl-3-pyridyl, 6-chloro-2-methyl-3-pyridyl, 2-chloro-6-methoxy-3-pyridyl, 6-chloro-2-methoxy-3-pyridyl, 5-methyl-6-chloro-3-pyridyl, 5-methoxy-6-chloro-3-pyridyl, 5-ethoxy-6-chloro-3-pyridyl, 5-chloro-6-methyl-3-pyridyl, 5-methoxy-6-methyl-3-pyridyl, 5-ethoxy-6-methyl-3-pyridyl, 5-chloro-6-methoxy-3-pyridyl, 5-chloro-6-ethoxy-3-pyridyl, 2,5,6-trimethyl-3-pyridyl, 2-pyrazinyl, 5-methyl-2-pyrazinyl, 6-methyl-2-pyrazinyl, 5-methoxy-2-pyrazinyl, 6-methoxy-2-pyrazinyl, 5-ethoxy-2-pyrazinyl, 6-ethoxy-2-pyrazinyl, 5-chloro-2-pyrazinyl, 6-chloro-2-pyrazinyl, 3-methyl-2-benzothienyl, 4-methyl-2-benzothienyl, 5-methyl-2-benzothienyl, 6-methyl-2-benzothienyl, 7-methyl-2-benzothienyl, 2-methyl-3-benzothienyl, 4-methyl-3-benzothienyl, 5-methyl-3-benzothienyl, 6-methyl-3-benzothienyl, 7-methyl-3-benzothienyl, 2-methyl-5-benzothienyl, 3-methyl-5-benzothienyl, 4-methyl-5-benzothienyl, 6-methyl-5-benzothienyl, 7-methyl-5-benzothienyl, 3-methoxy-2-benzothienyl, 4-methoxy-2-benzothienyl, 5-methoxy-2-benzothienyl, 6-methoxy-2-benzothienyl, 7-methoxy-2-benzothienyl, 2-methoxy-3-benzothienyl, 4-methoxy-3-benzothienyl, 5-methoxy-3-benzothienyl, 6-methoxy-3-benzothienyl, 7-methoxy-3-benzothienyl, 2-methoxy-5-benzothienyl, 3-methoxy-5-benzothienyl, 4-methoxy-5-benzothienyl, 6-methoxy-5-benzothienyl, 7-methoxy-5-benzothienyl, 3-chloro-2-benzothienyl, 4-chloro-2-benzothienyl, 5-chloro-2-benzothienyl, 6-chloro-2-benzothienyl, 7-chloro-2-benzothienyl, 2-chloro-3-benzothienyl, 4-chloro-3-benzothienyl, 5-chloro-3-benzothienyl, 6-chloro-3-benzothienyl, 7-chloro-3-benzothienyl, 2-chloro-5-benzothienyl, 3-chloro-5-benzothienyl, 4-chloro-5- benzothienyl, 6-chloro-5-benzothienyl, 7-chloro-5-benzothienyl, 3-fluoro-2-benzothienyl, 4-fluoro-2-benzothienyl, 5-fluoro-2-benzothienyl, 6-fluoro-2-benzothienyl, 7-fluoro-2-benzothienyl, 2-fluoro-3-benzothienyl, 4-fluoro-3-benzothienyl, 5-fluoro-3-benzothienyl, 6-fluoro-3-benzothienyl, 7-fluoro-3-benzothienyl, 2-fluoro-5-benzothienyl, 3-fluoro-5-benzothienyl, 4-fluoro-5-benzothienyl, 6-fluoro-5-benzothienyl, 7-fluoro-5-benzothienyl, 3-methyl-2-benzofuryl, 4-methyl-2-benzofuryl, 5-methyl-2-benzofuryl, 6-methyl-2-benzofuryl, 7-methyl-2-benzofuryl, 2-methyl-3-benzofuryl, 4-methyl-3-benzofuryl, 5-methyl-3-benzofuryl, 6-methyl-3-benzofuryl, 7-methyl-3-benzofuryl, 2-methyl-5-benzofuryl, 3-methyl-5-benzofuryl, 4-methyl-5-benzofuryl, 6-methyl-5-benzofuryl, 7-methyl-5-benzofuryl, 3-methoxy-2-benzofuryl, 4-methoxy-2-benzofuryl, 5-methoxy-2-benzofuryl, 6-methoxy-2-benzofuryl, 7-methoxy-2-benzofuryl, 2-methoxy-3-benzofuryl, 4-methoxy-3-benzofuryl, 5-methoxy-3-benzofuryl, 6-methoxy-3-benzofuryl, 7-methoxy-3-benzofuryl, 2-methoxy-5-benzofuryl, 3-methoxy-5-benzofuryl, 4-methoxy-5-benzofuryl, 6-methoxy-5-benzofuryl, 7-methoxy-5-benzofuryl, 3-chloro-2-benzofuryl, 4-chloro-2-benzofuryl, 5-chloro-2-benzofuryl, 6-chloro-2-benzofuryl, 7-chloro-2-benzofuryl, 2-chloro-3-benzofuryl, 4-chloro-3-benzofuryl, 5-chloro-3-benzofuryl, 6-chloro-3-benzofuryl, 7-chloro-3-benzofuryl, 2-chloro-5-benzofuryl, 3-chloro-5-benzofuryl, 4-chloro-5-benzofuryl, 6-chloro-5-benzofuryl, 7-chloro-5-benzofuryl, 3-fluoro-2-benzofuryl, 4-fluoro-2-benzofuryl, 5-fluoro-2-benzofuryl, 6-fluoro-2-benzofuryl, 7-fluoro-2-benzofuryl, 2-fluoro-3-benzofuryl, 4-fluoro-3-benzofuryl, 5-fluoro-3-benzofuryl, 6-fluoro-3-benzofuryl, 7-fluoro-3-benzofuryl, 2-fluoro-5-benzofuryl, 3-fluoro-5-benzofuryl, 4-fluoro-5-benzofuryl, 6-fluoro-5-benzofuryl, 7-fluoro-5-benzofuryl, 1-methyl-2-indolyl, 3-methyl-2-indolyl, 4-methyl-2-indolyl, 5-methyl-2-indolyl, 6-methyl-2-indolyl, 7-methyl-2-indolyl, 1-methyl-3-indolyl, 2-methyl-3-indolyl, 4-methyl-3-indolyl, 5-methyl-3-indolyl, 6-methyl-3-indolyl, 7-methyl-3-indolyl, 1-methyl-5-indolyl, 2-methyl-5-indolyl, 3-methyl-5-indolyl, 4-methyl-5-indolyl, 6-methyl-5-indolyl, 7-methyl-5-indolyl, 3-methoxy-2-indolyl, 4-methoxy-2-indolyl, 5-methoxy-2-indolyl, 6-methoxy-2-indolyl, 7-methoxy-2-indolyl, 2-methoxy-3-indolyl, 4-methoxy-3-indolyl, 5-methoxy-3-indolyl, 6-methoxy-3-indolyl, 7-methoxy-3-indolyl, 2-methoxy-5-indolyl, 3-methoxy-5-indolyl, 4-methoxy-5-indolyl, 6-methoxy-5-indolyl, 7-methoxy-5-indolyl, 3-chloro-2-indolyl, 4-chloro-2-indolyl, 5-chloro-2-indolyl, 6-chloro-2-indolyl, 7-chloro-2-indolyl, 2-chloro-3-indolyl, 4-chloro-3-indolyl, 5-chloro-3-indolyl, 6-chloro-3-indolyl, 7-chloro-3-indolyl, 2-chloro-5-indolyl, 3-chloro-5-indolyl, 4-chloro-5-indolyl, 6-chloro-5-indolyl, 7-chloro-5-indolyl, 3-fluoro-2-indolyl, 4-fluoro-2-indolyl, 5-fluoro-2-indolyl, 6-fluoro-2-indolyl, 7-fluoro-2-indolyl, 2-fluoro-3-indolyl, 4-fluoro-3-indolyl, 5-fluoro-3-indolyl, 6-fluoro-3-indolyl, 7-fluoro-3-indolyl, 2-fluoro-5-indolyl, 3-fluoro-5-indolyl, 4-fluoro-5-indolyl, 6-fluoro-5-indolyl, 7-fluoro-5-indolyl, 3-methyl-2-quinolyl, 4-methyl-2-quinolyl, 5-methyl-2-quinolyl, 6-methyl-2-quinolyl, 7-methyl-2-quinolyl, 8-methyl-2-quinolyl, 2-methyl-4-quinolyl, 3-methyl-4-quinolyl, 5-methyl-4-quinolyl, 6-methyl-4-quinolyl, 7-methyl-4-quinolyl, 8-methyl-4-quinolyl, 2-methyl-6-quinolyl, 3-methyl-6-quinolyl, 4-methyl-6-quinolyl, 5-methyl-6-quinolyl, 7-methyl-6-quinolyl, 8-methyl-6-quinolyl, 3-methoxy-2-quinolyl, 4-methoxy-2-quinolyl, 5-methoxy-2-quinolyl, 6-methoxy-2-quinolyl, 7-methoxy-2-quinolyl, 8-methoxy-2-quinolyl, 2-methoxy-4-quinolyl, 3-methoxy-4-quinolyl, 5-methoxy-4-quinolyl, 6-methoxy-4-quinolyl, 7-methoxy-4-quinolyl, 8-methoxy-4-quinolyl, 2-methoxy-6-quinolyl, 3-methoxy-6-quinolyl, 4-methoxy-6-quinolyl, 5-methoxy-6-quinolyl, 7-methoxy-6-quinolyl, 8-methoxy-6-quinolyl, 3-chloro-2-quinolyl, 4-chloro-2-quinolyl, 5-chloro-2-quinolyl, 6-chloro-2-quinolyl, 7-chloro-2-quinolyl, 8-chloro-2-quinolyl, 2-chloro-4-quinolyl, 3-chloro-4-quinolyl, 5-chloro-4-quinolyl, 6-chloro-4-quinolyl, 7-chloro-4-quinolyl, 8-chloro-4-quinolyl, 2-chloro-6-quinolyl, 3-chloro-6-quinolyl, 4-chloro-6-quinolyl, 5-chloro-6-quinolyl, 7-chloro-6-quinolyl, 8-chloro-6-quinolyl, 3-fluoro-2-quinolyl, 4-fluoro-2-quinolyl, 5-fluoro-2-quinolyl, 6-fluoro-2-quinolyl, 7-fluoro-2-quinolyl, 8-fluoro-2-quinolyl, 2-fluoro-4-quinolyl, 3-fluoro-4-quinolyl, 5-fluoro-4-quinolyl, 6-fluoro-4-quinolyl, 7-fluoro-4-quinolyl, 8-fluoro-4-quinolyl, 2-fluoro-6-quinolyl, 3-fluoro-6-quinolyl, 4-fluoro-6-quinolyl, 5-fluoro-6-quinolyl, 7-fluoro-6-quinolyl, and 8-fluoro-6-quinolyl.

In general formula (I), examples of further preferable X include NH and an oxygen atom, with NH being particularly preferable.

In general formula (I), examples of further preferable $R^1$ include $C_{1-6}$ alkyl, $C_{2-6}$ alkenyl, and $C_{2-6}$ alkynyl. Specific examples thereof include methyl, ethyl, propyl, isopropyl, butyl, 2-butyl, pentyl, 2-pentyl, hexyl, 2-hexyl, vinyl, propenyl, butenyl, butynyl, and pentenyl. Among them, $C_{3-5}$ alkyl, $C_{3-5}$ alkenyl, and $C_{3-5}$ alkynyl, more specifically, propyl, isopropyl, butyl, 2-butyl, pentyl, 2-pentyl, propenyl, butenyl, butynyl, and pentenyl are further preferable, with propyl, butyl, and pentyl being particularly preferable.

In general formula (I), examples of further preferable $R^2$ include hydroxyl, acetyloxy, propionyloxy, methoxycarbonyloxy, ethoxycarbonyloxy, propoxycarbonyloxy, and butoxycarbonyloxy, with hydroxyl, methoxycarbonyloxy, and ethoxycarbonyloxy being particularly preferable.

In general formula (I), examples of further preferable Y include a substituted or unsubstituted pyridine ring (e.g., 2-pyridyl, 3-pyridyl, and 4-pyridyl) and a pyrazine ring (e.g., 2-pyrazinyl and 3-pyrazinyl), with 3-pyridyl being particularly preferable. Examples of further preferable Y having a substituent include 2-methyl-3-pyridyl, 6-methyl-3-pyridyl, 2-ethyl-3-pyridyl, 6-ethyl-3-pyridyl, 2-methoxy-3-pyridyl, 6-methoxy-3-pyridyl, 2-ethoxy-3-pyridyl, 6-ethoxy-3-pyridyl, 2-chloro-3-pyridyl, 6-chloro-3-pyridyl, 6-dimethylamino-3-pyridyl, 6-(1-pyrrolidinyl)-3-pyridyl, 6-piperidino-3-pyridyl, 6-morpholino-3-pyridyl, 6-methylthio-3-pyridyl, 5,6-dimethyl-3-pyridyl, 5,6-dimethoxy-3-pyridyl, 2,6-dichloro-3-pyridyl, 5,6-dichloro-3-pyridyl, and 5-chloro-6-methoxy-3-pyridyl. Among them, 3-pyridyl, 6-methyl-3-pyridyl, 6-methoxy-3-pyridyl, 6-ethoxy-3-pyridyl, 6-chloro-3-pyridyl, 6-(1-pyrrolidinyl)-3-pyridyl, 6-morpholino-3-pyridyl, 2-methyl-3-pyridyl, 2-methoxy-3-pyridyl, and 2-chloro-3-pyridyl are particularly preferable.

Specific examples of the compounds in the scope of the present invention include the following.

TABLE 1

| X | $R^1$ | $R^2$ | Y |
|---|---|---|---|
| NH | propyl | OH | 2-pyridyl |
| NH | propyl | OH | 3-pyridyl |
| NH | propyl | OH | 4-pyridyl |
| NH | propyl | OH | 2-methyl-3-pyridyl |
| NH | propyl | OH | 4-methyl-3-pyridyl |
| NH | propyl | OH | 5-methyl-3-pyridyl |
| NH | propyl | OH | 6-methyl-3-pyridyl |
| NH | propyl | OH | 2-ethyl-3-pyridyl |
| NH | propyl | OH | 4-ethyl-3-pyridyl |

TABLE 1-continued

| X | R¹ | R² | Y |
|---|---|---|---|
| NH | propyl | OH | 5-ethyl-3-pyridyl |
| NH | propyl | OH | 6-ethyl-3-pyridyl |
| NH | propyl | OH | 2-methoxy-3-pyridyl |
| NH | propyl | OH | 4-methoxy-3-pyridyl |
| NH | propyl | OH | 5-methoxy-3-pyridyl |
| NH | propyl | OH | 6-methoxy-3-pyridyl |
| NH | propyl | OH | 2-ethoxy-3-pyridyl |
| NH | propyl | OH | 4-ethoxy-3-pyridyl |
| NH | propyl | OH | 5-ethoxy-3-pyridyl |
| NH | propyl | OH | 6-ethoxy-3-pyridyl |
| NH | propyl | OH | 2-chloro-3-pyridyl |
| NH | propyl | OH | 4-chloro-3-pyridyl |
| NH | propyl | OH | 5-chloro-3-pyridyl |
| NH | propyl | OH | 6-chloro-3-pyridyl |
| NH | propyl | OH | 2-fluoro-3-pyridyl |
| NH | propyl | OH | 4-fluoro-3-pyridyl |
| NH | propyl | OH | 5-fluoro-3-pyridyl |
| NH | propyl | OH | 6-fluoro-3-pyridyl |
| NH | propyl | OH | 2-dimethylamino-3-pyridyl |
| NH | propyl | OH | 4-dimethylamino-3-pyridyl |
| NH | propyl | OH | 5-dimethylamino-3-pyridyl |
| NH | propyl | OH | 6-dimethylamino-3-pyridyl |
| NH | propyl | OH | 2-(1-pyrrolidinyl)-3-pyridyl |
| NH | propyl | OH | 3-(1-pyrrolidinyl)-3-pyridyl |
| NH | propyl | OH | 5-(1-pyrrolidinyl)-3-pyridyl |
| NH | propyl | OH | 6-(1-pyrrolidinyl)-3-pyridyl |
| NH | propyl | OH | 2-piperidino-3-pyridyl |
| NH | propyl | OH | 4-piperidino-3-pyridyl |
| NH | propyl | OH | 5-piperidino-3-pyridyl |
| NH | propyl | OH | 6-piperidino-3-pyridyl |
| NH | propyl | OH | 2-morpholino-3-pyridyl |
| NH | propyl | OH | 4-morpholino-3-pyridyl |
| NH | propyl | OH | 5-morpholino-3-pyridyl |
| NH | propyl | OH | 6-morpholino-3-pyridyl |
| NH | propyl | OH | 2-hydroxy-3-pyridyl |
| NH | propyl | OH | 4-hydroxy-3-pyridyl |
| NH | propyl | OH | 5-hydroxy-3-pyridyl |
| NH | propyl | OH | 6-hydroxy-3-pyridyl |
| NH | propyl | OH | 2-mercapto-3-pyridyl |
| NH | propyl | OH | 4-mercapto-3-pyridyl |
| NH | propyl | OH | 5-mercapto-3-pyridyl |
| NH | propyl | OH | 6-mercapto-3-pyridyl |
| NH | propyl | OH | 2-methylthio-3-pyridyl |
| NH | propyl | OH | 4-methylthio-3-pyridyl |
| NH | propyl | OH | 5-methylthio-3-pyridyl |
| NH | propyl | OH | 6-methylthio-3-pyridyl |
| NH | propyl | OH | 2,6-dimethyl-3-pyridyl |
| NH | propyl | OH | 5,6-dimethyl-3-pyridyl |
| NH | propyl | OH | 2,6-diethyl-3-pyridyl |
| NH | propyl | OH | 5,6-diethyl-3-pyridyl |
| NH | propyl | OH | 2,6-dimethoxy-3-pyridyl |
| NH | propyl | OH | 5,6-dimethoxy-3-pyridyl |
| NH | propyl | OH | 2,6-diethoxy-3-pyridyl |
| NH | propyl | OH | 5,6-diethoxy-3-pyridyl |
| NH | propyl | OH | 2,6-dichloro-3-pyridyl |
| NH | propyl | OH | 5,6-dichloro-3-pyridyl |
| NH | propyl | OH | 5-chloro-6-methoxy-3-pyridyl |
| NH | propyl | OH | 5-chloro-6-ethoxy-3-pyridyl |
| NH | propyl | OH | 2-chloro-6-methyl-3-pyridyl |
| NH | propyl | OH | 6-chloro-2-methyl-3-pyridyl |
| NH | propyl | OH | 2-methyl-4-pyridyl |
| NH | propyl | OH | 2-ethyl-4-pyridyl |
| NH | propyl | OH | 2-methoxy-4-pyridyl |
| NH | propyl | OH | 2-ethoxy-4-pyridyl |
| NH | propyl | OH | 2-chloro-4-pyridyl |
| NH | propyl | OH | 2-dimethylamino-4-pyridyl |
| NH | propyl | OH | 2-(1-pyrrolidinyl)-4-pyridyl |
| NH | propyl | OH | 2-piperidino-4-pyridyl |
| NH | propyl | OH | 2-morpholino-4-pyridyl |
| NH | propyl | OH | 2-methylthio-4-pyridyl |
| NH | propyl | OH | 2-pyrazinyl |
| NH | propyl | OH | 5-methyl-2-pyrazinyl |
| NH | propyl | OH | 5-ethyl-2-pyrazinyl |
| NH | propyl | OH | 5-methoxy-2-pyrazinyl |
| NH | propyl | OH | 5-ethoxy-2-pyrazinyl |
| NH | propyl | OH | 5-chloro-2-pyrazinyl |
| NH | propyl | OH | 6-methyl-2-pyrazinyl |
| NH | propyl | OH | 6-methoxy-2-pyrazinyl |
| NH | propyl | OH | 6-chloro-2-pyrazinyl |
| NH | propyl | OCOOMe | 2-pyridyl |
| NH | propyl | OCOOMe | 3-pyridyl |
| NH | propyl | OCOOMe | 4-pyridyl |
| NH | propyl | OCOOMe | 2-methyl-3-pyridyl |
| NH | propyl | OCOOMe | 4-methyl-3-pyridyl |
| NH | propyl | OCOOMe | 5-methyl-3-pyridyl |
| NH | propyl | OCOOMe | 6-methyl-3-pyridyl |
| NH | propyl | OCOOMe | 2-ethyl-3-pyridyl |
| NH | propyl | OCOOMe | 4-ethyl-3-pyridyl |
| NH | propyl | OCOOMe | 5-ethyl-3-pyridyl |
| NH | propyl | OCOOMe | 6-ethyl-3-pyridyl |
| NH | propyl | OCOOMe | 2-methoxy-3-pyridyl |
| NH | propyl | OCOOMe | 4-methoxy-3-pyridyl |
| NH | propyl | OCOOMe | 5-methoxy-3-pyridyl |
| NH | propyl | OCOOMe | 6-methoxy-3-pyridyl |
| NH | propyl | OCOOMe | 2-ethoxy-3-pyridyl |
| NH | propyl | OCOOMe | 4-ethoxy-3-pyridyl |
| NH | propyl | OCOOMe | 5-ethoxy-3-pyridyl |
| NH | propyl | OCOOMe | 6-ethoxy-3-pyridyl |
| NH | propyl | OCOOMe | 2-chloro-3-pyridyl |
| NH | propyl | OCOOMe | 4-chloro-3-pyridyl |
| NH | propyl | OCOOMe | 5-chloro-3-pyridyl |
| NH | propyl | OCOOMe | 6-chloro-3-pyridyl |
| NH | propyl | OCOOMe | 2-fluoro-3-pyridyl |
| NH | propyl | OCOOMe | 4-fluoro-3-pyridyl |
| NH | propyl | OCOOMe | 5-fluoro-3-pyridyl |
| NH | propyl | OCOOMe | 6-fluoro-3-pyrjdyl |
| NH | propyl | OCOOMe | 2-dimethylamino-3-pyridyl |
| NH | propyl | OCOOMe | 4-dimethylamino-3-pyridyl1 |
| NH | propyl | OCOOMe | 5-dimethylamino-3-pyridyl |
| NH | propyl | OCOOMe | 6-dimethylamino-3-pyridyl |
| NH | propyl | OCOOMe | 2-(1-pyrrolidinyl)-3-pyridyl |
| NH | propyl | OCOOMe | 3-(1-pyrrolidinyl)-3-pyridyl |
| NH | propyl | OCOOMe | 5-(1-pyrrolidinyl)-3-pyridyl |
| NH | propyl | OCOOMe | 6-(1-pyrrolidinyl)-3-pyridyl |
| NH | propyl | OCOOMe | 2-piperidino-3-pyridyl |
| NH | propyl | OCOOMe | 4-piperidino-3-pyridyl |
| NH | propyl | OCOOMe | 5-piperidino-3-pyridyl |
| NH | propyl | OCOOMe | 6-piperidino-3-pyridyl |
| NH | propyl | OCOOMe | 2-morpholino-3-pyridyl |
| NH | propyl | OCOOMe | 4-morpholino-3-pyridyl |
| NH | propyl | OCOOMe | 5-morpholino-3-pyridyl |
| NH | propyl | OCOOMe | 6-morpholino-3-pyridyl |
| NH | propyl | OCOOMe | 2-hydroxy-3-pyridyl |
| NH | propyl | OCOOMe | 4-hydroxy-3-pyridyl |
| NH | propyl | OCOOMe | 5-hydroxy-3-pyridyl |
| NH | propyl | OCOOMe | 6-hydroxy-3-pyridyl |
| NH | propyl | OCOOMe | 2-mercapto-3-pyridyl |
| NH | propyl | OCOOMe | 4-mercapto-3-pyridyl |
| NH | propyl | OCOOMe | 5-mercapto-3-pyridyl |
| NH | propyl | OCOOMe | 6-mercapto-3-pyridyl |
| NH | propyl | OCOOMe | 2-methylthio-3-pyridyl |
| NH | propyl | OCOOMe | 4-methylthio-3-pyridyl |
| NH | propyl | OCOOMe | 5-methylthio-3-pyridyl |
| NH | propyl | OCOOMe | 6-methylthio-3-pyridyl |
| NH | propyl | OCOOMe | 2,6-dimethyl-3-pyridyl |
| NH | propyl | OCOOMe | 5,6-dimethyl-3-pyridyl |
| NH | propyl | OCOOMe | 2,6-diethyl-3-pyridyl |
| NH | propyl | OCOOMe | 5,6-diethyl-3-pyridyl |
| NH | propyl | OCOOMe | 2,6-dimethoxy-3-pyridyl |
| NH | propyl | OCOOMe | 5,6-dimethoxy-3-pyridyl |
| NH | propyl | OCOOMe | 2,6-diethoxy-3-pyridyl |
| NH | propyl | OCOOMe | 5,6-diethoxy-3-pyridyl |
| NH | propyl | OCOOMe | 2,6-dichloro-3-pyridyl |
| NH | propyl | OCOOMe | 5,6-dichloro-3-pyridyl |
| NH | propyl | OCOOMe | 5-chloro-6-methoxy-3-pyridyl |
| NH | propyl | OCOOMe | 5-chloro-6-ethoxy-3-pyridyl |
| NH | propyl | OCOOMe | 2-chloro-6-methyl-3-pyridyl |
| NH | propyl | OCOOMe | 6-chloro-2-methyl-3-pyridyl |
| NH | propyl | OCOOMe | 2-methyl-4-pyridyl |
| NH | propyl | OCOOMe | 2-ethyl-4-pyridyl |
| NH | propyl | OCOOMe | 2-methoxy-4-pyridyl |
| NH | propyl | OCOOMe | 2-ethoxy-4-pyridyl |
| NH | propyl | OCOOMe | 2-chloro-4-pyridyl |
| NH | propyl | OCOOMe | 2-dimethylamino-4-pyridyl |

TABLE 1-continued

| X | R¹ | R² | Y |
|---|---|---|---|
| NH | propyl | OCOOMe | 2-(1-pyrrolidinyl)-4-pyridyl |
| NH | propyl | OCOOMe | 2-piperidino-4-pyridyl |
| NH | propyl | OCOOMe | 2-morpholino-4-pyridyl |
| NH | propyl | OCOOMe | 2-methylthio-4-pyridyl |
| NH | propyl | OCOOMe | 2-pyrazinyl |
| NH | propyl | OCOOMe | 5-methyl-2-pyrazinyl |
| NH | propyl | OCOOMe | 5-ethyl-2-pyrazinyl |
| NH | propyl | OCOOMe | 5-methoxy-2-pyrazinyl |
| NH | propyl | OCOOMe | 5-ethoxy-2-pyrazinyl |
| NH | propyl | OCOOMe | 5-chloro-2-pyrazinyl |
| NH | propyl | OCOOMe | 6-methyl-2-pyrazinyl |
| NH | propyl | OCOOMe | 6-methoxy-2-pyrazinyl |
| NH | propyl | OCOOMe | 6-chloro-2-pyrazinyl |
| NH | propyl | OCOOEt | 2-pyridyl |
| NH | propyl | OCOOEt | 3-pyridyl |
| NH | propyl | OCOOEt | 4-pyridyl |
| NH | propyl | OCOOEt | 2-methyl-3-pyridyl |
| NH | propyl | OCOOEt | 4-methyl-3-pyridyl |
| NH | propyl | OCOOEt | 5-methyl-3-pyridyl |
| NH | propyl | OCOOEt | 6-methyl-3-pyridyl |
| NH | propyl | OCOOEt | 2-ethyl-3-pyridyl |
| NH | propyl | OCOOEt | 4-ethyl-3-pyridyl |
| NH | propyl | OCOOEt | 5-ethyl-3-pyridyl |
| NH | propyl | OCOOEt | 6-ethyl-3-pyridyl |
| NH | propyl | OCOOEt | 2-methoxy-3-pyridyl |
| NH | propyl | OCOOEt | 4-methoxy-3-pyridyl |
| NH | propyl | OCOOEt | 5-methoxy-3-pyridyl |
| NH | propyl | OCOOEt | 6-methoxy-3-pyridyl |
| NH | propyl | OCOOEt | 2-ethoxy-3-pyridyl |
| NH | propyl | OCOOEt | 4-ethoxy-3-pyridyl |
| NH | propyl | OCOOEt | 5-ethoxy-3-pyridyl |
| NH | propyl | OCOOEt | 6-ethoxy-3-pyridyl |
| NH | propyl | OCOOEt | 2-chloro-3-pyridyl |
| NH | propyl | OCOOEt | 4-chloro-3-pyridyl |
| NH | propyl | OCOOEt | 5-chloro-3-pyridyl |
| NH | propyl | OCOOEt | 6-chloro-3-pyridyl |
| NH | propyl | OCOOEt | 2-fluoro-3-pyridyl |
| NH | propyl | OCOOEt | 4-fluoro-3-pyridyl |
| NH | propyl | OCOOEt | 5-fluoro-3-pyridyl |
| NH | propyl | OCOOEt | 6-fluoro-3-pyridyl |
| NH | propyl | OCOOEt | 2-dimethylamino-3-pyridyl |
| NH | propyl | OCOOEt | 4-dimethylamino-3-pyridyl |
| NH | propyl | OCOOEt | 5-dimethylamino-3-pyridyl |
| NH | propyl | OCOOEt | 6-dimethylamino-3-pyridyl |
| NH | propyl | OCOOEt | 2-(1-pyrrolidinyl)-3-pyridyl |
| NH | propyl | OCOOEt | 3-(1-pyrrolidinyl)-3-pyridyl |
| NH | propyl | OCOOEt | 5-(1-pyrrolidinyl)-3-pyridyl |
| NH | propyl | OCOOEt | 6-(1-pyrrolidinyl)-3-pyridyl |
| NH | propyl | OCOOEt | 2-piperidino-3-pyridyl |
| NH | propyl | OCOOEt | 4-piperidino-3-pyridyl |
| NH | propyl | OCOOEt | 5-piperidino-3-pyridyl |
| NH | propyl | OCOOEt | 6-piperidino-3-pyridyl |
| NH | propyl | OCOOEt | 2-morpholino-3-pyridyl |
| NH | propyl | OCOOEt | 4-morpholino-3-pyridyl |
| NH | propyl | OCOOEt | 5-morpholino-3-pyridyl |
| NH | propyl | OCOOEt | 6-morpholino-3-pyridyl |
| NH | propyl | OCOOEt | 2-hydroxy-3-pyridyl |
| NH | propyl | OCOOEt | 4-hydroxy-3-pyridyl |
| NH | propyl | OCOOEt | 5-hydroxy-3-pyridyl |
| NH | propyl | OCOOEt | 6-hydroxy-3-pyridyl |
| NH | propyl | OCOOEt | 2-mercapto-3-pyridyl |
| NH | propyl | OCOOEt | 4-mercapto-3-pyridyl |
| NH | propyl | OCOOEt | 5-mercapto-3-pyridyl |
| NH | propyl | OCOOEt | 6-mercapto-3-pyridyl |
| NH | propyl | OCOOEt | 2-methylthio-3-pyridyl |
| NH | propyl | OCOOEt | 4-methylthio-3-pyridyl |
| NH | propyl | OCOOEt | 5-methylthio-3-pyridyl |
| NH | propyl | OCOOEt | 6-methylthio-3-pyridyl |
| NH | propyl | OCOOEt | 2,6-dimethyl-3-pyridyl |
| NH | propyl | OCOOEt | 5,6-dimethyl-3-pyridyl |
| NH | propyl | OCOOEt | 2,6-diethyl-3-pyridyl |
| NH | propyl | OCOOEt | 5,6-diethyl-3-pyridyl |
| NH | propyl | OCOOEt | 2,6-dimethoxy-3-pyridyl |
| NH | propyl | OCOOEt | 5,6-dimethoxy-3-pyridyl |
| NH | propyl | OCOOEt | 2,6-diethoxy-3-pyridyl |
| NH | propyl | OCOOEt | 5,6-diethoxy-3-pyridyl |
| NH | propyl | OCOOEt | 2,6-dichloro-3-pyridyl |
| NH | propyl | OCOOEt | 5,6-dichloro-3-pyridyl |
| NH | propyl | OCOOEt | 5-chloro-6-methoxy-3-pyridyl |
| NH | propyl | OCOOEt | 5-chloro-6-ethoxy-3-pyridyl |
| NH | propyl | OCOOEt | 2-chloro-6-methyl-3-pyridyl |
| NH | propyl | OCOOEt | 6-chloro-2-methyl-3-pyridyl |
| NH | propyl | OCOOEt | 2-methyl-4-pyridyl |
| NH | propyl | OCOOEt | 2-ethyl-4-pyridyl |
| NH | propyl | OCOOEt | 2-methoxy-4-pyridyl |
| NH | propyl | OCOOEt | 2-ethoxy-4-pyridyl |
| NH | propyl | OCOOEt | 2-chloro-4-pyridyl |
| NH | propyl | OCOOEt | 2-dimethylamino-4-pyridyl |
| NH | propyl | OCOOEt | 2-(1-pyrrolidinyl)-4-pyridyl |
| NH | propyl | OCOOEt | 2-piperidino-4-pyridyl |
| NH | propyl | OCOOEt | 2-morpholino-4-pyridyl |
| NH | propyl | OCOOEt | 2-methylthio-4-pyridyl |
| NH | propyl | OCOOEt | 2-pyrazinyl |
| NH | propyl | OCOOEt | 5-methyl-2-pyrazinyl |
| NH | propyl | OCOOEt | 5-ethyl-2-pyrazinyl |
| NH | propyl | OCOOEt | 5-methoxy-2-pyrazinyl |
| NH | propyl | OCOOEt | 5-ethoxy-2-pyrazinyl |
| NH | propyl | OCOOEt | 5-chloro-2-pyrazinyl |
| NH | propyl | OCOOEt | 6-methyl-2-pyrazinyl |
| NH | propyl | OCOOEt | 6-methoxy-2-pyrazinyl |
| NH | propyl | OCOOEt | 6-chloro-2-pyrazinyl |
| NH | n-butyl | OH | 2-pyridyl |
| NH | n-butyl | OH | 3-pyridyl |
| NH | n-butyl | OH | 4-pyridyl |
| NH | n-butyl | OH | 2-methyl-3-pyridyl |
| NH | n-butyl | OH | 4-methyl-3-pyridyl |
| NH | n-butyl | OH | 5-methyl-3-pyridyl |
| NH | n-butyl | OH | 6-methyl-3-pyridyl |
| NH | n-butyl | OH | 2-ethyl-3-pyridyl |
| NH | n-butyl | OH | 4-ethyl-3-pyridyl |
| NH | n-butyl | OH | 5-ethyl-3-pyridyl |
| NH | n-butyl | OH | 6-ethyl-3-pyridyl |
| NH | n-butyl | OH | 2-methoxy-3-pyridyl |
| NH | n-butyl | OH | 4-methoxy-3-pyridyl |
| NH | n-butyl | OH | 5-methoxy-3-pyridyl |
| NH | n-butyl | OH | 6-methoxy-3-pyridyl |
| NH | n-butyl | OH | 2-ethoxy-3-pyridyl |
| NH | n-butyl | OH | 4-ethoxy-3-pyridyl |
| NH | n-butyl | OH | 5-ethoxy-3-pyridyl |
| NH | n-butyl | OH | 6-ethoxy-3-pyridyl |
| NH | n-butyl | OH | 2-chloro-3-pyridyl |
| NH | n-butyl | OH | 4-chloro-3-pyridyl |
| NH | n-butyl | OH | 5-chloro-3-pyridyl |
| NH | n-butyl | OH | 6-chloro-3-pyridyl |
| NH | n-butyl | OH | 2-fluoro-3-pyridyl |
| NH | n-butyl | OH | 4-fluoro-3-pyridyl |
| NH | n-butyl | OH | 5-fluoro-3-pyridyl |
| NH | n-butyl | OH | 6-fluoro-3-pyridyl |
| NH | n-butyl | OH | 2-dimethylamino-3-pyridyl |
| NH | n-butyl | OH | 4-dimethylamino-3-pyridyl |
| NH | n-butyl | OH | 5-dimethylamino-3-pyridyl |
| NH | n-butyl | OH | 6-dimethylamino-3-pyridyl |
| NH | n-butyl | OH | 2-(1-pyrrolidinyl)-3-pyridyl |
| NH | n-butyl | OH | 3-(1-pyrrolidinyl)-3-pyridyl |
| NH | n-butyl | OH | 5-(1-pyrrolidinyl)-3-pyridyl |
| NH | n-butyl | OH | 6-(1-pyrrolidinyl)-3-pyridyl |
| NH | n-butyl | OH | 2-piperidino-3-pyridyl |
| NH | n-butyl | OH | 4-piperidino-3-pyridyl |
| NH | n-butyl | OH | 5-piperidino-3-pyridyl |
| NH | n-butyl | OH | 6-piperidino-3-pyridyl |
| NH | n-butyl | OH | 2-morpholino-3-pyridyl |
| NH | n-butyl | OH | 4-morpholino-3-pyridyl |
| NH | n-butyl | OH | 5-morpholino-3-pyridyl |
| NH | n-butyl | OH | 6-morpholino-3-pyridyl |
| NH | n-butyl | OH | 2-hydroxy-3-pyridyl |
| NH | n-butyl | OH | 4-hydroxy-3-pyridyl |
| NH | n-butyl | OH | 5-hydroxy-3-pyridyl |
| NH | n-butyl | OH | 6-hydroxy-3-pyridyl |
| NH | n-butyl | OH | 2-mercapto-3-pyridyl |
| NH | n-butyl | OH | 4-mercapto-3-pyridyl |
| NH | n-butyl | OH | 5-mercapto-3-pyridyl |
| NH | n-butyl | OH | 6-mercapto-3-pyridyl |
| NH | n-butyl | OH | 2-methylthio-3-pyridyl |
| NH | n-butyl | OH | 4-methylthio-3-pyridyl |

TABLE 1-continued

| X | R¹ | R² | Y |
|---|---|---|---|
| NH | n-butyl | OH | 5-methylthio-3-pyridyl |
| NH | n-butyl | OH | 6-methylthio-3-pyridyl |
| NH | n-butyl | OH | 2,6-dimethyl-3-pyridyl |
| NH | n-butyl | OH | 5,6-dimethyl-3-pyridyl |
| NH | n-butyl | OH | 2,6-diethyl-3-pyridyl |
| NH | n-butyl | OH | 5,6-diethyl-3-pyridyl |
| NH | n-butyl | OH | 2,6-dimethoxy-3-pyridyl |
| NH | n-butyl | OH | 5,6-dimethoxy-3-pyridyl |
| NH | n-butyl | OH | 2,6-diethoxy-3-pyridyl |
| NH | n-butyl | OH | 5,6-diethoxy-3-pyridyl |
| NH | n-butyl | OH | 2,6-dichloro-3-pyridyl |
| NH | n-butyl | OH | 5,6-dichloro-3-pyridyl |
| NH | n-butyl | OH | 5-chloro-6-methoxy-3-pyridyl |
| NH | n-butyl | OH | 5-chloro-6-ethoxy-3-pyridyl |
| NH | n-butyl | OH | 2-chloro-6-methyl-3-pyridyl |
| NH | n-butyl | OH | 6-chloro-2-methyl-3-pyridyl |
| NH | n-butyl | OH | 2-methyl-4-pyridyl |
| NH | n-butyl | OH | 2-ethyl-4-pyridyl |
| NH | n-butyl | OH | 2-methoxy-4-pyridyl |
| NH | n-butyl | OH | 2-ethoxy-4-pyridyl |
| NH | n-butyl | OH | 2-chloro-4-pyridyl |
| NH | n-butyl | OH | 2-dimethylamino-4-pyridyl |
| NH | n-butyl | OH | 2-(1-pyrrolidinyl)-4-pyridyl |
| NH | n-butyl | OH | 2-piperidino-4-pyridyl |
| NH | n-butyl | OH | 2-morpholino-4-pyridyl |
| NH | n-butyl | OH | 2-methylthio-4-pyridyl |
| NH | n-butyl | OH | 2-pyrazinyl |
| NH | n-butyl | OH | 5-methyl-2-pyrazinyl |
| NH | n-butyl | OH | 5-ethyl-2-pyrazinyl |
| NH | n-butyl | OH | 5-methoxy-2-pyrazinyl |
| NH | n-butyl | OH | 5-ethoxy-2-pyrazinyl |
| NH | n-butyl | OH | 5-chloro-2-pyrazinyl |
| NH | n-butyl | OH | 6-methyl-2-pyrazinyl |
| NH | n-butyl | OH | 6-methoxy-2-pyrazinyl |
| NH | n-butyl | OH | 6-chloro-2-pyrazinyl |
| NH | n-butyl | OCOOMe | 2-pyridyl |
| NH | n-butyl | OCOOMe | 3-pyridyl |
| NH | n-butyl | OCOOMe | 4-pyridyl |
| NH | n-butyl | OCOOMe | 2-methyl-3-pyridyl |
| NH | n-butyl | OCOOMe | 4-methyl-3-pyridyl |
| NH | n-butyl | OCOOMe | 5-methyl-3-pyridyl |
| NH | n-butyl | OCOOMe | 6-methyl-3-pyridyl |
| NH | n-butyl | OCOOMe | 2-ethyl-3-pyridyl |
| NH | n-butyl | OCOOMe | 4-ethyl-3-pyridyl |
| NH | n-butyl | OCOOMe | 5-ethyl-3-pyridyl |
| NH | n-butyl | OCOOMe | 6-ethyl-3-pyridyl |
| NH | n-butyl | OCOOMe | 2-methoxy-3-pyridyl |
| NH | n-butyl | OCOOMe | 4-methoxy-3-pyridyl |
| NH | n-butyl | OCOOMe | 5-methoxy-3-pyridyl |
| NH | n-butyl | OCOOMe | 6-methoxy-3-pyridyl |
| NH | n-butyl | OCOOMe | 2-ethoxy-3-pyridyl |
| NH | n-butyl | OCOOMe | 4-ethoxy-3-pyridyl |
| NH | n-butyl | OCOOMe | 5-ethoxy-3-pyridyl |
| NH | n-butyl | OCOOMe | 6-ethoxy-3-pyridyl |
| NH | n-butyl | OCOOMe | 2-chloro-3-pyridyl |
| NH | n-butyl | OCOOMe | 4-chloro-3-pyridyl |
| NH | n-butyl | OCOOMe | 5-chloro-3-pyridyl |
| NH | n-butyl | OCOOMe | 6-chloro-3-pyridyl |
| NH | n-butyl | OCOOMe | 2-fluoro-3-pyridyl |
| NH | n-butyl | OCOOMe | 4-fluoro-3-pyridyl |
| NH | n-butyl | OCOOMe | 5-fluoro-3-pyridyl |
| NH | n-butyl | OCOOMe | 6-fluoro-3-pyridyl |
| NH | n-butyl | OCOOMe | 2-dimethylamino-3-pyridyl |
| NH | n-butyl | OCOOMe | 4-dimethylamino-3-pyridyl |
| NH | n-butyl | OCOOMe | 5-dimethylamino-3-pyridyl |
| NH | n-butyl | OCOOMe | 6-dimethylamino-3-pyridyl |
| NH | n-butyl | OCOOMe | 2-(1-pyrrolidinyl)-3-pyridyl |
| NH | n-butyl | OCOOMe | 3-(1-pyrrolidinyl)-3-pyridyl |
| NH | n-butyl | OCOOMe | 5-(1-pyrrolidinyl)-3-pyridyl |
| NH | n-butyl | OCOOMe | 6-(1-pyrrolidinyl)-3-pyridyl |
| NH | n-butyl | OCOOMe | 2-piperidino-3-pyridyl |
| NH | n-butyl | OCOOMe | 4-piperidino-3-pyridyl |
| NH | n-butyl | OCOOMe | 5-piperidino-3-pyridyl |
| NH | n-butyl | OCOOMe | 6-piperidino-3-pyridyl |
| NH | n-butyl | OCOOMe | 2-morpholino-3-pyridyl |
| NH | n-butyl | OCOOMe | 4-morpholino-3-pyridyl |
| NH | n-butyl | OCOOMe | 5-morpholino-3-pyridyl |
| NH | n-butyl | OCOOMe | 6-morpholino-3-pyridyl |
| NH | n-butyl | OCOOMe | 2-hydroxy-3-pyridyl |
| NH | n-butyl | OCOOMe | 4-hydroxy-3-pyridyl |
| NH | n-butyl | OCOOMe | 5-hydroxy-3-pyridyl |
| NH | n-butyl | OCOOMe | 6-hydroxy-3-pyridyl |
| NH | n-butyl | OCOOMe | 2-mercapto-3-pyridyl |
| NH | n-butyl | OCOOMe | 4-mercapto-3-pyridyl |
| NH | n-butyl | OCOOMe | 5-mercapto-3-pyridyl |
| NH | n-butyl | OCOOMe | 6-mercapto-3-pyridyl |
| NH | n-butyl | OCOOMe | 2-methylthio-3-pyridyl |
| NH | n-butyl | OCOOMe | 4-methylthio-3-pyridyl |
| NH | n-butyl | OCOOMe | 5-methylthio-3-pyridyl |
| NH | n-butyl | OCOOMe | 6-methylthio-3-pyridyl |
| NH | n-butyl | OCOOMe | 2,6-dimethyl-3-pyridyl |
| NH | n-butyl | OCOOMe | 5,6-dimethyl-3-pyridyl |
| NH | n-butyl | OCOOMe | 2,6-diethyl-3-pyridyl |
| NH | n-butyl | OCOOMe | 5,6-diethyl-3-pyridyl |
| NH | n-butyl | OCOOMe | 2,6-dimethoxy-3-pyridyl |
| NH | n-butyl | OCOOMe | 5,6-dimethoxy-3-pyridyl |
| NH | n-butyl | OCOOMe | 2,6-diethoxy-3-pyridyl |
| NH | n-butyl | OCOOMe | 5,6-diethoxy-3-pyridyl |
| NH | n-butyl | OCOOMe | 2,6-dichloro-3-pyridyl |
| NH | n-butyl | OCOOMe | 5,6-dichloro-3-pyridyl |
| NH | n-butyl | OCOOMe | 5-chloro-6-methoxy-3-pyridyl |
| NH | n-butyl | OCOOMe | 5-chloro-6-ethoxy-3-pyridyl |
| NH | n-butyl | OCOOMe | 2-chloro-6-methyl-3-pyridyl |
| NH | n-butyl | OCOOMe | 6-chloro-2-methyl-3-pyridyl |
| NH | n-butyl | OCOOMe | 2-methyl-4-pyridyl |
| NH | n-butyl | OCOOMe | 2-ethyl-4-pyridyl |
| NH | n-butyl | OCOOMe | 2-methoxy-4-pyridyl |
| NH | n-butyl | OCOOMe | 2-ethoxy-4-pyridyl |
| NH | n-butyl | OCOOMe | 2-chloro-4-pyridyl |
| NH | n-butyl | OCOOMe | 2-dimethylamino-4-pyridyl |
| NH | n-butyl | OCOOMe | 2-(1-pyrrolidinyl)-4-pyridyl |
| NH | n-butyl | OCOOMe | 2-piperidino-4-pyridyl |
| NH | n-butyl | OCOOMe | 2-morpholino-4-pyridyl |
| NH | n-butyl | OCOOMe | 2-methylthio-4-pyridyl |
| NH | n-butyl | OCOOMe | 2-pyrazinyl |
| NH | n-butyl | OCOOMe | 5-methyl-2-pyrazinyl |
| NH | n-butyl | OCOOMe | 5-ethyl-2-pyrazinyl |
| NH | n-butyl | OCOOMe | 5-methoxy-2-pyrazinyl |
| NH | n-butyl | OCOOMe | 5-ethoxy-2-pyrazinyl |
| NH | n-butyl | OCOOMe | 5-chloro-2-pyrazinyl |
| NH | n-butyl | OCOOMe | 6-methyl-2-pyrazinyl |
| NH | n-butyl | OCOOMe | 6-methoxy-2-pyrazinyl |
| NH | n-butyl | OCOOMe | 6-chloro-2-pyrazinyl |
| NH | n-butyl | OCOOEt | 2-pyridyl |
| NH | n-butyl | OCOOEt | 3-pyridyl |
| NH | n-butyl | OCOOEt | 4-pyridyl |
| NH | n-butyl | OCOOEt | 2-methyl-3-pyridyl |
| NH | n-butyl | OCOOEt | 4-methyl-3-pyridyl |
| NH | n-butyl | OCOOEt | 5-methyl-3-pyridyl |
| NH | n-butyl | OCOOEt | 6-methyl-3-pyridyl |
| NH | n-butyl | OCOOEt | 2-ethyl-3-pyridyl |
| NH | n-butyl | OCOOEt | 4-ethyl-3-pyridyl |
| NH | n-butyl | OCOOEt | 5-ethyl-3-pyridyl |
| NH | n-butyl | OCOOEt | 6-ethyl-3-pyridyl |
| NH | n-butyl | OCOOEt | 2-methoxy-3-pyridyl |
| NH | n-butyl | OCOOEt | 4-methoxy-3-pyridyl |
| NH | n-butyl | OCOOEt | 5-methoxy-3-pyridyl |
| NH | n-butyl | OCOOEt | 6-methoxy-3-pyridyl |
| NH | n-butyl | OCOOEt | 2-ethoxy-3-pyridyl |
| NH | n-butyl | OCOOEt | 4-ethoxy-3-pyridyl |
| NH | n-butyl | OCOOEt | 5-ethoxy-3-pyridyl |
| NH | n-butyl | OCOOEt | 6-ethoxy-3-pyridyl |
| NH | n-butyl | OCOOEt | 2-chloro-3-pyridyl |
| NH | n-butyl | OCOOEt | 4-chloro-3-pyridyl |
| NH | n-butyl | OCOOEt | 5-chloro-3-pyridyl |
| NH | n-butyl | OCOOEt | 6-chloro-3-pyridyl |
| NH | n-butyl | OCOOEt | 2-fluoro-3-pyridyl |
| NH | n-butyl | OCOOEt | 4-fluoro-3-pyridyl |
| NH | n-butyl | OCOOEt | 5-fluoro-3-pyridyl |
| NH | n-butyl | OCOOEt | 6-fluoro-3-pyridyl |
| NH | n-butyl | OCOOEt | 2-dimethylamino-3-pyridyl |
| NH | n-butyl | OCOOEt | 4-dimethylamino-3-pyridyl |
| NH | n-butyl | OCOOEt | 5-dimethylamino-3-pyridyl |
| NH | n-butyl | OCOOEt | 6-dimethylamino-3-pyridyl |

TABLE 1-continued

| X | R¹ | R² | Y |
|---|---|---|---|
| NH | n-butyl | OCOOEt | 2-(1-pyrrolidinyl)-3-pyridyl |
| NH | n-butyl | OCOOEt | 3-(1-pyrrolidinyl)-3-pyridyl |
| NH | n-butyl | OCOOEt | 5-(1-pyrrolidinyl)-3-pyridyl |
| NH | n-butyl | OCOOEt | 6-(1-pyrrolidinyl)-3-pyridyl |
| NH | n-butyl | OCOOEt | 2-piperidino-3-pyridyl |
| NH | n-butyl | OCOOEt | 4-piperidino-3-pyridyl |
| NH | n-butyl | OCOOEt | 5-piperidino-3-pyridyl |
| NH | n-butyl | OCOOEt | 6-piperidino-3-pyridyl |
| NH | n-butyl | OCOOEt | 2-morpholino-3-pyridyl |
| NH | n-butyl | OCOOEt | 4-morpholino-3-pyridyl |
| NH | n-butyl | OCOOEt | 5-morpholino-3-pyridyl |
| NH | n-butyl | OCOOEt | 6-morpholino-3-pyridyl |
| NH | n-butyl | OCOOEt | 2-hydroxy-3-pyridyl |
| NH | n-butyl | OCOOEt | 4-hydroxy-3-pyridyl |
| NH | n-butyl | OCOOEt | 5-hydroxy-3-pyridyl |
| NH | n-butyl | OCOOEt | 6-hydroxy-3-pyridyl |
| NH | n-butyl | OCOOEt | 2-mercapto-3-pyridyl |
| NH | n-butyl | OCOOEt | 4-mercapto-3-pyridyl |
| NH | n-butyl | OCOOEt | 5-mercapto-3-pyridyl |
| NH | n-butyl | OCCOEt | 6-mercapto-3-pyridyl |
| NH | n-butyl | OCOOEt | 2-methylthio-3-pyridyl |
| NH | n-butyl | OCOOEt | 4-methylthio-3-pyridyl |
| NH | n-butyl | OCOOEt | 5-methylthio-3-pyridyl |
| NH | n-butyl | OCOOEt | 6-methylthio-3-pyridyl |
| NH | n-butyl | OCOOEt | 2,6-dimethyl-3-pyridyl |
| NH | n-butyl | OCOOEt | 5,6-dimethyl-3-pyridyl |
| NH | n-butyl | OCOOEt | 2,6-diethyl-3-pyridyl |
| NH | n-butyl | OCOOEt | 5,6-diethyl-3-pyridyl |
| NH | n-butyl | OCOOEt | 2,6-dimethoxy-3-pyridyl |
| NH | n-butyl | OCOOEt | 5,6-dimethoxy-3-pyridyl |
| NH | n-butyl | OCOOEt | 2,6-diethoxy-3-pyridyl |
| NH | n-butyl | OCOOEt | 5,6-diethoxy-3-pyridyl |
| NH | n-butyl | OCOOEt | 2,6-dichloro-3-pyridyl |
| NH | n-butyl | OCOOEt | 5,6-dichloro-3-pyridyl |
| NH | n-butyl | OCOOEt | 5-chloro-6-methoxy-3-pyridyl |
| NH | n-butyl | OCOOEt | 5-chloro-6-ethoxy-3-pyridyl |
| NH | n-butyl | OCOOEt | 2-chloro-6-methyl-3-pyridyl |
| NH | n-butyl | OCOOEt | 6-chloro-2-methyl-3-pyridyl |
| NH | n-butyl | OCOOEt | 2-methyl-4-pyridyl |
| NH | n-butyl | OCOOEt | 2-ethyl-4-pyridyl |
| NH | n-butyl | OCOOEt | 2-methoxy-4-pyridyl |
| NH | n-butyl | OCOOEt | 2-ethoxy-4-pyridyl |
| NH | n-butyl | OCOOEt | 2-chloro-4-pyridyl |
| NH | n-butyl | OCOOEt | 2-dimethylamino-4-pyridyl |
| NH | n-butyl | OCOOEt | 2-(1-pyrrolidinyl)-4-pyridyl |
| NH | n-butyl | OCOOEt | 2-piperidino-4-pyridyl |
| NH | n-butyl | OCOOEt | 2-morpholino-4-pyridyl |
| NH | n-butyl | OCOOEt | 2-methylthio-4-pyridyl |
| NH | n-butyl | OCOOEt | 2-pyrazinyl |
| NH | n-butyl | OCOOEt | 5-methyl-2-pyrazinyl |
| NH | n-butyl | OCOOEt | 5-ethyl-2-pyrazinyl |
| NH | n-butyl | OCOOEt | 5-methoxy-2-pyrazinyl |
| NH | n-butyl | OCOOEt | 5-ethoxy-2-pyrazinyl |
| NH | n-butyl | OCOOEt | 5-chloro-2-pyrazinyl |
| NH | n-butyl | OCOOEt | 6-methyl-2-pyrazinyl |
| NH | n-butyl | OCOOEt | 6-methoxy-2-pyrazinyl |
| NH | n-butyl | OCOOEt | 6-chloro-2-pyrazinyl |
| NH | n-pentyl | OH | 2-pyridyl |
| NH | n-pentyl | OH | 3-pyridyl |
| NH | n-pentyl | OH | 4-pyridyl |
| NH | n-pentyl | OH | 2-methyl-3-pyridyl |
| NH | n-pentyl | OH | 4-methyl-3-pyridyl |
| NH | n-pentyl | OH | 5-methyl-3-pyridyl |
| NH | n-pentyl | OH | 6-methyl-3-pyridyl |
| NH | n-pentyl | OH | 2-ethyl-3-pyridyl |
| NH | n-pentyl | OH | 4-ethyl-3-pyridyl |
| NH | n-pentyl | OH | 5-ethyl-3-pyridyl |
| NH | n-pentyl | OH | 6-ethyl-3-pyridyl |
| NH | n-pentyl | OH | 2-methoxy-3-pyridyl |
| NH | n-pentyl | OH | 4-methoxy-3-pyridyl |
| NH | n-pentyl | OH | 5-methoxy-3-pyridyl |
| NH | n-pentyl | OH | 6-methoxy-3-pyridyl |
| NH | n-pentyl | OH | 2-ethoxy-3-pyridyl |
| NH | n-pentyl | OH | 4-ethoxy-3-pyridyl |
| NH | n-pentyl | OH | 5-ethoxy-3-pyridyl |
| NH | n-pentyl | OH | 6-ethoxy-3-pyridyl |
| NH | n-pentyl | OH | 2-chloro-3-pyridyl |
| NH | n-pentyl | OH | 4-chloro-3-pyridyl |
| NH | n-pentyl | OH | 5-chloro-3-pyridyl |
| NH | n-pentyl | OH | 6-chloro-3-pyridyl |
| NH | n-pentyl | OH | 2-fluoro-3-pyridyl |
| NH | n-pentyl | OH | 4-fluoro-3-pyridyl |
| NH | n-pentyl | OH | 5-fluoro-3-pyridyl |
| NH | n-pentyl | OH | 6-fluoro-3-pyridyl |
| NH | n-pentyl | OH | 2-dimethylamino-3-pyridyl |
| NH | n-pentyl | OH | 4-dimethylamino-3-pyridyl |
| NH | n-pentyl | OH | 5-dimethylamino-3-pyridyl |
| NH | n-pentyl | OH | 6-dimethylamino-3-pyridyl |
| NH | n-pentyl | OH | 2-(1-pyrrolidinyl)-3-pyridyl |
| NH | n-pentyl | OH | 3-(1-pyrrolidinyl)-3-pyridyl |
| NH | n-pentyl | OH | 5-(1-pyrrolidinyl)-3-pyridyl |
| NH | n-pentyl | OH | 6-(1-pyrrolidinyl)-3-pyridyl |
| NH | n-pentyl | OH | 2-piperidino-3-pyridyl |
| NH | n-pentyl | OH | 4-piperidino-3-pyridyl |
| NH | n-pentyl | OH | 5-piperidino-3-pyridyl |
| NH | n-pentyl | OH | 6-piperidino-3-pyridyl |
| NH | n-pentyl | OH | 2-morpholino-3-pyridyl |
| NH | n-pentyl | OH | 4-morpholino-3-pyridyl |
| NH | n-pentyl | OH | 5-morpholino-3-pyridyl |
| NH | n-pentyl | OH | 6-morpholino-3-pyridyl |
| NH | n-pentyl | OH | 2-hydroxy-3-pyridyl |
| NH | n-pentyl | OH | 4-hydroxy-3-pyridyl |
| NH | n-pentyl | OH | 5-hydroxy-3-pyridyl |
| NH | n-pentyl | OH | 6-hydroxy-3-pyridyl |
| NH | n-pentyl | OH | 2-mercapto-3-pyridyl |
| NH | n-pentyl | OH | 4-mercapto-3-pyridyl |
| NH | n-pentyl | OH | 5-mercapto-3-pyridyl |
| NH | n-pentyl | OH | 6-mercapto-3-pyridyl |
| NH | n-pentyl | OH | 2-methylthio-3-pyridyl |
| NH | n-pentyl | OH | 4-methylthio-3-pyridyl |
| NH | n-pentyl | OH | 5-methylthio-3-pyridyl |
| NH | n-pentyl | OH | 6-methylthio-3-pyridyl |
| NH | n-pentyl | OH | 2,6-dimethyl-3-pyridyl |
| NH | n-pentyl | OH | 5,6-dimethyl-3-pyridyl |
| NH | n-pentyl | OH | 2,6-diethyl-3-pyridyl |
| NH | n-pentyl | OH | 5,6-diethyl-3-pyridyl |
| NH | n-pentyl | OH | 2,6-dimethoxy-3-pyridyl |
| NH | n-pentyl | OH | 5,6-dimethoxy-3-pyridyl |
| NH | n-pentyl | OH | 2,6-diethoxy-3-pyridyl |
| NH | n-pentyl | OH | 5,6-diethoxy-3-pyridyl |
| NH | n-pentyl | OH | 2,6-dichloro-3-pyridyl |
| NH | n-pentyl | OH | 5,6-dichloro-3-pyridyl |
| NH | n-pentyl | OH | 5-chloro-6-methoxy-3-pyridyl |
| NH | n-pentyl | OH | 5-chloro-6-ethoxy-3-pyridyl |
| NH | n-pentyl | OH | 2-chloro-6-methyl-3-pyridyl |
| NH | n-pentyl | OH | 6-chloro-2-methyl-3-pyridyl |
| NH | n-pentyl | OH | 2-methyl-4-pyridyl |
| NH | n-pentyl | OH | 2-ethyl-4-pyridyl |
| NH | n-pentyl | OH | 2-methoxy-4-pyridyl |
| NH | n-pentyl | OH | 2-ethoxy-4-pyridyl |
| NH | n-pentyl | OH | 2-chloro-4-pyridyl |
| NH | n-pentyl | OH | 2-dimethylamino-4-pyridyl |
| NH | n-pentyl | OH | 2-(1-pyrrolidinyl)-4-pyridyl |
| NH | n-pentyl | OH | 2-piperidino-4-pyridyl |
| NH | n-pentyl | OH | 2-morpholino-4-pyridyl |
| NH | n-pentyl | OH | 2-methylthio-4-pyridyl |
| NH | n-pentyl | OH | 2-pyrazinyl |
| NH | n-pentyl | OH | 5-methyl-2-pyrazinyl |
| NH | n-pentyl | OH | 5-ethyl-2-pyrazinyl |
| NH | n-pentyl | OH | 5-methoxy-2-pyrazinyl |
| NH | n-pentyl | OH | 5-ethoxy-2-pyrazinyl |
| NH | n-pentyl | OH | 5-chloro-2-pyrazinyl |
| NH | n-pentyl | OH | 6-methyl-2-pyrazinyl |
| NH | n-pentyl | OH | 6-methoxy-2-pyrazinyl |
| NH | n-pentyl | OH | 6-chloro-2-pyrazinyl |
| NH | n-pentyl | OCOOMe | 2-pyridyl |
| NH | n-pentyl | OCOOMe | 3-pyridyl |
| NH | n-pentyl | OCOOMe | 4-pyridyl |
| NH | n-pentyl | OCOOMe | 2-methyl-3-pyridyl |
| NH | n-pentyl | OCOOMe | 4-methyl-3-pyridyl |
| NH | n-pentyl | OCOOMe | 5-methyl-3-pyridyl |
| NH | n-pentyl | OCOOMe | 6-methyl-3-pyridyl |
| NH | n-pentyl | OCOOMe | 2-ethyl-3-pyridyl |
| NH | n-pentyl | OCOOMe | 4-ethyl-3-pyridyl |

TABLE 1-continued

| X | R¹ | R² | Y |
|---|---|---|---|
| NH | n-pentyl | OCOOMe | 5-ethyl-3-pyridyl |
| NH | n-pentyl | OCOOMe | 6-ethyl-3-pyridyl |
| NH | n-pentyl | OCOOMe | 2-methoxy-3-pyridyl |
| NH | n-pentyl | OCOOMe | 4-methoxy-3-pyridyl |
| NH | n-pentyl | OCOOMe | 5-methoxy-3-pyridyl |
| NH | n-pentyl | OCOOMe | 6-methoxy-3-pyridyl |
| NH | n-pentyl | OCOOMe | 2-ethoxy-3-pyridyl |
| NH | n-pentyl | OCOOMe | 4-ethoxy-3-pyridyl |
| NH | n-pentyl | OCOOMe | 5-ethoxy-3-pyridyl |
| NH | n-pentyl | OCOOMe | 6-ethoxy-3-pyridyl |
| NH | n-pentyl | OCOOMe | 2-chloro-3-pyridyl |
| NH | n-pentyl | OCOOMe | 4-chloro-3-pyridyl |
| NH | n-pentyl | OCOOMe | 5-chloro-3-pyridyl |
| NH | n-pentyl | OCOOMe | 6-chloro-3-pyridyl |
| NH | n-pentyl | OCOOMe | 2-fluoro-3-pyridyl |
| NH | n-pentyl | OCOOMe | 4-fluoro-3-pyridyl |
| NH | n-pentyl | OCOOMe | 5-fluoro-3-pyridyl |
| NH | n-pentyl | OCOOMe | 6-fluoro-3-pyridyl |
| NH | n-pentyl | OCOOMe | 2-dimethylamino-3-pyridyl |
| NH | n-pentyl | OCOOMe | 4-dimethylamino-3-pyridyl |
| NH | n-pentyl | OCOOMe | 5-dimethylamino-3-pyridyl |
| NH | n-pentyl | OCOOMe | 6-dimethylamino-3-pyridyl |
| NH | n-pentyl | OCOOMe | 2-(1-pyrrolidinyl)-3-pyridyl |
| NH | n-pentyl | OCOOMe | 3-(1-pyrrolidinyl)-3-pyridyl |
| NH | n-pentyl | OCOOMe | 5-(1-pyrrolidinyl)-3-pyridyl |
| NH | n-pentyl | OCOOMe | 6-(1-pyrrolidinyl)-3-pyridyl |
| NH | n-pentyl | OCOOMe | 2-piperidino-3-pyridyl |
| NH | n-pentyl | OCOOMe | 4-piperidino-3-pyridyl |
| NH | n-pentyl | OCOOMe | 5-piperidino-3-pyridyl |
| NH | n-pentyl | OCOOMe | 6-piperidino-3-pyridyl |
| NH | n-pentyl | OCOOMe | 2-morpholino-3-pyridyl |
| NH | n-pentyl | OCOOMe | 4-morpholino-3-pyridyl |
| NH | n-pentyl | OCOOMe | 5-morpholino-3-pyridyl |
| NH | n-pentyl | OCOOMe | 6-morpholino-3-pyridyl |
| NH | n-pentyl | OCOOMe | 2-hydroxy-3-pyridyl |
| NH | n-pentyl | OCOOMe | 4-hydroxy-3-pyridyl |
| NH | n-pentyl | OCOOMe | 5-hydroxy-3-pyridyl |
| NH | n-pentyl | OCOOMe | 6-hydroxy-3-pyridyl |
| NH | n-pentyl | OCOOMe | 2-mercapto-3-pyridyl |
| NH | n-pentyl | OCOOMe | 4-mercapto-3-pyridyl |
| NH | n-pentyl | OCOOMe | 5-mercapto-3-pyridyl |
| NH | n-pentyl | OCOOMe | 6-mercapto-3-pyridyl |
| NH | n-pentyl | OCOOMe | 2-methylthio-3-pyridyl |
| NH | n-pentyl | OCOOMe | 4-methylthio-3-pyridyl |
| NH | n-pentyl | OCOOMe | 5-methylthio-3-pyridyl |
| NH | n-pentyl | OCOOMe | 6-methylthio-3-pyridyl |
| NH | n-pentyl | OCOOMe | 2,6-dimethyl-3-pyridyl |
| NH | n-pentyl | OCOOMe | 5,6-dimethyl-3-pyridyl |
| NH | n-pentyl | OCOOMe | 2,6-diethyl-3-pyridyl |
| NH | n-pentyl | OCOOMe | 5,6-diethyl-3-pyridyl |
| NH | n-pentyl | OCOOMe | 2,6-dimethoxy-3-pyridyl |
| NH | n-pentyl | OCOOMe | 5,6-dimethoxy-3-pyridyl |
| NH | n-pentyl | OCOOMe | 2,6-diethoxy-3-pyridyl |
| NH | n-pentyl | OCOOMe | 5,6-diethoxy-3-pyridyl |
| NH | n-pentyl | OCOOMe | 2,6-dichloro-3-pyridyl |
| NH | n-pentyl | OCOOMe | 5,6-dichloro-3-pyridyl |
| NH | n-pentyl | OCOOMe | 5-chloro-6-methoxy-3-pyridyl |
| NH | n-pentyl | OCOOMe | 5-chloro-6-ethoxy-3-pyridyl |
| NH | n-pentyl | OCOOMe | 2-chloro-6-methyl-3-pyridyl |
| NH | n-pentyl | OCOOMe | 6-chloro-2-methyl-3-pyridyl |
| NH | n-pentyl | OCOOMe | 2-methyl-4-pyridyl |
| NH | n-pentyl | OCOOMe | 2-ethyl-4-pyridyl |
| NH | n-pentyl | OCOOMe | 2-methoxy-4-pyridyl |
| NH | n-pentyl | OCOOMe | 2-ethoxy-4-pyridyl |
| NH | n-pentyl | OCOOMe | 2-chloro-4-pyridyl |
| NH | n-pentyl | OCOOMe | 2-dimethylamino-4-pyridyl |
| NH | n-pentyl | OCOOMe | 2-(1-pyrrolidinyl)-4-pyridyl |
| NH | n-pentyl | OCOOMe | 2-piperidino-4-pyridyl |
| NH | n-pentyl | OCOOMe | 2-morpholino-4-pyridyl |
| NH | n-pentyl | OCOOMe | 2-methylthio-4-pyridyl |
| NH | n-pentyl | OCOOMe | 2-pyrazinyl |
| NH | n-pentyl | OCOOMe | 5-methyl-2-pyrazinyl |
| NH | n-pentyl | OCOOMe | 5-ethyl-2-pyrazinyl |
| NH | n-pentyl | OCOOMe | 5-methoxy-2-pyrazinyl |
| NH | n-pentyl | OCOOMe | 5-ethoxy-2-pyrazinyl |
| NH | n-pentyl | OCOOMe | 5-chloro-2-pyrazinyl |
| NH | n-pentyl | OCOOMe | 6-methyl-2-pyrazinyl |
| NH | n-pentyl | OCOOMe | 6-methoxy-2-pyrazinyl |
| NH | n-pentyl | OCOOMe | 6-chloro-2-pyrazinyl |
| NH | n-pentyl | OCOOEt | 2-pyridyl |
| NH | n-pentyl | OCOOEt | 3-pyridyl |
| NH | n-pentyl | OCOOEt | 4-pyridyl |
| NH | n-pentyl | OCOOEt | 2-methyl-3-pyridyl |
| NH | n-pentyl | OCOOEt | 4-methyl-3-pyridyl |
| NH | n-pentyl | OCOOEt | 5-methyl-3-pyridyl |
| NH | n-pentyl | OCOOEt | 6-methyl-3-pyridyl |
| NH | n-pentyl | OCOOEt | 2-ethyl-3-pyridyl |
| NH | n-pentyl | OCOOEt | 4-ethyl-3-pyridyl |
| NH | n-pentyl | OCOOEt | 5-ethyl-3-pyridyl |
| NH | n-pentyl | OCOOEt | 6-ethyl-3-pyridyl |
| NH | n-pentyl | OCOOEt | 2-methoxy-3-pyridyl |
| NH | n-pentyl | OCOOEt | 4-methoxy-3-pyridyl |
| NH | n-pentyl | OCOOEt | 5-methoxy-3-pyridyl |
| NH | n-pentyl | OCOOEt | 6-methoxy-3-pyridyl |
| NH | n-pentyl | OCOOEt | 2-ethoxy-3-pyridyl |
| NH | n-pentyl | OCOOEt | 4-ethoxy-3-pyridyl |
| NH | n-pentyl | OCOOEt | 5-ethoxy-3-pyridyl |
| NH | n-pentyl | OCOOEt | 6-ethoxy-3-pyridyl |
| NH | n-pentyl | OCOOEt | 2-chloro-3-pyridyl |
| NH | n-pentyl | OCOOEt | 4-chloro-3-pyridyl |
| NH | n-pentyl | OCOOEt | 5-chloro-3-pyridyl |
| NH | n-pentyl | OCOOEt | 6-chloro-3-pyridyl |
| NH | n-pentyl | OCOOEt | 2-fluoro-3-pyridyl |
| NH | n-pentyl | OCOOEt | 4-fluoro-3-pyridyl |
| NH | n-pentyl | OCOOEt | 5-fluoro-3-pyridyl |
| NH | n-pentyl | OCOOEt | 6-fluoro-3-pyridyl |
| NH | n-pentyl | OCOOEt | 2-dimethylamino-3-pyridyl |
| NH | n-pentyl | OCOOEt | 4-dimethylamino-3-pyridyl |
| NH | n-pentyl | OCOOEt | 5-dimethylamino-3-pyridyl |
| NH | n-pentyl | OCOOEt | 6-dimethylamino-3-pyridyl |
| NH | n-pentyl | OCOOEt | 2-(1-pyrrolidinyl)-3-pyridyl |
| NH | n-pentyl | OCOOEt | 3-(1-pyrrolidinyl)-3-pyridyl |
| NH | n-pentyl | OCOOEt | 5-(1-pyrrolidinyl)-3-pyridyl |
| NH | n-pentyl | OCOOEt | 6-(1-pyrrolidinyl)-3-pyridyl |
| NH | n-pentyl | OCOOEt | 2-piperidino-3-pyridyl |
| NH | n-pentyl | OCOOEt | 4-piperidino-3-pyridyl |
| NH | n-pentyl | OCOOEt | 5-piperidino-3-pyridyl |
| NH | n-pentyl | OCOOEt | 6-piperidino-3-pyridyl |
| NH | n-pentyl | OCOOEt | 2-morpholino-3-pyridyl |
| NH | n-pentyl | OCOOEt | 4-morpholino-3-pyridyl |
| NH | n-pentyl | OCOOEt | 5-morpholino-3-pyridyl |
| NH | n-pentyl | OCOOEt | 6-morpholino-3-pyridyl |
| NH | n-pentyl | OCOOEt | 2-hydroxy-3-pyridyl |
| NH | n-pentyl | OCOOEt | 4-hydroxy-3-pyridyl |
| NH | n-pentyl | OCOOEt | 5-hydroxy-3-pyridyl |
| NH | n-pentyl | OCOOEt | 6-hydroxy-3-pyridyl |
| NH | n-pentyl | OCOOEt | 2-mercapto-3-pyridyl |
| NH | n-pentyl | OCOOEt | 4-mercapto-3-pyridyl |
| NH | n-pentyl | OCOOEt | 5-mercapto-3-pyridyl |
| NH | n-pentyl | OCOOEt | 6-mercapto-3-pyridyl |
| NH | n-pentyl | OCOOEt | 2-methylthio-3-pyridyl |
| NH | n-pentyl | OCOOEt | 4-methylthio-3-pyridyl |
| NH | n-pentyl | OCOOEt | 5-methylthio-3-pyridyl |
| NH | n-pentyl | OCOOEt | 6-methylthio-3-pyridyl |
| NH | n-pentyl | OCOOEt | 2,6-dimethyl-3-pyridyl |
| NH | n-pentyl | OCOOEt | 5,6-dimethyl-3-pyridyl |
| NH | n-pentyl | OCOOEt | 2,6-diethyl-3-pyridyl |
| NH | n-pentyl | OCOOEt | 5,6-diethyl-3-pyridyl |
| NH | n-pentyl | OCOOEt | 2,6-dimethoxy-3-pyridyl |
| NH | n-pentyl | OCOOEt | 5,6-dimethoxy-3-pyridyl |
| NH | n-pentyl | OCOOEt | 2,6-diethoxy-3-pyridyl |
| NH | n-pentyl | OCOOEt | 5,6-diethoxy-3-pyridyl |
| NH | n-pentyl | OCOOEt | 2,6-dichloro-3-pyridyl |
| NH | n-pentyl | OCOOEt | 5,6-dichloro-3-pyridyl |
| NH | n-pentyl | OCOOEt | 5-chloro-6-methoxy-3-pyridyl |
| NH | n-pentyl | OCOOEt | 5-chloro-6-ethoxy-3-pyridyl |
| NH | n-pentyl | OCOOEt | 2-chloro-6-methyl-3-pyridyl |
| NH | n-pentyl | OCOOEt | 6-chloro-2-methyl-3-pyridyl |
| NH | n-pentyl | OCOOEt | 2-methyl-4-pyridyl |
| NH | n-pentyl | OCOOEt | 2-ethyl-4-pyridyl |
| NH | n-pentyl | OCOOEt | 2-methoxy-4-pyridyl |
| NH | n-pentyl | OCOOEt | 2-ethoxy-4-pyridyl |
| NH | n-pentyl | OCOOEt | 2-chloro-4-pyridyl |
| NH | n-pentyl | OCOOEt | 2-dimethylamino-4-pyridyl |

TABLE 1-continued

| X | R¹ | R² | Y |
|---|---|---|---|
| NH | n-pentyl | OCOOEt | 2-(1-pyrrolidinyl)-4-pyridyl |
| NH | n-pentyl | OCOOEt | 2-piperidino-4-pyridyl |
| NH | n-pentyl | OCOOEt | 2-morpholino-4-pyridyl |
| NH | n-pentyl | OCOOEt | 2-methylthio-4-pyridyl |
| NH | n-pentyl | OCOOEt | 2-pyrazinyl |
| NH | n-pentyl | OCOOEt | 5-methyl-2-pyrazinyl |
| NH | n-pentyl | OCOOEt | 5-ethyl-2-pyrazinyl |
| NH | n-pentyl | OCOOEt | 5-methoxy-2-pyrazinyl |
| NH | n-pentyl | OCOOEt | 5-ethoxy-2-pyrazinyl |
| NH | n-pentyl | OCOOEt | 5-chloro-2-pyrazinyl |
| NH | n-pentyl | OCOOEt | 6-methyl-2-pyrazinyl |
| NH | n-pentyl | OCOOEt 6-methoxy-2-pyrazinyl | |
| NH | n-pentyl | OCOOEt | 6-chloro-2-pyrazinyl |
| O | propyl | OH | 2-pyridyl |
| O | propyl | OH | 3-pyridyl |
| O | propyl | OH | 4-pyridyl |
| O | propyl | OH | 2-methyl-3-pyridyl |
| O | propyl | OH | 4-methyl-3-pyridyl |
| O | propyl | OH | 5-methyl-3-pyridyl |
| O | propyl | OH | 6-methyl-3-pyridyl |
| O | propyl | OH | 2-ethyl-3-pyridyl |
| O | propyl | OH | 4-ethyl-3-pyridyl |
| O | propyl | OH | 5-ethyl-3-pyridyl |
| O | propyl | OH | 6-ethyl-3-pyridyl |
| O | propyl | OH | 2-methoxy-3-pyridyl |
| O | propyl | OH | 4-methoxy-3-pyridyl |
| O | propyl | OH | 5-methoxy-3-pyridyl |
| O | propyl | OH | 6-methoxy-3-pyridyl |
| O | propyl | OH | 2-ethoxy-3-pyridyl |
| O | propyl | OH | 4-ethoxy-3-pyridyl |
| O | propyl | OH | 5-ethoxy-3-pyridyl |
| O | propyl | OH | 6-ethoxy-3-pyridyl |
| O | propyl | OH | 2-chloro-3-pyridyl |
| O | propyl | OH | 4-chloro-3-pyridyl |
| O | propyl | OH | 5-chloro-3-pyridyl |
| O | propyl | OH | 6-chloro-3-pyridyl |
| O | propyl | OH | 2-fluoro-3-pyridyl |
| O | propyl | OH | 4-fluoro-3-pyridyl |
| O | propyl | OH | 5-fluoro-3-pyridyl |
| O | propyl | OH | 6-fluoro-3-pyridyl |
| O | propyl | OH | 2-dimethylamino-3-pyridyl |
| O | propyl | OH | 4-dimethylamino-3-pyridyl |
| O | propyl | OH | 5-dimethylamino-3-pyridyl |
| O | propyl | OH | 6-dimethylamino-3-pyridyl |
| O | propyl | OH | 2-(1-pyrrolidinyl)-3-pyridyl |
| O | propyl | OH | 3-(1-pyrrolidinyl)-3-pyridyl |
| O | propyl | OH | 5-(1-pyrrolidinyl)-3-pyridyl |
| O | propyl | OH | 6-(1-pyrrolidinyl)-3-pyridyl |
| O | propyl | OH | 2-piperidino-3-pyridyl |
| O | propyl | OH | 4-piperidino-3-pyridyl |
| O | propyl | OH | 5-piperidino-3-pyridyl |
| O | propyl | OH | 6-piperidino-3-pyridyl |
| O | propyl | OH | 2-morpholino-3-pyridyl |
| O | propyl | OH | 4-morpholino-3-pyridyl |
| O | propyl | OH | 5-morpholino-3-pyridyl |
| O | propyl | OH | 6-morpholino-3-pyridyl |
| O | propyl | OH | 2-hydroxy-3-pyridyl |
| O | propyl | OH | 4-hydroxy-3-pyridyl |
| O | propyl | OH | 5-hydroxy-3-pyridyl |
| O | propyl | OH | 6-hydroxy-3-pyridyl |
| O | propyl | OH | 2-mercapto-3-pyridyl |
| O | propyl | OH | 4-mercapto-3-pyridyl |
| O | propyl | OH | 5-mercapto-3-pyridyl |
| O | propyl | OH | 6-mercapto-3-pyridyl |
| O | propyl | OH | 2-methylthio-3-pyridyl |
| O | propyl | OH | 4-methylthio-3-pyridyl |
| O | propyl | OH | 5-methylthio-3-pyridyl |
| O | propyl | OH | 6-methylthio-3-pyridyl |
| O | propyl | OH | 2,6-dimethyl-3-pyridyl |
| O | propyl | OH | 5,6-dimethyl-3-pyridyl |
| O | propyl | OH | 2,6-diethyl-3-pyridyl |
| O | propyl | OH | 5,6-diethyl-3-pyridyl |
| O | propyl | OH | 2,6-dimethoxy-3-pyridyl |
| O | propyl | OH | 5,6-dimethoxy-3-pyridyl |
| O | propyl | OH | 2,6-diethoxy-3-pyridyl |
| O | propyl | OH | 5,6-diethoxy-3-pyridyl |
| O | propyl | OH | 2,6-dichloro-3-pyridyl |
| O | propyl | OH | 5,6-dichloro-3-pyridyl |
| O | propyl | OH | 5-chloro-6-methoxy-3-pyridyl |
| O | propyl | OH | 5-chloro-6-ethoxy-3-pyridyl |
| O | propyl | OH | 2-chloro-6-methyl-3-pyridyl |
| O | propyl | OH | 6-chloro-2-methyl-3-pyridyl |
| O | propyl | OH | 2-methyl-4-pyridyl |
| O | propyl | OH | 2-ethyl-4-pyridyl |
| O | propyl | OH | 2-methoxy-4-pyridyl |
| O | propyl | OH | 2-ethoxy-4-pyridyl |
| O | propyl | OH | 2-chloro-4-pyridyl |
| O | propyl | OH | 2-dimethylamino-4-pyridyl |
| O | propyl | OH | 2-(1-pyrrolidinyl)-4-pyridyl |
| O | propyl | OH | 2-piperidino-4-pyridyl |
| O | propyl | OH | 2-morpholino-4-pyridyl |
| O | propyl | OH | 2-methylthio-4-pyridyl |
| O | propyl | OH | 2-pyrazinyl |
| O | propyl | OH | 5-methyl-2-pyrazinyl |
| O | propyl | OH | 5-ethyl-2-pyrazinyl |
| O | propyl | OH | 5-methoxy-2-pyrazinyl |
| O | propyl | OH | 5-ethoxy-2-pyrazinyl |
| O | propyl | OH | 5-chloro-2-pyrazinyl |
| O | propyl | OH | 6-methyl-2-pyrazinyl |
| O | propyl | OH | 6-methoxy-2-pyrazinyl |
| O | propyl | OH | 6-chloro-2-pyrazinyl |
| O | propyl | OCOOMe | 2-pyridyl |
| O | propyl | OCOOMe | 3-pyridyl |
| O | propyl | OCOOMe | 4-pyridyl |
| O | propyl | OCOOMe | 2-methyl-3-pyridyl |
| O | propyl | OCOOMe | 4-methyl-3-pyridyl |
| O | propyl | OCOOMe | 5-methyl-3-pyridyl |
| O | propyl | OCOOMe | 6-methyl-3-pyridyl |
| O | propyl | OCOOMe | 2-ethyl-3-pyridyl |
| O | propyl | OCOOMe | 4-ethyl-3-pyridyl |
| O | propyl | OCOOMe | 5-ethyl-3-pyridyl |
| O | propyl | OCOOMe | 6-ethyl-3-pyridyl |
| O | propyl | OCOOMe | 2-methoxy-3-pyridyl |
| O | propyl | OCOOMe | 4-methoxy-3-pyridyl |
| O | propyl | OCOOMe | 5-methoxy-3-pyridyl |
| O | propyl | OCOOMe | 6-methoxy-3-pyridyl |
| O | propyl | OCOOMe | 2-ethoxy-3-pyridyl |
| O | propyl | OCOOMe | 4-ethoxy-3-pyridyl |
| O | propyl | OCOOMe | 5-ethoxy-3-pyridyl |
| O | propyl | OCOOMe | 6-ethoxy-3-pyridyl |
| O | propyl | OCOOMe | 2-chloro-3-pyridyl |
| O | propyl | OCOOMe | 4-chloro-3-pyridyl |
| O | propyl | OCOOMe | 5-chloro-3-pyridyl |
| O | propyl | OCOOMe | 6-chloro-3-pyridyl |
| O | propyl | OCOOMe | 2-fluoro-3-pyridyl |
| O | propyl | OCOOMe | 4-fluoro-3-pyridyl |
| O | propyl | OCOOMe | 5-fluoro-3-pyridyl |
| O | propyl | OCOOMe | 6-fluoro-3-pyridyl |
| O | propyl | OCOOMe | 2-dimethylamino-3-pyridyl |
| O | propyl | OCOOMe | 4-dimethylamino-3-pyridyl |
| O | propyl | OCOOMe | 5-dimethylamino-3-pyridyl |
| O | propyl | OCOOMe | 6-dimethylamino-3-pyridyl |
| O | propyl | OCOOMe | 2-(1-pyrrolidinyl)-3-pyridyl |
| O | propyl | OCOOMe | 3-(1-pyrrolidinyl)-3-pyridyl |
| O | propyl | OCOOMe | 5-(1-pyrrolidinyl)-3-pyridyl |
| O | propyl | OCOOMe | 6-(1-pyrrolidinyl)-3-pyridyl |
| O | propyl | OCOOMe | 2-piperidino-3-pyridyl |
| O | propyl | OCOOMe | 4-piperidino-3-pyridyl |
| O | propyl | OCOOMe | 5-piperidino-3-pyridyl |
| O | propyl | OCOOMe | 6-piperidino-3-pyridyl |
| O | propyl | OCOOMe | 2-morpholino-3-pyridyl |
| O | propyl | OCOOMe | 4-morpholino-3-pyridyl |
| O | propyl | OCOOMe | 5-morpholino-3-pyridyl |
| O | propyl | OCOOMe | 6-morpholino-3-pyridyl |
| O | propyl | OCOOMe | 2-hydroxy-3-pyridyl |
| O | propyl | OCOOMe | 4-hydroxy-3-pyridyl |
| O | propyl | OCOOMe | 5-hydroxy-3-pyridyl |
| O | propyl | OCOOMe | 6-hydroxy-3-pyridyl |
| O | propyl | OCOOMe | 2-mercapto-3-pyridyl |
| O | propyl | OCOOMe | 4-mercapto-3-pyridyl |
| O | propyl | OCOOMe | 5-mercapto-3-pyridyl |
| O | propyl | OCOOMe | 6-mercapto-3-pyridyl |

TABLE 1-continued

| X | R¹ | R² | Y |
|---|---|---|---|
| O | propyl | OCOOMe | 2-methylthio-3-pyridyl |
| O | propyl | OCOOMe | 4-methylthio-3-pyridyl |
| O | propyl | OCOOMe | 5-methylthio-3-pyridyl |
| O | propyl | OCOOMe | 6-methylthio-3-pyridyl |
| O | propyl | OCOOMe | 2,6-dimethyl-3-pyridyl |
| O | propyl | OCOOMe | 5,6-dimethyl-3-pyridyl |
| O | propyl | OCOOMe | 2,6-diethyl-3-pyridyl |
| O | propyl | OCOOMe | 5,6-diethyl-3-pyridyl |
| O | propyl | OCOOMe | 2,6-dimethoxy-3-pyridyl |
| O | propyl | OCOOMe | 5,6-dimethoxy-3-pyridyl |
| O | propyl | OCOOMe | 2,6-diethoxy-3-pyridyl |
| O | propyl | OCOOMe | 5,6-diethoxy-3-pyridyl |
| O | propyl | OCOOMe | 2,6-dichloro-3-pyridyl |
| O | propyl | OCOOMe | 5,6-dichloro-3-pyridyl |
| O | propyl | OCOOMe | 5-chloro-6-methoxy-3-pyridyl |
| O | propyl | OCOOMe | 5-chloro-6-ethoxy-3-pyridyl |
| O | propyl | OCOOMe | 2-chloro-6-methyl-3-pyridyl |
| O | propyl | OCOOMe | 6-chloro-2-methyl-3-pyridyl |
| O | propyl | OCOOMe | 2-methyl-4-pyridyl |
| O | propyl | OCOOMe | 2-ethyl-4-pyridyl |
| O | propyl | OCOOMe | 2-methoxy-4-pyridyl |
| O | propyl | OCOOMe | 2-ethoxy-4-pyridyl |
| O | propyl | OCOOMe | 2-chloro-4-pyridyl |
| O | propyl | OCOOMe | 2-dimethylamino-4-pyridyl |
| O | propyl | OCOOMe | 2-(1-pyrrolidinyl)-4-pyridyl |
| O | propyl | OCOOMe | 2-piperidino-4-pyridyl |
| O | propyl | OCOOMe | 2-morpholino-4-pyridyl |
| O | propyl | OCOOMe | 2-methylthio-4-pyridyl |
| O | propyl | OCOOMe | 2-pyrazinyl |
| O | propyl | OCOOMe | 5-methyl-2-pyrazinyl |
| O | propyl | OCOOMe | 5-ethyl-2-pyrazinyl |
| O | propyl | OCOOMe | 5-methoxy-2-pyrazinyl |
| O | propyl | OCOOMe | 5-ethoxy-2-pyrazinyl |
| O | propyl | OCOOMe | 5-chloro-2-pyrazinyl |
| O | propyl | OCOOMe | 6-methyl-2-pyrazinyl |
| O | propyl | OCOOMe | 6-methoxy-2-pyrazinyl |
| O | propyl | OCOOMe | 6-chloro-2-pyrazinyl |
| O | propyl | OCOOEt | 2-pyridyl |
| O | propyl | OCOOEt | 3-pyridyl |
| O | propyl | OCOOEt | 4-pyridyl |
| O | propyl | OCOOEt | 2-methyl-3-pyridyl |
| O | propyl | OCOOEt | 4-methyl-3-pyridyl |
| O | propyl | OCOOEt | 5-methyl-3-pyridyl |
| O | propyl | OCOOEt | 6-methyl-3-pyridyl |
| O | propyl | OCOOEt | 2-ethyl-3-pyridyl |
| O | propyl | OCOOEt | 4-ethyl-3-pyridyl |
| O | propyl | OCOOEt | 5-ethyl-3-pyridyl |
| O | propyl | OCOOEt | 6-ethyl-3-pyridyl |
| O | propyl | OCOOEt | 2-methoxy-3-pyridyl |
| O | propyl | OCOOEt | 4-methoxy-3-pyridyl |
| O | propyl | OCOOEt | 5-methoxy-3-pyridyl |
| O | propyl | OCOOEt | 6-methoxy-3-pyridyl |
| O | propyl | OCOOEt | 2-ethoxy-3-pyridyl |
| O | propyl | OCOOEt | 4-ethoxy-3-pyridyl |
| O | propyl | OCOOEt | 5-ethoxy-3-pyridyl |
| O | propyl | OCOOEt | 6-ethoxy-3-pyridyl |
| O | propyl | OCOOEt | 2-chloro-3-pyridyl |
| O | propyl | OCOOEt | 4-chloro-3-pyridyl |
| O | propyl | OCOOEt | 5-chloro-3-pyridyl |
| O | propyl | OCOOEt | 6-chloro-3-pyridyl |
| O | propyl | OCOOEt | 2-fluoro-3-pyridyl |
| O | propyl | OCOOEt | 4-fluoro-3-pyridyl |
| O | propyl | OCOOEt | 5-fluoro-3-pyridyl |
| O | propyl | OCOOEt | 6-fluoro-3-pyridyl |
| O | propyl | OCOOEt | 2-dimethylamino-3-pyridyl |
| O | propyl | OCOOEt | 4-dimethylamino-3-pyridyl |
| O | propyl | OCOOEt | 6-dimethylamino-3-pyridyl |
| O | propyl | OCOOEt | 6-dimethylamino-3-pyridyl |
| O | propyl | OCOOEt | 2-(1-pyrrolidinyl)-3-pyridyl |
| O | propyl | OCOOEt | 3-(1-pyrrolidinyl)-3-pyridyl |
| O | propyl | OCOOEt | 5-(1-pyrrolidinyl)-3-pyridyl |
| O | propyl | OCOOEt | 6-(1-pyrrolidinyl)-3-pyridyl |
| O | propyl | OCOOEt | 2-piperidino-3-pyridyl |
| O | propyl | OCOOEt | 4-piperidino-3-pyridyl |
| O | propyl | OCOCEt | 5-piperidino-3-pyridyl |
| O | propyl | OCOOEt | 6-piperidino-3-pyridyl |
| O | propyl | OCOOEt | 2-morpholino-3-pyridyl |
| O | propyl | OCOOEt | 4-morpholino-3-pyridyl |
| O | propyl | OCOOEt | 5-morpholino-3-pyridyl |
| O | propyl | OCOOEt | 6-morpholino-3-pyridyl |
| O | propyl | OCOOEt | 2-hydroxy-3-pyridyl |
| O | propyl | OCOOEt | 4-hydroxy-3-pyridyl |
| O | propyl | OCOOEt | 5-hydroxy-3-pyridyl |
| O | propyl | OCOOEt | 6-hydroxy-3-pyridyl |
| O | propyl | OCOOEt | 2-mercapto-3-pyridyl |
| O | propyl | OCOOEt | 4-mercapto-3-pyridyl |
| O | propyl | OCOOEt | 5-mercapto-3-pyridyl |
| O | propyl | OCOOEt | 6-mercapto-3-pyridyl |
| O | propyl | OCOOEt | 2-methylthio-3-pyridyl |
| O | propyl | OCOOEt | 4-methylthio-3-pyridyl |
| O | propyl | OCOOEt | 5-methylthio-3-pyridyl |
| O | propyl | OOOOEt | 5-methylthio-3-pyridyl |
| O | propyl | OCOOEt | 2,6-dimethyl-3-pyridyl |
| O | propyl | OCOOEt | 5,6-dimethyl-3-pyridyl |
| O | propyl | OCOOEt | 2,6-diethyl-3-pyridyl |
| O | propyl | OCOOEt | 5,6-diethyl-3-pyridyl |
| O | propyl | OCOOEt | 2,6-dimethoxy-3-pyridyl |
| O | propyl | OCOOEt | 5,6-dimethoxy-3-pyridyl |
| O | propyl | OCOOEt | 2,6-diethoxy-3-pyridyl |
| O | propyl | OCOOEt | 5,6-diethoxy-3-pyridyl |
| O | propyl | OCOOEt | 2,6-dichloro-3-pyridyl |
| O | propyl | OCOOEt | 5,6-dichloro-3-pyridyl |
| O | propyl | OCOOEt | 5-chloro-6-methoxy-3-pyridyl |
| O | propyl | OCOOEt | 5-chloro-6-ethoxy-3-pyridyl |
| O | propyl | OCOOEt | 2-chloro-6-methyl-3-pyridyl |
| O | propyl | OCOOEt | 6-chloro-2-methyl-3-pyridyl |
| O | propyl | OCOOEt | 2-methyl-4-pyridyl |
| O | propyl | OCOOEt | 2-ethyl-4-pyridyl |
| O | propyl | OCOOEt | 2-methoxy-4-pyridyl |
| O | propyl | OCOOEt | 2-ethoxy-4-pyridyl |
| O | propyl | OCOOEt | 2-chloro-4-pyridyl |
| O | propyl | OCOOEt | 2-dimethylamino-4-pyridyl |
| O | propyl | OCOOEt | 2-(1-pyrrolidinyl)-4-pyridyl |
| O | propyl | OCOOEt | 2-piperidino-4-pyridyl |
| O | propyl | OCOOEt | 2-morpholino-4-pyridyl |
| O | propyl | OCOOEt | 2-methylthio-4-pyridyl |
| O | propyl | OCOOEt | 2-pyrazinyl |
| O | propyl | OCOOEt | 5-methyl-2-pyrazinyl |
| O | propyl | OCOOEt | 5-ethyl-2-pyrazinyl |
| O | propyl | OCOOEt | 5-methoxy-2-pyrazinyl |
| O | propyl | OCOOEt | 5-ethoxy-2-pyrazinyl |
| O | propyl | OCOOEt | 5-chloro-2-pyrazinyl |
| O | propyl | OCOOEt | 6-methyl-2-pyrazinyl |
| O | propyl | OCOOEt | 6-methoxy-2-pyrazinyl |
| O | propyl | OCOOEt | 6-chloro-2-pyrazinyl |
| O | n-butyl | OH | 2-pyridyl |
| O | n-butyl | OH | 3-pyridyl |
| O | n-butyl | OH | 4-pyridyl |
| O | n-butyl | OH | 2-methyl-3-pyridyl |
| O | n-butyl | OH | 4-methyl-3-pyridyl |
| O | n-butyl | OH | 5-methyl-3-pyridyl |
| O | n-hntyl | OH | 6-methyl-3-pyridyl |
| O | n-butyl | OH | 2-ethyl-3-pyridyl |
| O | n-butyl | OH | 4-ethyl-3-pyridyl |
| O | n-butyl | OH | 5-ethyl-3-pyridyl |
| O | n-butyl | OH | 6-ethyl-3-pyridyl |
| O | n-butyl | OH | 2-methoxy-3-pyridyl |
| O | n-butyl | OH | 4-methoxy-3-pyridyl |
| O | n-butyl | OH | 5-methoxy-3-pyridyl |
| O | n-butyl | OH | 6-methoxy-3-pyridyl |
| O | n-butyl | OH | 2-ethoxy-3-pyridyl |
| O | n-butyl | OH | 4-ethoxy-3-pyridyl |
| O | n-butyl | OH | 5-ethoxy-3-pyridyl |
| O | n-butyl | OH | 6-ethoxy-3-pyridyl |
| O | n-butyl | OH | 2-chloro-3-pyridyl |
| O | n-butyl | OH | 4-chloro-3-pyridyl |
| O | n-butyl | OH | 5-chloro-3-pyridyl |
| O | n-butyl | OH | 6-chloro-3-pyridyl |
| O | n-butyl | OH | 2-flouro-3-pyridyl |
| O | n-butyl | OH | 4-flouro-3-pyridyl |
| O | n-butyl | OH | 5-flouro-3-pyridyl |
| O | n-butyl | OH | 6-fluoro-3-pyridyl |
| O | n-butyl | OH | 2-dimethylamino-3-pyridyl |
| O | n-butyl | OH | 4-dimethylamino-3-pyridyl |

TABLE 1-continued

| X | R¹ | R² | Y |
|---|---|---|---|
| O | n-butyl | OH | 5-dimethylamino-3-pyridyl |
| O | n-butyl | OH | 6-dimethylamino-3-pyridyl |
| O | n-butyl | OH | 2-(1-pyrrolidinyl)-3-pyridyl |
| O | n-butyl | OH | 3-(1-pyrrolidinyl)-3-pyridyl |
| O | n-butyl | OH | 5-(1-pyrrolidinyl)-3-pyridyl |
| O | n-butyl | OH | 6-(1-pyrrolidinyl)-3-pyridyl |
| O | n-butyl | OH | 2-piperidino-3-pyridyl |
| O | n-butyl | OH | 4-piperidino-3-pyridyl |
| O | n-butyl | OH | 5-piperidino-3-pyridyl |
| O | n-butyl | OH | 6-piperidino-3-pyridyl |
| O | n-butyl | OH | 2-morpholino-3-pyridyl |
| O | n-butyl | OH | 4-morpholino-3-pyridyl |
| O | n-butyl | OH | 5-morpholino-3-pyridyl |
| O | n-butyl | OH | 6-morpholino-3-pyridyl |
| O | n-butyl | OH | 2-hydroxy-3-pyridyl |
| O | n-butyl | OH | 4-hydroxy-3-pyridyl |
| O | n-butyl | OH | 5-hydroxy-3-pyridyl |
| O | n-butyl | OH | 6-hydroxy-3-pyridyl |
| O | n-butyl | OH | 2-mercapto-3-pyridyl |
| O | n-butyl | OH | 4-mercapto-3-pyridyl |
| O | n-butyl | OH | 5-mercapto-3-pyridyl |
| O | n-butyl | OH | 6-mercapto-3-pyridyl |
| O | n-butyl | OH | 2-methylthio-3-pyridyl |
| O | n-butyl | OH | 4-methylthio-3-pyridyl |
| O | n-butyl | OH | 5-methylthio-3-pyridyl |
| O | n-butyl | OH | 6-methylthio-3-pyridyl |
| O | n-butyl | OH | 2,6-dimethyl-3-pyridyl |
| O | n-butyl | OH | 5,6-dimethyl-3-pyridyl |
| O | n-butyl | OH | 2,6-diethyl-3-pyridyl |
| O | n-butyl | OH | 5,6-diethyl-3-pyridyl |
| O | n-butyl | OH | 2,6-dimethoxy-3-pyridyl |
| O | n-butyl | OH | 5,6-dimethoxy-3-pyridyl |
| O | n-butyl | OH | 2,6-diethoxy-3-pyridyl |
| O | n-butyl | OH | 5,6-diethoxy-3-pyridyl |
| O | n-butyl | OH | 2,6-dichloro-3-pyridyl |
| O | n-butyl | OH | 5,6-dichloro-3-pyridyl |
| O | n-butyl | OH | 5-chloro-6-methoxy-3-pyridyl |
| O | n-butyl | OH | 5-chloro-6-ethoxy-3-pyridyl |
| O | n-butyl | OH | 2-chloro-6-methyl-3-pyridyl |
| O | n-butyl | OH | 6-chloro-2-methyl-3-pyridyl |
| O | n-butyl | OH | 2-methyl-4-pyridyl |
| O | n-butyl | OH | 2-ethyl-4-pyridyl |
| O | n-butyl | OH | 2-methoxy-4-pyridyl |
| O | n-butyl | OH | 2-ethoxy-4-pyridyl |
| O | n-butyl | OH | 2-chloro-4-pyridyl |
| O | n-butyl | OH | 2-dimethylamino-4-pyridyl |
| O | n-butyl | OH | 2-(1-pyrrolidinyl1)-4-pyridyl |
| O | n-butyl | OH | 2-piperidino-4-pyridyl |
| O | n-butyl | OH | 2-morpholino-4-pyridyl |
| O | n-butyl | OH | 2-methylthio-4-pyridyl |
| O | n-butyl | OH | 2-pyrazinyl |
| O | n-butyl | OH | 5-methyl-2-pyrazinyl |
| O | n-butyl | OH | 5-ethyl-2-pyrazinyl |
| O | n-butyl | OH | 5-methoxy-2-pyrazinyl |
| O | n-butyl | OH | 5-ethoxy-2-pyrazinyl |
| O | n-butyl | OH | 5-chloro-2-pyrazinyl |
| O | n-butyl | OH | 6-methyl-2-pyrazinyl |
| O | n-butyl | OH | 6-methoxy-2-pyrazinyl |
| O | n-butyl | OH | 6-chloro-2-pyrazinyl |
| O | n-butyl | OCOOMe | 2-pyridyl |
| O | n-butyl | OCOOMe | 3-pyridyl |
| O | n-butyl | OCOOMe | 4-pyridyl |
| O | n-butyl | OCOOMe | 2-methyl-3-pyridyl |
| O | n-butyl | OCOOMe | 4-methyl-3-pyridyl |
| O | n-butyl | OCOOMe | 5-methyl-3-pyridyl |
| O | n-butyl | OCOOMe | 6-methyl-3-pyridyl |
| O | n-butyl | OCOOMe | 2-ethyl-3-pyridyl |
| O | n-butyl | OCOOMe | 4-ethyl-3-pyridyl |
| O | n-butyl | OCOOMe | 5-ethyl-3-pyridyl |
| O | n-butyl | OCOOMe | 6-ethyl-3-pyridyl |
| O | n-butyl | OCOOMe | 2-methoxy-3-pyridyl |
| O | n-butyl | OCOOMe | 4-methoxy-3-pyridyl |
| O | n-butyl | OCOOMe | 5-methoxy-3-pyridyl |
| O | n-butyl | OCOOMe | 6-methoxy-3-pyridyl |
| O | n-butyl | OCOOMe | 2-ethoxy-3-pyridyl |
| O | n-butyl | OCOOMe | 4-ethoxy-3-pyridyl |
| O | n-butyl | OCOOMe | 5-ethoxy-3-pyridyl |
| O | n-butyl | OCOOMe | 6-ethoxy-3-pyridyl |
| O | n-butyl | OCOOMe | 2-chloro-3-pyridyl |
| O | n-butyl | OCOOMe | 4-chloro-3-pyridyl |
| O | n-butyl | OCOOMe | 5-chloro-3-pyridyl |
| O | n-butyl | OCOOMe | 6-chloro-3-pyridyl |
| O | n-butyl | OCOOMe | 2-fluoro-3-pyridyl |
| O | n-butyl | OCOOMe | 4-fluoro-3-pyridyl |
| O | n-butyl | OCOOMe | 5-fluoro-3-pyridyl |
| O | n-butyl | OCOOMe | 6-fluoro-3-pyridyl |
| O | n-butyl | OCOOMe | 2-dimethylamino-3-pyridyl |
| O | n-butyl | OCOOMe | 4-dimethylamino-3-pyridyl |
| O | n-butyl | OCOOMe | 5-dimethylamino-3-pyridyl |
| O | n-butyl | OCOOMe | 6-dimethylamino-3-pyridyl |
| O | n-butyl | OCOOMe | 2-(1-pyrrolidinyl)-3-pyridyl |
| O | n-butyl | OCOOMe | 3-(1-pyrrolidinyl)-3-pyridyl |
| O | n-butyl | OCOOMe | 5-(1-pyrrolidinyl)-3-pyridyl |
| O | n-butyl | OCOOMe | 6-(1-pyrrolidinyl)-3-pyridyl |
| O | n-butyl | OCOOMe | 2-piperidino-3-pyridyl |
| O | n-butyl | OCOOMe | 4-piperidino-3-pyridyl |
| O | n-butyl | OCOOMe | 5-piperidino-3-pyridyl |
| O | n-butyl | OCOOMe | 6-piperidino-3-pyridyl |
| O | n-butyl | OCOOMe | 2-morpholino-3-pyridyl |
| O | n-butyl | OCOOMe | 4-morpholino-3-pyridyl |
| O | n-butyl | OCOOMe | 5-morpholino-3-pyridyl |
| O | n-butyl | OCOOMe | 6-morpholino-3-pyridyl |
| O | n-butyl | OCOOMe | 2-hydroxy-3-pyridyl |
| O | n-butyl | OCOOMe | 4-hydroxy-3-pyridyl |
| O | n-butyl | OCOOMe | 5-hydroxy-3-pyridyl |
| O | n-butyl | OCOOMe | 6-hydroxy-3-pyridyl |
| O | n-butyl | OCOOMe | 2-mercapto-3-pyridyl |
| O | n-butyl | OCOOMe | 4-mercapto-3-pyridyl |
| O | n-butyl | OCOOMe | 5-mercapto-3-pyridyl |
| O | n-butyl | OCOOMe | 6-mercapto-3-pyridyl |
| O | n-butyl | OCOOMe | 2-methylthio-3-pyridyl |
| O | n-butyl | OCOOMe | 4-methylthio-3-pyridyl |
| O | n-butyl | OCOOMe | 5-methylthio-3-pyridyl |
| O | n-butyl | OCOOMe | 6-methylthio-3-pyridyl |
| O | n-butyl | OCOOMe | 2,6-dimethyl-3-pyridyl |
| O | n-butyl | OCOOMe | 5,6-dimethyl-3-pyridyl |
| O | n-butyl | OCOOMe | 2,6-diethyl-3-pyridyl |
| O | n-butyl | OCOOMe | 5,6-diethyl-3-pyridyl |
| O | n-butyl | OCOOMe | 2,6-dimethoxy-3-pyridyl |
| O | n-butyl | OCOOMe | 5,6-dimethoxy-3-pyridyl |
| O | n-butyl | OCOOMe | 2,6-diethoxy-3-pyridyl |
| O | n-butyl | OCOOMe | 5,6-diethoxy-3-pyridyl |
| O | n-butyl | OCOOMe | 2,6-dichloro-3-pyridyl |
| O | n-butyl | OCOOMe | 5,6-dichloro-3-pyridyl |
| O | n-butyl | OCOOMe | 5-chloro-6-methoxy-3-pyridyl |
| O | n-butyl | OCOOMe | 5-chloro-6-ethoxy-3-pyridyl |
| O | n-butyl | OCOOMe | 2-chloro-6-methyl-3-pyridyl |
| O | n-butyl | OCOOMe | 6-chloro-2-methyl-3-pyridyl |
| O | n-butyl | OCOOMe | 2-methyl-4-pyridyl |
| O | n-butyl | OCOOMe | 2-ethyl-4-pyridyl |
| O | n-butyl | OCOOMe | 2-methoxy-4-pyridyl |
| O | n-butyl | OCOOMe | 2-ethoxy-4-pyridyl |
| O | n-butyl | OCOOMe | 2-chloro-4-pyridyl |
| O | n-butyl | OCOOMe | 2-dimethylamino-4-pyridyl |
| O | n-bvtyl | OCOOMe | 2-(1-pyrrolidinyl)-4-pyridyl |
| O | n-butyl | OCOOMe | 2-piperidino-4-pyridyl |
| O | n-butyl | OCOOMe | 2-morpholino-4-pyridyl |
| O | n-butyl | OCOOMe | 2-methylthio-4-pyridyl |
| O | n-butyl | OCOOMe | 2-pyrazinyl |
| O | n-butyl | OCOOMe | 5-methyl-2-pyrazinyl |
| O | n-butyl | OCOOMe | 5-ethyl-2-pyrazinyl |
| O | n-butyl | OCOOMe | 5-methoxy-2-pyrazinyl |
| O | n-butyl | OCOOMe | 5-ethoxy-2-pyrazinyl |
| O | n-butyl | OCOOMe | 5-chloro-2-pyrazinyl |
| O | n-butyl | OCOOMe | 6-methyl-2-pyrazinyl |
| O | n-butyl | OCOOMe | 6-methoxy-2-pyrazinyl |
| O | n-butyl | OCOOMe | 6-chloro-2-pyrazinyl |
| O | n-butyl | OCOOEt | 2-pyridyl |
| O | n-butyl | OCOOEt | 3-pyridyl |
| O | n-butyl | OCOOEt | 4-pyridyl |
| O | n-butyl | OCOOEt | 2-methyl-3-pyridyl |
| O | n-butyl | OCOOEt | 4-methyl-3-pyridyl |
| O | n-butyl | OCOOEt | 5-methyl-3-pyridyl |
| O | n-butyl | OCOOEt | 6-methyl-3-pyridyl |

TABLE 1-continued

| X | R¹ | R² | Y |
|---|---|---|---|
| O | n-butyl | OCOOEt | 2-ethyl-3-pyridyl |
| O | n-butyl | OCOOEt | 4-ethyl-3-pyridyl |
| O | n-butyl | OCOOEt | 5-ethyl-3-pyridyl |
| O | n-butyl | OCOOEt | 6-ethyl-3-pyridyl |
| O | n-butyl | OCOOEt | 2-methoxy-3-pyridyl |
| O | n-butyl | OCOOEt | 4-methoxy-3-pyridyl |
| O | n-butyl | OCOOEt | 5-methoxy-3-pyridyl |
| O | n-butyl | OCOOEt | 6-methoxy-3-pyridyl |
| O | n-butyl | OCOOEt | 2-ethoxy-3-pyridyl |
| O | n-butyl | OCOOEt | 4-ethoxy-3-pyridyl |
| O | n-butyl | OCOOEt | 5-ethoxy-3-pyridyl |
| O | n-butyl | OCOOEt | 6-ethoxy-3-pyridyl |
| O | n-butyl | OCOOEt | 2-chloro-3-pyridyl |
| O | n-butyl | OCOOEt | 4-chloro-3-pyridyl |
| O | n-butyl | OCOOEt | 5-chloro-3-pyridyl |
| O | n-butyl | OCOOEt | 6-chloro-3-pyridyl |
| O | n-butyl | OCOOEt | 2-fluoro-3-pyridyl |
| O | n-butyl | OCOOEt | 4-fluoro-3-pyridyl |
| O | n-butyl | OCOOEt | 5-fluoro-3-pyridyl |
| O | n-butyl | OCOOEt | 6-fluoro-3-pyridyl |
| O | n-butyl | OCOOEt | 2-dimethylamino-3-pyridyl |
| O | n-butyl | OCOOEt | 4-dimethylamino-3-pyridyl |
| O | n-butyl | OCOOEt | 5-dimethylamino-3-pyridyl |
| O | n-butyl | OCOOEt | 6-dimethylamino-3-pyridyl |
| O | n-butyl | OCOOEt | 2-(1-pyrrolidinyl)-3-pyridyl |
| O | n-butyl | OCOOEt | 3-(1-pyrrolidinyl)-3-pyridyl |
| O | n-butyl | OCOOEt | 5-(1-pyrrolidinyl)-3-pyridyl |
| O | n-butyl | OCOOEt | 6-(1-pyrrolidinyl)-3-pyridyl |
| O | n-butyl | OCOOEt | 2-piperidino-3-pyridyl |
| O | n-butyl | OCOOEt | 4-piperidino-3-pyridyl |
| O | n-butyl | OCOOEt | 5-piperidino-3-pyridyl |
| O | n-butyl | OCOOEt | 6-piperidino-3-pyridyl |
| O | n-butyl | OCOOEt | 2-morpholino-3-pyridyl |
| O | n-butyl | OCOOEt | 4-morpholino-3-pyridyl |
| O | n-butyl | OCOOEt | 5-morpholino-3-pyridyl |
| O | n-butyl | OCOOEt | 6-morpholino-3-pyridyl |
| O | n-butyl | OCOOEt | 2-hydroxy-3-pyridyl |
| O | n-butyl | OCOOEt | 4-hydroxy-3-pyridyl |
| O | n-butyl | OCOOEt | 5-hydroxy-3-pyridyl |
| O | n-butyl | OCOOEt | 6-hydroxy-3-pyridyl |
| O | n-butyl | OCOOEt | 2-mercapto-3-pyridyl |
| O | n-butyl | OCOOEt | 4-mercapto-3-pyridyl |
| O | n-butyl | OCOOEt | 5-mercapto-3-pyridyl |
| O | n-butyl | OCOOEt | 6-mercapto-3-pyridyl |
| O | n-butyl | OCOOEt | 2-methylthio-3-pyridyl |
| O | n-butyl | OCOOEt | 4-methylthio-3-pyridyl |
| O | n-butyl | OCOOEt | 5-methylthio-3-pyridyl |
| O | n-butyl | OCOOEt | 6-methylthio-3-pyridyl |
| O | n-butyl | OCOOEt | 2,6-dimethyl-3-pyridyl |
| O | n-butyl | OCOOEt | 5,6-dimethyl-3-pyridyl |
| O | n-butyl | OCOOEt | 2,6-diethyl-3-pyridyl |
| O | n-butyl | OCOOEt | 5,6-diethyl-3-pyridyl |
| O | n-butyl | OCOOEt | 2,6-dimethoxy-3-pyridyl |
| O | n-butyl | OCOOEt | 5,6-dimethoxy-3-pyridyl |
| O | n-butyl | OCOOEt | 2,6-diethoxy-3-pyridyl |
| O | n-butyl | OCOOEt | 5,6-diethoxy-3-pyridyl |
| O | n-butyl | OCOOEt | 2,6-dichloro-3-pyridyl |
| O | n-butyl | OCOOEt | 5,6-dichloro-3-pyridyl |
| O | n-butyl | OCOOEt | 5-chloro-6-methoxy-3-pyridyl |
| O | n-butyl | OCOOEt | 5-chloro-6-ethoxy-3-pyridyl |
| O | n-butyl | OCOOEt | 2-chloro-6-methyl-3-pyridyl |
| O | n-butyl | OCOOEt | 6-chloro-2-methyl-3-pyridyl |
| O | n-butyl | OCOOEt | 2-methyl-4-pyridyl |
| O | n-butyl | OCOOEt | 2-ethyl-4-pyridyl |
| O | n-butyl | OCOOEt | 2-methoxy-4-pyridyl |
| O | n-butyl | OCOOEt | 2-ethoxy-4-pyridyl |
| O | n-butyl | OCOOEt | 2-chloro-4-pyridyl |
| O | n-butyl | OCOOEt | 2-dimethylamino-4-pyridyl |
| O | n-butyl | OCOOEt | 2-(1-pyrrolidinyl)-4-pyridyl |
| O | n-butyl | OCOOEt | 2-piperidino-4-pyridyl |
| O | n-butyl | OCOOEt | 2-morpholino-4-pyridyl |
| O | n-butyl | OCOOEt | 2-methylthio-4-pyridyl |
| O | n-butyl | OCOOEt | 2-pyrazinyl |
| O | n-butyl | OCOOEt | 5-methyl-2-pyrazinyl |
| O | n-butyl | OCOOEt | 5-ethyl-2-pyrazinyl |
| O | n-butyl | OCOOEt | 5-methoxy-2-pyrazinyl |
| O | n-butyl | OCOOEt | 5-ethoxy-2-pyrazinyl |
| O | n-butyl | OCOOEt | 5-chloro-2-pyrazinyl |
| O | n-butyl | OCOOEt | 6-methyl-2-pyrazinyl |
| O | n-butyl | OCOOEt | 6-methoxy-2-pyrazinyl |
| O | n-butyl | OCOOEt | 6-chloro-2-pyrazinyl |
| O | n-pentyl | OH | 2-pyridyl |
| O | n-pentyl | OH | 3-pyridyl |
| O | n-pentyl | OH | 4-pyridyl |
| O | n-pentyl | OH | 2-methyl-3-pyridyl |
| O | n-pentyl | OH | 4-methyl-3-pyridyl |
| O | n-pentyl | OH | 5-methyl-3-pyridyl |
| O | n-pentyl | OH | 6-methyl-3-pyridyl |
| O | n-pentyl | OH | 2-ethyl-3-pyridyl |
| O | n-pentyl | OH | 4-ethyl-3-pyridyl |
| O | n-pentyl | OH | 5-ethyl-3-pyridyl |
| O | n-pentyl | OH | 6-ethyl-3-pyridyl |
| O | n-pentyl | OH | 2-methoxy-3-pyridyl |
| O | n-pentyl | OH | 4-methoxy-3-pyridyl |
| O | n-pentyl | OH | 5-methoxy-3-pyridyl |
| O | n-pentyl | OH | 6-methoxy-3-pyridyl |
| O | n-pentyl | OH | 2-ethoxy-3-pyridyl |
| O | n-pentyl | OH | 4-ethoxy-3-pyridyl |
| O | n-pentyl | OH | 5-ethoxy-3-pyridyl |
| O | n-pentyl | OH | 6-ethoxy-3-pyridyl |
| O | n-pentyl | OH | 2-chloro-3-pyridyl |
| O | n-pentyl | OH | 4-chloro-3-pyridyl |
| O | n-pentyl | OH | 5-chloro-3-pyridyl |
| O | n-pentyl | OH | 6-chloro-3-pyridyl |
| O | n-pentyl | OH | 2-fluoro-3-pyridyl |
| O | n-pentyl | OH | 4-fluoro-3-pyridyl |
| O | n-pentyl | OH | 5-fluoro-3-pyridyl |
| O | n-pentyl | OH | 6-fluoro-3-pyridyl |
| O | n-pentyl | OH | 2-dimethylamino-3-pyridyl |
| O | n-pentyl | OH | 4-dimethylamino-3-pyridyl |
| O | n-pentyl | OH | 5-dimethylamino-3-pyridyl |
| O | n-pentyl | OH | 6-dimethylamino-3-pyridyl |
| O | n-pentyl | OH | 2-(1-pyrrolidinyl)-3-pyridyl |
| O | n-pentyl | OH | 3-(1-pyrrolidinyl)-3-pyridyl |
| O | n-pentyl | OH | 5-(1-pyrrolidinyl)-3-pyridyl |
| O | n-pentyl | OH | 6-(1-pyrrolidinyl)-3-pyridyl |
| O | n-pentyl | OH | 2-piperidino-3-pyridyl |
| O | n-pentyl | OH | 4-piperidino-3-pyridyl |
| O | n-pentyl | OH | 5-piperidino-3-pyridyl |
| O | n-pentyl | OH | 6-piperidino-3-pyridyl |
| O | n-pentyl | OH | 2-morpholino-3-pyridyl |
| O | n-pentyl | OH | 4-morpholino-3-pyridyl |
| O | n-pentyl | OH | 5-morpholino-3-pyridyl |
| O | n-pentyl | OH | 6-morpholino-3-pyridyl |
| O | n-pentyl | OH | 2-hydroxy-3-pyridyl |
| O | n-pentyl | OH | 4-hydroxy-3-pyridyl |
| O | n-pentyl | OH | 5-hydroxy-3-pyridyl |
| O | n-pentyl | OH | 6-hydroxy-3-pyridyl |
| O | n-pentyl | OH | 2-mercapto-3-pyridyl |
| O | n-pentyl | OH | 4-mercapto-3-pyridyl |
| O | n-pentyl | OH | 5-mercapto-3-pyridyl |
| O | n-pentyl | OH | 6-mercapto-3-pyridyl |
| O | n-pentyl | OH | 2-methylthio-3-pyridyl |
| O | n-pentyl | OH | 4-methylthio-3-pyridyl |
| O | n-pentyl | OH | 5-methylthio-3-pyridyl |
| O | n-pentyl | OH | 6-methylthio-3-pyridyl |
| O | n-pentyl | OH | 2,6-dimethyl-3-pyridyl |
| O | n-pentyl | OH | 5,6-dimethyl-3-pyridyl |
| O | n-pentyl | OH | 2,6-diethyl-3-pyridyl |
| O | n-pentyl | OH | 5,6-diethyl-3-pyridyl |
| O | n-pentyl | OH | 2,6-dimethoxy-3-pyridyl |
| O | n-pentyl | OH | 5,6-dimethoxy-3-pyridyl |
| O | n-pentyl | OH | 2,6-diethoxy-3-pyridyl |
| O | n-pentyl | OH | 5,6-diethoxy-3-pyridyl |
| O | n-pentyl | OH | 2,6-dichloro-3-pyridyl |
| O | n-pentyl | OH | 5,6-dichloro-3-pyridyl |
| O | n-pentyl | OH | 5-chloro-6-methoxy-3-pyridyl |
| O | n-pentyl | OH | 5-chloro-6-ethoxy-3-pyridyl |
| O | n-pentyl | OH | 2-chloro-6-methyl-3-pyridyl |
| O | n-pentyl | OH | 6-chloro-2-methyl-3-pyridyl |
| O | n-pentyl | OH | 2-methyl-4-pyridyl |
| O | n-pentyl | OH | 2-ethyl-4-pyridyl |
| O | n-pentyl | OH | 2-methoxy-4-pyridyl |
| O | n-pentyl | OH | 2-ethoxy-4-pyridyl |

TABLE 1-continued

| X | R¹ | R² | Y |
|---|---|---|---|
| O | n-pentyl | OH | 2-chloro-4-pyridyl |
| O | n-pentyl | OH | 2-dimethylamino-4-pyridyl |
| O | n-pentyl | OH | 2-(1-pyrrolidinyl)-4-pyridyl |
| O | n-pentyl | OH | 2-piperidino-4-pyridyl |
| O | n-pentyl | OH | 2-morpholino-4-pyridyl |
| O | n-pentyl | OH | 2-methylthio-4-pyridyl |
| O | n-pentyl | OH | 2-pyrazinyl |
| O | n-pentyl | OH | 5-methyl-2-pyrazinyl |
| O | n-pentyl | OH | 5-ethyl-2-pyrazinyl |
| O | n-pentyl | OH | 5-methoxy-2-pyrazinyl |
| O | n-pentyl | OH | 5-ethoxy-2-pyrazinyl |
| O | n-pentyl | OH | 5-chloro-2-pyrazinyl |
| O | n-pentyl | OH | 6-methyl-2-pyrazinyl |
| O | n-pentyl | OH | 6-methoxy-2-pyrazinyl |
| O | n-pentyl | OH | 6-chloro-2-pyrazinyl |
| O | n-pentyl | OCOOMe | 2-pyridyl |
| O | n-pentyl | OCOOMe | 3-pyridyl |
| O | n-pentyl | OCOOMe | 4-pyridyl |
| O | n-pentyl | OCOOMe | 2-methyl-3-pyridyl |
| O | n-pentyl | OCOOMe | 4-methyl-3-pyridyl |
| O | n-pentyl | OCOOMe | 5-methyl-3-pyridyl |
| O | n-pentyl | OCOOMe | 6-methyl-3-pyridyl |
| O | n-pentyl | OCOOMe | 2-ethyl-3-pyridyl |
| O | n-pentyl | OCOOMe | 4-ethyl-3-pyridyl |
| O | n-pentyl | OCOOMe | 5-ethyl-3-pyridyl |
| O | n-pentyl | OCOOMe | 6-ethyl-3-pyridyl |
| O | n-pentyl | OCOOMe | 2-methoxy-3-pyridyl |
| O | n-pentyl | OCOOMe | 4-methoxy-3-pyridyl |
| O | n-pentyl | OCOOMe | 5-methoxy-3-pyridyl |
| O | n-pentyl | OCOOMe | 6-methoxy-3-pyridyl |
| O | n-pentyl | OCOOMe | 2-ethoxy-3-pyridyl |
| O | n-pentyl | OCOOMe | 4-ethoxy-3-pyridyl |
| O | n-pentyl | OCOOMe | 5-ethoxy-3-pyridyl |
| O | n-pentyl | OCOOMe | 6-ethoxy-3-pyridyl |
| O | n-pentyl | OCOOMe | 2-chloro-3-pyridyl |
| O | n-pentyl | OCOOMe | 4-chloro-3-pyridyl |
| O | n-pentyl | OCOOMe | 5-chloro-3-pyridyl |
| O | n-pentyl | OCOOMe | 6-chloro-3-pyridyl |
| O | n-pentyl | OCOOMe | 2-fluoro-3-pyridyl |
| O | n-pentyl | OCOOMe | 4-fluoro-3-pyridyl |
| O | n-pentyl | OCOOMe | 5-fluoro-3-pyridyl |
| O | n-pentyl | OCOOMe | 6-fluoro-3-pyridyl |
| O | n-pentyl | OCOOMe | 2-dimethylamino-3-pyridyl |
| O | n-pentyl | OCOOMe | 4-dimethylamino-3-pyridyl |
| O | n-pentyl | OCOOMe | 5-dimethylamino-3-pyridyl |
| O | n-pentyl | OCOOMe | 6-dimethylamino-3-pyridyl |
| O | n-pentyl | OCOOMe | 2-(1-pyrrolidinyl)-3-pyridyl |
| O | n-pentyl | OCOOMe | 3-(1-pyrrolidinyl)-3-pyridyl |
| O | n-pentyl | OCOOMe | 5-(1-pyrrolidinyl)-3-pyridyl |
| O | n-pentyl | OCOOMe | 6-(1-pyrrolidinyl)-3-pyridyl |
| O | n-pentyl | OCOOMe | 2-piperidino-3-pyridyl |
| O | n-pentyl | OCOOMe | 4-piperidino-3-pyridyl |
| O | n-pentyl | OCOOMe | 5-piperidino-3-pyridyl |
| O | n-pentyl | OCOOMe | 6-piperidino-3-pyridyl |
| O | n-pentyl | OCOOMe | 2-morpholino-3-pyridyl |
| O | n-pentyl | OCOOMe | 4-morpholino-3-pyridyl |
| O | n-pentyl | OCOOMe | 5-morpholino-3-pyridyl |
| O | n-pentyl | OCOOMe | 6-morpholino-3-pyridyl |
| O | n-pentyl | OCOOMe | 2-hydroxy-3-pyridyl |
| O | n-pentyl | OCOOMe | 4-hydroxy-3-pyridyl |
| O | n-pentyl | OCOOMe | 5-hydroxy-3-pyridyl |
| O | n-pentyl | OCOOMe | 6-hydroxy-3-pyridyl |
| O | n-pentyl | OCOOMe | 2-mercapto-3-pyridyl |
| O | n-pentyl | OCOOMe | 4-mercapto-3-pyridyl |
| O | n-pentyl | OCOOMe | 5-mercapto-3-pyridyl |
| O | n-pentyl | OCOOMe | 6-mercapto-3-pyridyl |
| O | n-pentyl | OCOOMe | 2-methylthio-3-pyridyl |
| O | n-pentyl | OCOOMe | 4-methylthio-3-pyridyl |
| O | n-pentyl | OCOOMe | 5-methylthio-3-pyridyl |
| O | n-pentyl | OCOOMe | 6-methylthio-3-pyridyl |
| O | n-pentyl | OCOOMe | 2,6-dimethyl-3-pyridyl |
| O | n-pentyl | OCOOMe | 5,6-dimethyl-3-pyridyl |
| O | n-pentyl | OCOOMe | 2,6-diethyl-3-pyridyl |
| O | n-pentyl | OCOOMe | 5,6-diethyl-3-pyridyl |
| O | n-pentyl | OCOOMe | 2,6-dimethoxy-3-pyridyl |
| O | n-pentyl | OCOOMe | 5,6-dimethoxy-3-pyridyl |
| O | n-pentyl | OCOOMe | 2,6-diethoxy-3-pyridyl |
| O | n-pentyl | OCOOMe | 5,6-diethoxy-3-pyridyl |
| O | n-pentyl | OCOOMe | 2,6-dichloro-3-pyridyl |
| O | n-pentyl | OCOOMe | 5,6-dichloro-3-pyridyl |
| O | n-pentyl | OCOOMe | 5-chloro-6-methoxy-3-pyridyl |
| O | n-pentyl | OCOOMe | 5-chloro-6-methoxy-3-pyridyl |
| O | n-pentyl | OCOOMe | 2-chloro-6-methyl-3-pyridyl |
| O | n-pentyl | OCOOMe | 6-chloro-2-methyl-3-pyridyl |
| O | n-pentyl | OCOOMe | 2-methyl-4-pyridyl |
| O | n-pentyl | OCOOMe | 2-ethyl-4-pyridyl |
| O | n-pentyl | OCOOMe | 2-methoxy-4-pyridyl |
| O | n-pentyl | OCOOMe | 2-ethoxy-4-pyridyl |
| O | n-pentyl | OCOOMe | 2-chloro-4-pyridyl |
| O | n-pentyl | OCOOMe | 2-dimethylamino-4-pyridyl |
| O | n-pentyl | OCOOMe | 2-(1-pyrrolidinyl)-4-pyridyl |
| O | n-pentyl | OCOOMe | 2-piperidino-4-pyridyl |
| O | n-pentyl | OCOOMe | 2-morpholino-4-pyridyl |
| O | n-pentyl | OCOOMe | 2-methylthio-4-pyridyl |
| O | n-pentyl | OCOOMe | 2-pyrazinyl |
| O | n-pentyl | OCOOMe | 5-methyl-2-pyrazinyl |
| O | n-pentyl | OCOOMe | 5-ethyl-2-pyrazinyl |
| O | n-pentyl | OCOOMe | 5-methoxy-2-pyrazinyl |
| O | n-pentyl | OCOOMe | 5-ethoxy-2-pyrazinyl |
| O | n-pentyl | OCOOMe | 5-chloro-2-pyrazinyl |
| O | n-pentyl | OCOOMe | 6-methyl-2-pyrazinyl |
| O | n-pentyl | OCOOMe | 6-methoxy-2-pyrazinyl |
| O | n-pentyl | OCOOMe | 6-chloro-2-pyrazinyl |
| O | n-pentyl | OCOOEt | 2-pyridyl |
| O | n-pentyl | OCOOEt | 3-pyridyl |
| O | n-pentyl | OCOOEt | 4-pyridyl |
| O | n-pentyl | OCOOEt | 2-methyl-3-pyridyl |
| O | n-pentyl | OCOOEt | 4-methyl-3-pyridyl |
| O | n-pentyl | OCOOEt | 5-methyl-3-pyridyl |
| O | n-pentyl | OCOOEt | 6-methyl-3-pyridyl |
| O | n-pentyl | OCOOEt | 2-ethyl-3-pyridyl |
| O | n-pentyl | OCOOEt | 4-ethyl-3-pyridyl |
| O | n-pentyl | OCOOEt | 5-ethyl-3-pyridyl |
| O | n-pentyl | OCOOEt | 6-ethyl-3-pyridyl |
| O | n-pentyl | OCOOEt | 2-methoxy-3-pyridyl |
| O | n-pentyl | OCOOEt | 4-methoxy-3-pyridyl |
| O | n-pentyl | OCOOEt | 5-methoxy-3-pyridyl |
| O | n-pentyl | OCOOEt | 6-methoxy-3-pyridyl |
| O | n-pentyl | OCOOEt | 2-ethoxy-3-pyridyl |
| O | n-pentyl | OCOOEt | 4-ethoxy-8-pyridyl |
| O | n-pentyl | OCOOEt | 5-ethoxy-3-pyridyl |
| O | n-pentyl | OCOOEt | 6-ethoxy-3-pyridyl |
| O | n-pentyl | OCOOEt | 2-chloro-3-pyridyl |
| O | n-pentyl | OCOOEt | 4-chloro-3-pyridyl |
| O | n-pentyl | OCOOEt | 5-chloro-3-pyridyl |
| O | n-pentyl | OCOOEt | 6-chloro-3-pyridyl |
| O | n-pentyl | OCOOEt | 2-fluoro-3-pyridyl |
| O | n-pentyl | OCOOEt | 4-fluoro-3-pyridyl |
| O | n-pentyl | OCOOEt | 5-fluoro-3-pyridyl |
| O | n-pentyl | OCOOEt | 6-fluoro-3-pyridyl |
| O | n-pentyl | OCOOEt | 2-dimethylamino-3-pyridyl |
| O | n-pentyl | OCOOEt | 4-dimethylamino-3-pyridyl |
| O | n-pentyl | OCOOEt | 5-dimethylamino-3-pyridyl |
| O | n-pentyl | OCOOEt | 6-dimethylamino-3-pyridyl |
| O | n-pentyl | OCOOEt | 2-(1-pyrrolidinyl)-3-pyridyl |
| O | n-pentyl | OCOOEt | 3-(1-pyrrolidinyl)-3-pyridyl |
| O | n-pentyl | OCOOEt | 5-(1-pyrrolidinyl)-3-pyridyl |
| O | n-pentyl | OCOOEt | 6-(1-pyrrolidinyl)-3-pyridyl |
| O | n-pentyl | OCOOEt | 2-piperidino-3-pyridyl |
| O | n-pentyl | OCOOEt | 4-piperidino-3-pyridyl |
| O | n-pentyl | OCOOEt | 5-piperidino-3-pyridyl |
| O | n-pentyl | OCOOEt | 6-piperidino-3-pyridyl |
| O | n-pentyl | OCOOEt | 2-morpholino-3-pyridyl |
| O | n-pentyl | OCOOEt | 4-morpholino-3-pyridyl |
| O | n-pentyl | OCOOEt | 5-morpholino-3-pyridyl |
| O | n-pentyl | OCOOEt | 6-morpholino-3-pyridyl |
| O | n-pentyl | OCOOEt | 2-hydroxy-3-pyridyl |
| O | n-pentyl | OCOOEt | 4-hydroxy-3-pyridyl |
| O | n-pentyl | OCOOEt | 5-hydroxy-3-pyridyl |
| O | n-pentyl | OCOOEt | 6-hydroxy-3-pyridyl |
| O | n-pentyl | OCOOEt | 2-mercapto-3-pyridyl |
| O | n-pentyl | OCOOEt | 4-mercapto-3-pyridyl |
| O | n-pentyl | OCOOEt | 5-mercapto-3-pyridyl |
| O | n-pentyl | OCOOEt | 6-mercapto-3-pyridyl |

TABLE 1-continued

| X | R¹ | R² | Y |
|---|----|----|---|
| O | n-pentyl | OCOOEt | 2-methylthio-3-pyridyl |
| O | n-pentyl | OCOOEt | 4-methylthio-3-pyridyl |
| O | n-pentyl | OCOOEt | 5-methylthio-3-pyridyl |
| O | n-pentyl | OCOOEt | 6-methylthio-3-pyridyl |
| O | n-pentyl | OCOOEt | 2,6-dimethyl-3-pyridyl |
| O | n-pentyl | OCOOEt | 5,6-dimethyl-3-pyridyl |
| O | n-pentyl | OCOOEt | 2,6-diethyl-3-pyridyl |
| O | n-pentyl | OCOOEt | 5,6-diethyl-3-pyridyl |
| O | n-pentyl | OCOOEt | 2,6-dimethoxy-3-pyridyl |
| O | n-pentyl | OCOOEt | 5,6-dimethoxy-3-pyridyl |
| O | n-pentyl | OCOOEt | 2,6-diethoxy-3-pyridyl |
| O | n-pentyl | OCOOEt | 5,6-diethoxy-3-pyridyl |
| O | n-pentyl | OCOOEt | 2,6-dichloro-3-pyridyl |
| O | n-pentyl | OCOOEt | 5,6-dichloro-3-pyridyl |
| O | n-pentyl | OCOOEt | 5-chloro-6-methoxy-3-pyridyl |
| O | n-pentyl | OCOOEt | 5-chloro-6-ethoxy-3-pyridyl |
| O | n-pentyl | OCOOEt | 2-chloro-6-methyl-3-pyridyl |
| O | n-pentyl | OCOOEt | 6-chloro-2-methyl-3-pyridyl |
| O | n-pentyl | OCOOEt | 2-methyl-4-pyridyl |
| O | n-pentyl | OCOOEt | 2-ethyl-4-pyridyl |
| O | n-pentyl | OCOOEt | 2-methoxy-4-pyridyl |
| O | n-pentyl | OCOOEt | 2-ethoxy-4-pyridyl |
| O | n-pentyl | OCOOEt | 2-chloro-4-pyridyl |
| O | n-pentyl | OCOOEt | 2-dimethylamino-4-pyridyl |
| O | n-pentyl | OCOOEt | 2-(1-pyrrolidinyl)-4-pyridyl |
| O | n-pentyl | OCOOEt | 2-piperidino-4-pyridyl |
| O | n-pentyl | OCOOEt | 2-morpholino-4-pyridyl |
| O | n-pentyl | OCOOEt | 2-methylthio-4-pyridyl |
| O | n-pentyl | OCOOEt | 2-pyrazinyl |
| O | n-pentyl | OCOOEt | 5-methyl-2-pyrazinyl |
| O | n-pentyl | OCOOEt | 5-ethyl-2-pyrazinyl |
| O | n-pentyl | OCOOEt | 5-methoxy-2-pyrazinyl |
| O | n-pentyl | OCOOEt | 5-ethoxy-2-pyrazinyl |
| O | n-pentyl | OCOOEt | 5-chloro-2-pyrazinyl |
| O | n-pentyl | OCOOEt | 6-methyl-2-pyrazinyl |
| O | n-pentyl | OCOOEt | 6-methoxy-2-pyrazinyl |
| O | n-pentyl | OCOOEt | 6-chloro-2-pyrazinyl |
| S | propyl | OH | 2-pyridyl |
| S | propyl | OH | 3-pyridyl |
| S | propyl | OH | 4-pyridyl |
| S | propyl | OH | 2-methyl-3-pyridyl |
| S | propyl | OH | 4-methyl-3-pyridyl |
| S | propyl | OH | 5-methyl-3-pyridyl |
| S | propyl | OH | 6-methyl-3-pyridyl |
| S | propyl | OH | 2-ethyl-3-pyridyl |
| S | propyl | OH | 4-ethyl-3-pyridyl |
| S | propyl | OH | 5-ethyl-3-pyridyl |
| S | propyl | OH | 6-ethyl-3-pyridyl |
| S | propyl | OH | 2-methoxy-3-pyridyl |
| S | propyl | OH | 4-methoxy-3-pyridyl |
| S | propyl | OH | 5-methoxy-3-pyridyl |
| S | propyl | OH | 6-methoxy-3-pyridyl |
| S | propyl | OH | 2-ethoxy-3-pyridyl |
| S | propyl | OH | 4-ethoxy-3-pyridyl |
| S | propyl | OH | 5-ethoxy-3-pyridyl |
| S | propyl | OH | 6-ethoxy-3-pyridyl |
| S | propyl | OH | 2-chloro-3-pyridyl |
| S | propyl | OH | 4-chloro-3-pyridyl |
| S | propyl | OH | 5-chloro-3-pyridyl |
| S | propyl | OH | 6-chloro-3-pyridyl |
| S | propyl | OH | 2-fluoro-3-pyridyl |
| S | propyl | OH | 4-fluoro-3-pyridyl |
| S | propyl | OH | 5-fluoro-3-pyridyl |
| S | propyl | OH | 6-fluoro-3-pyridyl |
| S | propyl | OH | 2-dimethylamino-3-pyridyl |
| S | propyl | OH | 4-dimethylamino-3-pyridyl |
| S | propyl | OH | 5-dimethylamino-3-pyridyl |
| S | propyl | OH | 6-dimethylamino-3-pyridyl |
| S | propyl | OH | 2-(1-pyrrolidinyl)-3-pyridyl |
| S | propyl | OH | 3-(1-pyrrolidinyl)-3-pyridyl |
| S | propyl | OH | 5-(1-pyrrolidinyl)-3-pyridyl |
| S | propyl | OH | 6-(1-pyrrolidinyl)-3-pyridyl |
| S | propyl | OH | 2-piperidino-3-pyridyl |
| S | propyl | OH | 4-piperidino-3-pyridyl |
| S | propyl | OH | 5-piperidino-3-pyridyl |
| S | propyl | OH | 6-piperidino-3-pyridyl |
| S | propyl | OH | 2-morpholino-3-pyridyl |
| S | propyl | OH | 4-morpholino-3-pyridyl |
| S | propyl | OH | 5-morpholino-3-pyridyl |
| S | propyl | OH | 6-morpholino-3-pyridyl |
| S | propyl | OH | 2-hydroxy-3-pyridyl |
| S | propyl | OH | 4-hydroxy-3-pyridyl |
| S | propyl | OH | 5-hydroxy-3-pyridyl |
| S | propyl | OH | 6-hydroxy-3-pyridyl |
| S | propyl | OH | 2-mercapto-3-pyridyl |
| S | propyl | OH | 4-mercapto-3-pyridyl |
| S | propyl | OH | 5-mercapto-3-pyridyl |
| S | propyl | OH | 6-mercapto-3-pyridyl |
| S | propyl | OH | 2-methylthio-3-pyridyl |
| S | propyl | OH | 4-methylthio-3-pyridyl |
| S | propyl | OH | 5-methylthio-3-pyridyl |
| S | propyl | OH | 6-methylthio-3-pyridyl |
| S | propyl | OH | 2,6-dimethyl-3-pyridyl |
| S | propyl | OH | 5,6-dimethyl-3-pyridyl |
| S | propyl | OH | 2,6-diethyl-3-pyridyl |
| S | propyl | OH | 5,6-diethyl-3-pyridyl |
| S | propyl | OH | 2,6-dimethoxy-3-pyridyl |
| S | propyl | OH | 5,6-dimethoxy-3-pyridyl |
| S | propyl | OH | 2,6-diethoxy-3-pyridyl |
| S | propyl | OH | 5,6-diethoxy-3-pyridyl |
| S | propyl | OH | 2,6-dichloro-3-pyridyl |
| S | propyl | OH | 5,6-dichloro-3-pyridyl |
| S | propyl | OH | 5-chloro-6-methoxy-3-pyridyl |
| S | propyl | OH | 5-chloro-6-ethoxy-3-pyridyl |
| S | propyl | OH | 2-chloro-6-methyl-3-pyridyl |
| S | propyl | OH | 6-chloro-2-methyl-3-pyridyl |
| S | propyl | OH | 2-methyl-4-pyridyl |
| S | propyl | OH | 2-ethyl-4-pyridyl |
| S | propyl | OH | 2-methoxy-4-pyridyl |
| S | propyl | OH | 2-ethoxy-4-pyridyl |
| S | propyl | OH | 2-chloro-4-pyridyl |
| S | propyl | OH | 2-dimethylamino-4-pyridyl |
| S | propyl | OH | 2-(1-pyrrolidinyl)-4-pyridyl |
| S | propyl | OH | 2-piperidino-4-pyridyl |
| S | propyl | OH | 2-morpholino-4-pyridyl |
| S | prapyl | OH | 2-methylthio-4-pyridyl |
| S | propyl | OH | 2-pyrazinyl |
| S | propyl | OH | 5-methyl-2-pyrazinyl |
| S | propyl | OH | 5-ethyl-2-pyrazinyl |
| S | propyl | OH | 5-methoxy-2-pyrazinyl |
| S | propyl | OH | 5-ethoxy-2-pyrazinyl |
| S | propyl | OH | 5-chloro-2-pyrazinyl |
| S | propyl | OH | 6-methyl-2-pyrazinyl |
| S | propyl | OH | 6-methoxy-2-pyrazinyl |
| S | propyl | OH | 6-chloro-2-pyrazinyl |
| S | propyl | OCOOMe | 2-pyridyl |
| S | propyl | OCOOMe | 3-pyridyl |
| S | propyl | OCOOMe | 4-pyridyl |
| S | propyl | OCOOMe | 2-methyl-3-pyridyl |
| S | propyl | OCOOMe | 4-methyl-3-pyridyl |
| S | propyl | OCOOMe | 5-methyl-3-pyridyl |
| S | propyl | OCOOMe | 6-methyl-3-pyridyl |
| S | propyl | OCOOMe | 2-ethyl-3-pyridyl |
| S | propyl | OCOOMe | 4-ethyl-3-pyridyl |
| S | propyl | OCOOMe | 5-ethyl-3-pyridyl |
| S | propyl | OCOOMe | 6-ethyl-3-pyridyl |
| S | propyl | OCOOMe | 2-methoxy-3-pyridyl |
| S | propyl | OCOOMe | 4-methoxy-3-pyridyl |
| S | propyl | OCOOMe | 5-methoxy-3-pyridyl |
| S | propyl | OCOOMe | 6-methoxy-3-pyridyl |
| S | propyl | OCOOMe | 2-ethoxy-3-pyridyl |
| S | propyl | OCOOMe | 4-ethoxy-3-pyridyl |
| S | propyl | OCOOMe | 5-ethoxy-3-pyridyl |
| S | propyl | OCOOMe | 6-ethoxy-3-pyridyl |
| S | propyl | OCOOMe | 2-chloro-3-pyridyl |
| S | propyl | OCOOMe | 4-chloro-3-pyridyl |
| S | propyl | OCOOMe | 5-chloro-3-pyridyl |
| S | propyl | OCOOMe | 6-chloro-3-pyridyl |
| S | propyl | OCOOMe | 2-fluoro-3-pyridyl |
| S | propyl | OCOOMe | 4-fluoro-3-pyridyl |
| S | propyl | OCOOMe | 5-fluoro-3-pyridyl |
| S | propyl | OOOOMe | 6-fluoro-3-pyridyl |
| S | propyl | OCOOMe | 2-dimethylamino-3-pyridyl |
| S | propyl | OCOOMe | 4-dimethylamino-3-pyridyl |

TABLE 1-continued

| X | R¹ | R² | Y |
|---|---|---|---|
| S | propyl | OCOOMe | 5-dimethylamino-3-pyridyl |
| S | propyl | OCOOMe | 6-dimethylamino-3-pyridyl |
| S | propyl | OCOOMe | 2-(1-pyrrolidinyl)-3-pyridyl |
| S | propyl | OCOOMe | 3-(1-pyrrolidinyl)-3-pyridyl |
| S | propyl | OCOOMe | 5-(1-pyrrolidinyl)-3-pyridyl |
| S | propyl | OCOOMe | 6-(1-pyrrolidinyl)-3-pyridyl |
| S | propyl | OCOOMe | 2-piperidino-3-pyridyl |
| S | propyl | OCOOMe | 4-piperidino-3-pyridyl |
| S | propyl | OCOOMe | 5-piperidino-3-pyridyl |
| S | propyl | OCOOMe | 6-piperidino-3-pyridyl |
| S | propyl | OCOOMe | 2-morpholino-3-pyridyl |
| S | propyl | OCOOMe | 4-morpholino-3-pyridyl |
| S | propyl | OCOOMe | 5-morpholino-3-pyridyl |
| S | propyl | OCOOMe | 6-morpholino-3-pyridyl |
| S | propyl | OCOOMe | 2-hydroxy-3-pyridyl |
| S | propyl | OCOOMe | 4-hydroxy-3-pyridyl |
| S | propyl | OCOOMe | 5-hydroxy-3-pyridyl |
| S | propyl | OCOOMe | 6-hydroxy-3-pyridyl |
| S | propyl | OCOOMe | 2-mercapto-3-pyridyl |
| S | propyl | OCOOMe | 4-mercapto-3-pyridyl |
| S | propyl | OCOOMe | 5-mercapto-3-pyridyl |
| S | propyl | OCOOMe | 6-mercapto-3-pyridyl |
| S | propyl | OCOOMe | 2-methylthio-3-pyridyl |
| S | propyl | OCOOMe | 4-methylthio-3-pyridyl |
| S | propyl | OCOOMe | 5-methylthio-3-pyridyl |
| S | propyl | OCOOMe | 6-methylthio-3-pyridyl |
| S | propyl | OCOOMe | 2,6-dimethyl-3-pyridyl |
| S | propyl | OCOOMe | 5,6-dimethyl-3-pyridyl |
| S | propyl | OCOOMe | 2,6-diethyl-3-pyridyl |
| S | propyl | OCOOMe | 5,6-diethyl-3-pyridyl |
| S | propyl | OCOOMe | 2,6-dimethoxy-3-pyridyl |
| S | propyl | OCOOMe | 5,6-dimethoxy-3-pyridyl |
| S | propyl | OCOOMe | 2,6-diethoxy-3-pyridyl |
| S | propyl | OCOOMe | 5,6-diethoxy-3-pyridyl |
| S | propyl | OCOOMe | 2,6-dichloro-3-pyridyl |
| S | propyl | OCOOMe | 5,6-dichloro-3-pyridyl |
| S | propyl | OCOOMe | 5-chloro-6-methoxy-3-pyridyl |
| S | propyl | OCOOMe | 5-chloro-6-ethoxy-3-pyridyl |
| S | propyl | OCOOMe | 2-chloro-6-methyl-3-pyridyl |
| S | propyl | OCOOMe | 6-chloro-2-methyl-3-pyridyl |
| S | propyl | OCOOMe | 2-methyl-4-pyridyl |
| S | propyl | OCOOMe | 2-ethyl-4-pyridyl |
| S | propyl | OCOOMe | 2-methoxy-4-pyridyl |
| S | propyl | OCOOMe | 2-ethoxy-4-pyridyl |
| S | propyl | OCOOMe | 2-chloro-4-pyridyl |
| S | propyl | OCOOMe | 2-dimethylamino-4-pyridyl |
| S | propyl | OCOOMe | 2-(1-pyrrolidinyl)-4-pyridyl |
| S | propyl | OCOOMe | 2-piperidino-4-pyridyl |
| S | propyl | OCOOMe | 2-morpholino-4-pyridyl |
| S | propyl | OCOOMe | 2-methylthio-4-pyridyl |
| S | propyl | OCOOMe | 2-pyrazinyl |
| S | propyl | OCOOMe | 5-methyl-2-pyrazinyl |
| S | propyl | OCOOMe | 5-ethyl-2-pyrazinyl |
| S | propyl | OCOOMe | 5-methoxy-2-pyrazinyl |
| S | propyl | OCOOMe | 5-ethoxy-2-pyrazinyl |
| S | propyl | OCOOMe | 5-chloro-2-pyrazinyl |
| S | propyl | OCOOMe | 6-methyl-2-pyrazinyl |
| S | propyl | OCOOMe | 6-methoxy-2-pyrazinyl |
| S | propyl | OCOOMe | 6-chloro-2-pyrazinyl |
| S | propyl | OCOOEt | 2-pyridyl |
| S | propyl | OCOOEt | 3-pyridyl |
| S | propyl | OCOOEt | 4-pyridyl |
| S | propyl | OCOOEt | 2-methyl-3-pyridyl |
| S | propyl | OCOOEt | 4-methyl-3-pyridyl |
| S | propyl | OCOOEt | 5-methyl-3-pyridyl |
| S | propyl | OCOOEt | 6-methyl-3-pyridyl |
| S | propyl | OCOOEt | 2-ethyl-3-pyridyl |
| S | propyl | OCOOEt | 4-ethyl-3-pyridyl |
| S | propyl | OCOOEt | 5-ethyl-3-pyridyl |
| S | propyl | OCOOEt | 6-ethyl-3-pyridyl |
| S | propyl | OCOOEt | 2-methoxy-3-pyridyl |
| S | propyl | OCOOEt | 4-methoxy-3-pyridyl |
| S | propyl | OCOOEt | 5-methoxy-3-pyridyl |
| S | propyl | OCOOEt | 6-methoxy-3-pyridyl |
| S | propyl | OCOOEt | 2-ethoxy-3-pyridyl |
| S | propyl | OCOOEt | 4-ethoxy-3-pyridyl |
| S | propyl | OCOOEt | 5-ethoxy-3-pyridyl |
| S | propyl | OCOOEt | 6-ethoxy-3-pyridyl |
| S | propyl | OCOOEt | 2-chloro-3-pyridyl |
| S | propyl | OCOOEt | 4-chloro-3-pyridyl |
| S | propyl | OCOOEt | 5-chloro-3-pyridyl |
| S | propyl | OCOOEt | 6-chloro-3-pyridyl |
| S | propyl | OCOOEt | 2-fluoro-3-pyridyl |
| S | propyl | OCOOEt | 4-fluoro-3-pyridyl |
| S | propyl | OCOOEt | 5-fluoro-3-pyridyl |
| S | propyl | OCOOEt | 6-fluoro-3-pyridyl |
| S | propyl | OCOOEt | 2-dimethylamino-3-pyridyl |
| S | propyl | OCOOEt | 4-dimethylamino-3-pyridyl |
| S | propyl | OCOOEt | 5-dimethylamino-3-pyridyl |
| S | propyl | OCOOEt | 6-dimethylamino-3-pyridyl |
| S | propyl | OCOOEt | 2-(1-pyrrolidinyl)-3-pyridyl |
| S | propyl | OCOOEt | 3-(1-pyrrolidinyl)-3-pyridyl |
| S | propyl | OCOOEt | 5-(1-pyrrolidinyl)-3-pyridyl |
| S | propyl | OCOOEt | 6-(1-pyrrolidinyl)-3-pyridyl |
| S | propyl | OCOOEt | 2-piperidino-3-pyridyl |
| S | propyl | OCOOEt | 4-piperidino-3-pyridyl |
| S | propyl | OCOOEt | 5-piperidino-3-pyridyl |
| S | propyl | OCOOEt | 6-piperidino-3-pyridyl |
| S | propyl | OCOOEt | 2-morpholino-3-pyridyl |
| S | propyl | OCOOEt | 4-morpholino-3-pyridyl |
| S | propyl | OCOOEt | 5-morpholino-3-pyridyl |
| S | propyl | OCOOEt | 6-morpholino-3-pyridyl |
| S | propyl | OCOOEt | 2-hydroxy-3-pyridyl |
| S | propyl | OCOOEt | 4-hydroxy-3-pyridyl |
| S | propyl | OCOOEt | 5-hydroxy-3-pyridyl |
| S | propyl | OCOOEt | 6-hydroxy-3-pyridyl |
| S | propyl | OCOOEt | 2-mercapto-3-pyridyl |
| S | propyl | OCOOEt | 4-mercapto-3-pyridyl |
| S | propyl | OCOOEt | 5-mercapto-3-pyridyl |
| S | propyl | OCOOEt | 6-mercapto-3-pyridyl |
| S | propyl | OCOOEt | 2-methylthio-3-pyridyl |
| S | propyl | OCOOEt | 4-methylthio-3-pyridyl |
| S | propyl | OCOOEt | 5-methylthio-3-pyridyl |
| S | propyl | OCOOEt | 6-methylthio-3-pyridyl |
| S | propyl | OCOOEt | 2,6-dimethyl-3-pyridyl |
| S | propyl | OCOOEt | 5,6-dimethyl-3-pyridyl |
| S | propyl | OCOOEt | 2,6-diethyl-3-pyridyl |
| S | propyl | OCOOEt | 5,6-diethyl-3-pyridyl |
| S | propyl | OCOOEt | 2,6-dimethoxy-3-pyridyl |
| S | propyl | OCOOEt | 5,6-dimethoxy-3-pyridyl |
| S | propyl | OCOOEt | 2,6-diethoxy-3-pyridyl |
| S | propyl | OCOOEt | 5,6-diethoxy-3-pyridyl |
| S | propyl | OCOOEt | 2,6-dichloro-3-pyridyl |
| S | propyl | OCOOEt | 5,6-dichloro-3-pyridyl |
| S | propyl | OCOOEt | 5-chloro-6-methoxy-3-pyridyl |
| S | propyl | OCOOEt | 5-chloro-6-ethoxy-3-pyridyl |
| S | propyl | OCOOEt | 2-chloro-6-methyl-3-pyridyl |
| S | propyl | OCOOEt | 6-chloro-2-methyl-3-pyridyl |
| S | propyl | OCOOEt | 2-methyl-4-pyridyl |
| S | propyl | OCOOEt | 2-ethyl-4-pyridyl |
| S | propyl | OCOOEt | 2-methoxy-4-pyridyl |
| S | propyl | OCOOEt | 2-ethoxy-4-pyridyl |
| S | propyl | OCOOEt | 2-chloro-4-pyridyl |
| S | propyl | OCOOEt | 2-dimethylamino-4-pyridyl |
| S | propyl | OCOOEt | 2-(1-pyrrolidinyl)-4-pyridyl |
| S | propyl | OCOOEt | 2-piperidino-4-pyridyl |
| S | propyl | OCOOEt | 2-morpholino-4-pyridyl |
| S | propyl | OCOOEt | 2-methylthio-4-pyridyl |
| S | propyl | OCOOEt | 2-pyrazinyl |
| S | propyl | OCOOEt | 5-methyl-2-pyrazinyl |
| S | propyl | OCOOEt | 5-ethyl-2-pyrazinyl |
| S | propyl | OCOOEt | 5-methoxy-2-pyrazinyl |
| S | propyl | OCOOEt | 5-ethoxy-2-pyrazinyl |
| S | propyl | OCOOEt | 5-chloro-2-pyrazinyl |
| S | propyl | OCOOEt | 6-methyl-2-pyrazinyl |
| S | propyl | OCOOEt | 6-methoxy-2-pyrazinyl |
| S | propyl | OCOOEt | 6-chloro-2-pyrazinyl |
| S | n-butyl | OH | 2-pyridyl |
| S | n-butyl | OH | 3-pyridyl |
| S | n-butyl | OH | 4-pyridyl |
| S | n-butyl | OH | 2-methyl-3-pyridyl |
| S | n-butyl | OH | 4-methyl-3-pyridyl |
| S | n-butyl | OH | 5-methyl-3-pyridyl |
| S | n-butyl | OH | 6-methyl-3-pyridyl |

TABLE 1-continued

| X | R¹ | R² | Y |
|---|---|---|---|
| S | n-butyl | OH | 2-ethyl-3-pyridyl |
| S | n-butyl | OH | 4-ethyl-3-pyridyl |
| S | n-butyl | OH | 5-ethyl-3-pyridyl |
| S | n-butyl | OH | 6-ethyl-3-pyridyl |
| S | n-butyl | OH | 2-methoxy-3-pyridyl |
| S | n-butyl | OH | 4-methoxy-3-pyridyl |
| S | n-butyl | OH | 5-methoxy-3-pyridyl |
| S | n-butyl | OH | 6-methoxy-3-pyridyl |
| S | n-butyl | OH | 2-ethoxy-3-pyridyl |
| S | n-butyl | OH | 4-ethoxy-3-pyridyl |
| S | n-butyl | OH | 5-ethoxy-3-pyridyl |
| S | n-butyl | OH | 6-ethoxy-3-pyridyl |
| S | n-butyl | OH | 2-chloro-3-pyridyl |
| S | n-butyl | OH | 4-chloro-3-pyridyl |
| S | n-butyl | OH | 5-chloro-3-pyridyl |
| S | n-butyl | OH | 6-chloro-3-pyridyl |
| S | n-butyl | OH | 2-fluoro-3-pyridyl |
| S | n-butyl | OH | 4-fluoro-3-pyridyl |
| S | n-butyl | OH | 5-fluoro-3-pyridyl |
| S | n-butyl | OH | 6-fluoro-3-pyridyl |
| S | n-butyl | OH | 2-dimethylamino-3-pyridyl |
| S | n-butyl | OH | 4-dimethylamino-3-pyridyl |
| S | n-butyl | OH | 5-dimethylamino-3-pyridyl |
| S | n-butyl | OH | 6-dimethylamino-3-pyridyl |
| S | n-butyl | OH | 2-(1-pyrrolidinyl)-3-pyridyl |
| S | n-butyl | OH | 3-(1-pyrrolidinyl)-3-pyridyl |
| S | n-butyl | OH | 5-(1-pyrrolidinyl)-3-pyridyl |
| S | n-butyl | OH | 6-(1-pyrrolidinyl)-3-pyridyl |
| S | n-butyl | OH | 2-piperidino-3-pyridyl |
| S | n-butyl | OH | 4-piperidino-3-pyridyl |
| S | n-butyl | OH | 5-piperidino-3-pyridyl |
| S | n-butyl | OH | 6-piperidino-3-pyridyl |
| S | n-butyl | OH | 2-morpholino-3-pyridyl |
| S | n-butyl | OH | 4-morpholino-3-pyridyl |
| S | n-butyl | OH | 5-morpholino-3-pyridyl |
| S | n-butyl | OH | 6-morpholino-3-pyridyl |
| S | n-butyl | OH | 2-hydroxy-3-pyridyl |
| S | n-butyl | OH | 4-hydroxy-3-pyridyl |
| S | n-butyl | OH | 5-hydroxy-3-pyridyl |
| S | n-butyl | OH | 6-hydroxy-3-pyridyl |
| S | n-butyl | OH | 2-mercapto-3-pyridyl |
| S | n-butyl | OH | 4-mercapto-3-pyridyl |
| S | n-butyl | OH | 5-mercapto-3-pyridyl |
| S | n-butyl | OH | 6-mercapto-3-pyridyl |
| S | n-butyl | OH | 2-methylthio-3-pyridyl |
| S | n-butyl | OH | 4-methylthio-3-pyridyl |
| S | n-butyl | OH | 5-methylthio-3-pyridyl |
| S | n-butyl | OH | 6-methylthio-3-pyridyl |
| S | n-butyl | OH | 2,6-dimethyl-3-pyridyl |
| S | n-butyl | OH | 5,6-dimethyl-3-pyridyl |
| S | n-butyl | OH | 2,6-diethyl-3-pyridyl |
| S | n-butyl | OH | 5,6-diethyl-3-pyridyl |
| S | n-butyl | OH | 2,6-dimethoxy-3-pyridyl |
| S | n-butyl | OH | 5,6-dimethoxy-3-pyridyl |
| S | n-butyl | OH | 2,6-diethoxy-3-pyridyl |
| S | n-butyl | OH | 5,6-diethoxy-3-pyridyl |
| S | n-butyl | OH | 2,6-dichloro-3-pyridyl |
| S | n-butyl | OH | 5,6-dichloro-3-pyridyl |
| S | n-butyl | OH | 5-chloro-6-methoxy-3-pyridyl |
| S | n-butyl | OH | 5-chloro-6-ethoxy-3-pyridyl |
| S | n-butyl | OH | 2-chloro-6-methyl-3-pyridyl |
| S | n-butyl | OH | 6-chloro-2-methyl-3-pyridyl |
| S | n-butyl | OH | 2-methyl-4-pyridyl |
| S | n-butyl | OH | 2-ethyl-4-pyridyl |
| S | n-butyl | OH | 2-methoxy-4-pyridyl |
| S | n-butyl | OH | 2-ethoxy-4-pyridyl |
| S | n-butyl | OH | 2-chloro-4-pyridyl |
| S | n-butyl | OH | 2-dimethylamino-4-pyridyl |
| S | n-butyl | OH | 2-(1-pyrrolidinyl)-4-pyridyl |
| S | n-butyl | OH | 2-piperidino-4-pyridyl |
| S | n-butyl | OH | 2-morpholino-4-pyridyl |
| S | n-butyl | OH | 2-methylthio-4-pyridyl |
| S | n-butyl | OH | 2-pyrazinyl |
| S | n-butyl | OH | 5-methyl-2-pyrazinyl |
| S | n-butyl | OH | 5-ethyl-2-pyrazinyl |
| S | n-butyl | OH | 5-methoxy-2-pyrazinyl |
| S | n-butyl | OH | 5-ethoxy-2-pyrazinyl |
| S | n-butyl | OH | 5-chloro-2-pyrazinyl |
| S | n-butyl | OH | 6-methyl-2-pyrazinyl |
| S | n-butyl | OH | 6-methoxy-2-pyrazinyl |
| S | n-butyl | OH | 6-chloro-2-pyrazinyl |
| S | n-butyl | OCOOMe | 2-pyridyl |
| S | n-butyl | OCOOMe | 3-pyridyl |
| S | n-butyl | OCOOMe | 4-pyridyl |
| S | n-butyl | OCOOMe | 2-methyl-3-pyridyl |
| S | n-butyl | OCOOMe | 4-methyl-3-pyridyl |
| S | n-butyl | OCOOMe | 5-methyl-3-pyridyl |
| S | n-butyl | OCOOMe | 6-methyl-3-pyridyl |
| S | n-butyl | OCOOMe | 2-ethyl-3-pyridyl |
| S | n-butyl | OCOOMe | 4-ethyl-3-pyridyl |
| S | n-butyl | OCOOMe | 5-ethyl-3-pyridyl |
| S | n-butyl | OCOOMe | 6-ethyl-3-pyridyl |
| S | n-butyl | OCOOMe | 2-methoxy-8-pyridyl |
| S | n-butyl | OCOOMe | 4-methoxy-3-pyridyl |
| S | n-butyl | OCOOMe | 5-methoxy-3-pyridyl |
| S | n-butyl | OCOOMe | 6-methoxy-3-pyridyl |
| S | n-butyl | OCOOMe | 2-ethoxy-3-pyridyl |
| S | n-butyl | OCOOMe | 4-ethoxy-3-pyridyl |
| S | n-butyl | OCOOMe | 5-ethoxy-3-pyridyl |
| S | n-butyl | OCOOMe | 6-ethoxy-3-pyridyl |
| S | n-butyl | OCOOMe | 2-chloro-3-pyridyl |
| S | n-butyl | OCOOMe | 4-chloro-3-pyridyl |
| S | n-butyl | OCOOMe | 5-chloro-3-pyridyl |
| S | n-butyl | OCOOMe | 6-chloro-3-pyridyl |
| S | n-butyl | OCOOMe | 2-fluoro-3-pyridyl |
| S | n-butyl | OCOOMe | 4-fluoro-3-pyridyl |
| S | n-butyl | OCOOMe | 5-fluoro-3-pyridyl |
| S | n-butyl | OCOOMe | 6-fluoro-3-pyridyl |
| S | n-butyl | OCOOMe | 2-dimethylamino-3-pyridyl |
| S | n-butyl | OCOOMe | 4-dimethylamino-3-pyridyl |
| S | n-butyl | OCOOMe | 5-dimethylamino-3-pyridyl |
| S | n-butyl | OCOOMe | 6-dimethylamino-3-pyridyl |
| S | n-butyl | OCOOMe | 2-(1-pyrrolidinyl)-3-pyridyl |
| S | n-butyl | OCOOMe | 3-(1-pyrrolidinyl)-3-pyridyl |
| S | n-butyl | OCOOMe | 5-(1-pyrrolidinyl)-3-pyridyl |
| S | n-butyl | OCOOMe | 6-(1-pyrrolidinyl)-3-pyridyl |
| S | n-butyl | OCOOMe | 2-piperidino-3-pyridyl |
| S | n-butyl | OCOOMe | 4-piperidino-3-pyridyl |
| S | n-butyl | OCOOMe | 5-piperidino-3-pyridyl |
| S | n-butyl | OCOOMe | 6-piperidino-3-pyridyl |
| S | n-butyl | OCOOMe | 2-morpholino-3-pyridyl |
| S | n-butyl | OCOOMe | 4-morpholino-3-pyridyl |
| S | n-butyl | OCOOMe | 5-morpholino-3-pyridyl |
| S | n-butyl | OCOOMe | 6-morpholino-3-pyridyl |
| S | n-butyl | OCOOMe | 2-hydroxy-3-pyridyl |
| S | n-butyl | OCOOMe | 4-hydroxy-3-pyridyl |
| S | n-butyl | OCOOMe | 5-hydroxy-3-pyridyl |
| S | n-butyl | OCOOMe | 6-hydroxy-3-pyridyl |
| S | n-butyl | OCOOMe | 2-mercapto-3-pyridyl |
| S | n-butyl | OCOOMe | 4-mercapto-3-pyridyl |
| S | n-butyl | OCOOMe | 5-mercapto-3-pyridyl |
| S | n-butyl | OCOOMe | 6-mercapto-3-pyridyl |
| S | n-butyl | OCOOMe | 2-methylthio-3-pyridyl |
| S | n-butyl | OCOOMe | 4-methylthio-3-pyridyl |
| S | n-butyl | OCOOMe | 5-methylthio-3-pyridyl |
| S | n-butyl | OCOOMe | 6-methylthio-3-pyridyl |
| S | n-butyl | OCOOMe | 2,6-dimethyl-3-pyridyl |
| S | n-butyl | OCOOMe | 5,6-dimethyl-3-pyridyl |
| S | n-butyl | OCOOMe | 2,6-diethyl-3-pyridyl |
| S | n-butyl | OCOOMe | 5,6-diethyl-3-pyridyl |
| S | n-butyl | OCOOMe | 2,6-dimethoxy-3-pyridyl |
| S | n-butyl | OCOOMe | 5,6-dimethoxy-3-pyridyl |
| S | n-butyl | OCOOMe | 2,6-diethoxy-3-pyridyl |
| S | n-butyl | OCOOMe | 5,6-diethoxy-3-pyridyl |
| S | n-butyl | OCOOMe | 2,6-dichloro-3-pyridyl |
| S | n-butyl | OCOOMe | 5,6-dichloro-3-pyridyl |
| S | n-butyl | OCOOMe | 5-chloro-6-methoxy-3-pyridyl |
| S | n-butyl | OCOOMe | 5-chloro-6-ethoxy-3-pyridyl |
| S | n-butyl | OCOOMe | 2-chloro-6-methyl-3-pyridyl |
| S | n-butyl | OCOOMe | 6-chloro-2-methyl-3-pyridyl |
| S | n-butyl | OCOOMe | 2-methyl-4-pyridyl |
| S | n-butyl | OCOOMe | 2-ethyl-4-pyridyl |
| S | n-butyl | OCOOMe | 2-methoxy-4-pyridyl |
| S | n-butyl | OCOOMe | 2-ethoxy-4-pyridyl |

TABLE 1-continued

| X | R¹ | R² | Y |
|---|---|---|---|
| S | n-butyl | OCOOMe | 2-chloro-4-pyridyl |
| S | n-butyl | OCOOMe | 2-dimethylamino-4-pyridyl |
| S | n-butyl | OCOOMe | 2-(1-pyrrolidinyl)-4-pyridyl |
| S | n-butyl | OCOOMe | 2-piperidino-4-pyridyl |
| S | n-butyl | OCOOMe | 2-morpholino-4-pyridyl |
| S | n-butyl | OCOOMe | 2-methylthio-4-pyridyl |
| S | n-butyl | OCOOMe | 2-pyrazinyl |
| S | n-butyl | OCOOMe | 5-methyl-2-pyrazinyl |
| S | n-butyl | OCOOMe | 5-ethyl-2-pyrazinyl |
| S | n-butyl | OCOOMe | 5-methoxy-2-pyrazinyl |
| S | n-butyl | OCOOMe | 5-ethoxy-2-pyrazinyl |
| S | n-butyl | OCOOMe | 5-chloro-2-pyrazinyl |
| S | n-butyl | OCOOMe | 6-methyl-2-pyrazinyl |
| S | n-butyl | OCOOMe | 6-methoxy-2-pyrazinyl |
| S | n-butyl | OCOOMe | 6-chloro-2-pyrazinyl |
| S | n-butyl | OCOOEt | 2-pyridyl |
| S | n-butyl | OCOOEt | 3-pyridyl |
| S | n-butyl | OCOOEt | 4-pyridyl |
| S | n-butyl | OCOOEt | 2-methyl-3-pyridyl |
| S | n-butyl | OCOOEt | 4-methyl-3-pyridyl |
| S | n-butyl | OCOOEt | 5-methyl-3-pyridyl |
| S | n-butyl | OCOOEt | 6-methyl-3-pyridyl |
| S | n-butyl | OCOOEt | 2-ethyl-3-pyridyl |
| S | n-butyl | OCOOEt | 4-ethyl-3-pyridyl |
| S | n-butyl | OCOOEt | 5-ethyl-3-pyridyl |
| S | n-butyl | OCOOEt | 6-ethyl-3-pyridyl |
| S | n-butyl | OCOOEt | 2-methoxy-3-pyridyl |
| S | n-butyl | OCOOEt | 4-methoxy-3-pyridyl |
| S | n-butyl | OCOOEt | 5-methoxy-3-pyridyl |
| S | n-butyl | OCOCEt | 6-methoxy-3-pyridyl |
| S | n-butyl | OCOOEt | 2-ethoxy-3-pyridyl |
| S | n-butyl | OCOOEt | 4-ethoxy-3-pyridyl |
| S | n-butyl | OCOOEt | 5-ethoxy-3-pyridyl |
| S | n-butyl | OCOOEt | 6-ethoxy-3-pyridyl |
| S | n-butyl | OCOOEt | 2-chloro-3-pyridyl |
| S | n-butyl | OCOOEt | 4-chloro-3-pyridyl |
| S | n-butyl | OCOOEt | 5-chloro-3-pyridyl |
| S | n-butyl | OCOOEt | 6-chloro-3-pyridyl |
| S | n-butyl | OCOOEt | 2-fluoro-3-pyridyl |
| S | n-butyl | OCOOEt | 4-fluoro-3-pyridyl |
| S | n-butyl | OCOOEt | 5-fluoro-3-pyridyl |
| S | n-butyl | OCOOEt | 6-fluoro-3-pyridyl |
| S | n-butyl | OCOOEt | 2-dimethylamino-3-pyridyl |
| S | n-butyl | OCOOEt | 4-dimethylamino-3-pyridyl |
| S | n-butyl | OCOOEt | 5-dimethylamino-3-pyridyl |
| S | n-butyl | OCOOEt | 6-dimethylamino-3-pyridyl |
| S | n-butyl | OCOOEt | 2-(1-pyrrolidinyl)-3-pyridyl |
| S | n-butyl | OCCOEt | 3-(1-pyrrolidinyl)-3-pyridyl |
| S | n-butyl | OCOOEt | 5-(1-pyrrolidinyl)-3-pyridyl |
| S | n-butyl | OCOOEt | 6-(1-pyrrolidinyl)-3-pyridyl |
| S | n-butyl | OCOOEt | 2-piperidino-3-pyridyl |
| S | n-butyl | OCOOEt | 4-piperidino-3-pyridyl |
| S | n-butyl | OCOOEt | 5-piperidino-3-pyridyl |
| S | n-butyl | OCOOEt | 6-piperidinio-3-pyridyl |
| S | n-butyl | OCOOEt | 2-morpholino-3-pyridyl |
| S | n-butyl | OCOOEt | 4-morpholino-3-pyridyl |
| S | n-butyl | OCOOEt | 5-morpholino-3-pyridyl |
| S | n-butyl | OCOOEt | 6-morpholino-3-pyridyl |
| S | n-butyl | OCOOEt | 2-hydroxy-3-pyridyl |
| S | n-butyl | OCOOEt | 4-hydroxy-3-pyridyl |
| S | n-butyl | OCOOEt | 5-hydroxy-3-pyridyl |
| S | n-butyl | OCOOEt | 6-hydroxy-3-pyridyl |
| S | n-butyl | OCOOEt | 2-mercapto-3-pyridyl |
| S | n-butyl | OCOOEt | 4-mercapto-3-pyridyl |
| S | n-butyl | OCOOEt | 5-mercapto-3-pyridyl |
| S | n-butyl | OCOOEt | 6-mercapto-3-pyridyl |
| S | n-butyl | OCOOEt | 2-methylthio-3-pyridyl |
| S | n-butyl | OCOOEt | 4-methylthio-3-pyridyl |
| S | n-butyl | OCOOEt | 5-methylthio-3-pyridyl |
| S | n-butyl | OCOOEt | 6-methylthio-3-pyridyl |
| S | n-butyl | OCOOEt | 2,6-dimethyl-3-pyridyl |
| S | n-butyl | OCOOEt | 5,6-dimethyl-3-pyridyl |
| S | n-butyl | OCOOEt | 2,6-diethyl-3-pyridyl |
| S | n-butyl | OCOOEt | 5,6-diethyl-3-pyridyl |
| S | n-butyl | OCOOEt | 2,6-dimethoxy-3-pyridyl |
| S | n-butyl | OCOOEt | 5,6-dimethoxy-3-pyridyl |
| S | n-butyl | OCOOEt | 2,6-diethoxy-3-pyridyl |
| S | n-butyl | OCOOEt | 5,6-diethoxy-3-pyridyl |
| S | n-butyl | OCOOEt | 2,6-dichloro-3-pyridyl |
| S | n-butyl | OCOOEt | 5,6-dichloro-3-pyridyl |
| S | n-butyl | OCOOEt | 5-chloro-6-methoxy-3-pyridyl |
| S | n-butyl | OCOOEt | 5-chloro-6-ethoxy-3-pyridyl |
| S | n-butyl | OCOOEt | 2-chloro-6-methyl-3-pyridyl |
| S | n-butyl | OCOOEt | 6-chloro-2-methyl-3-pyridyl |
| S | n-butyl | OCOOEt | 2-methyl-4-pyridyl |
| S | n-butyl | OCOOEt | 2-ethyl-4-pyridyl |
| S | n-butyl | OCOOEt | 2-methoxy-4-pyridyl |
| S | n-butyl | OCOOEt | 2-ethoxy-4-pyridyl |
| S | n-butyl | OCOOEt | 2-chloro-4-pyridyl |
| S | n-butyl | OCOOEt | 2-dimethylamino-4-pyridyl |
| S | n-butyl | OCOOEt | 2-(1-pyrrolidinyl)-4-pyridyl |
| S | n-butyl | OCOOEt | 2-piperidino-4-pyridyl |
| S | n-butyl | OCOOEt | 2-morpholino-4-pyridyl |
| S | n-butyl | OCOOEt | 2-methylthio-4-pyridyl |
| S | n-butyl | OCOOEt | 2-pyrazinyl |
| S | n-butyl | OCOOEt | 5-methyl-2-pyrazinyl |
| S | n-butyl | OCOOEt | 5-ethyl-2-pyrazinyl |
| S | n-butyl | OCOOEt | 5-methoxy-2-pyrazinyl |
| S | n-butyl | OCOOEt | 5-ethoxy-2-pyrazinyl |
| S | n-butyl | OCOOEt | 5-chloro-2-pyrazinyl |
| S | n-butyl | OCOOEt | 6-methyl-2-pyrazinyl |
| S | n-butyl | OCOOEt | 6-methoxy-2-pyrazinyl |
| S | n-butyl | OCOOEt | 6-chloro-2-pyrazinyl |
| S | n-pentyl | OH | 2-pyridyl |
| S | n-pentyl | OH | 3-pyridyl |
| S | n-pentyl | OH | 4-pyridyl |
| S | n-pentyl | OH | 2-methyl-3-pyridyl |
| S | n-pentyl | OH | 4-methyl-3-pyridyl |
| S | n-pentyl | OH | 5-methyl-3-pyridyl |
| S | n-pentyl | OH | 6-methyl-3-pyridyl |
| S | n-pentyl | OH | 2-ethyl-3-pyridyl |
| S | n-pentyl | OH | 4-ethyl-3-pyridyl |
| S | n-pentyl | OH | 5-ethyl-3-pyridyl |
| S | n-pentyl | OH | 6-ethyl-3-pyridyl |
| S | n-pentyl | OH | 2-methoxy-3-pyridyl |
| S | n-pentyl | OH | 4-methoxy-3-pyridyl |
| S | n-pentyl | OH | 5-methoxy-3-pyridyl |
| S | n-pentyl | OH | 6-methoxy-3-pyridyl |
| S | n-pentyl | OH | 2-ethoxy-3-pyridyl |
| S | n-pentyl | OH | 4-ethoxy-3-pyridyl |
| S | n-pentyl | OH | 5-ethoxy-3-pyridyl |
| S | n-pentyl | OH | 6-ethoxy-3-pyridyl |
| S | n-pentyl | OH | 2-chloro-3-pyridyl |
| S | n-pentyl | OH | 4-chloro-3-pyridyl |
| S | n-pentyl | OH | 5-chloro-3-pyridyl |
| S | n-pentyl | OH | 6-chloro-3-pyridyl |
| S | n-pentyl | OH | 2-fluoro-3-pyridyl |
| S | n-pentyl | OH | 4-fluoro-3-pyridyl |
| S | n-pentyl | OH | 5-fluoro-3-pyridyl |
| S | n-pentyl | OH | 6-fluoro-3-pyridyl |
| S | n-pentyl | OH | 2-dimethylamino-3-pyridyl |
| S | n-pentyl | OH | 4-dimethylamino-3-pyridyl |
| S | n-pentyl | OH | 5-dimethylamino-3-pyridyl |
| S | n-pentyl | OH | 6-dimethylamino-3-pyridyl |
| S | n-pentyl | OH | 2-(1-pyrrolidinyl)-3-pyridyl |
| S | n-pentyl | OH | 3-(1-pyrrolidinyl)-3-pyridyl |
| S | n-pentyl | OH | 5-(1-pyrrolidinyl)-3-pyridyl |
| S | n-pentyl | OH | 6-(1-pyrrolidinyl)-3-pyridyl |
| S | n-pentyl | OH | 2-piperidino-3-pyridyl |
| S | n-pentyl | OH | 4-piperidino-3-pyridyl |
| S | n-pentyl | OH | 5-piperidino-3-pyridyl |
| S | n-pentyl | OH | 6-piperidino-3-pyridyl |
| S | n-pentyl | OH | 2-morpholino-3-pyridyl |
| S | n-pentyl | OH | 4-morpholino-3-pyridyl |
| S | n-pentyl | OH | 5-morpholino-3-pyridyl |
| S | n-pentyl | OH | 6-morpholino-3-pyridyl |
| S | n-pentyl | OH | 2-hydroxy-3-pyridyl |
| S | n-pentyl | OH | 4-hydroxy-3-pyridyl |
| S | n-pentyl | OH | 5-hydroxy-3-pyridyl |
| S | n-pentyl | OH | 6-hydroxy-3-pyridyl |
| S | n-pentyl | OH | 2-mercapto-3-pyridyl |
| S | n-pentyl | OH | 4-mercapto-3-pyridyl |
| S | n-pentyl | OH | 5-mercapto-3-pyridyl |
| S | n-pentyl | OH | 6-mercapto-3-pyridyl |

TABLE 1-continued

| X | R¹ | R² | Y |
|---|----|----|---|
| S | n-pentyl | OH | 2-methylthio-3-pyridyl |
| S | n-pentyl | OH | 4-methylthio-3-pyridyl |
| S | n-pentyl | OH | 5-methylthio-3-pyridyl |
| S | n-pentyl | OH | 6-methylthio-3-pyridyl |
| S | n-pentyl | OH | 2,6-dimethyl-3-pyridyl |
| S | n-pentyl | OH | 5,6-dimethyl-3-pyridyl |
| S | n-pentyl | OH | 2,6-diethyl-3-pyridyl |
| S | n-pentyl | OH | 5,6-diethyl-3-pyridyl |
| S | n-pentyl | OH | 2,6-dimethoxy-3-pyridyl |
| S | n-pentyl | OH | 5,6-dimethoxy-3-pyridyl |
| S | n-pentyl | OH | 2,6-diethoxy-3-pyridyl |
| S | n-pentyl | OH | 5,6-diethoxy-3-pyridyl |
| S | n-pentyl | OH | 2,6-dichloro-3-pyridyl |
| S | n-pentyl | OH | 5,6-dichloro-3-pyridyl |
| S | n-pentyl | OH | 5-chloro-6-methoxy-3-pyridyl |
| S | n-pentyl | OH | 5-chloro-6-ethoxy-3-pyridyl |
| S | n-pentyl | OH | 2-chloro-6-methyl-3-pyridyl |
| S | n-pentyl | OH | 6-chloro-2-methyl-3-pyridyl |
| S | n-pentyl | OH | 2-methyl-4-pyridyl |
| S | n-pentyl | OH | 2-ethyl-4-pyridyl |
| S | n-pentyl | OH | 2-methoxy-4-pyridyl |
| S | n-pentyl | OH | 2-ethoxy-4-pyridyl |
| S | n-pentyl | OH | 2-chloro-4-pyridyl |
| S | n-pentyl | OH | 2-dimethylamino-4-pyridyl |
| S | n-pentyl | OH | 2-(1-pyrrolidinyl)-4-pyridyl |
| S | n-pentyl | OH | 2-piperidino-4-pyridyl |
| S | n-pentyl | OH | 2-morpholino-4-pyridyl |
| S | n-pentyl | OH | 2-methylthio-4-pyridyl |
| S | n-pentyl | OH | 2-pyrazinyl |
| S | n-pentyl | OH | 5-methyl-2-pyrazinyl |
| S | n-pentyl | OH | 5-ethyl-2-pyrazinyl |
| S | n-pentyl | OH | 5-methoxy-2-pyrazinyl |
| S | n-pentyl | OH | 5-ethoxy-2-pyrazinyl |
| S | n-pentyl | OH | 5-chloro-2-pyrazinyl |
| S | n-pentyl | OH | 6-methyl-2-pyrazinyl |
| S | n-pentyl | OH | 6-methoxy-2-pyrazinyl |
| S | n-pentyl | OH | 6-chloro-2-pyrazinyl |
| S | n-pentyl | OCOOMe | 2-pyridyl |
| S | n-pentyl | OCOOMe | 3-pyridyl |
| S | n-pentyl | OCOOMe | 4-pyridyl |
| S | n-pentyl | OCOOMe | 2-methyl-3-pyridyl |
| S | n-pentyl | OCOOMe | 4-methyl-3-pyridyl |
| S | n-pentyl | OCOOMe | 5-methyl-3-pyridyl |
| S | n-pentyl | OCOOMe | 6-methyl-3-pyridyl |
| S | n-pentyl | OCOOMe | 2-ethyl-3-pyridyl |
| S | n-pentyl | OCOOMe | 4-ethyl-3-pyridyl |
| S | n-pentyl | OCOOMe | 5-ethyl-3-pyridyl |
| S | n-pentyl | OCOOMe | 6-ethyl-3-pyridyl |
| S | n-pentyl | OCOOMe | 2-methoxy-3-pyridyl |
| S | n-pentyl | OCOOMe | 4-methoxy-3-pyridyl |
| S | n-pentyl | OCOOMe | 5-methoxy-3-pyridyl |
| S | n-pentyl | OCOOMe | 6-methoxy-3-pyridyl |
| S | n-pentyl | OCOOMe | 2-ethoxy-3-pyridyl |
| S | n-pentyl | OCOOMe | 4-ethoxy-3-pyridyl |
| S | n-pentyl | OCOOMe | 5-ethoxy-3-pyridyl |
| S | n-pentyl | OCOOMe | 6-ethoxy-3-pyridyl |
| S | n-pentyl | OCOOMe | 2-chloro-3-pyridyl |
| S | n-pentyl | OCOOMe | 4-chloro-3-pyridyl |
| S | n-pentyl | OCOOMe | 5-chloro-3-pyridyl |
| S | n-pentyl | OCOOMe | 6-chloro-3-pyridyl |
| S | n-pentyl | OCOOMe | 2-fluoro-3-pyridyl |
| S | n-pentyl | OCOOMe | 4-fluoro-3-pyridyl |
| S | n-pentyl | OCOOMe | 5-fluoro-3-pyridyl |
| S | n-pentyl | OCOOMe | 6-fluoro-3-pyridyl |
| S | n-pentyl | OCOOMe | 2-dimethylamino-3-pyridyl |
| S | n-pentyl | OCOOMe | 4-dimethylamino-3-pyridyl |
| S | n-pentyl | OCOOMe | 5-dimethylamino-3-pyridyl |
| S | n-pentyl | OCOOMe | 6-dimethylamino-3-pyridyl |
| S | n-pentyl | OCOOMe | 2-(1-pyrrolidinyl)-3-pyridyl |
| S | n-pentyl | OCOOMe | 3-(1-pyrrolidinyl)-3-pyridyl |
| S | n-pentyl | OCOOMe | 5-(1-pyrrolidinyl)-3-pyridyl |
| S | n-pentyl | OCOOMe | 6-(1-pyrrolidinyl)-3-pyridyl |
| S | n-pentyl | OCOOMe | 2-piperidino-3-pyridyl |
| S | n-pentyl | OCOOMe | 4-piperidino-3-pyridyl |
| S | n-pentyl | OCOOMe | 5-piperidino-3-pyridyl |
| S | n-pentyl | OCOOMe | 6-piperidino-3-pyridyl |
| S | n-pentyl | OCOOMe | 2-morpholino-3-pyridyl |
| S | n-pentyl | OCOOMe | 4-morpholino-3-pyridyl |
| S | n-pentyl | OCOOMe | 5-morpholino-3-pyridyl |
| S | n-pentyl | OCOOMe | 6-morpholino-3-pyridyl |
| S | n-pentyl | OCOOMe | 2-hydroxy-3-pyridyl |
| S | n-pentyl | OCOOMe | 4-hydroxy-3-pyridyl |
| S | n-pentyl | OCOOMe | 5-hydroxy-3-pyridyl |
| S | n-pentyl | OCOOMe | 6-hydroxy-3-pyridyl |
| S | n-pentyl | OCOOMe | 2-mercapto-3-pyridyl |
| S | n-pentyl | OCOOMe | 4-mercapto-3-pyridyl |
| S | n-pentyl | OCOOMe | 5-mercapto-3-pyridyl |
| S | n-pentyl | OCOOMe | 6-mercapto-3-pyridyl |
| S | n-pentyl | OCOOMe | 2-methylthio-3-pyridyl |
| S | n-pentyl | OCOOMe | 4-methylthio-3-pyridyl |
| S | n-pentyl | OCOOMe | 5-methylthio-3-pyridyl |
| S | n-pentyl | OCOOMe | 6-methylthio-3-pyridyl |
| S | n-pentyl | OCOOMe | 2,6-dimethyl-3-pyridyl |
| S | n-pentyl | OCOOMe | 5,6-dimethyl-3-pyridyl |
| S | n-pentyl | OCOOMe | 2,6-diethyl-3-pyridyl |
| S | n-pentyl | OCOOMe | 5,6-diethyl-3-pyridyl |
| S | n-pentyl | OCOOMe | 2,6-dimethoxy-3-pyridyl |
| S | n-pentyl | OCOOMe | 5,6-dimethoxy-3-pyridyl |
| S | n-pentyl | OCOOMe | 2,6-diethoxy-3-pyridyl |
| S | n-pentyl | OCOOMe | 5,6-diethoxy-3-pyridyl |
| S | n-pentyl | OCOOMe | 2,6-dichloro-3-pyridyl |
| S | n-pentyl | OCOOMe | 5,6-dichloro-3-pyridyl |
| S | n-pentyl | OCOOMe | 5-chloro-6-methoxy-3-pyridyl |
| S | n-pentyl | OCOOMe | 5-chloro-6-ethoxy-3-pyridyl |
| S | n-pentyl | OCOOMe | 2-chloro-6-methyl-3-pyridyl |
| S | n-pentyl | OCOOMe | 6-chloro-2-methyl-3-pyridyl |
| S | n-pentyl | OCOOMe | 2-methyl-4-pyridyl |
| S | n-pentyl | OCOOMe | 2-ethyl-4-pyridyl |
| S | n-pentyl | OCOOMe | 2-methoxy-4-pyridyl |
| S | n-pentyl | OCOOMe | 2-ethoxy-4-pyridyl |
| S | n-pentyl | OCOOMe | 2-chloro-4-pyridyl |
| S | n-pentyl | OCOOMe | 2-dimethylamino-4-pyridyl |
| S | n-pentyl | OCOOMe | 2-(1-pyrrolidinyl)-4-pyridyl |
| S | n-pentyl | OCOOMe | 2-piperidino-4-pyridyl |
| S | n-pentyl | OCOOMe | 2-morpholino-4-pyridyl |
| S | n-pentyl | OCOOMe | 2-methylthio-4-pyridyl |
| S | n-pentyl | OCOOMe | 2-pyrazinyl |
| S | n-pentyl | OCOOMe | 5-methyl-2-pyrazinyl |
| S | n-pentyl | OCOOMe | 5-ethyl-2-pyrazinyl |
| S | n-pentyl | OCOOMe | 5-methoxy-2-pyrazinyl |
| S | n-pentyl | OCOOMe | 5-ethoxy-2-pyrazinyl |
| S | n-pentyl | OCOOMe | 5-chloro-2-pyrazinyl |
| S | n-pentyl | OCOOMe | 6-methyl-2-pyrazinyl |
| S | n-pentyl | OCOOMe | 6-methoxy-2-pyrazinyl |
| S | n-pentyl | OCOOMe | 6-chloro-2-pyrazinyl |
| S | n-pentyl | OCOOEt | 2-pyridyl |
| S | n-pentyl | OCOOEt | 3-pyridyl |
| S | n-pentyl | OCOOEt | 4-pyridyl |
| S | n-pentyl | OCOOEt | 2-methyl-3-pyridyl |
| S | n-pentyl | OCOOEt | 4-methyl-3-pyridyl |
| S | n-pentyl | OCOOEt | 5-methyl-3-pyridyl |
| S | n-pentyl | OCOOEt | 6-methyl-3-pyridyl |
| S | n-pentyl | OCOOEt | 2-ethyl-3-pyridyl |
| S | n-pentyl | OCOOEt | 4-ethyl-3-pyridyl |
| S | n-pentyl | OCOOEt | 5-ethyl-3-pyridyl |
| S | n-pentyl | OCOOEt | 6-ethyl-3-pyridyl |
| S | n-pentyl | OCOOEt | 2-methoxy-3-pyridyl |
| S | n-pentyl | OCOOEt | 4-methoxy-3-pyridyl |
| S | n-pentyl | OCOOEt | 5-methoxy-3-pyridyl |
| S | n-pentyl | OCOOEt | 6-methoxy-3-pyridyl |
| S | n-pentyl | OCOOEt | 2-ethoxy-3-pyridyl |
| S | n-pentyl | OCOOEt | 4-ethoxy-3-pyridyl |
| S | n-pentyl | OCOOEt | 5-ethoxy-3-pyridyl |
| S | n-pentyl | OCOOEt | 6-ethoxy-3-pyridyl |
| S | n-pentyl | OCOOEt | 2-chloro-3-pyridyl |
| S | n-pentyl | OCOOEt | 4-chloro-3-pyridyl |
| S | n-pentyl | OCOOEt | 5-chloro-3-pyridyl |
| S | n-pentyl | OCOOEt | 6-chloro-3-pyridyl |
| S | n-pentyl | OCOOEt | 2-fluoro-3-pyridyl |
| S | n-pentyl | OCOOEt | 4-fluoro-3-pyridyl |
| S | n-pentyl | OCOOEt | 5-fluoro-3-pyridyl |
| S | n-pentyl | OCOOEt | 6-fluoro-3-pyridyl |
| S | n-pentyl | OCOOEt | 2-dimethylamino-3-pyridyl |
| S | n-pentyl | OCOOEt | 4-dimethylamino-3-pyridyl |

TABLE 1-continued

| X | R¹ | R² | Y |
|---|---|---|---|
| S | n-pentyl | OCOOEt | 5-dimethylamino-3-pyridyl |
| S | n-pentyl | OCOOEt | 6-dimethylamino-3-pyridyl |
| S | n-pentyl | OCOOEt | 2-(1-pyrrolidinyl)-3-pyridyl |
| S | n-pentyl | OCOOEt | 3-(1-pyrrolidinyl)-3-pyridyl |
| S | n-pentyl | OCOOEt | 5-(1-pyrrolidinyl)-3-pyridyl |
| S | n-pentyl | OCOOEt | 6-(1-pyrrolidinyl)-3-pyridyl |
| S | n-pentyl | OCOOEt | 2-piperidino-3-pyridyl |
| S | n-pentyl | OCOOEt | 4-piperidino-3-pyridyl |
| S | n-pentyl | OCOOEt | 5-piperidino-3-pyridyl |
| S | n-pentyl | OCOOEt | 6-piperidino-3-pyridyl |
| S | n-pentyl | OCOOEt | 2-morpholino-3-pyridyl |
| S | n-pentyl | OCOOEt | 4-morpholino-3-pyridyl |
| S | n-pentyl | OCOOEt | 5-morpholino-3-pyridyl |
| S | n-pentyl | OCOOEt | 6-morpholino-3-pyridyl |
| S | n-pentyl | OCOOEt | 2-hydroxy-3-pyridyl |
| S | n-pentyl | OCOOEt | 4-hydroxy-3-pyridyl |
| S | n-pentyl | OCOOEt | 5-hydroxy-3-pyridyl |
| S | n-pentyl | OCOOEt | 6-hydroxy-3-pyridyl |
| S | n-pentyl | OCOOEt | 2-mercapto-3-pyridyl |
| S | n-pentyl | OCOOEt | 4-mercapto-3-pyridyl |
| S | n-pentyl | OCOOEt | 5-mercapto-3-pyridyl |
| S | n-pentyl | OCOOEt | 6-mercapto-3-pyridyl |
| S | n-pentyl | OCOOEt | 2-methylthio-3-pyridyl |
| S | n-pentyl | OCOOEt | 4-methylthio-3-pyridyl |
| S | n-pentyl | OCOOEt | 5-methylthio-3-pyridyl |
| S | n-pentyl | OCOOEt | 6-methylthio-3-pyridyl |
| S | n-pentyl | OCOOEt | 2,6-dimethyl-3-pyridyl |
| S | n-pentyl | OCOOEt | 5,6-dimethyl-3-pyridyl |
| S | n-pentyl | OCOOEt | 2,6-diethyl-3-pyridyl |
| S | n-pentyl | OCOOEt | 5,6-diethyl-3-pyridyl |
| S | n-pentyl | OCOOEt | 2,6-dimethoxy-3-pyridyl |
| S | n-pentyl | OCOOEt | 5,6-dimethoxy-3-pyridyl |
| S | n-pentyl | OCOOEt | 2,6-diethoxy-3-pyridyl |
| S | n-pentyl | OCOOEt | 5,6-diethoxy-3-pyridyl |
| S | n-pentyl | OCOOEt | 2,6-dichloro-3-pyridyl |
| S | n-pentyl | OCOOEt | 5,6-dichloro-3-pyridyl |
| S | n-pentyl | OCOOEt | 5-chloro-6-methoxy-3-pyridyl |
| S | n-pentyl | OCOOEt | 5-chloro-6-ethoxy-3-pyridyl |
| S | n-pentyl | OCOOEt | 2-chloro-6-methyl-3-pyridyl |
| S | n-pentyl | OCOOEt | 6-chloro-2-methyl-3-pyridyl |
| S | n-pentyl | OCOOEt | 2-methyl-4-pyridyl |
| S | n-pentyl | OCOOEt | 2-ethyl-4-pyridyl |
| S | n-pentyl | OCOOEt | 2-methoxy-4-pyridyl |
| S | n-pentyl | OCOOEt | 2-ethoxy-4-pyridyl |
| S | n-pentyl | OCOOEt | 2-chloro-4-pyridyl |
| S | n-pentyl | OCOOEt | 2-dimethylamino-4-pyridyl |
| S | n-pentyl | OCOOEt | 2-(1-pyrrolidinyl)-4-pyridyl |
| S | n-pentyl | OCOOEt | 2-piperidino-4-pyridyl |
| S | n-pentyl | OCOOEt | 2-morpholino-4-pyridyl |
| S | n-pentyl | OCOOEt | 2-methylthio-4-pyridyl |
| S | n-pentyl | OCOOEt | 2-pyrazinyl |
| S | n-pentyl | OCOOEt | 5-methyl-2-pyrazinyl |
| S | n-pentyl | OCOOEt | 5-ethyl-2-pyrazinyl |
| S | n-pentyl | OCOOEt | 5-methoxy-2-pyrazinyl |
| S | n-pentyl | OCOOEt | 5-ethoxy-2-pyrazinyl |
| S | n-pentyl | OCOOEt | 5-chloro-2-pyrazinyl |
| S | n-pentyl | OCOOEt | 6-methyl-2-pyrazinyl |
| S | n-pentyl | OCOOEt | 6-methoxy-2-pyrazinyl |
| S | n-pentyl | OCOOEt | 6-chloro-2-pyrazinyl |
| NH | 2-methoxyethyl | OH | 3-pyridyl |
| NH | 2-methoxyethyl | OH | 4-pyridyl |
| NH | 2-methoxyethyl | OH | 2-methyl-3-pyridyl |
| NH | 2-methoxyethyl | OH | 6-methyl-3-pyridyl |
| NH | 2-methoxyethyl | OH | 2-ethyl-3-pyridyl |
| NH | 2-methoxyethyl | OH | 6-ethyl-3-pyridyl |
| NH | 2-methoxyethyl | OH | 6-methoxy-3-pyridyl |
| NH | 2-methoxyethyl | OH | 6-ethoxy-3-pyridyl |
| NH | 2-methoxyethyl | OH | 2-chloro-3-pyridyl |
| NH | 2-methoxyethyl | OH | 6-chloro-3-pyridyl |
| NH | 2-methoxyethyl | OH | 5,6-dimethyl-3-pyridyl |
| NH | 2-methoxyethyl | OH | 5,6-dimethoxy-3-pyridyl |
| NH | 2-methoxyethyl | OH | 5,6-dichloro-3-pyridyl |
| NH | 2-methoxyethyl | OH | 6-dimethylamino-3-pyridyl |
| NH | 2-methoxyethyl | OH | 6-(1-pyrrolidinyl)-3-pyridyl |
| NH | 2-methoxyethyl | OH | 6-piperidino-3-pyridyl |
| NH | 2-methoxyethyl | OH | 6-morpholino-3-pyridyl |
| NH | 2-methoxyethyl | OH | 6-methylthio-3-pyridyl |
| NH | 2-methoxyethyl | OH | 2-pyrazinyl |
| NH | 2-methoxyethyl | OH | 5-methyl-2-pyrazinyl |
| NH | 3-methoxypropyl | OH | 3-pyridyl |
| NH | 3-methoxypropyl | OH | 4-pyridyl |
| NH | 3-methoxypropyl | OH | 2-methyl-3-pyridyl |
| NH | 3-methoxypropyl | OH | 6-methyl-3-pyridyl |
| NH | 3-methoxypropyl | OH | 2-ethyl-3-pyridyl |
| NH | 3-methoxypropyl | OH | 6-ethyl-3-pyridyl |
| NH | 3-methoxypropyl | OH | 2-methoxy-3-pyridyl |
| NH | 3-methoxypropyl | OH | 6-methoxy-3-pyridyl |
| NH | 3-methoxypropyl | OH | 6-ethoxy-3-pyridyl |
| NH | 3-methoxypropyl | OH | 2-chloro-3-pyridyl |
| NH | 3-methoxypropyl | OH | 6-chloro-3-pyridyl |
| NH | 3-methoxypropyl | OH | 5,6-dimethyl-3-pyridyl |
| NH | 3-methoxypropyl | OH | 5,6-dimethoxy-3-pyridyl |
| NH | 3-methoxypropyl | OH | 5,6-dichloro-3-pyridyl |
| NH | 3-methoxypropyl | OH | 6-dimethylamino-3-pyridyl |
| NH | 3-methoxypropyl | OH | 6-(1-pyrrolidinyl)-3-pyridyl |
| NH | 3-methoxypropyl | OH | 6-piperidino-3-pyridyl |
| NH | 3-methoxypropyl | OH | 6-morpholino-3-pyridyl |
| NH | 3-methoxypropyl | OH | 6-methylthio-3-pyridyl |
| NH | 3-methoxypropyl | OH | 2-pyrazinyl |
| NH | 3-methoxypropyl | OH | 5-methyl-2-pyrazinyl |
| O | 2-methoxyethyl | OH | 3-pyridyl |
| O | 2-methoxyethyl | OH | 4-pyridyl |
| O | 2-methoxyethyl | OH | 2-methyl-3-pyridyl |
| O | 2-methoxyethyl | OH | 6-methyl-3-pyridyl |
| O | 2-methoxyethyl | OH | 2-ethyl-3-pyridyl |
| O | 2-methoxyethyl | OH | 6-ethyl-3-pyridyl |
| O | 2-methoxyethyl | OH | 6-methoxy-3-pyridyl |
| O | 2-methoxyethyl | OH | 6-ethoxy-3-pyridyl |
| O | 2-methoxyethyl | OH | 2-chloro-3-pyridyl |
| O | 2-methoxyethyl | OH | 6-chloro-3-pyridyl |
| O | 2-methoxyethyl | OH | 5,6-dimethyl-3-pyridyl |
| O | 2-methoxyethyl | OH | 5,6-dimethoxy-3-pyridyl |
| O | 2-methoxyethyl | OH | 5,6-dichloro-3-pyridyl |
| O | 2-methoxyethyl | OH | 6-dimethylamino-3-pyridyl |
| O | 2-methoxyethyl | OH | 6-(1-pyrrolidinyl)-3-pyridyl |
| O | 2-methoxyethyl | OH | 6-piperidino-3-pyridyl |
| O | 2-methoxyethyl | OH | 6-morpholino-3-pyridyl |
| O | 2-methoxyethyl | OH | 6-methylthio-3-pyridyl |
| O | 2-methoxyethyl | OH | 2-pyrazinyl |
| O | 2-methoxyethyl | OH | 5-methyl-2-pyrazinyl |
| O | 3-methoxypropyl | OH | 3-pyridyl |
| O | 3-methoxypropyl | OH | 4-pyridyl |
| O | 3-methoxypropyl | OH | 2-methyl-3-pyridyl |
| O | 3-methoxypropyl | OH | 6-methyl-3-pyridyl |
| O | 3-methoxypropyl | OH | 2-ethyl-3-pyridyl |
| O | 3-methoxypropyl | OH | 6-ethyl-3-pyridyl |
| O | 3-methoxypropyl | OH | 2-methoxy-3-pyridyl |
| O | 3-methoxypropyl | OH | 6-methoxy-3-pyridyl |
| O | 3-methoxypropyl | OH | 6-ethoxy-3-pyridyl |
| O | 3-methoxypropyl | OH | 2-chloro-3-pyridyl |
| O | 3-methoxypropyl | OH | 6-chloro-3-pyridyl |
| O | 3-methoxypropyl | OH | 5,6-dimethyl-3-pyridyl |
| O | 3-methoxypropyl | OH | 5,6-dimethoxy-3-pyridyl |
| O | 3-methoxypropyl | OH | 5,6-dichloro-3-pyridyl |
| O | 3-methoxypropyl | OH | 6-dimethylamino-3-pyridyl |
| O | 3-methoxypropyl | OH | 6-(1-pyrrolidinyl)-3-pyridyl |
| O | 3-methoxypropyl | OH | 6-piperidino-3-pyridyl |
| O | 3-methoxypropyl | OH | 6-morpholino-3-pyridyl |
| O | 3-methoxypropyl | OH | 6-methylthio-3-pyridyl |
| O | 3-methoxypropyl | OH | 2-pyrazinyl |
| O | 3-methoxypropyl | OH | 5-methyl-2-pyrazinyl |
| S | 2-methoxyethyl | OH | 3-pyridyl |
| S | 2-methoxyethyl | OH | 4-pyridyl |
| S | 2-methoxyethyl | OH | 2-methyl-3-pyridyl |
| S | 2-methoxyethyl | OH | 6-methyl-3-pyridyl |
| S | 2-methoxyethyl | OH | 2-ethyl-3-pyridyl |
| S | 2-methoxyethyl | OH | 6-ethyl-3-pyridyl |
| S | 2-methoxyethyl | OH | 6-methoxy-3-pyridyl |
| S | 2-methoxyethyl | OH | 6-ethoxy-3-pyridyl |
| S | 2-methoxyethyl | OH | 2-chloro-3-pyridyl |
| S | 2-methoxyethyl | OH | 6-chloro-3-pyridyl |
| S | 2-methoxyethyl | OH | 5,6-dimethyl-3-pyridyl |
| S | 2-methoxyethyl | OH | 5,6-dimethoxy-3-pyridyl |
| S | 2-methoxyethyl | OH | 5,6-dichloro-3-pyridyl |

TABLE 1-continued

| X | R¹ | R² | Y |
|---|---|---|---|
| S | 2-methoxyethyl | OH | 6-dimethylamino-3-pyridyl |
| S | 2-methoxyethyl | OH | 6-(1-pyrrolidinyl)-3-pyridyl |
| S | 2-methoxyethyl | OH | 6-piperidino-3-pyridyl |
| S | 2-methoxyethyl | OH | 6-morpholino-3-pyridyl |
| S | 2-methoxyethyl | OH | 6-methylthio-3-pyridyl |
| S | 2-methoxyethyl | OH | 2-pyrazinyl |
| S | 2-methoxyethyl | OH | 5-methyl-2-pyrazinyl |
| S | 2-hydroxyethyl | OH | 3-pyridyl |
| S | 2-hydroxyethyl | OH | 4-pyridyl |
| S | 2-hydroxyethyl | OH | 2-methyl-3-pyridyl |
| S | 2-hydroxyethyl | OH | 6-methyl-3-pyridyl |
| S | 2-hydroxyethyl | OH | 2-ethyl-3-pyridyl |
| S | 2-hydroxyethyl | OH | 6-ethyl-3-pyridyl |
| S | 2-hydroxyethyl | OH | 2-methoxy-3-pyridyl |
| S | 2-hydxoxyethyl | OH | 6-methoxy-3-pyridyl |
| S | 2-hydroxyethyl | OH | 6-ethoxy-3-pyridyl |
| S | 2-hydroxyethyl | OH | 2-chloro-3-pyridyl |
| S | 2-hydroxyethyl | OH | 6-chloro-3-pyridyl |
| S | 2-hydroxyethyl | OH | 5,6-dimethyl-3-pyridyl |
| S | 2-hydroxyethyl | OH | 5,6-dimethoxy-3-pyridyl |
| S | 2-hydroxyethyl | OH | 5,6-dichloro-3-pyridyl |
| S | 2-hydroxyethyl | OH | 6-dimethylamino-3-pyridyl |
| S | 2-hydroxyethyl | OH | 6-(1-pyrrolidinyl)-3-pyridyl |
| S | 2-hydroxyethyl | OH | 6-piperidino-3-pyridyl |
| S | 2-hydroxyethyl | OH | 6-morpholino-3-pyridyl |
| S | 2-hydroxyethyl | OH | 6-methylthio-3-pyridyl |
| S | 2-hydroxyethyl | OH | 2-pyrazinyl |
| S | 2-hydroxyethyl | OH | 5-methyl-2-pyrazinyl |
| NH | propyl | OH | 1-naphthyl |
| NH | propyl | OH | 2-naphthyl |
| NH | propyl | OH | 2-pyrrolyl |
| NH | propyl | OH | 3-pyrrolyl |
| NH | propyl | OH | 2-furyl |
| NH | propyl | OH | 3-furyl |
| NH | propyl | OH | 2-thienyl |
| NH | propyl | OH | 3-thienyl |
| NH | propyl | OH | 3-pyrazolyl |
| NH | propyl | OH | 4-pyrazolyl |
| NH | propyl | OH | 2-imidazolyl |
| NH | propyl | OH | 4-imidazolyl |
| NH | propyl | OH | 2-oxazolyl |
| NH | propyl | OH | 4-oxazolyl |
| NH | propyl | OH | 5-oxazolyl |
| NH | propyl | OH | 2-thiazolyl |
| NH | propyl | OH | 4-thiazolyl |
| NH | propyl | OH | 5-thiazolyl |
| NH | propyl | OH | 2-pyrimidinyl |
| NH | propyl | OH | 4-pyrimidinyl |
| NH | propyl | OH | 5-pyrimidinyl |
| NH | propyl | OH | 2-indolyl |
| NH | propyl | OH | 3-indolyl |
| NH | propyl | OH | 5-indolyl |
| NH | propyl | OH | 6-indolyl |
| NH | propyl | OH | 5-benzimidazolyl |
| NH | propyl | OH | 2-benzofuryl |
| NH | propyl | OH | 3-indazolyl |
| NH | propyl | OH | 2-benzoxazolyl |
| NH | propyl | OH | 4-fluoro-1-naphthyl |
| NH | propyl | OH | 5-chloro-2-thienyl |
| NH | propyl | OH | 4-methyl-1-naphthyl |
| NH | propyl | OH | 1-methyl-2-pyrrolyl |
| NH | propyl | OH | 2-methyl-3-furyl |
| NH | propyl | OH | 5-methyl-2-thienyl |
| NH | propyl | OH | 4-methyl-5-imidazolyl |
| NH | propyl | OH | 1-methyl-3-indolyl |
| NH | propyl | OH | 2-methoxy-1-naphthyl |
| NH | propyl | OH | 3-methoxy-2-naphthyl |
| NH | propyl | OH | 6-ethoxy-2-naphthyl |
| NH | propyl | OH | 5-methoxy-3-indolyl |
| NH | propyl | OH | 1,4-dimethoxy-2-naphthyl |
| NH | propyl | OH | 5,6-dimethoxy-2-indolyl |
| NH | propyl | OH | 5-methoxy-1-methyl-2-indolyl |
| NH | propyl | OCOOMe | 1-naphthyl |
| NH | propyl | OCOOMe | 2-naphthyl |
| NH | propyl | OCOOMe | 2-pyrrolyl |
| NH | propyl | OCOOMe | 3-pyrrolyl |
| NH | propyl | OCOOMe | 2-furyl |
| NH | propyl | OCOOMe | 3-furyl |
| NH | propyl | OCOOMe | 2-thienyl |
| NH | propyl | OCOOMe | 3-thienyl |
| NH | propyl | OCOOMe | 3-pyrazolyl |
| NH | propyl | OCOOMe | 4-pyrazolyl |
| NH | propyl | OCOOMe | 2-imidazolyl |
| NH | propyl | OCOOMe | 4-imidazolyl |
| NH | propyl | OCOOMe | 2-oxazolyl |
| NH | propyl | OCOOMe | 4-oxazolyl |
| NH | propyl | OCOOMe | 5-oxazolyl |
| NH | propyl | OCOOMe | 2-thiazolyl |
| NH | propyl | OCOOMe | 4-thiazolyl |
| NH | propyl | OCOOMe | 5-thiazolyl |
| NH | propyl | OCOOMe | 2-pyrimidinyl |
| NH | propyl | OCOOMe | 4-pyrimidinyl |
| NH | propyl | OCOOMe | 5-pyrimidinyl |
| NH | propyl | OCOOMe | 2-indolyl |
| NH | propyl | OCOOMe | 3-indolyl |
| NH | propyl | OCOOMe | 5-indolyl |
| NH | propyl | OCOOMe | 6-indolyl |
| NH | propyl | OCOOMe | 5-benzimidazolyl |
| NH | propyl | OCOOMe | 2-benzofuryl |
| NH | propyl | OCOOMe | 3-indazolyl |
| NH | propyl | OCOOMe | 2-benzoxazolyl |
| NH | propyl | OCOOMe | 4-fluoro-1-naphthyl |
| NH | propyl | OCOOMe | 5-chloro-2-thienyl |
| NH | propyl | OCOOMe | 4-methyl-1-naphthyl |
| NH | propyl | OCOOMe | 1-methyl-2-pyrrolyl |
| NH | propyl | OCOOMe | 2-methyl-3-furyl |
| NH | propyl | OCOOMe | 5-methyl-2-thienyl |
| NH | propyl | OCOOMe | 4-methyl-5-imidazolyl |
| NH | propyl | OCOOMe | 1-methyl-3-indolyl |
| NH | propyl | OCOOMe | 2-methoxy-1-naphthyl |
| NH | propyl | OCOOMe | 3-methoxy-2-naphthyl |
| NH | propyl | OCOOMe | 6-ethoxy-2-naphthyl |
| NH | propyl | OCOOMe | 5-methoxy-3-indolyl |
| NH | propyl | OCOOMe | 1,4-dimethoxy-2-naphthyl |
| NH | propyl | OCOOMe | 5,6-dimethoxy-2-indolyl |
| NH | propyl | OCOOMe | 5-methoxy-1-methyl-2-indolyl |
| NH | propyl | OCOOEt | 1-naphthyl |
| NH | propyl | OCOOEt | 2-naphthyl |
| NH | propyl | OCOOEt | 2-pyrrolyl |
| NH | propyl | OCOOEt | 3-pyrrolyl |
| NH | propyl | OCOOEt | 2-furyl |
| NH | propyl | OCOOEt | 3-furyl |
| NH | propyl | OCOOEt | 2-thienyl |
| NH | propyl | OCOOEt | 3-thienyl |
| NH | propyl | OCOOEt | 3-pyrazolyl |
| NH | propyl | OCOOEt | 4-pyrazolyl |
| NH | propyl | OCOOEt | 2-imidazolyl |
| NH | propyl | OCOOEt | 4-imidazolyl |
| NH | propyl | OCOOEt | 2-oxazolyl |
| NH | propyl | OCOOEt | 4-oxazolyl |
| NH | propyl | OCOOEt | 5-oxazolyl |
| NH | propyl | OCOOEt | 2-thiazolyl |
| NH | propyl | OCOOEt | 4-thiazolyl |
| NH | propyl | OCOOEt | 5-thiazolyl |
| NH | propyl | OCOOEt | 2-pyrimidinyl |
| NH | propyl | OCOOEt | 4-pyrimidinyl |
| NH | propyl | OCOOEt | 5-pyrimidinyl |
| NH | propyl | OCOOEt | 2-indolyl |
| NH | propyl | OCOOEt | 3-indolyl |
| NH | propyl | OCOOEt | 5-indolyl |
| NH | propyl | OCOOEt | 6-indolyl |
| NH | propyl | OCOOEt | 5-benzimidazolyl |
| NH | propyl | OCOOEt | 2-benzofuryl |
| NH | propyl | OCOOEt | 3-indazolyl |
| NH | propyl | OCOOEt | 2-benzoxazolyl |
| NH | propyl | OCOOEt | 4-fluoro-1-naphthyl |
| NH | propyl | OCOOEt | 5-chloro-2-thienyl |
| NH | propyl | OCOOEt | 4-methyl-1-naphthyl |
| NH | propyl | OCOOEt | 1-methyl-2-pyrrolyl |
| NH | propyl | OCOOEt | 2-methyl-3-furyl |
| NH | propyl | OCOOEt | 5-methyl-2-thienyl |
| NH | propyl | OCOOEt | 4-methyl-5-imidazolyl |
| NH | propyl | OCOOEt | 1-methyl-3-indolyl |
| NH | propyl | OCOOEt | 2-methoxy-1-naphthyl |

TABLE 1-continued

| X | R¹ | R² | Y |
|---|---|---|---|
| NH | propyl | OCOOEt | 3-methoxy-2-naphthyl |
| NH | propyl | OCOOEt | 6-ethoxy-2-naphthyl |
| NH | propyl | OCOOEt | 5-methoxy-3-indolyl |
| NH | propyl | OCOOEt | 1,4-dimethoxy-2-naphthyl |
| NH | propyl | OCOOEt | 5,6-dimethoxy-2-indolyl |
| NH | propyl | OCOOEt | 5-methoxy-1-methyl-2-indolyl |
| NH | n-butyl | OH | 1-naphthyl |
| NH | n-butyl | OH | 2-naphthyl |
| NH | n-butyl | OH | 2-pyrrolyl |
| NH | n-butyl | OH | 3-pyrrolyl |
| NH | n-butyl | OH | 2-furyl |
| NH | n-butyl | OH | 3-furyl |
| NH | n-butyl | OH | 2-thienyl |
| NH | n-butyl | OH | 3-thienyl |
| NH | n-butyl | OH | 3-pyrazolyl |
| NH | n-butyl | OH | 4-pyrazolyl |
| NH | n-butyl | OH | 2-imidazolyl |
| NH | n-butyl | OH | 4-imidazolyl |
| NH | n-butyl | OH | 2-oxazolyl |
| NH | n-butyl | OH | 4-oxazolyl |
| NH | n-butyl | OH | 5-oxazolyl |
| NH | n-butyl | OH | 2-thiazolyl |
| NH | n-butyl | OH | 4-thiazolyl |
| NH | n-butyl | OH | 5-thiazolyl |
| NH | n-butyl | OH | 2-pyrimidinyl |
| NH | n-butyl | OH | 4-pyrimidinyl |
| NH | n-butyl | OH | 5-pyrimidinyl |
| NH | n-butyl | OH | 2-indolyl |
| NH | n-butyl | OH | 3-indolyl |
| NH | n-butyl | OH | 5-indolyl |
| NH | n-butyl | OH | 6-indolyl |
| NH | n-butyl | OH | 5-benzimidazolyl |
| NH | n-butyl | OH | 2-benzofuryl |
| NH | n-butyl | OH | 3-indazolyl |
| NH | n-butyl | OH | 2-benzoxazolyl |
| NH | n-butyl | OH | 4-fluoro-1-naphthyl |
| NH | n-butyl | OH | 5-chloro-2-thienyl |
| NH | n-butyl | OH | 4-methyl-1-nahthyl |
| NH | n-butyl | OH | 1-methyl-2-pyrrolyl |
| NH | n-butyl | OH | 2-methyl-3-furyl |
| NH | n-butyl | OH | 5-methyl-2-thienyl |
| NH | n-butyl | OH | 4-methyl-5-imidazolyl |
| NH | n-butyl | OH | 1-methyl-3-indolyl |
| NH | n-butyl | OH | 2-methoxy-1-naphthyl |
| NH | n-butyl | OH | 3-methoxy-2-naphthyl |
| NH | n-butyl | OH | 6-ethoxy-2-naphthyl |
| NH | n-butyl | OH | 5-methoxy-3-indolyl |
| NH | n-butyl | OH | 1,4-dimethoxy-2-naphthyl |
| NH | n-butyl | OH | 5,6-dimethoxy-2-indolyl |
| NH | n-butyl | OH | 5-methoxy-1-methyl-2-indolyl |
| NH | n-butyl | OCOOMe | 1-naphthyl |
| NH | n-butyl | OCOOMe | 2-naphthyl |
| NH | n-butyl | OCOOMe | 2-pyrrolyl |
| NH | n-butyl | OCOOMe | 3-pyrrolyl |
| NH | n-butyl | OCOOMe | 2-furyl |
| NH | n-butyl | OCOOMe | 3-furyl |
| NH | n-butyl | OCOOMe | 2-thienyl |
| NH | n-butyl | OCOOMe | 3-thienyl |
| NH | n-butyl | OCOOMe | 3-pyrazolyl |
| NH | n-butyl | OCOOMe | 4-pyrazolyl |
| NH | n-butyl | OCOOMe | 2-imidazolyl |
| NH | n-butyl | OCOOMe | 4-imidazolyl |
| NH | n-butyl | OCOOMe | 2-oxazolyl |
| NH | n-butyl | OCOOMe | 4-oxazolyl |
| NH | n-butyl | OCOOMe | 5-oxazolyl |
| NH | n-butyl | OCOOMe | 2-thiazolyl |
| NH | n-butyl | OCOOMe | 4-thiazolyl |
| NH | n-butyl | OCOOMe | 5-thiazolyl |
| NH | n-butyl | OCOOMe | 2-pyrimidinyl |
| NH | n-butyl | OCOOMe | 4-pyrimidinyl |
| NH | n-butyl | OCOOMe | 5-pyrimidinyl |
| NH | n-butyl | OCOOMe | 2-indolyl |
| NH | n-butyl | OCOOMe | 3-indolyl |
| NH | n-butyl | OCOOMe | 5-indolyl |
| NH | n-butyl | OCOOMe | 6-indolyl |
| NH | n-butyl | OCOOMe | 5-benzimidazolyl |
| NH | n-butyl | OCOOMe | 2-benzofuryl |
| NH | n-butyl | OCOOMe | 3-indazolyl |
| NH | n-butyl | OCOOMe | 2-benzoxazolyl |
| NH | n-butyl | OCOOMe | 4-fluoro-1-naphthyl |
| NH | n-butyl | OCOOMe | 5-chloro-2-thienyl |
| NH | n-butyl | OCOOMe | 4-methyl-1-naphthyl |
| NH | n-butyl | OCOOMe | 1-methyl-2-pyrrolyl |
| NH | n-butyl | OCOOMe | 2-methyl-3-furyl |
| NH | n-butyl | OCOOMe | 5-methyl-2-thienyl |
| NH | n-butyl | OCOOMe | 4-methyl-5-imidazolyl |
| NH | n-butyl | OCOOMe | 1-methyl-3-indolyl |
| NH | n-butyl | OCOOMe | 2-methoxy-1-naphthyl |
| NH | n-butyl | OCOOMe | 3-methoxy-2-naphthyl |
| NH | n-butyl | OCOOMe | 6-ethoxy-2-naphthyl |
| NH | n-butyl | OCOOMe | 5-methoxy-3-indolyl |
| NH | n-butyl | OCOOMe | 1,4-dimethoxy-2-naphthyl |
| NH | n-butyl | OCOOMe | 5,6-dimethoxy-2-indolyl |
| NH | n-butyl | OCOOMe | 5-methoxy-1-methyl-2-indolyl |
| NH | n-butyl | OCOOEt | 1-naphthyl |
| NH | n-butyl | OCOOEt | 2-naphthyl |
| NH | n-butyl | OCOOEt | 2-pyrrolyl |
| NH | n-butyl | OCOOEt | 3-pyrrolyl |
| NH | n-butyl | OCOOEt | 2-furyl |
| NH | n-butyl | OCOOEt | 3-furyl |
| NH | n-butyl | OCOOEt | 2-thienyl |
| NH | n-butyl | OCOOEt | 3-thienyl |
| NH | n-butyl | OCOOEt | 3-pyrazolyl |
| NH | n-butyl | OCOOEt | 4-pyrazolyl |
| NH | n-butyl | OCOOEt | 2-imidazolyl |
| NH | n-butyl | OCOOEt | 4-imidazolyl |
| NH | n-butyl | OCOOEt | 2-oxazolyl |
| NH | n-butyl | OCOOEt | 4-oxazolyl |
| NH | n-butyl | OCOOEt | 5-oxazolyl |
| NH | n-butyl | OCOOEt | 2-thiazolyl |
| NH | n-butyl | OCOOEt | 4-thiazolyl |
| NH | n-butyl | OCOOEt | 5-thiazolyl |
| NH | n-butyl | OCOOEt | 2-pyrimidinyl |
| NH | n-butyl | OCOOEt | 4-pyrimidinyl |
| NH | n-butyl | OCOOEt | 5-pyrimidinyl |
| NH | n-butyl | OCOOEt | 2-indolyl |
| NH | n-butyl | OCOOEt | 3-indolyl |
| NH | n-butyl | OCOOEt | 5-indolyl |
| NH | n-butyl | OCOOEt | 6-indolyl |
| NH | n-butyl | OCOOEt | 5-benzimidazolyl |
| NH | n-butyl | OCOOEt | 2-benzofuryl |
| NH | n-butyl | OCOOEt | 3-indazolyl |
| NH | n-butyl | OCOOEt | 2-benzoxazolyl |
| NH | n-butyl | OCOOEt | 4-fluoro-1-naphthyl |
| NH | n-butyl | OCOOEt | 5-chloro-2-thienyl |
| NH | n-butyl | OCOOEt | 4-methyl-1-naphthyl |
| NH | n-butyl | OCOOEt | 1-methyl-2-pyrrolyl |
| NH | n-butyl | OCOOEt | 2-methyl-3-furyl |
| NH | n-butyl | OCOOEt | 5-methyl-2-thienyl |
| NH | n-butyl | OCOOEt | 4-methyl-5-imidazolyl |
| NH | n-butyl | OCOOEt | 1-methyl-3-indolyl |
| NH | n-butyl | OCOOEt | 2-methoxy-1-naphthyl |
| NH | n-butyl | OCOOEt | 3-methoxy-2-naphthyl |
| NH | n-butyl | OCOOEt | 6-ethoxy-2-naphthyl |
| NH | n-butyl | OCOOEt | 5-methoxy-3-indolyl |
| NH | n-butyl | OCOOEt | 1,4-dimethoxy-2-naphthyl |
| NH | n-butyl | OCOOEt | 5,6-dimethoxy-2-indolyl |
| NH | n-butyl | OCOOEt | 5-methoxy-1-methyl-2-indolyl |
| NH | n-pentyl | OH | 1-naphthyl |
| NH | n-pentyl | OH | 2-naphthyl |
| NH | n-pentyl | OH | 2-pyrrolyl |
| NH | n-pentyl | OH | 3-pyrrolyl |
| NH | n-pentyl | OH | 2-furyl |
| NH | n-pentyl | OH | 3-furyl |
| NH | n-pentyl | OH | 2-thienyl |
| NH | n-pentyl | OH | 3-thienyl |
| NH | n-pentyl | OH | 3-pyrazolyl |
| NH | n-pentyl | OH | 4-pyrazolyl |
| NH | n-pentyl | OH | 2-imidazolyl |
| NH | n-pentyl | OH | 4-imidazolyl |
| NH | n-pentyl | OH | 2-oxazolyl |
| NH | n-pentyl | OH | 4-oxazolyl |
| NH | n-pentyl | OH | 5-oxazolyl |
| NH | n-pentyl | OH | 2-thiazolyl |

TABLE 1-continued

| X | R¹ | R² | Y |
|---|---|---|---|
| NH | n-pentyl | OH | 4-thiazolyl |
| NH | n-pentyl | OH | 5-thiazolyl |
| NH | n-pentyl | OH | 2-pyrimidinyl |
| NH | n-pentyl | OH | 4-pyrimidinyl |
| NH | n-pentyl | OH | 5-pyrimidinyl |
| NH | n-pentyl | OH | 2-indolyl |
| NH | n-pentyl | OH | 3-indolyl |
| NH | n-pentyl | OH | 5-indolyl |
| NH | n-pentyl | OH | 6-indolyl |
| NH | n-pentyl | OH | 5-benzimidazolyl |
| NH | n-pentyl | OH | 2-benzofuryl |
| NH | n-pentyl | OH | 3-indazolyl |
| NH | n-pentyl | OH | 2-benzoxazolyl |
| NH | n-pentyl | OH | 4-fluoro-1-naphthyl |
| NH | n-pentyl | OH | 5-chloro-2-thienyl |
| NH | n-pentyl | OH | 4-methyl-1-naphthyl |
| NH | n-pentyl | OH | 1-methyl-2-pyrrolyl |
| NH | n-pentyl | OH | 2-methyl-3-furyl |
| NH | n-pentyl | OH | 5-methyl-2-thienyl |
| NH | n-pentyl | OH | 4-methyl-5-imidazolyl |
| NH | n-pentyl | OH | 1-methyl-3-indolyl |
| NH | n-pentyl | OH | 2-methoxy-1-naphthyl |
| NH | n-pentyl | OH | 3-methoxy-2-naphthyl |
| NH | n-pentyl | OH | 6-ethoxy-2-naphthyl |
| NH | n-pentyl | OH | 5-methoxy-3-indolyl |
| NH | n-pentyl | OH | 1,4-dimethoxy-2-naphthyl |
| NH | n-pentyl | OH | 5,6-dimethoxy-2-indolyl |
| NH | n-pentyl | OH | 5-methoxy-1-methyl-2-indolyl |
| NH | n-pentyl | OCOOMe | 1-naphthyl |
| NH | n-pentyl | OCOOMe | 2-naphthyl |
| NH | n-pentyl | OCOOMe | 2-pyrrolyl |
| NH | n-pentyl | OCOOMe | 3-pyrrolyl |
| NH | n-pentyl | OCOOMe | 2-furyl |
| NH | n-pentyl | OCOOMe | 3-furyl |
| NH | n-pentyl | OCOOMe | 2-thienyl |
| NH | n-pentyl | OCOOMe | 3-thienyl |
| NH | n-pentyl | OCOOMe | 3-pyrazolyl |
| NH | n-pentyl | OCOOMe | 4-pyrazolyl |
| NH | n-pentyl | OCOOMe | 2-imidazolyl |
| NH | n-pentyl | OCOOMe | 4-imidazolyl |
| NH | n-pentyl | OCOOMe | 2-oxazolyl |
| NH | n-pentyl | OCOOMe | 4-oxazolyl |
| NH | n-pentyl | OCOOMe | 5-oxazolyl |
| NH | n-pentyl | OCOOMe | 2-thiazolyl |
| NH | n-pentyl | OCOOMe | 4-thiazolyl |
| NH | n-pentyl | OCOOMe | 5-thiazolyl |
| NH | n-pentyl | OCOOMe | 2-pyrimidinyl |
| NH | n-pentyl | OCOOMe | 4-pyrimidinyl |
| NH | n-pentyl | OCOOMe | 5-pyrimidinyl |
| NH | n-pentyl | OCOOMe | 2-indolyl |
| NH | n-pentyl | OCOOMe | 3-indolyl |
| NH | n-pentyl | OCOOMe | 5-indolyl |
| NH | n-pentyl | OCOOMe | 6-indolyl |
| NH | n-pentyl | OCOOMe | 5-benzimidazolyl |
| NH | n-pentyl | OCOOMe | 2-benzofuryl |
| NH | n-pentyl | OCOOMe | 3-indazolyl |
| NH | n-pentyl | OCOOMe | 2-benzoxazolyl |
| NH | n-pentyl | OCOOMe | 4-fluoro-1-naphthyl |
| NH | n-pentyl | OCOOMe | 5-chloro-2-thienyl |
| NH | n-pentyl | OCOOMe | 4-methyl-1-naphthyl |
| NH | n-pentyl | OCOOMe | 1-methyl-2-pyrrolyl |
| NH | n-pentyl | OCOOMe | 2-methyl-3-furyl |
| NH | n-pentyl | OCOOMe | 5-methyl-2-thienyl |
| NH | n-pentyl | OCOOMe | 4-methyl-5-imidazolyl |
| NH | n-pentyl | OCOOMe | 1-methyl-3-indolyl |
| NH | n-pentyl | OCOOMe | 2-methoxy-1-naphthyl |
| NH | n-pentyl | OCOOMe | 3-methoxy-2-naphthyl |
| NH | n-pentyl | OCOOMe | 6-ethoxy-2-naphthyl |
| NH | n-pentyl | OCOOMe | 5-methoxy-3-indolyl |
| NH | n-pentyl | OCOOMe | 1,4-dimethoxy-2-naphthyl |
| NH | n-pentyl | OCOOMe | 5,6-dimethoxy-2-indolyl |
| NH | n-pentyl | OCOOMe | 5-methoxy-1-methyl-2-indolyl |
| NH | n-pentyl | OCOOEt | 1-naphthyl |
| NH | n-pentyl | OCOOEt | 2-naphthyl |
| NH | n-pentyl | OCOOEt | 2-pyrrolyl |
| NH | n-pentyl | OCOOEt | 3-pyrrolyl |
| NH | n-pentyl | OCOOEt | 2-furyl |
| NH | n-pentyl | OCOOEt | 3-furyl |
| NH | n-pentyl | OCOOEt | 2-thienyl |
| NH | n-pentyl | OCOOEt | 3-thienyl |
| NH | n-pentyl | OCOOEt | 3-pyrazolyl |
| NH | n-pentyl | OCOOEt | 4-pyrazolyl |
| NH | n-pentyl | OCOOEt | 2-imidazolyl |
| NH | n-pentyl | OCOOEt | 4-imidazolyl |
| NH | n-pentyl | OCOOEt | 2-oxazolyl |
| NH | n-pentyl | OCOOEt | 4-oxazolyl |
| NH | n-pentyl | OCOOEt | 5-oxazolyl |
| NH | n-pentyl | OCOOEt | 2-thiazolyl |
| NH | n-pentyl | OCOOEt | 4-thiazolyl |
| NH | n-pentyl | OCOOEt | 5-thiazolyl |
| NH | n-pentyl | OCOOEt | 2-pyrimidinyl |
| NH | n-pentyl | OCOOEt | 4-pyrimidinyl |
| NH | n-pentyl | OCOOEt | 5-pyrimidinyl |
| NH | n-pentyl | OCOOEt | 2-indolyl |
| NH | n-pentyl | OCOOEt | 3-indolyl |
| NH | n-pentyl | OCOOEt | 5-indolyl |
| NH | n-pentyl | OCOOEt | 6-indolyl |
| NH | n-pentyl | OCOOEt | 5-benzimidazolyl |
| NH | n-pentyl | OCOOEt | 2-benzofuryl |
| NH | n-pentyl | OCOOEt | 3-indazolyl |
| NH | n-pentyl | OCOOEt | 2-benzoxazolyl |
| NH | n-pentyl | OCOOEt | 4-fluoro-1-naphthyl |
| NH | n-pentyl | OCOOEt | 5-chloro-2-thienyl |
| NH | n-pentyl | OCOOEt | 4-methyl-1-naphthyl |
| NH | n-pentyl | OCOOEt | 1-methyl-2-pyrrolyl |
| NH | n-pentyl | OCOOEt | 2-methyl-3-furyl |
| NH | n-pentyl | OCOOEt | 5-methyl-2-thienyl |
| NH | n-pentyl | OCOOEt | 4-methyl-5-imidazolyl |
| NH | n-pentyl | OCOOEt | 1-methyl-3-indolyl |
| NH | n-pentyl | OCOOEt | 2-methoxy-1-naphthyl |
| NH | n-pentyl | OCOOEt | 3-methoxy-2-naphthyl |
| NH | n-pentyl | OCOOEt | 6-ethoxy-2-naphthyl |
| NH | n-pentyl | OCOOEt | 5-methoxy-3-indolyl |
| NH | n-pentyl | OCOOEt | 1,4-dimethoxy-2-naphthyl |
| NH | n-pentyl | OCOOEt | 5,6-dimethoxy-2-indolyl |
| NH | n-pentyl | OCOOEt | 5-methoxy-1-methyl-2-indolyl |
| O | propyl | OH | 1-naphthyl |
| O | propyl | OH | 2-naphthyl |
| O | propyl | OH | 2-pyrrolyl |
| O | propyl | OH | 3-pyrrolyl |
| O | propyl | OH | 2-furyl |
| O | propyl | OH | 3-furyl |
| O | propyl | OH | 2-thienyl |
| O | propyl | OH | 3-thienyl |
| O | propyl | OH | 3-pyrazolyl |
| O | propyl | OH | 4-pyrazolyl |
| O | propyl | OH | 2-imidazolyl |
| O | propyl | OH | 4-imidazolyl |
| O | propyl | OH | 2-oxazolyl |
| O | propyl | OH | 4-oxazolyl |
| O | propyl | OH | 5-oxazolyl |
| O | propyl | OH | 2-thiazolyl |
| O | propyl | OH | 4-thiazolyl |
| O | propyl | OH | 5-thiazolyl |
| O | propyl | OH | 2-pyrimidinyl |
| O | propyl | OH | 4-pyrimidinyl |
| O | propyl | OH | 5-pyrimidinyl |
| O | propyl | OH | 2-indolyl |
| O | propyl | OH | 3-indolyl |
| O | propyl | OH | 5-indolyl |
| O | propyl | OH | 6-indolyl |
| O | propyl | OH | 5-benzimidazolyl |
| O | propyl | OH | 2-benzofuryl |
| O | propyl | OH | 3-indazolyl |
| O | propyl | OH | 2-benzoxazolyl |
| O | propyl | OH | 4-fluoro-1-naphthyl |
| O | propyl | OH | 5-chloro-2-thienyl |
| O | propyl | OH | 4-methyl-1-naphthyl |
| O | propyl | OH | 1-methyl-2-pyrrolyl |
| O | propyl | OH | 2-methyl-3-furyl |
| O | propyl | OH | 5-methyl-2-thienyl |
| O | propyl | OH | 4-methyl-5-imidazolyl |
| O | propyl | OH | 1-methyl-3-indolyl |
| O | propyl | OH | 2-methoxy-1-naphthyl |

TABLE 1-continued

| X | R¹ | R² | Y |
|---|---|---|---|
| O | propyl | OH | 3-methoxy-2-naphthyl |
| O | propyl | OH | 6-ethoxy-2-naphthyl |
| O | propyl | OH | 5-methoxy-3-indolyl |
| O | propyl | OH | 1,4-dimethoxy-2-naphthyl |
| O | propyl | OH | 5,6-dimethoxy-2-indolyl |
| O | propyl | OH | 5-methoxy-1-methyl-2-indolyl |
| O | propyl | OCOOMe | 1-naphthyl |
| O | propyl | OCOOMe | 2-naphthyl |
| O | propyl | OCOOMe | 2-pyrrolyl |
| O | propyl | OCOOMe | 3-pyrrolyl |
| O | propyl | OCOOMe | 2-furyl |
| O | propyl | OCOOMe | 3-furyl |
| O | propyl | OCOOMe | 2-thienyl |
| O | propyl | OCOOMe | 3-thienyl |
| O | propyl | OCOOMe | 3-pyrazolyl |
| O | propyl | OCOOMe | 4-pyrazolyl |
| O | propyl | OCOOMe | 2-imidazolyl |
| O | propyl | OCOOMe | 4-imidazolyl |
| O | propyl | OCOOMe | 2-oxazolyl |
| O | propyl | OCOOMe | 4-oxazolyl |
| O | propyl | OCOOMe | 5-oxazolyl |
| O | propyl | OCOOMe | 2-thiazolyl |
| O | propyl | OCOOMe | 4-thiazolyl |
| O | propyl | OCOOMe | 5-thiazolyl |
| O | propyl | OCOOMe | 2-pyrimidinyl |
| O | propyl | OCOOMe | 4-pyrimidinyl |
| O | propyl | OCOOMe | 5-pyrimidinyl |
| O | propyl | OCOOMe | 2-indolyl |
| O | propyl | OCOOMe | 3-indolyl |
| O | propyl | OCOOMe | 5-indolyl |
| O | propyl | OCOOMe | 6-indolyl |
| O | propyl | OCOOMe | 5-benzimidazolyl |
| O | propyl | OCOOMe | 2-benzofuryl |
| O | propyl | OCOOMe | 3-indazolyl |
| O | propyl | OCOOMe | 2-benzoxazolyl |
| O | propyl | OCOOMe | 4-fluoro-1-naphthyl |
| O | propyl | OCOOMe | 5-chloro-2-thienyl |
| O | propyl | OCOOMe | 4-methyl-1-naphthyl |
| O | propyl | OCOOMe | 1-methyl-2-pyrrolyl |
| O | propyl | OCOOMe | 2-methyl-3-furyl |
| O | propyl | OCOOMe | 5-methyl-2-thienyl |
| O | propyl | OCOOMe | 4-methyl-5-imidazolyl |
| O | propyl | OCOOMe | 1-methyl-3-indolyl |
| O | propyl | OCOOMe | 2-methoxy-1-naphthyl |
| O | propyl | OCOOMe | 3-methoxy-2-naphthyl |
| O | propyl | OCOOMe | 6-ethoxy-2-naphthyl |
| O | propyl | OCOOMe | 5-methoxy-3-indolyl |
| O | propyl | OCOOMe | 1,4-dimethoxy-2-naphthyl |
| O | propyl | OCOOMe | 5,6-dimethoxy-2-indolyl |
| O | propyl | OCOOMe | 5-methoxy-1-methyl-2-indolyl |
| O | propyl | OCOOEt | 1-naphthyl |
| O | propyl | OCOOEt | 2-naphthyl |
| O | propyl | OCOOEt | 2-pyrrolyl |
| O | propyl | OCOOEt | 3-pyrrolyl |
| O | propyl | OCOOEt | 2-furyl |
| O | propyl | OCOOEt | 3-furyl |
| O | propyl | OCOOEt | 2-thienyl |
| O | propyl | OCOOEt | 3-thienyl |
| O | propyl | OCOOEt | 3-pyrazolyl |
| O | propyl | OCOOEt | 4-pyrazolyl |
| O | propyl | OCOOEt | 2-imidazolyl |
| O | propyl | OCOOEt | 4-imidazolyl |
| O | propyl | OCOOEt | 2-oxazolyl |
| O | propyl | OCOOEt | 4-oxazolyl |
| O | propyl | OCOOEt | 5-oxazolyl |
| O | propyl | OCOOEt | 2-thiazolyl |
| O | propyl | OCOOEt | 4-thiazolyl |
| O | propyl | OCOOEt | 5-thiazolyl |
| O | propyl | OCOOEt | 2-pyrimidinyl |
| O | propyl | OCOOEt | 4-pyrimidinyl |
| O | propyl | OCOOEt | 5-pyrimidinyl |
| O | propyl | OCOOEt | 2-indolyl |
| O | propyl | OCOOEt | 3-indolyl |
| O | propyl | OCOOEt | 5-indolyl |
| O | propyl | OCOOEt | 6-indolyl |
| O | propyl | OCOOEt | 5-benzimidazolyl |
| O | propyl | OCOOEt | 2-benzofuryl |
| O | propyl | OCOOEt | 3-indazolyl |
| O | propyl | OCOOEt | 2-benzoxazolyl |
| O | propyl | OCOOEt | 4-fluoro-1-naphthyl |
| O | propyl | OCOOEt | 5-chloro-2-thienyl |
| O | propyl | OCOOEt | 4-methyl-1-naphthyl |
| O | propyl | OCOOEt | 1-methyl-2-pyrrolyl |
| O | propyl | OCOOEt | 2-methyl-3-furyl |
| O | propyl | OCOOEt | 5-methyl-2-thienyl |
| O | propyl | OCOOEt | 4-methyl-5-imidazolyl |
| O | propyl | OCOOEt | 1-methyl-3-indolyl |
| O | propyl | OCOOEt | 2-methoxy-1-naphthyl |
| O | propyl | OCOOEt | 3-methoxy-2-naphthyl |
| O | propyl | OCOOEt | 6-ethoxy-2-naphthyl |
| O | propyl | OCOOEt | 5-methoxy-3-indolyl |
| O | propyl | OCOOEt | 1,4-dimethoxy-2-naphthyl |
| O | propyl | OCOOEt | 5,6-dimethoxy-2-indolyl |
| O | propyl | OCOOEt | 5-methoxy-1-methyl-2-indolyl |
| O | n-butyl | OH | 1-naphthyl |
| O | n-butyl | OH | 2-naphthyl |
| O | n-butyl | OH | 2-pyrrolyl |
| O | n-butyl | OH | 3-pyrrolyl |
| O | n-butyl | OH | 2-furyl |
| O | n-butyl | OH | 3-furyl |
| O | n-butyl | OH | 2-thienyl |
| O | n-butyl | OH | 3-thienyl |
| O | n-butyl | OH | 3-pyrazolyl |
| O | n-butyl | OH | 4-pyrazolyl |
| O | n-butyl | OH | 2-imidazolyl |
| O | n-butyl | OH | 4-imidazolyl |
| O | n-butyl | OH | 2-oxazolyl |
| O | n-butyl | OH | 4-oxazolyl |
| O | n-butyl | OH | 5-oxazolyl |
| O | n-butyl | OH | 2-thiazolyl |
| O | n-butyl | OH | 4-thiazolyl |
| O | n-butyl | OH | 5-thiazolyl |
| O | n-butyl | OH | 2-pyrimidinyl |
| O | n-butyl | OH | 4-pyrimidinyl |
| O | n-butyl | OH | 5-pyrimidinyl |
| O | n-butyl | OH | 2-indolyl |
| O | n-butyl | OH | 3-indolyl |
| O | n-butyl | OH | 5-indolyl |
| O | n-butyl | OH | 6-indolyl |
| O | n-butyl | OH | 5-benzimidazolyl |
| O | n-butyl | OH | 2-benzofuryl |
| O | n-butyl | OH | 3-indazolyl |
| O | n-butyl | OH | 2-benzoxazolyl |
| O | n-butyl | OH | 4-fluoro-1-naphthyl |
| O | n-butyl | OH | 5-chloro-2-thienyl |
| O | n-butyl | OH | 4-methyl-1-naphthyl |
| O | n-butyl | OH | 1-methyl-2-pyrrolyl |
| O | n-butyl | OH | 2-methyl-3-furyl |
| O | n-butyl | OH | 5-methyl-2-thienyl |
| O | n-butyl | OH | 4-methyl-5-imidazolyl |
| O | n-butyl | OH | 1-methyl-3-indolyl |
| O | n-butyl | OH | 2-methoxy-1-naphthyl |
| O | n-butyl | OH | 3-methoxy-2-naphthyl |
| O | n-butyl | OH | 6-ethoxy-2-naphthyl |
| O | n-butyl | OH | 5-methoxy-3-indolyl |
| O | n-butyl | OH | 1,4-dimethoxy-2-naphthyl |
| O | n-butyl | OH | 5,6-dimethoxy-2-indolyl |
| O | n-butyl | OH | 5-methoxy-1-methyl-2-indolyl |
| O | n-butyl | OCOOMe | 1-naphthyl |
| O | n-butyl | OCOOMe | 2-naphthyl |
| O | n-butyl | OCOOMe | 2-pyrrolyl |
| O | n-butyl | OCOOMe | 3-pyrrolyl |
| O | n-butyl | OCOOMe | 2-furyl |
| O | n-butyl | OCOOMe | 3-furyl |
| O | n-butyl | OCOOMe | 2-thienyl |
| O | n-butyl | OCOOMe | 3-thienyl |
| O | n-butyl | OCOOMe | 3-pyrazolyl |
| O | n-butyl | OCOOMe | 4-pyrazolyl |
| O | n-butyl | OCOOMe | 2-imidazolyl |
| O | n-butyl | OCOOMe | 4-imidazolyl |
| O | n-butyl | OCOOMe | 2-oxazolyl |
| O | n-butyl | OCOOMe | 4-oxazolyl |
| O | n-butyl | OCOOMe | 5-oxazolyl |
| O | n-butyl | OCOOMe | 2-thiazolyl |

TABLE 1-continued

| X | R¹ | R² | Y |
|---|---|---|---|
| O | n-butyl | OCOOMe | 4-thiazolyl |
| O | n-butyl | OCOOMe | 5-thiazolyl |
| O | n-butyl | OCOOMe | 2-pyrimidinyl |
| O | n-butyl | OCOOMe | 4-pyrimidinyl |
| O | n-butyl | OCOOMe | 5-pyrimidinyl |
| O | n-butyl | OCOOMe | 2-indolyl |
| O | n-butyl | OCOOMe | 3-indolyl |
| O | n-butyl | OCOOMe | 5-indolyl |
| O | n-butyl | OCOOMe | 6-indolyl |
| O | n-butyl | OCOOMe | 5-benzimidazolyl |
| O | n-butyl | OCOOMe | 2-benzofuryl |
| O | n-butyl | OCOOMe | 3-indazolyl |
| O | n-butyl | OCOOMe | 2-benzoxazolyl |
| O | n-butyl | OCOOMe | 4-fluoro-1-naphthyl |
| O | n-butyl | OCOOMe | 5-chloro-2-thienyl |
| O | n-butyl | OCOOMe | 4-methyl-1-naphthyl |
| O | n-butyl | OCOOMe | 1-methyl-2-pyrrolyl |
| O | n-butyl | OCOOMe | 2-methyl-3-furyl |
| O | n-butyl | OCOOMe | 5-methyl-2-thienyl |
| O | n-butyl | OCOOMe | 4-methyl-5-imidazolyl |
| O | n-butyl | OCOOMe | 1-methyl-3-indolyl |
| O | n-butyl | OCOOMe | 2-methoxy-1-naphthyl |
| O | n-butyl | OCOOMe | 3-methoxy-2-naphthyl |
| O | n-butyl | OCOOMe | 6-ethoxy-2-naphthyl |
| O | n-butyl | OCOOMe | 5-methoxy-3-indolyl |
| O | n-butyl | OCOOMe | 1,4-dimethoxy-2-naphthyl |
| O | n-butyl | OCOOMe | 5,6-dimethoxy-2-indolyl |
| O | n-butyl | OCOOMe | 5-methoxy-1-methyl-2-indolyl |
| O | n-butyl | OCOOEt | 1-naphthyl |
| O | n-butyl | OCOOEt | 2-naphthyl |
| O | n-butyl | OCOOEt | 2-pyrrolyl |
| O | n-butyl | OCOOEt | 3-pyrrolyl |
| O | n-butyl | OCOOEt | 2-furyl |
| O | n-butyl | OCOOEt | 3-furyl |
| O | n-butyl | OCOOEt | 2-thienyl |
| O | n-butyl | OCOOEt | 3-thienyl |
| O | n-butyl | OCOOEt | 3-pyrazolyl |
| O | n-butyl | OCOOEt | 4-pyrazolyl |
| O | n-butyl | OCOOEt | 2-imidazolyl |
| O | n-butyl | OCOOEt | 4-imidazolyl |
| O | n-butyl | OCOOEt | 2-oxazolyl |
| O | n-butyl | OCOOEt | 4-oxazolyl |
| O | n-butyl | OCOOEt | 5-oxazolyl |
| O | n-butyl | OCOOEt | 2-thiazolyl |
| O | n-butyl | OCOOEt | 4-thiazolyl |
| O | n-butyl | OCOOEt | 5-thiazolyl |
| O | n-butyl | OCOOEt | 2-pyrimidinyl |
| O | n-butyl | OCOOEt | 4-pyrimidinyl |
| O | n-butyl | OCOOEt | 5-pyrimidinyl |
| O | n-butyl | OCOOEt | 2-indolyl |
| O | n-butyl | OCOOEt | 3-indolyl |
| O | n-butyl | OCOOEt | 5-indolyl |
| O | n-butyl | OCOOEt | 6-indolyl |
| O | n-butyl | OCOOEt | 5-benzimidazolyl |
| O | n-butyl | OCOOEt | 2-benzofuryl |
| O | n-butyl | OCOOEt | 3-indazolyl |
| O | n-butyl | OCOOEt | 2-benzoxazolyl |
| O | n-butyl | OCOOEt | 4-fluoro-1-naphthyl |
| O | n-butyl | OCOOEt | 5-chloro-2-thienyl |
| O | n-butyl | OCOOEt | 4-methyl-1-naphthyl |
| O | n-butyl | OCOOEt | 1-methyl-2-pyrrolyl |
| O | n-butyl | OCOOEt | 2-methyl-3-furyl |
| O | n-butyl | OCOOEt | 5-methyl-2-thienyl |
| O | n-butyl | OCOOEt | 4-methyl-5-imidazolyl |
| O | n-butyl | OCOOEt | 1-methyl-3-indolyl |
| O | n-butyl | OCOOEt | 2-methoxy-1-naphthyl |
| O | n-butyl | OCOOEt | 3-methoxy-2-naphthyl |
| O | n-butyl | OCOOEt | 6-ethoxy-2-naphthyl |
| O | n-butyl | OCOOEt | 5-methoxy-3-indolyl |
| O | n-butyl | OCOOEt | 1,4-dimethoxy-2-naphthyl |
| O | n-butyl | OCOOEt | 5,6-dimethoxy-2-indolyl |
| O | n-butyl | OCOOEt | 5-methoxy-1-methyl-2-indolyl |
| O | n-pentyl | OH | 1-naphthyl |
| O | n-pentyl | OH | 2-naphthyl |
| O | n-pentyl | OH | 2-pyrrolyl |
| O | n-pentyl | OH | 3-pyrrolyl |
| O | n-pentyl | OH | 2-furyl |
| O | n-pentyl | OH | 3-furyl |
| O | n-pentyl | OH | 2-thienyl |
| O | n-pentyl | OH | 3-thienyl |
| O | n-pentyl | OH | 3-pyrazolyl |
| O | n-pentyl | OH | 4-pyrazolyl |
| O | n-pentyl | OH | 2-imidazolyl |
| O | n-pentyl | OH | 4-imidazolyl |
| O | n-pentyl | OH | 2-oxazolyl |
| O | n-pentyl | OH | 4-oxazolyl |
| O | n-pentyl | OH | 5-oxazolyl |
| O | n-pentyl | OH | 2-thiazolyl |
| O | n-pentyl | OH | 4-thiazolyl |
| O | n-pentyl | OH | 5-thiazolyl |
| O | n-pentyl | OH | 2-pyrimidinyl |
| O | n-pentyl | OH | 4-pyrimidinyl |
| O | n-pentyl | OH | 5-pyrimidinyl |
| O | n-pentyl | OH | 2-indolyl |
| O | n-pentyl | OH | 3-indolyl |
| O | n-pentyl | OH | 5-indolyl |
| O | n-pentyl | OH | 6-indolyl |
| O | n-pentyl | OH | 5-benzimidazolyl |
| O | n-pentyl | OH | 2-benzofuryl |
| O | n-pentyl | OH | 3-indazolyl |
| O | n-pentyl | OH | 2-benzoxazolyl |
| O | n-pentyl | OH | 4-fluoro-1-naphthyl |
| O | n-pentyl | OH | 5-chloro-2-thienyl |
| O | n-pentyl | OH | 4-methyl-1-naphthyl |
| O | n-pentyl | OH | 1-methyl-2-pyrrolyl |
| O | n-pentyl | OH | 2-methyl-3-furyl |
| O | n-pentyl | OH | 5-methyl-2-thienyl |
| O | n-pentyl | OH | 4-methyl-5-imidazolyl |
| O | n-pentyl | OH | 1-methyl-3-indolyl |
| O | n-pentyl | OH | 2-methoxy-1-naphthyl |
| O | n-pentyl | OH | 3-methoxy-2-naphthyl |
| O | n-pentyl | OH | 6-ethoxy-2-naphthyl |
| O | n-pentyl | OH | 5-methoxy-3-indolyl |
| O | n-pentyl | OH | 1,4-dimethoxy-2-naphthyl |
| O | n-pentyl | OH | 5,6-dimethoxy-2-indolyl |
| O | n-pentyl | OH | 5-methoxy-1-methyl-2-indolyl |
| O | n-pentyl | OCOOMe | 1-naphthyl |
| O | n-pentyl | OCOOMe | 2-naphthyl |
| O | n-pentyl | OCOOMe | 2-pyrrolyl |
| O | n-pentyl | OCOOMe | 3-pyrrolyl |
| O | n-pentyl | OCOOMe | 2-furyl |
| O | n-pentyl | OCOOMe | 3-furyl |
| O | n-pentyl | OCOOMe | 2-thienyl |
| O | n-pentyl | OCOOMe | 3-thienyl |
| O | n-pentyl | OCOOMe | 3-pyrazolyl |
| O | n-pentyl | OCOOMe | 4-pyrazolyl |
| O | n-pentyl | OCOOMe | 2-imidazolyl |
| O | n-pentyl | OCOOMe | 4-imidazolyl |
| O | n-pentyl | OCOOMe | 2-oxazolyl |
| O | n-pentyl | OCOOMe | 4-oxazolyl |
| O | n-pentyl | OCOOMe | 5-oxazolyl |
| O | n-pentyl | OCOOMe | 2-thiazolyl |
| O | n-pentyl | OCOOMe | 4-thiazolyl |
| O | n-pentyl | OCOOMe | 5-thiazolyl |
| O | n-pentyl | OCOOMe | 2-pyrimidinyl |
| O | n-pentyl | OCOOMe | 4-pyrimidinyl |
| O | n-pentyl | OCOOMe | 5-pyrimidinyl |
| O | n-pentyl | OCOOMe | 2-indolyl |
| O | n-pentyl | OCOOMe | 3-indolyl |
| O | n-pentyl | OCOOMe | 5-indolyl |
| O | n-pentyl | OCOOMe | 6-indolyl |
| O | n-pentyl | OCOOMe | 5-benzimidazolyl |
| O | n-pentyl | OCOOMe | 2-benzofuryl |
| O | n-pentyl | OCOOMe | 3-indazolyl |
| O | n-pentyl | OCOOMe | 2-benzoxazolyl |
| O | n-pentyl | OCOOMe | 4-fluoro-1-naphthyl |
| O | n-pentyl | OCOOMe | 5-chloro-2-thienyl |
| O | n-pentyl | OCOOMe | 4-methyl-1-naphthyl |
| O | n-pentyl | OCOOMe | 1-methyl-2-pyrrolyl |
| O | n-pentyl | OCOOMe | 2-methyl-3-furyl |
| O | n-pentyl | OCOOMe | 5-methyl-2-thienyl |
| O | n-pentyl | OCOOMe | 4-methyl-5-imidazolyl |
| O | n-pentyl | OCOOMe | 1-methyl-3-indolyl |
| O | n-pentyl | OCOOMe | 2-methoxy-1-naphthyl |

TABLE 1-continued

| X | R¹ | R² | Y |
|---|---|---|---|
| O | n-pentyl | OCOOMe | 3-methoxy-2-naphthyl |
| O | n-pentyl | OCOOMe | 6-ethoxy-2-naphthyl |
| O | n-pentyl | OCOOMe | 5-methoxy-3-indolyl |
| O | n-pentyl | OCOOMe | 1,4-dimethoxy-2-naphthyl |
| O | n-pentyl | OCOOMe | 5,6-dimethoxy-2-indolyl |
| O | n-pentyl | OCOOMe | 5-methoxy-1-methyl-2-indolyl |
| O | n-pentyl | OCOOEt | 1-naphthyl |
| O | n-pentyl | OCOOEt | 2-naphthyl |
| O | n-pentyl | OCOOEt | 2-pyrrolyl |
| O | n-pentyl | OCOOEt | 3-pyrrolyl |
| O | n-pentyl | OCOOEt | 2-furyl |
| O | n-pentyl | OCOOEt | 3-furyl |
| O | n-pentyl | OCOOEt | 2-thienyl |
| O | n-pentyl | OCOOEt | 3-thienyl |
| O | n-pentyl | OCOOEt | 3-pyrazolyl |
| O | n-pentyl | OCOOEt | 4-pyrazolyl |
| O | n-pentyl | OCOOEt | 2-imidazolyl |
| O | n-pentyl | OCOOEt | 4-imidazolyl |
| O | n-pentyl | OCOOEt | 2-oxazolyl |
| O | n-pentyl | OCOOEt | 4-oxazolyl |
| O | n-pentyl | OCOOEt | 5-oxazolyl |
| O | n-pentyl | OCOOEt | 2-thiazolyl |
| O | n-pentyl | OCOOEt | 4-thiazolyl |
| O | n-pentyl | OCOOEt | 5-thiazolyl |
| O | n-pentyl | OCOOEt | 2-pyrimidinyl |
| O | n-pentyl | OCOOEt | 4-pyrimidinyl |
| O | n-pentyl | OCOOEt | 5-pyrimidinyl |
| O | n-pentyl | OCOOEt | 2-indolyl |
| O | n-pentyl | OCOOEt | 3-indolyl |
| O | n-pentyl | OCOOEt | 5-indolyl |
| O | n-pentyl | OCOOEt | 6-indolyl |
| O | n-pentyl | OCOOEt | 5-benzimidazolyl |
| O | n-pentyl | OCOOEt | 2-benzofuryl |
| O | n-pentyl | OCOOEt | 3-indazolyl |
| O | n-pentyl | OCOOEt | 2-benzoxazolyl |
| O | n-pentyl | OCOOEt | 4-fluoro-1-naphthyl |
| O | n-pentyl | OCOOEt | 5-chloro-2-thienyl |
| O | n-pentyl | OCOOEt | 4-methyl-1-naphthyl |
| O | n-pentyl | OCOOEt | 1-methyl-2-pyrrolyl |
| O | n-pentyl | OCOOEt | 2-methyl-3-furyl |
| O | n-pentyl | OCOOEt | 5-methyl-2-thienyl |
| O | n-pentyl | OCOOEt | 4-methyl-5-imidazolyl |
| O | n-pentyl | OCOOEt | 1-methyl-3-indolyl |
| O | n-pentyl | OCOOEt | 2-methoxy-1-naphthyl |
| O | n-pentyl | OCOOEt | 3-methoxy-2-naphthyl |
| O | n-pentyl | OCOOEt | 6-ethoxy-2-naphthyl |
| O | n-pentyl | OCOOEt | 5-methoxy-3-indolyl |
| O | n-pentyl | OCOOEt | 1,4-dimethoxy-2-naphthyl |
| O | n-pentyl | OCOOEt | 5,6-dimethoxy-2-indolyl |
| O | n-pentyl | OCOOEt | 5-methoxy-1-methyl-2-indolyl |
| S | propyl | OH | 1-naphthyl |
| S | propyl | OH | 2-naphthyl |
| S | propyl | OH | 2-pyrrolyl |
| S | propyl | OH | 3-pyrrolyl |
| S | propyl | OH | 2-furyl |
| S | propyl | OH | 3-furyl |
| S | propyl | OH | 2-thienyl |
| S | propyl | OH | 3-thienyl |
| S | propyl | OH | 3-pyrazolyl |
| S | propyl | OH | 4-pyrazolyl |
| S | propyl | OH | 2-imidazolyl |
| S | propyl | OH | 4-imidazolyl |
| S | propyl | OH | 2-oxazolyl |
| S | propyl | OH | 4-oxazolyl |
| S | propyl | OH | 5-oxazolyl |
| S | propyl | OH | 2-thiazolyl |
| S | propyl | OH | 4-thiazolyl |
| S | propyl | OH | 5-thiazolyl |
| S | propyl | OH | 2-pyrimidinyl |
| S | propyl | OH | 4-pyrimidinyl |
| S | propyl | OH | 5-pyrimidinyl |
| S | propyl | OH | 2-indolyl |
| S | propyl | OH | 3-indolyl |
| S | propyl | OH | 5-indolyl |
| S | propyl | OH | 6-indolyl |
| S | propyl | OH | 5-benzimidazolyl |
| S | propyl | OH | 2-benzofuryl |
| S | propyl | OH | 3-indazolyl |
| S | propyl | OH | 2-benzoxazolyl |
| S | propyl | OH | 4-fluoro-1-naphthyl |
| S | propyl | OH | 5-chloro-2-thienyl |
| S | propyl | OH | 4-methyl-1-naphthyl |
| S | propyl | OH | 1-methyl-2-pyrrolyl |
| S | propyl | OH | 2-methyl-3-furyl |
| S | propyl | OH | 5-methyl-2-thienyl |
| S | propyl | OH | 4-methyl-5-imidazolyl |
| S | propyl | OH | 1-methyl-3-indolyl |
| S | propyl | OH | 2-methoxy-1-naphthyl |
| S | propyl | OH | 3-methoxy-2-naphthyl |
| S | propyl | OH | 6-ethoxy-2-naphthyl |
| S | propyl | OH | 5-methoxy-3-indolyl |
| S | propyl | OH | 1,4-dimethoxy-2-naphthyl |
| S | propyl | OH | 5,6-dimethoxy-2-indolyl |
| S | propyl | OH | 5-methoxy-1-methyl-2-indolyl |
| S | propyl | OCOOMe | 1-naphthyl |
| S | propyl | OCOOMe | 2-naphthyl |
| S | propyl | OCOOMe | 2-pyrrolyl |
| S | propyl | OCOOMe | 3-pyrrolyl |
| S | propyl | OCOOMe | 2-furyl |
| S | propyl | OCOOMe | 3-furyl |
| S | propyl | OCOOMe | 2-thienyl |
| S | propyl | OCOOMe | 3-thienyl |
| S | propyl | OCOOMe | 3-pyrazolyl |
| S | propyl | OCOOMe | 4-pyrazolyl |
| S | propyl | OCOOMe | 2-imidazolyl |
| S | propyl | OCOOMe | 4-imidazolyl |
| S | propyl | OCOOMe | 2-oxazolyl |
| S | propyl | OCOOMe | 4-oxazolyl |
| S | propyl | OCOOMe | 5-oxazolyl |
| S | propyl | OCOOMe | 2-thiazolyl |
| S | propyl | OCOOMe | 4-thiazolyl |
| S | propyl | OCOOMe | 5-thiazolyl |
| S | propyl | OCOOMe | 2-pyrimidinyl |
| S | propyl | OCOOMe | 4-pyrimidinyl |
| S | propyl | OCOOMe | 5-pyrimidinyl |
| S | propyl | OCOOMe | 2-indolyl |
| S | propyl | OCOOMe | 3-indolyl |
| S | propyl | OCOOMe | 5-indolyl |
| S | propyl | OCOOMe | 6-indolyl |
| S | propyl | OCOOMe | 5-benzimidazolyl |
| S | propyl | OCOOMe | 2-benzofuryl |
| S | propyl | OCOOMe | 3-indazolyl |
| S | propyl | OCOOMe | 2-benzoxazolyl |
| S | propyl | OCOOMe | 4-fluoro-1-naphthyl |
| S | propyl | OCOOMe | 5-chloro-2-thienyl |
| S | propyl | OCOOMe | 4-methyl-1-naphthyl |
| S | propyl | OCOOMe | 1-methyl-2-pyrrolyl |
| S | propyl | OCOOMe | 2-methyl-3-furyl |
| S | propyl | OCOOMe | 5-methyl-2-thienyl |
| S | propyl | OCOOMe | 4-methyl-5-imidazolyl |
| S | propyl | OCOOMe | 1-methyl-3-indolyl |
| S | propyl | OCOOMe | 2-methoxy-1-naphthyl |
| S | propyl | OCOOMe | 3-methoxy-2-naphthyl |
| S | propyl | OCOOMe | 6-ethoxy-2-naphthyl |
| S | propyl | OCOOMe | 5-methoxy-3-indolyl |
| S | propyl | OCOOMe | 1,4-dimethoxy-2-naphthyl |
| S | propyl | OCOOMe | 5,6-dimethoxy-2-indolyl |
| S | propyl | OCOOMe | 5-methoxy-1-methyl-2-indolyl |
| S | propyl | OCOOEt | 1-naphthyl |
| S | propyl | OCOOEt | 2-naphthyl |
| S | propyl | OCOOEt | 2-pyrrolyl |
| S | propyl | OCOOEt | 3-pyrrolyl |
| S | propyl | OCOOEt | 2-furyl |
| S | propyl | OCOOEt | 3-furyl |
| S | propyl | OCOOEt | 2-thienyl |
| S | propyl | OCOOEt | 3-thienyl |
| S | propyl | OCOOEt | 3-pyrazolyl |
| S | propyl | OCOOEt | 4-pyrazolyl |
| S | propyl | OCOOEt | 2-imidazolyl |
| S | propyl | OCOOEt | 4-imidazolyl |
| S | propyl | OCOOEt | 2-oxazolyl |
| S | propyl | OCOOEt | 4-oxazolyl |
| S | propyl | OCOOEt | 5-oxazolyl |
| S | propyl | OCOOEt | 2-thiazolyl |

TABLE 1-continued

| X | R¹ | R² | Y |
|---|---|---|---|
| S | propyl | OCOOEt | 4-thiazolyl |
| S | propyl | OCOOEt | 5-thiazolyl |
| S | propyl | OCOOEt | 2-pyrimidinyl |
| S | propyl | OCOOEt | 4-pyrimidinyl |
| S | propyl | OCOOEt | 5-pyrimidinyl |
| S | propyl | OCOOEt | 2-indolyl |
| S | propyl | OCOOEt | 3-indolyl |
| S | propyl | OCOOEt | 5-indolyl |
| S | propyl | OCOOEt | 6-indolyl |
| S | propyl | OCOOEt | 5-benzimidazolyl |
| S | propyl | OCOOEt | 2-benzofuryl |
| S | propyl | OCOOEt | 3-indazolyl |
| S | propyl | OCOOEt | 2-benzoxazolyl |
| S | propyl | OCOOEt | 4-fluoro-1-naphthyl |
| S | propyl | OCOOEt | 5-chloro-2-thienyl |
| S | propyl | OCOOEt | 4-methyl-1-naphthyl |
| S | propyl | OCOOEt | 1-methyl-2-pyrrolyl |
| S | propyl | OCOOEt | 2-methyl-3-furyl |
| S | propyl | OCOOEt | 5-methyl-2-thienyl |
| S | propyl | OCOOEt | 4-methyl-5-imidazolyl |
| S | propyl | OCOOEt | 1-methyl-3-indolyl |
| S | propyl | OCOOEt | 2-methoxy-1-naphthyl |
| S | propyl | OCOOEt | 3-methoxy-2-naphthyl |
| S | propyl | OCOOEt | 6-ethoxy-2-naphthyl |
| S | propyl | OCOOEt | 5-methoxy-3-indolyl |
| S | propyl | OCOOEt | 1,4-dimethoxy-2-naphthyl |
| S | propyl | OCOOEt | 5,6-dimethoxy-2-indolyl |
| S | propyl | OCOOEt | 5-methoxy-1-methyl-2-indolyl |
| S | n-butyl | OH | 1-naphthyl |
| S | n-butyl | OH | 2-naphthyl |
| S | n-butyl | OH | 2-pyrrolyl |
| S | n-butyl | OH | 3-pyrrolyl |
| S | n-butyl | OH | 2-furyl |
| S | n-butyl | OH | 3-furyl |
| S | n-butyl | OH | 2-thienyl |
| S | n-butyl | OH | 3-thienyl |
| S | n-butyl | OH | 3-pyrazolyl |
| S | n-butyl | OH | 4-pyrazolyl |
| S | n-butyl | OH | 2-imidazolyl |
| S | n-butyl | OH | 4-imidazolyl |
| S | n-butyl | OH | 2-oxazolyl |
| S | n-butyl | OH | 4-oxazolyl |
| S | n-butyl | OH | 5-oxazolyl |
| S | n-butyl | OH | 2-thiazolyl |
| S | n-butyl | OH | 4-thiazolyl |
| S | n-butyl | OH | 5-thiazolyl |
| S | n-butyl | OH | 2-pyrimidinyl |
| S | n-butyl | OH | 4-pyrimidinyl |
| S | n-butyl | OH | 5-pyrimidinyl |
| S | n-butyl | OH | 2-indolyl |
| S | n-butyl | OH | 3-indolyl |
| S | n-butyl | OH | 5-indolyl |
| S | n-butyl | OH | 6-indolyl |
| S | n-butyl | OH | 5-benzimidazolyl |
| S | n-butyl | OH | 2-benzofuryl |
| S | n-butyl | OH | 3-indazolyl |
| S | n-butyl | OH | 2-benzoxazolyl |
| S | n-butyl | OH | 4-fluoro-1-naphthyl |
| S | n-butyl | OH | 5-chloro-2-thienyl |
| S | n-butyl | OH | 4-methyl-1-naphthyl |
| S | n-butyl | OH | 1-methyl-2-pyrrolyl |
| S | n-butyl | OH | 2-methyl-3-furyl |
| S | n-butyl | OH | 5-methyl-2-thienyl |
| S | n-butyl | OH | 4-methyl-5-imidazolyl |
| S | n-butyl | OH | 1-methyl-3-indolyl |
| S | n-butyl | OH | 2-methoxy-1-naphthyl |
| S | n-butyl | OH | 3-methoxy-2-naphthyl |
| S | n-butyl | OH | 6-ethoxy-2-naphthyl |
| S | n-butyl | OH | 5-methoxy-3-indolyl |
| S | n-butyl | OH | 1,4-dimethoxy-2-naphthyl |
| S | n-butyl | OH | 5,6-dimethoxy-2-indolyl |
| S | n-butyl | OH | 5-methoxy-1-methyl-2-indolyl |
| S | n-butyl | OCOOMe | 1-naphthyl |
| S | n-butyl | OCOOMe | 2-naphthyl |
| S | n-butyl | OCOOMe | 2-pyrrolyl |
| S | n-butyl | OCOOMe | 3-pyrrolyl |
| S | n-butyl | OCOOMe | 2-furyl |
| S | n-butyl | OCOOMe | 3-furyl |
| S | n-butyl | OCOOMe | 2-thienyl |
| S | n-butyl | OCOOMe | 3-thienyl |
| S | n-butyl | OCOOMe | 3-pyrazolyl |
| S | n-butyl | OCOOMe | 4-pyrazolyl |
| S | n-butyl | OCOOMe | 2-imidazolyl |
| S | n-butyl | OCOOMe | 4-imidazolyl |
| S | n-butyl | OCOOMe | 2-oxazolyl |
| S | n-butyl | OCOOMe | 4-oxazolyl |
| S | n-butyl | OCOOMe | 5-oxazolyl |
| S | n-butyl | OCOOMe | 2-thiazolyl |
| S | n-butyl | OCOOMe | 4-thiazolyl |
| S | n-butyl | OCOOMe | 5-thiazolyl |
| S | n-butyl | OCOOMe | 2-pyrimidinyl |
| S | n-butyl | OCOOMe | 4-pyrimidinyl |
| S | n-butyl | OCOOMe | 5-pyrimidinyl |
| S | n-butyl | OCOOMe | 2-indolyl |
| S | n-butyl | OCOOMe | 3-indolyl |
| S | n-butyl | OCOOMe | 5-indolyl |
| S | n-butyl | OCOOMe | 6-indolyl |
| S | n-butyl | OCOOMe | 5-benzimidazolyl |
| S | n-butyl | OCOOMe | 2-benzofuryl |
| S | n-butyl | OCOOMe | 3-indazolyl |
| S | n-butyl | OCOOMe | 2-benzoxazolyl |
| S | n-butyl | OCOOMe | 4-fluoro-1-naphthyl |
| S | n-butyl | OCOOMe | 5-chloro-2-thienyl |
| S | n-butyl | OCOOMe | 4-methyl-1-naphthyl |
| S | n-butyl | OCOOMe | 1-methyl-2-pyrrolyl |
| S | n-butyl | OCOOMe | 2-methyl-3-furyl |
| S | n-butyl | OCOOMe | 5-methyl-2-thienyl |
| S | n-butyl | OCOOMe | 4-methyl-5-imidazolyl |
| S | n-butyl | OCOOMe | 1-methyl-3-indolyl |
| S | n-butyl | OCOOMe | 2-methoxy-1-naphthyl |
| S | n-butyl | OCOOMe | 3-methoxy-2-naphthyl |
| S | n-butyl | OCOOMe | 6-ethoxy-2-naphthyl |
| S | n-butyl | OCOOMe | 5-methoxy-3-indolyl |
| S | n-butyl | OCOOMe | 1,4-dimethoxy-2-naphthyl |
| S | n-butyl | OCOOMe | 5,6-dimethoxy-2-indolyl |
| S | n-butyl | OCOOMe | 5-methoxy-1-methyl-2-indolyl |
| S | n-butyl | OCOOEt | 1-naphthyl |
| S | n-butyl | OCOOEt | 2-naphthyl |
| S | n-butyl | OCOOEt | 2-pyrrolyl |
| S | n-butyl | OCOOEt | 3-pyrrolyl |
| S | n-butyl | OCOOEt | 2-furyl |
| S | n-butyl | OCOOEt | 3-furyl |
| S | n-butyl | OCOOEt | 2-thienyl |
| S | n-butyl | OCOOEt | 3-thienyl |
| S | n-butyl | OCOOEt | 3-pyrazolyl |
| S | n-butyl | OCOOEt | 4-pyrazolyl |
| S | n-butyl | OCOOEt | 2-imidazolyl |
| S | n-butyl | OCOOEt | 4-imidazolyl |
| S | n-butyl | OCOOEt | 2-oxazolyl |
| S | n-butyl | OCOOEt | 4-oxazolyl |
| S | n-butyl | OCOOEt | 5-oxazolyl |
| S | n-butyl | OCOOEt | 2-thiazolyl |
| S | n-butyl | OCOOEt | 4-thiazolyl |
| S | n-butyl | OCOOEt | 5-thiazolyl |
| S | n-butyl | OCOOEt | 2-pyrimidinyl |
| S | n-butyl | OCOOEt | 4-pyrimidinyl |
| S | n-butyl | OCOOEt | 5-pyrimidinyl |
| S | n-butyl | OCOOEt | 2-indolyl |
| S | n-butyl | OCOOEt | 3-indolyl |
| S | n-butyl | OCOOEt | 5-indolyl |
| S | n-butyl | OCOOEt | 6-indolyl |
| S | n-butyl | OCOOEt | 5-benzimidazolyl |
| S | n-butyl | OCOOEt | 2-benzofuryl |
| S | n-butyl | OCOOEt | 3-indazolyl |
| S | n-butyl | OCOOEt | 2-benzoxazolyl |
| S | n-butyl | OCOOEt | 4-fluoro-1-naphthyl |
| S | n-butyl | OCOOEt | 5-chloro-2-thienyl |
| S | n-butyl | OCOOEt | 4-methyl-1-naphthyl |
| S | n-butyl | OCOOEt | 1-methyl-2-pyrrolyl |
| S | n-butyl | OCOOEt | 2-methyl-3-furyl |
| S | n-butyl | OCOOEt | 5-methyl-2-thienyl |
| S | n-butyl | OCOOEt | 4-methyl-5-imidazolyl |
| S | n-butyl | OCOOEt | 1-methyl-3-indolyl |
| S | n-butyl | OCOOEt | 2-methoxy-2-naphthyl |

TABLE 1-continued

| X | R¹ | R² | Y |
|---|----|----|---|
| S | n-butyl | OCOOEt | 3-methoxy-2-naphthyl |
| S | n-butyl | OCOOEt | 6-ethoxy-2-naphthyl |
| S | n-butyl | OCOOEt | 5-methoxy-3-indolyl |
| S | n-butyl | OCOOEt | 1,4-dimethoxy-2-naphthyl |
| S | n-butyl | OCOOEt | 5,6-dimethoxy-2-indolyl |
| S | n-butyl | OCOOEt | 5-methoxy-1-methyl-2-indolyl |
| S | n-pentyl | OH | 1-naphthyl |
| S | n-pentyl | OH | 2-naphthyl |
| S | n-pentyl | OH | 2-pyrrolyl |
| S | n-pentyl | OH | 3-pyrrolyl |
| S | n-pentyl | OH | 2-furyl |
| S | n-pentyl | OH | 3-furyl |
| S | n-pentyl | OH | 2-thienyl |
| S | n-pentyl | OH | 3-thienyl |
| S | n-pentyl | OH | 3-pyrazolyl |
| S | n-pentyl | OH | 4-pyrazolyl |
| S | n-pentyl | OH | 2-imidazolyl |
| S | n-pentyl | OH | 4-imidazolyl |
| S | n-pentyl | OH | 2-oxazolyl |
| S | n-pentyl | OH | 4-oxazolyl |
| S | n-pentyl | OH | 5-oxazolyl |
| S | n-pentyl | OH | 2-thiazolyl |
| S | n-pentyl | OH | 4-thiazolyl |
| S | n-pentyl | OH | 5-thiazolyl |
| S | n-pentyl | OH | 2-pyrimidinyl |
| S | n-pentyl | OH | 4-pyrimidinyl |
| S | n-pentyl | OH | 5-pyrimidinyl |
| S | n-pentyl | OH | 2-indolyl |
| S | n-pentyl | OH | 3-indolyl |
| S | n-pentyl | OH | 5-indolyl |
| S | n-pentyl | OH | 6-indolyl |
| S | n-pentyl | OH | 5-benzimidazolyl |
| S | n-pentyl | OH | 2-benzofuryl |
| S | n-pentyl | OH | 3-indazolyl |
| S | n-pentyl | OH | 2-benzoxazolyl |
| S | n-pentyl | OH | 4-fluoro-1-naphthyl |
| S | n-pentyl | OH | 5-chloro-2-thienyl |
| S | n-pentyl | OH | 4-methyl-1-naphthyl |
| S | n-pentyl | OH | 1-methyl-2-pyrrolyl |
| S | n-pentyl | OH | 2-methyl-3-furyl |
| S | n-pentyl | OH | 5-methyl-2-thienyl |
| S | n-pentyl | OH | 4-methyl-5-imidazolyl |
| S | n-pentyl | OH | 1-methyl-3-indolyl |
| S | n-pentyl | OH | 2-methoxy-1-naphthyl |
| S | n-pentyl | OH | 3-methoxy-2-naphthyl |
| S | n-pentyl | OH | 6-ethoxy-2-naphthyl |
| S | n-pentyl | OH | 5-methoxy-3-indolyl |
| S | n-pentyl | OH | 1,4-dimethoxy-2-naphthyl |
| S | n-pentyl | OH | 5,6-dimethoxy-2-indolyl |
| S | n-pentyl | OH | 5-methoxy-1-methyl-2-indolyl |
| S | n-pentyl | OCOOMe | 1-naphthyl |
| S | n-pentyl | OCOOMe | 2-naphthyl |
| S | n-pentyl | OCOOMe | 2-pyrrolyl |
| S | n-pentyl | OCOOMe | 3-pyrrolyl |
| S | n-pentyl | OCOOMe | 2-furyl |
| S | n-pentyl | OCOOMe | 3-furyl |
| S | n-pentyl | OCOOMe | 2-thienyl |
| S | n-pentyl | OCOOMe | 3-thienyl |
| S | n-pentyl | OCOOMe | 3-pyrazolyl |
| S | n-pentyl | OCOOMe | 4-pyrazolyl |
| S | n-pentyl | OCOOMe | 2-imidazolyl |
| S | n-pentyl | OCOOMe | 4-imidazolyl |
| S | n-pentyl | OCOOMe | 2-oxazolyl |
| S | n-pentyl | OCOOMe | 4-oxazolyl |
| S | n-pentyl | OCOOMe | 5-oxazolyl |
| S | n-pentyl | OCOOMe | 2-thiazolyl |
| S | n-pentyl | OCOOMe | 4-thiazolyl |
| S | n-pentyl | OCOOMe | 5-thiazolyl |
| S | n-pentyl | OCOOMe | 2-pyrimidinyl |
| S | n-pentyl | OCOOMe | 4-pyrimidinyl |
| S | n-pentyl | OCOOMe | 5-pyrimidinyl |
| S | n-pentyl | OCOOMe | 2-indolyl |
| S | n-pentyl | OCOOMe | 3-indolyl |
| S | n-pentyl | OCOOMe | 5-indolyl |
| S | n-pentyl | OCOOMe | 6-indolyl |
| S | n-pentyl | OCOOMe | 5-benzimidazolyl |
| S | n-pentyl | OCOOMe | 2-benzofuryl |
| S | n-pentyl | OCOOMe | 3-indazolyl |
| S | n-pentyl | OCOOMe | 2-benzoxazolyl |
| S | n-pentyl | OCOOMe | 4-fluoro-1-naphthyl |
| S | n-pentyl | OCOOMe | 5-chloro-2-thienyl |
| S | n-pentyl | OCOOMe | 4-methyl-1-naphthyl |
| S | n-pentyl | OCOOMe | 1-methyl-2-pyrrolyl |
| S | n-pentyl | OCOOMe | 2-methyl-3-furyl |
| S | n-pentyl | OCOOMe | 5-methyl-2-thienyl |
| S | n-pentyl | OCOOMe | 4-methyl-5-imidazolyl |
| S | n-pentyl | OCOOMe | 1-methyl-3-indolyl |
| S | n-pentyl | OCOOMe | 2-methoxy-1-naphthyl |
| S | n-pentyl | OCOOMe | 3-methoxy-2-naphthyl |
| S | n-pentyl | OCOOMe | 6-ethoxy-2-naphthyl |
| S | n-pentyl | OCOOMe | 5-methoxy-3-indolyl |
| S | n-pentyl | OCOOMe | 1,4-dimethoxy-2-naphthyl |
| S | n-pentyl | OCOOMe | 5,6-dimethoxy-2-indolyl |
| S | n-pentyl | OCOOMe | 5-methoxy-1-methyl-2-indolyl |
| S | n-pentyl | OCOOEt | 1-naphthyl |
| S | n-pentyl | OCOOEt | 2-naphthyl |
| S | n-pentyl | OCOOEt | 2-pyrrolyl |
| S | n-pentyl | OCOOEt | 3-pyrrolyl |
| S | n-pentyl | OCOOEt | 2-furyl |
| S | n-pentyl | OCOOEt | 3-furyl |
| S | n-pentyl | OCOOEt | 2-thienyl |
| S | n-pentyl | OCOOEt | 3-thienyl |
| S | n-pentyl | OCOOEt | 3-pyrazolyl |
| S | n-pentyl | OCOOEt | 4-pyrazolyl |
| S | n-pentyl | OCOOEt | 2-imidazolyl |
| S | n-pentyl | OCOOEt | 4-imidazolyl |
| S | n-pentyl | OCOOEt | 2-oxazolyl |
| S | n-pentyl | OCOOEt | 4-oxazolyl |
| S | n-pentyl | OCOOEt | 5-oxazolyl |
| S | n-pentyl | OCOOEt | 2-thiazolyl |
| S | n-pentyl | OCOOEt | 4-thiazolyl |
| S | n-pentyl | OCOOEt | 5-thiazolyl |
| S | n-pentyl | OCOOEt | 2-pyrimidinyl |
| S | n-pentyl | OCOOEt | 4-pyrimidinyl |
| S | n-pentyl | OCOOEt | 5-pyrimidinyl |
| S | n-pentyl | OCOOEt | 2-indolyl |
| S | n-pentyl | OCOOEt | 3-indolyl |
| S | n-pentyl | OCOOEt | 5-indolyl |
| S | n-pentyl | OCOOEt | 6-indolyl |
| S | n-pentyl | OCOOEt | 5-benzimidazolyl |
| S | n-pentyl | OCOOEt | 2-benzofuryl |
| S | n-pentyl | OCOOEt | 3-indazolyl |
| S | n-pentyl | OCOOEt | 2-benzoxazolyl |
| S | n-pentyl | OCOOEt | 4-fluoro-1-naphthyl |
| S | n-pentyl | OCOOEt | 5-chloro-2-thienyl |
| S | n-pentyl | OCOOEt | 4-methyl-1-naphthyl |
| S | n-pentyl | OCOOEt | 1-methyl-2-pyrrolyl |
| S | n-pentyl | OCOOEt | 2-methyl-3-furyl |
| S | n-pentyl | OCOOEt | 5-methyl-2-thienyl |
| S | n-pentyl | OCOOEt | 4-methyl-5-imidazolyl |
| S | n-pentyl | OCOOEt | 1-methyl-3-indolyl |
| S | n-pentyl | OCOOEt | 2-methoxy-1-naphthyl |
| S | n-pentyl | OCOOEt | 3-methoxy-2-naphthyl |
| S | n-pentyl | OCOOEt | 6-ethoxy-2-naphthyl |
| S | n-pentyl | OCOOEt | 5-methoxy-3-indolyl |
| S | n-pentyl | OCOOEt | 1,4-dimethoxy-2-naphthyl |
| S | n-pentyl | OCOOEt | 5,6-dimethoxy-2-indolyl |
| S | n-pentyl | OCOOEt | 5-methoxy-1-methyl-2-indolyl |
| NH | 2-methoxyethyl | OH | 1-naphthyl |
| NH | 2-methoxyethyl | OH | 2-naphthyl |
| NH | 2-methoxyethyl | OH | 2-pyrrolyl |
| NH | 2-methoxyethyl | OH | 3-pyrrolyl |
| NH | 2-methoxyethyl | OH | 2-furyl |
| NH | 2-methoxyethyl | OH | 3-furyl |
| NH | 2-methoxyethyl | OH | 2-thienyl |
| NH | 2-methoxyethyl | OH | 3-thienyl |
| NH | 2-methoxyethyl | OH | 3-pyrazolyl |
| NH | 2-methoxyethyl | OH | 4-pyrazolyl |
| NH | 2-methoxyethyl | OH | 2-imidazolyl |
| NH | 2-methoxyethyl | OH | 4-imidazolyl |
| NH | 2-methoxyethyl | OH | 2-oxazolyl |
| NH | 2-methoxyethyl | OH | 4-oxazolyl |
| NH | 2-methoxyethyl | OH | 5-oxazolyl |
| NH | 2-methoxyethyl | OH | 2-thiazolyl |

TABLE 1-continued

| X | R¹ | R² | Y |
|---|---|---|---|
| NH | 2-methoxyethyl | OH | 4-thiazolyl |
| NH | 2-methoxyethyl | OH | 5-thiazolyl |
| NH | 2-methoxyethyl | OH | 2-pyrimidinyl |
| NH | 2-methoxyethyl | OH | 4-pyrimidinyl |
| NH | 2-methoxyethyl | OH | 5-pyrimidinyl |
| NH | 2-methoxyethyl | OH | 2-indolyl |
| NH | 2-methoxyethyl | OH | 3-indolyl |
| NH | 2-methoxyethyl | OH | 5-indolyl |
| NH | 2-methoxyethyl | OH | 6-indolyl |
| NH | 2-methoxyethyl | OH | 5-benzimidazolyl |
| NH | 2-methoxyethyl | OH | 2-benzofuryl |
| NH | 2-methoxyethyl | OH | 3-indazolyl |
| NH | 2-methoxyethyl | OH | 2-benzoxazolyl |
| NH | 2-methoxyethyl | OH | 4-fluoro-1-naphthyl |
| NH | 2-methoxyethyl | OH | 5-chloro-2-thienyl |
| NH | 2-methoxyethyl | OH | 4-methyl-1-naphthyl |
| NH | 2-methoxyethyl | OH | 1-methyl-2-pyrrolyl |
| NH | 2-methoxyethyl | OH | 2-methyl-3-furyl |
| NH | 2-methoxyethyl | OH | 5-methyl-2-thienyl |
| NH | 2-methoxyethyl | OH | 4-methyl-5-imidazolyl |
| NH | 2-methoxyethyl | OH | 1-methyl-3-indolyl |
| NH | 2-methoxyethyl | OH | 2-methoxy-1-naphthyl |
| NH | 2-methoxyethyl | OH | 3-methoxy-2-naphthyl |
| NH | 2-methoxyethyl | OH | 6-ethoxy-2-naphthyl |
| NH | 2-methoxyethyl | OH | 5-methoxy-3-indolyl |
| NH | 2-methoxyethyl | OH | 1,4-dimethoxy-2-naphthyl |
| NH | 2-methoxyethyl | OH | 5,6-dimethoxy-2-indolyl |
| NH | 2-methoxyethyl | OH | 5-methoxy-1-methyl-2-indolyl |
| NH | 3-methoxypropyl | OH | 1-naphthyl |
| NH | 3-methoxypropyl | OH | 2-naphthyl |
| NH | 3-methoxypropyl | OH | 2-pyrrolyl |
| NH | 3-methoxypropyl | OH | 3-pyrrolyl |
| NH | 3-methoxypropyl | OH | 2-furyl |
| NH | 3-methoxypropyl | OH | 3-furyl |
| NH | 3-methoxypropyl | OH | 2-thienyl |
| NH | 3-methoxypropyl | OH | 3-thienyl |
| NH | 3-methoxypropyl | OH | 3-pyrazolyl |
| NH | 3-methoxypropyl | OH | 4-pyrazolyl |
| NH | 3-methoxypropyl | OH | 2-imidazolyl |
| NH | 3-methoxypropyl | OH | 4-imidazolyl |
| NH | 3-methoxypropyl | OH | 2-oxazolyl |
| NH | 3-methoxypropyl | OH | 4-oxazolyl |
| NH | 3-methoxypropyl | OH | 5-oxazolyl |
| NH | 3-methoxypropyl | OH | 2-thiazolyl |
| NH | 3-methoxypropyl | OH | 4-thiazolyl |
| NH | 3-methoxypropyl | OH | 5-thiazolyl |
| NH | 3-methoxypropyl | OH | 2-pyrimidinyl |
| NH | 3-methoxypropyl | OH | 4-pyrimidinyl |
| NH | 3-methoxypropyl | OH | 5-pyrimidinyl |
| NH | 3-methoxypropyl | OH | 2-indolyl |
| NH | 3-methoxypropyl | OH | 3-indolyl |
| NH | 3-methoxypropyl | OH | 5-indolyl |
| NH | 3-methoxypropyl | OH | 6-indolyl |
| NH | 3-methoxypropyl | OH | 5-benzimidazolyl |
| NH | 3-methoxypropyl | OH | 2-benzofuryl |
| NH | 3-methoxypropyl | OH | 3-indazolyl |
| NH | 3-methoxypropyl | OH | 2-benzoxazolyl |
| NH | 3-methoxypropyl | OH | 4-fluoro-1-naphthyl |
| NH | 3-methoxypropyl | OH | 5-chloro-2-thienyl |
| NH | 3-methoxypropyl | OH | 4-methyl-1-naphthyl |
| NH | 3-methoxypropyl | OH | 1-methyl-2-pyrrolyl |
| NH | 3-methoxypropyl | OH | 2-methyl-3-furyl |
| NH | 3-methoxypropyl | OH | 5-methyl-2-thienyl |
| NH | 3-methoxypropyl | OH | 4-methyl-5-imidazolyl |
| NH | 3-methoxypropyl | OH | 1-methyl-3-indolyl |
| NH | 3-methoxypropyl | OH | 2-methoxy-1-naphthyl |
| NH | 3-methoxypropyl | OH | 3-methoxy-2-naphthyl |
| NH | 3-methoxypropyl | OH | 6-ethoxy-2-naphthyl |
| NH | 3-methoxypropyl | OH | 5-methoxy-3-indolyl |
| NH | 3-methoxypropyl | OH | 1,4-dimethoxy-2-naphthyl |
| NH | 3-methoxypropyl | OH | 5,6-dimethoxy-2-indolyl |
| NH | 3-methoxypropyl | OH | 5-methoxy-1-methyl-2-indolyl |
| O | 2-methoxyethyl | OH | 1-naphthyl |
| O | 2-methoxyethyl | OH | 2-naphthyl |
| O | 2-methoxyethyl | OH | 2-pyrrolyl |
| O | 2-methoxyethyl | OH | 3-pyrrolyl |
| O | 2-methoxyethyl | OH | 2-furyl |
| O | 2-methoxyethyl | OH | 3-furyl |
| O | 2-methoxyethyl | OH | 2-thienyl |
| O | 2-methoxyethyl | OH | 3-thienyl |
| O | 2-methoxyethyl | OH | 3-pyrazolyl |
| O | 2-methoxyethyl | OH | 4-pyrazolyl |
| O | 2-methoxyethyl | OH | 2-imidazolyl |
| O | 2-methoxyethyl | OH | 4-imidazolyl |
| O | 2-methoxyethyl | OH | 2-oxazolyl |
| O | 2-methoxyethyl | OH | 4-oxazolyl |
| O | 2-methoxyethyl | OH | 5-oxazolyl |
| O | 2-methoxyethyl | OH | 2-thiazolyl |
| O | 2-methoxyethyl | OH | 4-thiazolyl |
| O | 2-methoxyethyl | OH | 5-thiazolyl |
| O | 2-methoxyethyl | OH | 2-pyrimidinyl |
| O | 2-methoxyethyl | OH | 4-pyrimidinyl |
| O | 2-methoxyethyl | OH | 5-pyrimidinyl |
| O | 2-methoxyethyl | OH | 2-indolyl |
| O | 2-methoxyethyl | OH | 3-indolyl |
| O | 2-methoxyethyl | OH | 5-indolyl |
| O | 2-methoxyethyl | OH | 6-indolyl |
| O | 2-methoxyethyl | OH | 5-benzimidazolyl |
| O | 2-methoxyethyl | OH | 2-benzofuryl |
| O | 2-methoxyethyl | OH | 3-indazolyl |
| O | 2-methoxyethyl | OH | 2-benzoxazolyl |
| O | 2-methoxyethyl | OH | 4-fluoro-1-naphthyl |
| O | 2-methoxyethyl | OH | 5-chloro-2-thienyl |
| O | 2-methoxyethyl | OH | 4-methyl-1-naphthyl |
| O | 2-methoxyethyl | OH | 1-methyl-2-pyrrolyl |
| O | 2-methoxyethyl | OH | 2-methyl-3-furyl |
| O | 2-methoxyethyl | OH | 5-methyl-2-thienyl |
| O | 2-methoxyethyl | OH | 4-methyl-5-imidazolyl |
| O | 2-methoxyethyl | OH | 1-methyl-3-indolyl |
| O | 2-methoxyethyl | OH | 2-methoxy-1-naphthyl |
| O | 2-methoxyethyl | OH | 3-methoxy-2-naphthyl |
| O | 2-methoxyethyl | OH | 6-ethoxy-2-naphthyl |
| O | 2-methoxyethyl | OH | 5-methoxy-3-indolyl |
| O | 2-methoxyethyl | OH | 1,4-dimethoxy-2-naphthyl |
| O | 2-methoxyethyl | OH | 5,6-dimethoxy-2-indolyl |
| O | 2-methoxyethyl | OH | 5-methoxy-1-methyl-2-indolyl |
| O | 3-methoxypropyl | OH | 1-naphthyl |
| O | 3-methoxypropyl | OH | 2-naphthyl |
| O | 3-methoxypropyl | OH | 2-pyrrolyl |
| O | 3-methoxypropyl | OH | 3-pyrrolyl |
| O | 3-methoxypropyl | OH | 2-furyl |
| O | 3-methoxypropyl | OH | 3-furyl |
| O | 3-methoxypropyl | OH | 2-thienyl |
| O | 3-methoxypropyl | OH | 3-thienyl |
| O | 3-methoxypropyl | OH | 3-pyrazolyl |
| O | 3-methoxypropyl | OH | 4-pyrazolyl |
| O | 3-methoxypropyl | OH | 2-imidazolyl |
| O | 3-methoxypropyl | OH | 4-imidazolyl |
| O | 3-methoxypropyl | OH | 2-oxazolyl |
| O | 3-methoxypropyl | OH | 4-oxazolyl |
| O | 3-methoxypropyl | OH | 5-oxazolyl |
| O | 3-methoxypropyl | OH | 2-thiazolyl |
| O | 3-methoxypropyl | OH | 4-thiazolyl |
| O | 3-methoxypropyl | OH | 5-thiazolyl |
| O | 3-methoxypropyl | OH | 2-pyrimidinyl |
| O | 3-methoxypropyl | OH | 4-pyrimidinyl |
| O | 3-methoxypropyl | OH | 5-pyrimidinyl |
| O | 3-methoxypropyl | OH | 2-indolyl |
| O | 3-methoxypropyl | OH | 3-indolyl |
| O | 3-methoxypropyl | OH | 5-indolyl |
| O | 3-methoxypropyl | OH | 6-indolyl |
| O | 3-methoxypropyl | OH | 5-benzimidazolyl |
| O | 3-methoxypropyl | OH | 2-benzofuryl |
| O | 3-methoxypropyl | OH | 3-indazolyl |
| O | 3-methoxypropyl | OH | 2-benzoxazolyl |
| O | 3-methoxypropyl | OH | 4-fluoro-1-naphthyl |
| O | 3-methoxypropyl | OH | 5-chloro-2-thienyl |
| O | 3-methoxypropyl | OH | 4-methyl-1-naphthyl |
| O | 3-methoxypropyl | OH | 1-methyl-2-pyrrolyl |
| O | 3-methoxypropyl | OH | 2-methyl-3-furyl |
| O | 3-methoxypropyl | OH | 5-methyl-2-thienyl |
| O | 3-methoxypropyl | OH | 4-methyl-5-imidazolyl |
| O | 3-methoxypropyl | OH | 1-methyl-3-indolyl |
| O | 3-methoxypropyl | OH | 2-methoxy-1-naphthyl |

TABLE 1-continued

| X | R¹ | R² | Y |
|---|---|---|---|
| O | 3-methoxypropyl | OH | 3-methoxy-2-naphthyl |
| O | 3-methoxypropyl | OH | 6-ethoxy-2-naphthyl |
| O | 3-methoxypropyl | OH | 5-methoxy-3-indolyl |
| O | 3-methoxypropyl | OH | 1,4-dimethoxy-2-naphthyl |
| O | 3-methoxypropyl | OH | 5,6-dimethoxy-2-indolyl |
| O | 3-methoxypropyl | OH | 5-methoxy-1-methyl-2-indolyl |
| S | 2-methoxyethyl | OH | 1-naphthyl |
| S | 2-methoxyethyl | OH | 2-naphthyl |
| S | 2-methoxyethyl | OH | 2-pyrrolyl |
| S | 2-methoxyethyl | OH | 3-pyrrolyl |
| S | 2-methoxyethyl | OH | 2-furyl |
| S | 2-methoxyethyl | OH | 3-furyl |
| S | 2-methoxyethyl | OH | 2-thienyl |
| S | 2-methoxyethyl | OH | 3-thienyl |
| S | 2-methoxyethyl | OH | 3-pyrazolyl |
| S | 2-methoxyethyl | OH | 4-pyrazolyl |
| S | 2-methoxyethyl | OH | 2-imidazolyl |
| S | 2-methoxyethyl | OH | 4-imidazolyl |
| S | 2-methoxyethyl | OH | 2-oxazolyl |
| S | 2-methoxyethyl | OH | 4-oxazolyl |
| S | 2-methoxyethyl | OH | 5-oxazolyl |
| S | 2-methoxyethyl | OH | 2-thiazolyl |
| S | 2-methoxyethyl | OH | 4-thiazolyl |
| S | 2-methoxyethyl | OH | 5-thiazolyl |
| S | 2-methoxyethyl | OH | 2-pyrimidinyl |
| S | 2-methoxyethyl | OH | 4-pyrimidinyl |
| S | 2-methoxyethyl | OH | 5-pyrimidinyl |
| S | 2-methoxyethyl | OH | 2-indolyl |
| S | 2-methoxyethyl | OH | 3-indolyl |
| S | 2-methoxyethyl | OH | 5-indolyl |
| S | 2-methoxyethyl | OH | 6-indolyl |
| S | 2-methoxyethyl | OH | 5-benzimidazolyl |
| S | 2-methoxyethyl | OH | 2-benzofuryl |
| S | 2-methoxyethyl | OH | 3-indazolyl |
| S | 2-methoxyethyl | OH | 2-benzoxazolyl |
| S | 2-methoxyethyl | OH | 4-fluoro-1-naphthyl |
| S | 2-methoxyethyl | OH | 5-chloro-2-thienyl |
| S | 2-methoxyethyl | OH | 4-methyl-1-naphthyl |
| S | 2-methoxyethyl | OH | 1-methyl-2-pyrrolyl |
| S | 2-methoxyethyl | OH | 2-methyl-3-furyl |
| S | 2-methoxyethyl | OH | 5-methyl-2-thienyl |
| S | 2-methoxyethyl | OH | 4-methyl-5-imidazolyl |
| S | 2-methoxyethyl | OH | 1-methyl-3-indolyl |
| S | 2-methoxyethyl | OH | 2-methoxy-1-naphthyl |
| S | 2-methoxyethyl | OH | 3-methoxy-2-naphthyl |
| S | 2-methoxyethyl | OH | 6-ethoxy-2-naphthyl |
| S | 2-methoxyethyl | OH | 5-methoxy-3-indolyl |
| S | 2-methoxyethyl | OH | 1,4-dimethoxy-2-naphthyl |
| S | 2-methoxyethyl | OH | 5,6-dimethoxy-2-indolyl |
| S | 2-methoxyethyl | OH | 5-methoxy-1-methyl-2-indolyl |
| S | 2-hydroxyethyl | OH | 1-naphthyl |
| S | 2-hydroxyethyl | OH | 2-naphthyl |
| S | 2-hydroxyethyl | OH | 2-pyrrolyl |
| S | 2-hydroxyethyl | OH | 3-pyrrolyl |
| S | 2-hydroxyethyl | OH | 2-furyl |
| S | 2-hydroxyethyl | OH | 3-furyl |
| S | 2-hydroxyethyl | OH | 2-thienyl |
| S | 2-hydroxyethyl | OH | 3-thienyl |
| S | 2-hydroxyethyl | OH | 3-pyrazolyl |
| S | 2-hydroxyethyl | OH | 4-pyrazolyl |
| S | 2-hydroxyethyl | OH | 2-imidazolyl |
| S | 2-hydroxyethyl | OH | 4-imidazolyl |
| S | 2-hydroxyethyl | OH | 2-oxazolyl |
| S | 2-hydroxyethyl | OH | 4-oxazolyl |
| S | 2-hydroxyethyl | OH | 5-oxazolyl |
| S | 2-hydroxyethyl | OH | 2-thiazolyl |
| S | 2-hydroxyethyl | OH | 4-thiazolyl |
| S | 2-hydroxyethyl | OH | 5-thiazolyl |
| S | 2-hydroxyethyl | OH | 2-pyrimidinyl |
| S | 2-hydroxyethyl | OH | 4-pyrimidinyl |
| S | 2-hydroxyethyl | OH | 5-pyrimidinyl |
| S | 2-hydroxyethyl | OH | 2-indolyl |
| S | 2-hydroxyethyl | OH | 3-indolyl |
| S | 2-hydroxyethyl | OH | 5-indolyl |
| S | 2-hydroxyethyl | OH | 6-indolyl |
| S | 2-hydroxyethyl | OH | 5-benzimidazolyl |
| S | 2-hydroxyethyl | OH | 2-benzofuryl |
| S | 2-hydroxyethyl | OH | 3-indazolyl |
| S | 2-hydroxyethyl | OH | 2-benzoxazolyl |
| S | 2-hydroxyethyl | OH | 4-fluoro-1-naphthyl |
| S | 2-hydroxyethyl | OH | 5-chloro-2-thienyl |
| S | 2-hydroxyethyl | OH | 4-methyl-1-naphthyl |
| S | 2-hydroxyethyl | OH | 1-methyl-2-pyrrolyl |
| S | 2-hydroxyethyl | OH | 2-methyl-3-furyl |
| S | 2-hydroxyethyl | OH | 5-methyl-2-thienyl |
| S | 2-hydroxyethyl | OH | 4-methyl-5-imidazolyl |
| S | 2-hydroxyethyl | OH | 1-methyl-3-indolyl |
| S | 2-hydroxyethyl | OH | 2-methoxy-1-naphthyl |
| S | 2-hydroxyethyl | OH | 3-methoxy-2-naphthyl |
| S | 2-hydroxyethyl | OH | 6-ethoxy-2-naphthyl |
| S | 2-hydroxyethyl | OH | 5-methoxy-3-indolyl |
| S | 2-hydroxyethyl | OH | 1,4-dimethoxy-2-naphthyl |
| S | 2-hydroxyethyl | OH | 5,6-dimethoxy-2-indolyl |
| S | 2-hydroxyethyl | OH | 5-methoxy-1-methyl-2-indolyl |

A compound in which $R^2$ represents acyloxy or alkoxycarbonyloxy according to the present invention is equivalent to ester of a compound in which $R^2$ represents hydroxyl. The compound is a prodrug that is aimed at improving solubility, absorbency, and biostability of a compound in which $R^2$ represents hydroxyl. That is, the above ester is metabolized in a living organism to an active form compound in which $R^2$ is hydroxyl. A compound represented by general formula (I) and a tautomer thereof are chemically equivalent. The adenine derivative according to the present invention includes the tautomer. For example, when $R^2$ represent hydroxyl, a compound represented by general formula (I) is a hydroxy derivative represented by general formula (II):

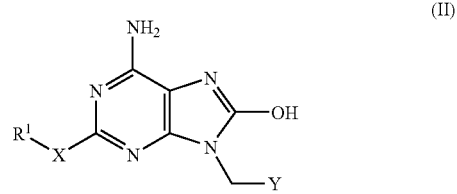

(II)

wherein $R^1$, X, and Y are as defined in general formula (I). An example of a tautomer of this derivative is an oxo derivative represented by general formula (III):

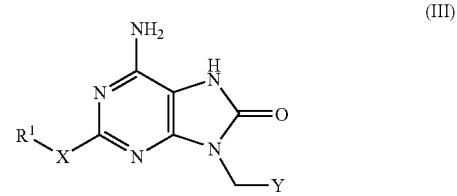

(III)

wherein $R^1$, X, and Y are as defined in general formula (I).

An embodiment of a process for producing these adenine derivatives is hereafter described in detail.

(1) When R² is OH

A compound (IV) is allowed to react with Y—CH₂-Hal (wherein Y is as defined in general formula (II) and Hal represents a halogen atom) in the presence of a base, thereby synthesizing a 9-substitution product (V). Examples of the aforementioned bases that can be used include alkali metal salt or alkaline earth metal salt of carbonic acid such as potassium carbonate, metal hydroxides such as sodium hydroxide and potassium hydroxide, metal hydrides such as sodium hydride, and alkoxides such as potassum t-butoxide. Examples of the aforementioned solvents that can be used include aprotic solvents such as dimethylformamide, dimethyl sulfoxide, tetrahydrofuran, and 1,4-dioxane. Reaction temperature can be between room temperature and reflux temperature of the solvent.

Subsequently, when X represents NH, a compound (V) is allowed to react with a corresponding R¹—NH₂ (wherein R¹ is as defined above) in the presence or absence of a base, thereby synthesizing a 2-substitution product (VI). Examples of bases that can be used include tertiary amines such as triethylamine, diisopropylethylamine, and 4-dimethylaminopyridine. Examples of solvents that can be used include aprotic solvents, such as tetrahydrofuran, 1,4-dioxane, and diglyme, and alcoholic solvents such as propanol or butanol. Alternatively, reaction may be carried out in the absence of a solvent. Reaction temperature can be between 50° C. and reflux temperature of the solvent.

When X represents an oxygen atom or sulfur atom, a compound (V) is allowed to react with a corresponding R¹—OH or R¹—SH in the presence of a base, thereby synthesizing a 2-substitution product (VI). Examples of bases that can be used include alkali metals such as sodium or potassium and alkali metal hydrides such as sodium hydride. Examples of solvents that can be used include aprotic solvents such as dimethylformamide, dimethyl sulfoxide, tetrahydrofuran, 1,4-dioxane, and diglyme. Alternatively, reaction may be carried out in the absence of a solvent. Reaction temperature can be between 50° C. and reflux temperature of the solvent.

In a process for producing a compound (VI) from a compound (IV), a compound (VI) can be obtained by first synthesizing a 2-substitution product (V'), followed by the reaction between the 2-substitution product (V') and Y—CH₂-Hal (wherein Y is as defined in general formula (II) and Hal represents a halogen atom).

A compound (VII) can be synthesized by reacting a compound (VI) with bromine. Examples of solvents that can be used include, halogenated solvents such as carbon tetrachloride, dichloromethane or chloroform, and acetic acid. Reaction temperature can be between 0° C. and reflux temperature of the solvent. Alternatively, a reaction assistant such as sodium acetate may be additionally used in the reaction.

A compound (IX) can be synthesized through hydrolysis of a compound (VII) under acidic conditions. Examples of acids that can be used include hydrochloric acid and hydrobromic acid. Reaction temperature can be between 50° C. and reflux temperature of the solvent. Alternatively, a compound (VII) is allowed to react with sodium methoxide to prepare a compound (VIII), and the resultant is treated with acid for demethylation. Thus, a compound (IX) can be obtained.

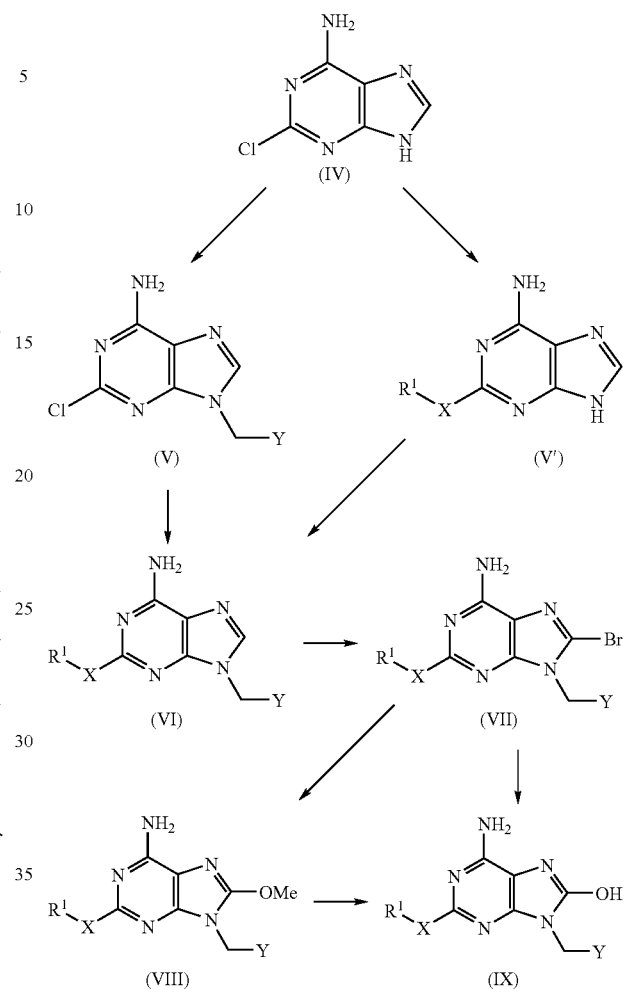

A compound (X) can be synthesized by reacting a compound (VII) with sodium hydrosulfide (sodium hydrogensulfide). Examples of solvents that can be used include alcoholic solvents such as ethanol, propanol, and butanol. Reaction temperature can be between 50° C. and reflux temperature of the solvent.

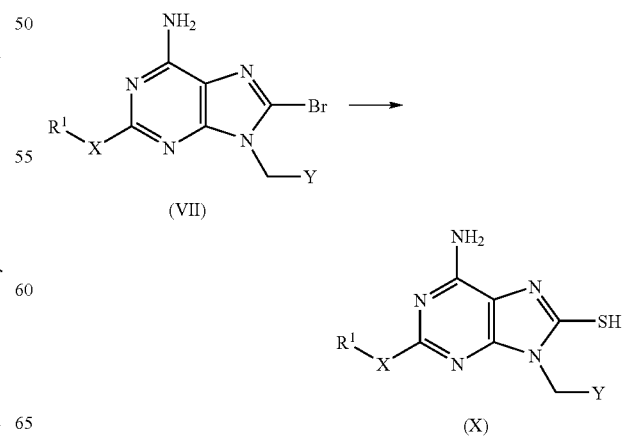

A compound (XI) can be obtained by allowing the compound (IX) to react with acyl chloride or chloroformate ester corresponding to $R^2$ in the presence of a base. Examples of bases that can be used include tertiary amines such as triethylamine, diisopropylethylamine, or 4-dimethylaminopyridine. Examples of solvents that can be used include aprotic solvents such as tetrahydrofuran, 1,4-dioxane, and dichloromethane. Reaction temperature can be between 0° C. and reflux temperature of the solvent (In the formula, $R^4$ represents $C_{1-7}$ alkyl or $C_{1-7}$ alkoxy).

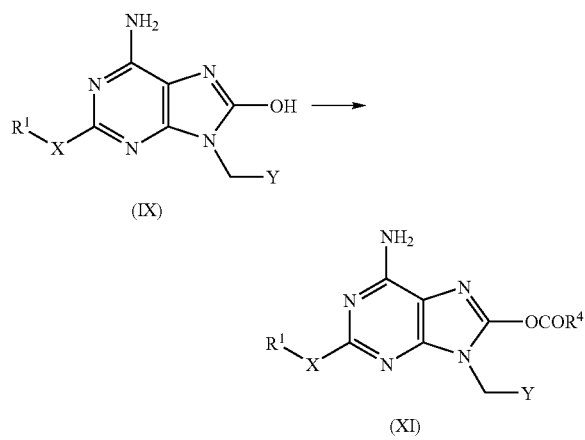

The thus obtained adenine derivative according to the present invention can be used as a pharmaceutically acceptable salt such as sodium salt, potassium salt, calcium salt, hydrochloride, hydrobromate, sulfate, nitrate, acetate, methanesulfonate, toluenesulfonate, citrate, fumarate, or maleate.

The adenine derivative according to the present invention is useful as a therapeutic agent for viral diseases such as hepatitis B, hepatitis C, and AIDS, cancerous diseases, and diseases resulting from type 2 helper T cells. It can be used in various dosage forms, for example, oral preparations such as a tablet, capsule, or powder. In addition, it can be parenteral injection or external preparation. The pharmaceutical preparation according to the present invention can be any substance selected from the group consisting of a compound represented by general formula (I), a tautomer thereof, and a pharmaceutically acceptable salt thereof. A hydrate or solvate thereof may also be used. Alternatively, two or more of these substances may be used in combinations. A substance itself that is selected from the aforementioned group may be administered as a pharmaceutical preparation according to the present invention. In general, however, it is preferably administered in a form of a pharmaceutical composition comprising, as an active ingredient, the aforementioned substance and a pharmaceutically acceptable additive for pharmaceutical preparations.

A pharmaceutical composition for organisms can be easily produced in accordance with a process that is common in the field of pharmaceutical preparations, wherein the aforementioned substance as an active ingredient is mixed with at least one pharmaceutically acceptable additive for pharmaceutical preparations. A route for administering the pharmaceutical preparation according to the present invention is not particularly limited. Preferably, the most effective route is suitably selected for therapy and/or prevention. Examples of pharmaceutical compositions that are suitable for oral administration include capsules, powders, tablets, granules, fine grains, syrups, liquids, and suspensions. Examples of pharmaceutical compositions that are suitable for parenteral administration include inhalants, sprays, intrarectal preparations, parenteral injections, drops, pastes, creams, percutaneous absorbents, transmucosal absorbents, eye drops, nasal drops, ear drops, tapes, and medical applications. It should be noted that the forms of the pharmaceutical preparation according to the present invention are not limited thereto.

Among the pharmaceutical compositions suitable for oral administration, for example, liquid preparations such as emulsions and syrups can be produced using additives for pharmaceutical preparations. Examples thereof include: water; saccharine such as sucrose, sorbit, and fructose; glycols such as polyethylene glycol and propylene glycol; oils such as sesame oil, olive oil, and soybean oil; antiseptics such as p-hydroxybenzoate; and flavors such as strawberry flavor and peppermint. Solid preparations such as capsules, tablets, powders, and granules can be produced using: for example, excipients such as lactose, glucose, sucrose, and mannite; disintegrators such as starch and sodium alginate; lubricants such as magnesium stearate and talc; binders such as polyvinyl alcohol, hydroxypropylcellulose, and gelatin; surfactants such as fatty acid ester; and plasticizers such as glycerin.

Among pharmaceutical compositions suitable for parenteral administration, liquid preparations such as parenteral injections, drops, and eye drops can be preferably produced as sterilized isotonic liquid preparations. For example, parenteral injections can be produced using an aqueous medium comprising a mixture of a salt solution, a glucose solution, or salt water and a glucose solution. Intrarectal preparations can be generally produced in a form of suppository using, for example, a carrier such as cacao butter, hydrogenated fat, or hydrogenated carboxylic acid. Sprays can be prepared using nonirritating carriers that allow the aforementioned substances as active ingredients to be dispersed as fine particles to facilitate absorption. Examples of such carriers include lactose and glycerin. A form of aerosol or dry powder preparation can be selected. Also, at least one additive for pharmaceutical preparations selected from diluent, flavor, antiseptics, excipient, disintegrator, lubricant, binder, surfactant, plasticizer, and the like as exemplified in the production of oral preparation can be suitably used to produce a pharmaceutical composition for parenteral administration. It should be noted that additives for pharmaceutical preparations that are used to produce the pharmaceutical preparation according to the present invention are not limited to the aforementioned substances. Any substance can be used as long as it is available to persons skilled in the art.

The dose of the adenine derivative according to the present invention is suitably determined depending on, for example, sex, age, body weight, type of disease, or symptom of a patient. The dose is generally in the range of 0.001 to 100 mg/kg per day, and preferably in the range of 0.01 to 10 mg/kg. Administration can be made in single or several separate doses.

This description includes part or all of the content as disclosed in the description of Japanese Patent Application No. 2001-118232, which is a priority document of the present application.

BEST MODES FOR CARRYING OUT THE INVENTION

Figure 1:
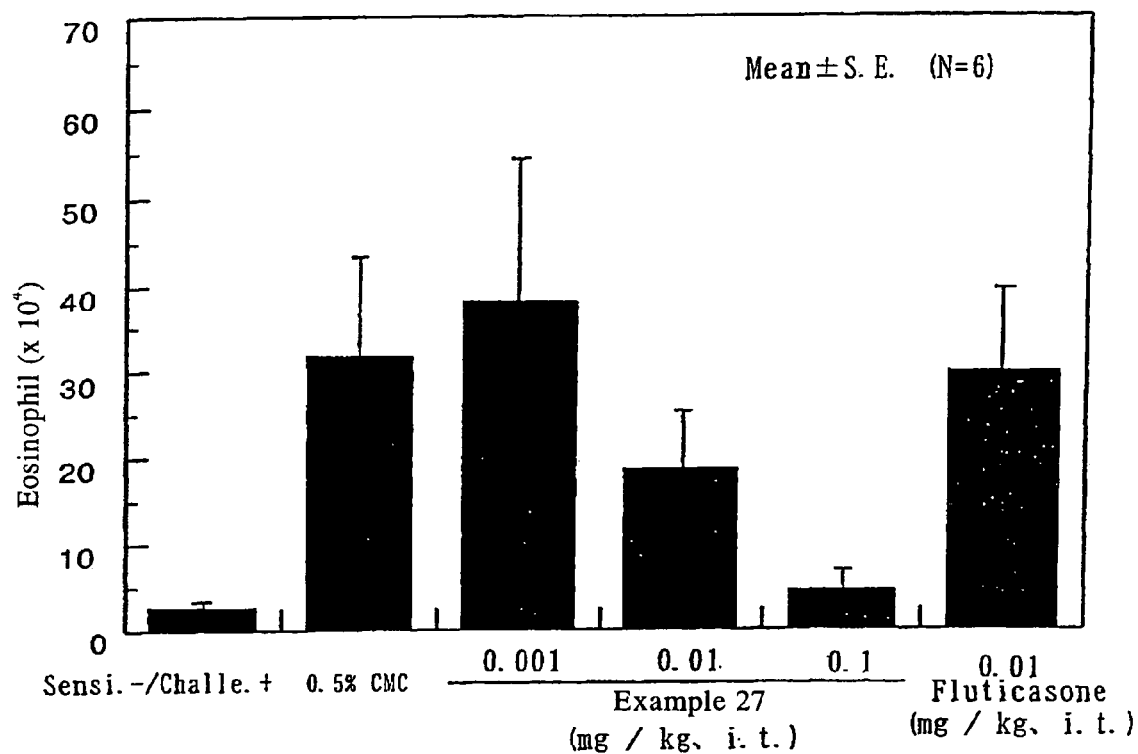
FIG. 1 is a diagram showing the result of evaluation for the medicinal effect of the compound according to the present invention in a rat model of eosinophil leukocytic infiltration.

The present invention is hereafter described in detail with reference to the examples, although the technical scope of the present invention is not limited thereto.

Reference Example 1

2-Butoxyadenine

Sodium (13.6 g, 0.59 mol) was added to butanol (480 ml), the temperature of the mixture was raised to 90° C. to completely dissolve sodium therein. Subsequently, 2-chloroadenine (4.0 g, 23.6 mmol) was added, and the resultant was heated under reflux for 9 hours. After the reaction solution was cooled to 4° C., water (400 ml) was added thereto, and the resultant was vigorously stirred for 30 minutes. The separated layer of butanol was concentrated under reduced pressure, water (400 ml) was added to the residue, and concentrated hydrochloric acid was added dropwide under ice cooling to neutralize the product. The precipitated solid was collected by filtration, the resulting solid was added to ethanol (70 ml), and the resultant was heated under reflux for 30 minutes. The product was cooled to room temperature, and the precipitated solid was then collected by filtration. Thus, 3.72 g of the title compound was obtained (yield: 76%).

Reference Example 2

8-Bromo-2-butoxy-9-(6-chloro-3-pyridylmethyl) adenine

Potassium carbonate (2.85 g, 20.6 mmol) and 2-chloro-5-chloromethylpyridine (3.33 g, 20.6 mmol) were added to the DMF solution (125 ml) of 2-butoxyadenine (2.60 g, 12.5 mmol) obtained in Reference Example 1. The resultant was stirred while heating at 80° C. for 2.5 hours. The reaction solution was concentrated under reduced pressure, water (100 ml) was added thereto, and the resultant was neutralized with 1N hydrochloric acid. The precipitated solid was collected by filtration. The resulting solid was dissolved in methylene chloride (100 ml), hexane (150 ml) was added under ice cooling, and the precipitated crystal was collected by filtration. Thus, 2-butoxy-9-(6-chloro-3-pyridylmethyl) adenine was obtained (yield: 3.12 g). Bromine (1.92 ml, 37.5 mmol) was added to an acetic acid suspension (186 ml) comprising sodium acetate (3.05 g, 37.2 mmol) and 2-butoxy-9-(6-chloro-3-pyridylmethyl)adenine (3.1 g, 9.31 mmol) at room temperature, and the resultant was allowed to react for 4 hours. The reaction solution was removed by distillation under reduced pressure, water (200 ml) was added to the residue, and the resultant was neutralized with 5N sodium hydroxide under ice cooling. The precipitated crystal was collected by filtration, and crude crystal was recrystalized with the aid of methanol. The resultant was dried under reduced pressure at 40° C. for 15 hours. Thus, 2.38 g of the title compound was obtained as a white powdery crystal (yield: 62%).

Reference Example 3

2-Butoxy-9-(6-chloro-3-pyridylmethyl)-8-methoxyadenine

Sodium (614 mg, 26.7 mmol) was added and completely dissolved in methanol (110 ml). 8-Bromo-2-butoxy-9-(6-chloro-3-pyridylmethyl)adenine (2.2 g, 5.34 mmol) obtained in Reference Example 2 was added to the resulting solution, and the mixture was heated under reflux for 3.5 hours. The reaction solution was concentrated under reduced pressure, water (100 ml) was added to the residue, and the resultant was neutralized with concentrated hydrochloric acid under ice cooling. The precipitated solid was collected by filtration and washed with water (20 ml). This solid was recrystalized with the aid of ethyl acetate (30 ml) to obtain 1.26 g of the title compound as a white powdery crystal (yield: 65.0%).

Reference Example 4

2-Butoxy-9-(6-methoxy-3-pyridylmethyl)adenine

Sodium (415 mg, 18.0 mmol) was added and completely dissolved in methanol (18 ml). Thereafter, 2-butoxy-9-(6-chloro-3-pyridylmethyl)adenine (300 mg, 0.90 mmol) was added thereto, and the resultant was heated under reflux for 24 hours. The reaction solution was concentrated under reduced pressure, water (30 ml) was added to the residue, and the resultant was neutralized with concentrated hydrochloric acid under ice cooling. The precipitated solid was collected by filtration, and crude crystal was purified by silica gel column chromatography (methylene chloride:methanol=50:1) to obtain 148 mg of the title compound (yield: 50%).

Reference Example 5

2-Butylaminoadenine

2-Chloroadenine (6.0 g, 35.4 mmol) and butylamine (30 ml) were placed in an autoclave (200 ml), and the content of the autoclave was allowed to react at 130° C. for 150 hours. The reaction solution was concentrated under reduced pressure, and water was poured into the residue to precipitate a solid. The precipitated solid was sequentially washed with methylene chloride and methanol. Thus, 2.08 g of the title compound was obtained as a yellowish orange powdery solid (yield: 30%).

EXAMPLE 1

2-Butoxy-9-(6-chloro-3-pyridylmethyl)-8-hydroxyadenine

The compound (1.26 g, 3.47 mmol) obtained in Reference Example 3 was added to concentrated hydrochloric acid (70 ml), and the mixture was allowed to react at room temperature for 2 hours. The reaction solution was concentrated under reduced pressure, water (130 ml) was added to the residue, and the resultant was neutralized with an aqueous solution of 5N sodium hydroxide under ice cooling. The precipitated crystal was collected by filtration and then dried. Thus, 1.20 g of the title compound was obtained as a white powdery crystal (yield: 99%).

$^1$H NMR (DMSO-$d_6$) δ 10.14 (1H, brs), 8.40 (1H, d, J=2.4 Hz), 7.76 (1H, dd, J=2.4, 8.4 Hz), 7.49 (1H, d, J=8.4 Hz), 6.55 (2H, brs), 4.91 (2H, s), 4.14 (2H, t, J=6.5 Hz), 1.67–1.57 (2H, m), 1.44–1.30 (2H, m), 0.90 (3H, t, J=7.3 Hz).

EXAMPLE 2

2-Butoxy-8-hydroxy-9-(6-methoxy-3-pyridylmethyl)adenine

The title compound was obtained in the same manner as in Example 1 using a corresponding starting material.

$^1$H NMR (DMSO-$d_6$) δ 10.09 (1H, brs), 8.16 (1H, d, J=2.4 Hz), 7.65 (1H, dd, J=2.4, 8.4 Hz), 6.78 (1H, d, J=8.4 Hz), 6.49 (2H, brs), 4.80 (2H, s), 4.15 (2H, t, J=6.6 Hz), 3.81 (3H, s), 1.66–1.58 (2H, m), 1.42–1.34 (2H, m), 0.91 (3H, t, J=7.3 Hz).

EXAMPLE 3

2-Butoxy-9-(6-ethoxy-3-pyridylmethyl)-8-hydroxyadenine

The title compound was obtained in the same manner as in Example 1 using a corresponding starting material.

$^1$H NMR (DMSO-$d_6$) δ 10.06 (1H, brs), 8.14 (1H, d, J=2.4 Hz), 7.64 (1H, dd, J=2.4, 8.6 Hz), 6.75 (1H, d, J=8.6 Hz), 6.48 (2H, brs), 4.80 (2H, s), 4.26 (2H, q, J=7.2 Hz), 4.15 (2H, t, J=6.6 Hz), 1.68–1.58 (2H, m), 1.42–1.34 (2H, m), 1.28 (3H, t, J=7.2 Hz), 0.91 (3H, t, J=7.3 Hz).

EXAMPLE 4

2-Butoxy-9-(6-n-butoxy-3-pyridylmethyl)-8-hydroxyadenine

The title compound was obtained in the same manner as in Example 1 using a corresponding starting material.

$^1$H NMR (DMSO-$d_6$) δ 10.25 (1H, brs), 8.13 (1H, d, J=1.9 Hz), 7.63 (1H, dd, J=1.9, 8.4 Hz), 6.75 (1H, d, J=8.4 Hz), 6.53 (2H, brs), 4.79 (2H, s), 4.23–4.12 (4H, m), 1.68–1.60 (4H, m), 1.42–1.34 (4H, m), 0.94–0.88 (6H, m).

EXAMPLE 5

2-Butoxy-9-(2-chloro-3-pyridylmethyl)-8-hydroxyadenine

The title compound was obtained in the same manner as in Example 1 using a corresponding starting material.

$^1$H NMR (DMSO-$d_6$) δ 10.15 (1H, brs), 8.36–8.33 (1H, m), 7.52–7.50 (1H, m), 7.41–7.36 (1H, m), 6.53 (2H, brs), 4.94 (2H, s), 4.07 (2H, t, J=6.6 Hz), 1.62–1.52 (2H,m), 1.37–1.23 (2H, m), 0.87 (3H, t, J=7.3 Hz).

EXAMPLE 6

2-Butoxy-8-hydroxy-9-(2-methoxy-3-pyridylmethyl)adenine

The title compound was obtained in the same manner as in Example 1 using a corresponding starting material.

$^1$H NMR (DMSO-$d_6$) δ 10.06 (1H, brs), 8.08–8.06 (1H, m), 7.21–7.19 (1H, m), 6.93–6.88 (1H, m), 6.47 (2H, brs), 4.80 (2H, s), 4.08 (2H, t, J=6.5 Hz), 3.92 (3H, s), 1.60–1.52 (2H, m), 1.38–1.29 (2H, m), 0.87 (3H, t, J=7.3 Hz).

EXAMPLE 7

2-Butoxy-9-(6-chloro-5-methoxy-3-pyridylmethyl)-8-hydroxyadenine

The title compound was obtained in the same manner as in Example 1 using a corresponding starting material.

$^1$H NMR (DMSO-$d_6$) δ 10.06 (1H, brs), 8.12 (1H, d, J=1.9 Hz), 7.85 (1H, d, J=1.9 Hz), 6.49 (2H, brs), 4.83 (2H, s), 4.16 (2H, t, J=6.6 Hz), 3.91 (3H, s), 1.66–1.61 (2H, m), 1.42–1.34 (2H, m), 0.91 (3H, t, J=7.3 Hz).

EXAMPLE 8

2-Butoxy-8-hydroxy-9-(3-pyridylmethyl)adenine

Potassium carbonate (1.1 g, 8 mmol) and 3-chloromethylpyridine hydrochloride (660 mg, 5 mmol) were added to a DMF solution (30 ml) comprising 2-chloroadenine (520 mg, 3 mmol), and the resultant was stirred while heating at 80° C. for 3 hours. The reaction solution was concentrated under reduced pressure, water was added thereto, and the precipitated solid was collected by filtration. Thus, 2-chloro-9-(3-pyridylmethyl)adenine was obtained (yield: 759 mg). Sodium (750 mg, 30 mmol) was added to butanol (50 ml), and the temperature of the mixture was raised to 90° C. to completely dissolve sodium therein. Subsequently, 2-chloro-9-(3-pyridylmethyl)adenine (430 mg, 1.5 mmol) was added thereto, and the resultant was heated under reflux for 2 hours. The solvent was concentrated under reduced pressure, water was added to the residue, and concentrated hydrochloric acid was added dropwise under ice cooling to neutralize the solution. Liquid separation was carried out with the addition of methylene chloride, and the organic layer was concentrated under reduced pressure. Acetic acid (30 ml) was added to the residue to dissolve it, bromine (660 mg, 5.5 mmol) was added thereto, and the resultant was allowed to react at room temperature all day and night. The reaction solution was removed by distillation under reduced pressure, and the residue was purified by silica gel column chromatography (methylene chloride:methanol=10:1). Thus, 310 mg of 8-bromo-2-butoxy-9-(3-pyridylmethyl)adenine was obtained. Subsequently, the title compound was obtained in the same manner as in Reference Example 3 and Example 1.

$^1$H NMR (DMSO-$d_6$) δ 10.22 (1H, brs), 8.56 (1H, d, J=1.9 Hz), 8.49–8.47 (1H, m), 7.71–7.67 (1H, m), 7.38–7.33 (1H, m), 6.54 (2H, brs), 4.90 (2H, s), 4.14 (2H, t, J=6.6 Hz), 1.65–1.57 (2H, m), 1.41–1.33 (2H, m), 0.90 (3H, t, J=7.3 Hz).

EXAMPLE 9

2-Butoxy-8-hydroxy-9-(4-pyridylmethyl)adenine

The title compound was obtained in the same manner as in Example 1 using a corresponding starting material.

$^1$H NMR (DMSO-$d_6$) δ 10.20 (1H, brs), 8.70–8.68 (2H, m), 7.29–7.27 (2H, m), 6.48 (2H, brs), 4.92 (2H, s), 4.16 (2H, t, J=6.6 Hz), 1.63–1.55 (2H, m), 1.40–1.32 (2H, m), 0.89 (3H, t, J=7.3 Hz).

EXAMPLE 10

2-Butoxy-9-(pyrazin-2-ylmethyl)-8-methoxyadenine

The title compound was obtained in the same manner as in Example 1 using a corresponding starting material.

$^1$H NMR (DMSO-$d_6$) δ 10.02 (1H, brs), 8.66 (1H, s), 8.56–8.53 (2H, m), 6.48 (2H, brs), 5.05 (2H, s), 4.06 (2H, t, J=6.6 Hz), 1.59–1.51 (2H, m), 1.37–1.29 (2H, m), 0.87 (3H, t, J=7.3 Hz).

EXAMPLE 11

2-Butoxy-9-(5,6-dichloro-3-pyridylmethyl)-8-hydroxyadenine

Concentrated hydrochloric acid (4 ml) was added to a butanol suspension (4 ml) comprising 2-n-butoxy-8-bromo-9-(5,6-dichloro-3-pyridylmethyl)-8-hydroxyadenine (150 mg, 0.34 mmol) obtained in the same manner as in Reference Example 2, and the resultant was allowed to react at 70° C. for 9 hours. The reaction solution was concentrated under reduced pressure, water (30 ml) was added to the residue under ice cooling, and the solution was neutralized with an aqueous solution of 1N sodium hydroxide. The precipitated solid was collected by filtration, crude crystal was purified by silica gel column chromatography (methylene chloride:methanol=25:1), and 45 mg of the title compound was obtained as a white powdery crystal (yield: 35%).

$^1$H NMR (DMSO-$d_6$) δ 10.16 (1H, brs), 8.36 (1H, d, J=1.9 Hz), 8.06 (1H, d, J=1.9 Hz), 6.52 (2H, brs), 4.93 (2H, s), 4.13 (2H, t, J=6.6 Hz), 1.64–1.58 (2H, m), 1.40–1.32 (2H, m), 0.90 (3H, t, J=7.3 Hz).

EXAMPLE 12

2-Butoxy-9-(2,6-dichloro-3-pyridylmethyl)-8-hydroxyadenine

The title compound was obtained in the same manner as in Example 11 using a corresponding starting material.

$^1$H NMR (DMSO-$d_6$) δ 10.12 (1H, brs), 7.66 (1H, d, J=8.4 Hz), 7.52 (1H, d, J=8.4 Hz), 6.52 (2H, brs), 4.92 (2H, s), 4.08 (2H, t, J=6.6 Hz), 1.60–1.52 (2H, m), 1.37–1.29 (2H, m), 0.88 (3H, t, J=7.4 Hz).

EXAMPLE 13

2-Butoxy-9-(6-piperidino-3-pyridylmethyl)-8-hydroxyadenine

The compound (100 mg, 0.29 mmol) obtained in Example 1 was added to piperidine (3 ml), and the resultant was allowed to react at 90° C. for 30 hours. The reaction solution was concentrated under reduced pressure, and methylene chloride (50 ml) was added to the residue to precipitate a solid. The precipitated solid was collected by filtration and washed with water. Thus, 56 mg of the title compound was obtained as a white powdery solid (yield: 49%).

$^1$H NMR (DMSO-$d_6$) δ 9.79 (1H, brs), 8.09 (1H, d, J=2.4 Hz), 7.47 (1H, dd, J=2.4, 8.6 Hz), 6.75 (1H, d, J=8.6 Hz), 6.44 (2H, brs), 4.70 (2H, s), 4.17 (2H, t, J=6.5 Hz), 3.48–3.44 (4H, m), 1.67–1.35 (10H, m), 0.92 (3H, t, J=7.3 Hz).

EXAMPLE 14

2-Butoxy-9-(6-(1-pyrrolidinyl)-3-pyridylmethyl)-8-hydroxyadenine

The title compound was obtained in the same manner as in Example 13 using the compound obtained in Example 1 and pyrrolidine.

$^1$H NMR (DMSO-$d_6$) δ 10.03 (1H, brs), 8.07 (1H, d, J=2.4 Hz), 7.46 (1H, dd, J=2.4, 8.6 Hz), 6.45 (2H, brs), 6.37 (1H, d, J=8.6 Hz), 4.69 (2H, s), 4.16 (2H, t, J=6.6 Hz), 3.33–3.29 (4H, m), 1.93–1.88 (4H, m), 1.67–1.59 (2H, m), 1.43–1.35 (2H, m), 0.92 (3H, t, J=7.3 Hz).

EXAMPLE 15

2-Butoxy-9-(6-morpholino-3-pyridylmethyl)-8-hydroxyadenine

The title compound was obtained in the same manner as in Example 13 using the compound obtained in Example 1 and morpholine.

$^1$H NMR (DMSO-$d_6$) δ 10.01 (1H, brs), 8.14 (1H, d, J=2.4 Hz), 7.53 (1H, dd, J=2.4, 8.6 Hz), 6.78 (1H, d, J=8.6 Hz), 6.45 (2H, brs), 4.73 (2H, s), 4.16 (2H, t, J=6.6 Hz), 3.66 (4H, t, J=4.9 Hz), 3.38 (4H, t, J=4.9 Hz), 1.67–1.61 (2H, m), 1.43–1.35 (2H, m), 0.92 (3H, t, J=7.3 Hz).

EXAMPLE 16

2-Butoxy-9-(6-dimethylamino-3-pyridylmethyl)-8-hydroxyadenine

The title compound was obtained in the same manner as in Example 13 using the compound obtained in Example 1 and an aqueous solution of 40% dimethylamine.

$^1$H NMR (DMSO-$d_6$) δ 10.12 (1H, brs), 8.09 (1H, d, J=2.4 Hz), 7.48 (1H, dd, J=2.4, 8.9 Hz), 6.57 (1H, d, J=8.9 Hz), 6.49 (2H, brs), 4.70 (2H, s), 4.16 (2H, t, J=6.6 Hz), 2.97 (6H, s), 1.70–1.46 (2H, m), 1.43–1.33 (2H, m), 0.92 (3H, t, J=7.3 Hz).

EXAMPLE 17

2-Butylamino-9-(6-chloro-3-pyridylmethyl)-8-hydroxyadenine

The title compound was obtained in the same manner as in Example 11 using the compound obtained in Reference Example 5.

$^1$H NMR (DMSO-$d_6$) δ 10.10 (1H, brs), 8.56 (1H, d, J=1.9 Hz), 8.49–8.47 (1H, m), 7.71–7.67 (1H, m), 7.38–7.33 (1H, m), 6.50 (2H, brs), 4.90 (2H, s), 4.14 (2H, t, J=6.6 Hz), 1.67–1.57 (2H, m), 1.41–1.30 (2H, m), 0.90 (3H, t, J=7.3 Hz).

EXAMPLE 18

2-Butylamino-9-(2-chloro-3-pyridylmethyl)-8-hydroxyadenine

The title compound was obtained in the same manner as in Example 11 using the compound obtained in Reference Example 5.

$^1$H NMR (DMSO-$d_6$) δ 9.76 (1H, brs), 8.35–8.32 (1H, m), 7.47–7.36 (2H, m), 6.23 (1H, brt, J=5.7 Hz), 6.07 (2H, s), 4.88 (2H, s), 3.13–3.05 (2H, m), 1.43–1.27 (2H, m), 1.24–1.16 (2H, m), 0.82 (3H, t, J=7.3 Hz).

EXAMPLE 19

2-Butylamino-8-hydroxy-9-(6-methoxy-3-pyridylmethyl)adenine

The title compound was obtained in the same manner as in Example 11 using the compound obtained in Reference Example 5.

$^1$H NMR (DMSO-$d_6$) δ 10.07 (1H, brs), 8.17 (1H, d, J=2.4 Hz), 7.67 (1H, dd, J=2.4, 8.4 Hz), 6.82–6.76 (2H, m), 6.60 (2H, brs), 4.78 (2H, s), 3.81 (3H, s), 3.25–3.17 (2H, m), 1.54–1.43 (2H, m), 1.38–1.25 (2H, m), 0.89 (3H, t, J=7.3 Hz).

EXAMPLE 20

2-Butylamino-8-hydroxy-9-(2-pyridylmethyl)adenine

The title compound was obtained in the same manner as in Example 11 using the compound obtained in Reference Example 5.

$^1$H NMR (DMSO-$d_6$) δ 10.88 (1H, s), 8.56–8.54 (1H, m), 8.05–7.89 (3H, m), 7.46–7.41 (2H, m), 5.05 (3H, s), 3.19–3.14 (2H, m), 1.44–1.21 (4H, m), 0.81 (3H, t, J=7.3 Hz).

EXAMPLE 21

2-Butylamino-8-hydroxy-9-(3-pyridylmethyl)adenine

The title compound was obtained in the same manner as in Example 11 using the compound obtained in Reference Example 5.

$^1$H NMR (DMSO-$d_6$) δ 9.78 (1H, brs), 8.55 (1H, d, J=2.4 Hz), 8.47 (1H, dd, J=1.9, 4.9 Hz), 7.68 (1H, d, J=7.8 Hz), 7.34 (1H, dd, J=4.9, 7.8 Hz), 6.21 (1H, brt, J=5.5 Hz), 6.05 (2H, brs), 4.84 (2H, s), 3.20–3.12 (2H, m), 1.47–1.39 (2H, m), 1.32–1.24 (2H, m), 0.87 (3H, t, J=7.3 Hz).

EXAMPLE 22

2-Butylamino-8-hydroxy-9-(4-pyridylmethyl)adenine

The title compound was obtained in the same manner as in Example 11 using the compound obtained in Reference Example 5.

$^1$H NMR (DMSO-$d_6$) δ 11.05 (1H, brs), 8.76 (2H, d, J=8.7 Hz), 8.09–7.88 (3H, m), 7.73 (2H, d, J=8.7 Hz), 5.09 (2H, s), 3.22–3.17 (2H, m), 1.47–1.32 (2H, m), 1.29–1.18 (2H, m), 0.82 (3H, t, J=7.4 Hz).

EXAMPLE 23

2-Butylamino-9-(2,6-dichloro-3-pyridylmethyl)-8-hydroxyadenine

The title compound was obtained in the same manner as in Example 11 using the compound obtained in Reference Example 5.

$^1$H NMR (DMSO-$d_6$) δ 9.82 (1H, brs), 7.61–7.51 (2H, m), 6.23 (1H, brt, J=5.4 Hz), 6.08 (2H, s), 4.87 (2H, s), 3.12–3.05 (2H, m), 1.40–1.19 (4H, m), 0.82 (3H, t, J=7.3 Hz).

EXAMPLE 24

2-Butylamino-9-(6-dimethylamino-3-pyridylmethyl)-8-hydroxyadenine

The title compound was obtained in the same manner as in Example 13 using the compound obtained in Example 17 and an aqueous solution of 40% dimethylamine.

$^1$H NMR (DMSO-$d_6$) δ 9.61 (1H, brs), 8.10 (1H, d, J=2.2 Hz), 7.49 (1H, dd, J=2.2, 8.6 Hz), 6.56 (1H, d, J=8.6 Hz), 6.18 (1H, brt, J=5.7 Hz), 5.97 (2H, brs), 4.65 (2H, s), 3.22–3.15 (2H, m), 2.97 (6H, s), 1.53–1.42 (2H, m), 1.38–1.24 (2H, m), 0.89 (3H, t, J=7.3 Hz).

EXAMPLE 25

2-Butoxy-8-hydroxy-9-(6-methyl-3-pyridylmethyl)adenine

The title compound was obtained in the same manner as in Example 1 using a corresponding starting material.

$^1$H NMR (DMSO-$d_6$) δ 9.95 (1H, s), 8.42 (1H, d, J=2.2 Hz), 7.58 (1H, dd, J=2.2, 8.1 Hz), 7.20 (1H, d, J=8.1 Hz), 6.46 (2H, brs), 4.84 (2H, s), 4.14 (2H, t, J=6.6 Hz), 2.41 (3H, s), 1.62 (2H, m), 1.37 (2H, m), 0.90 (3H, t, J=7.3 Hz).

EXAMPLE 26

2-Butoxy-8-hydroxy-9-(2-methyl-3-pyridylmethyl)adenine

The title compound was obtained in the same manner as in Example 1 using a corresponding starting material.

$^1$H NMR (DMSO-$d_6$) δ 10.01 (1H, brs), 8.33 (1H, d, J=3.1 Hz), 7.39 (1H, d, J=6.4 Hz), 7.15 (1H, dd, J=3.1, 6.4 Hz), 6.49 (2H, brs), 4.88 (2H, s), 4.10 (2H, t, J=6.6 Hz), 2.59 (3H, s), 1.59 (2H, m), 1.34 (2H, m), 0.88 (3H, t, J=7.3 Hz).

EXAMPLE 27

2-Butylamino-8-hydroxy-9-(6-methyl-3-pyridylmethyl)adenine

The title compound was obtained in the same manner as in Example 11 using the compound obtained in Reference Example 5.

$^1$H NMR (DMSO-$d_6$) δ 9.78 (1H, s), 8.42 (1H, d, J=2.2 Hz), 7.57 (1H, dd, J=2.2, 8.0 Hz), 7.19 (1H, d, J=8.0 Hz), 6.22 (1H, t, J=7.1 Hz), 6.09 (2H, brs), 4.78 (2H, s), 3.16 (2H, m), 2.41 (3H, s), 1.44 (2H, m), 1.28 (2H, m), 0.87 (3H, t, J=9.6 Hz).

EXAMPLE 28

2-Butylamino-8-hydroxy-9-(2-methyl-3-pyridylmethyl)adenine

The title compound was obtained in the same manner as in Example 11 using the compound obtained in Reference Example 5.

$^1$H NMR (DMSO-$d_6$) δ 9.70 (1H, s), 8.32 (1H, d, J=3.1 Hz), 7.37 (1H, d, J=7.7 Hz), 7.14 (1H, dd, J=3.1, 7.7 Hz), 6.20 (1H, t, J=6.4 Hz), 6.0 (2H, brs), 4.82 (2H, s), 3.12 (2H, m), 2.60 (3H, s), 1.39 (2H, m), 1.25 (2H, m), 0.84 (3H, t, J=7.1 Hz).

EXAMPLE 29

2-Butylamino-9-(2-chloro-6-methyl-3-pyridylmethyl)-8-hydroxyadenine

The title compound was obtained in the same manner as in Example 11 using the compound obtained in Reference Example 5.

$^1$H NMR (DMSO-$d_6$) δ 9.74 (1H, brs), 7.33 (1H, d, J=5.8 Hz), 7.22 (1H, d, J=5.8 Hz), 6.24 (1H, m), 6.06 (2H, brs), 4.83 (2H, s), 3.09 (2H, m), 2.42 (3H, s), 1.37 (2H, m), 1.25 (2H, m), 0.82 (3H, t, J=5.5 Hz).

EXAMPLE 30

2-Butylamino-8-hydroxy-9-(6-hydroxy-3-pyridylmethyl)adenine

The title compound was obtained in the same manner as in Example 11 using the compound obtained in Reference Example 5.

$^1$H NMR (DMSO-$d_6$) δ 11.50 (1H, brs), 9.61 (1H, brs), 7.45 (1H, dd, J=2.6, 9.5 Hz), 7.28 (1H, d, J=2.6 Hz), 6.28 (1H, d, J=9.5 Hz), 6.22 (1H, t, J=6.2 Hz), 6.00 (2H, brs), 4.53 (2H, s), 3.17 (2H, q, J=6.2 Hz), 1.45 (2H, m), 1.30 (2H, m), 0.88 (3H, t, J=7.3 Hz).

EXAMPLE 31

8-Hydroxy-2-(2-methoxy)ethoxy-9-(3-pyridylmethyl)adenine

The title compound was obtained in the same manner as in Example 1 using a corresponding starting material.

$^1$H NMR (DMSO-$d_6$) δ 10.02 (1H, brs), 8.57 (1H, s), 8.48 (1H, d, J=4.8 Hz), 7.70 (1H, d, J=6.1 Hz), 7.36 (1H, dd, J=4.8, 6.1 Hz), 6.50 (2H, brs), 4.90 (2H, s), 4.27 (2H, t, J=4.6 Hz), 3.59 (2H, t, J=4.6 Hz), 3.27 (3H, s).

EXAMPLE 32

8-Hydroxy-2-methoxy-9-(3-pyridylmethyl)adenine

The title compound was obtained in the same manner as in Example 1.

$^1$H NMR (DMSO-$d_6$) δ 10.04 (1H, brs), 8.57 (1H, s), 8.48 (1H, d, J=4.8 Hz), 7.71 (1H, d, J=6.1 Hz), 7.35 (1H, dd, J=4.8, 6.1 Hz), 6.53 (2H, brs), 4.90 (2H, s), 3.76 (3H, s).

EXAMPLE 33

2-Butylamino-8-ethoxycarbonyloxy-9-(6-methoxy-3-pyridylmethyl)adenine

Triethylamine (100 μL, 0.75 mmol), ethyl chloroformate (67 μL, 0.70 mmol), and dimethylaminopyridine (20 mg, 0.17 mmol) were added to a solution (15 ml) of the compound (200 mg, 0.58 mmol) obtained in Example 19 in methylene chloride in that order, and the resultant was allowed to react at room temperature for 15 hours. Water was added to the reaction solution to extract an organic layer. The organic layer was washed with an aqueous solution of 5% citric acid and 10% saline solution and dried over anhydrous sodium sulfate. The solvent was then removed by distillation. Hexane was added to the residue, and the solid was precipitated, followed by collection by filtration. Thus, 170 mg of the title compound was obtained as a white powdery solid (yield: 71%).

$^1$H NMR (CDCl$_3$) δ 8.33 (1H, d, J=1.9 Hz), 7.75 (1H, dd, J=1.9, 8.4 Hz), 6.15 (2H, brs), 6.67 (1H, d, J=8.4 Hz), 4.87 (2H, s), 4.71 (1H, brt, J=5.4 Hz), 4.46 (2H, q, J=7.1 Hz), 3.90 (3H, s), 3.41–3.34 (2H, m), 1.60–1.35 (7H, m), 0.96 (3H, t, J=7.3 Hz).

EXAMPLE 34

2-Butylamino-9-(6-chloro-3-pyridylmethyl)-8-ethoxycarbonyloxyadenine

The title compound was obtained in the same manner as in Example 33 using the compound obtained in Example 17 and ethyl chloroformate.

$^1$H NMR (CDCl$_3$) δ 8.55 (1H, d, J=2.4 Hz), 7.81 (1H, dd, J=2.4, 8.4 Hz), 7.27 (1H, d, J=8.4 Hz), 6.06 (2H, brs), 4.93 (2H, s), 4.83 (1H, brt, J=5.5 Hz), 4.47 (2H, q, J=7.1 Hz), 3.40–3.32 (2H, m), 1.59–1.36 (7H, m), 0.95 (3H, t, J=7.3 Hz).

EXAMPLE 35

2-Butylamino-8-isopropoxycarbonyloxy-9-(6-methoxy-3-pyridylmethyl)adenine

The title compound was obtained in the same manner as in Example 33 using the compound obtained in Example 19 and isopropyl chloroformate.

$^1$H NMR (CDCl$_3$) δ 8.32 (1H, d, J=2.2 Hz), 7.74 (1H, dd, J=2.2, 8.9 Hz), 6.68 (1H, d, J=8.9 Hz), 6.08 (2H, brs), 5.23–5.13 (1H, m), 4.89 (1H, brt, J=5.8 Hz), 4.87 (2H, s), 3.91 (3H, s), 3.42–3.35 (2H, m), 1.60–1.52 (2H, m), 1.48–1.37 (8H, m), 0.96 (3H, t, J=7.3 Hz).

EXAMPLE 36

2-Butylamino-9-(6-chloro-3-pyridylmethyl)-8-isopropoxycarbonyloxyadenine.

The title compound was obtained in the same manner as in Example 33 using the compound obtained in Example 17 and isopropyl chloroformate.

$^1$H NMR (CDCl$_3$) δ 8.55 (1H, d, J=1.9 Hz), 7.80 (1H, dd, J=1.9, 8.4 Hz), 7.27 (1H, d, J=8.4 Hz), 6.14 (2H, brs), 5.24–5.14 (1H, m), 4.96–4.92 (3H, m), 3.40–3.33 (2H, m), 1.62–1.51 (2H, m), 1.45–1.34 (8H, m), 0.95 (3H, t, J=7.3 Hz).

EXAMPLE 37

2-Butoxy-8-ethoxycarbonyloxy-9-(6-methoxy-3-pyridylmethyl)adenine

The title compound was obtained in the same manner as in Example 33 using the compound obtained in Example 2 and ethyl chloroformate.

$^1$H NMR (CDCl$_3$) δ 8.33 (1H, d, J=2.4 Hz), 7.75 (1H, dd, J=2.4, 8.1 Hz), 6.68 (1H, d, J=8.1 Hz), 6.15 (2H, brs), 4.93 (2H, s), 4.48 (2H, q, J=7.1 Hz), 4.30 (2H, t, J=6.6 Hz), 3.90 (3H, s), 1.83–1.72 (2H, m), 1.53–1.43 (5H, m), 0.98 (3H, t, J=7.3 Hz).

EXAMPLE 38

2-Butoxy-9-(6-chloro-3-pyridylmethyl)-8-ethoxycarbonyloxyadenine

The title compound was obtained in the same manner as in Example 33 using the compound obtained in Example 1 and ethyl chloroformate.

$^1$H NMR (CDCl$_3$) δ 8.56 (1H, d, J=2.4 Hz), 7.81 (1H, dd, J=2.4, 8.4 Hz), 7.29 (1H, d, J=8.4 Hz), 7.28 (2H, brs), 4.99 (2H, s), 4.49 (2H, q, J=7.0 Hz), 4.28 (2H, t, J=6.6 Hz), 1.81–1.71 (2H, m), 1.52–1.43 (5H, m), 0.97 (3H, t, J=7.3 Hz).

EXAMPLE 39

2-Butoxy-9-(2-chloro-3-pyridylmethyl)-8-ethoxycarbonyloxyadenine

The title compound was obtained in the same manner as in Example 33 using the compound obtained in Example 5 and ethyl chloroformate.

$^1$H NMR (DMSO-d$_6$) δ 8.37–8.35 (1H, m), 7.73–7.69 (1H, m), 7.41–7.37 (1H, m), 7.09 (2H, brs), 4.95 (2H, s), 4.39 (2H, q, J=7.2 Hz), 4.12 (2H, t, J=6.6 Hz), 1.61–1.53 (2H, m), 1.37–1.29 (5H, m), 0.87 (3H, t, J=7.3 Hz).

EXAMPLE 40

2-Butoxy-8-methoxycarbonyloxy-9-(3-pyridylmethyl)adenine

The title compound was obtained in the same manner as in Example 33 using the compound obtained in Example 8 and methyl chloroformate.

$^1$H NMR (CDCl$_3$) δ 8.77 (1H, d, J=2.2 Hz), 8.56–8.53 (1H, m), 7.85–7.81 (1H, m), 7.25 (2H, brs), 7.24–7.22 (1H, m), 5.02 (2H, s), 4.30 (2H, t, J=6.6 Hz), 4.05 (3H, s), 1.82–1.72 (2H, m), 1.53–1.42 (2H, m), 0.97 (3H, t, J=7.3 Hz).

EXAMPLE 41

2-Butoxy-8-(n-pentyloxy)carbonyloxy-9-(3-pyridylmethyl)adenine

The title compound was obtained in the same manner as in Example 33 using the compound obtained in Example 8 and n-pentyl chloroformate.

$^1$H NMR (DMSO-d$_6$) δ 8.59 (1H, d, J=1.9 Hz), 8.51–8.48 (1H, m), 7.75–7.72 (1H, m), 7.39–7.34 (1H, m), 7.07 (2H, brs), 4.92 (2H, s), 4.32 (2H, t, J=6.6 Hz), 4.18 (2H, t, J=6.5 Hz), 1.71–1.61 (4H, m), 1.41–1.31 (6H, m), 0.93–0.85 (6H, m).

EXAMPLE 42

2-Butoxy-8-(cyclohexyloxy)carbonyloxy-9-(3-pyridylmethyl)adenine

The title compound was obtained in the same manner as in Example 33 using the compound obtained in Example 8 and cyclohexyl chloroformate.

$^1$H NMR (DMSO-d$_6$) δ 8.60 (1H, d, J=1.9 Hz), 8.51–8.49 (1H, m), 7.76–7.72 (1H, m), 7.39–7.35 (1H, m), 7.07 (2H, brs), 4.96–4.93 (3H, m), 4.18 (2H, t, J=6.5 Hz), 1.86–1.58 (8H, m), 1.44–1.33 (6H, m), 0.91 (3H, t, J=7.4 Hz).

EXAMPLE 43

8-(Allyloxy)carbonyloxy-2-butoxy-9-(3-pyridylmethyl)adenine

The title compound was obtained in the same manner as in Example 33 using the compound obtained in Example 8 and allyl chloroformate.

$^1$H NMR (DMSO-d$_6$) δ 8.61 (1H, d, J=1.9 Hz), 8.51–8.49 (1H, m), 7.77–7.74 (1H, m), 7.39–7.35 (1H, m), 7.25 (1H, dd, J=6.5, 13.8 Hz), 7.03 (2H, brs), 5.06 (1H, dd, J=1.9, 13.8 Hz), 4.93 (2H, s), 4.86 (1H, dd, J=1.9, 6.5 Hz), 4.19 (2H, t, J=6.6 Hz), 1.64–1.41 (2H, m), 1.39–1.33 (2H, m), 0.91 (3H, t, J=7.4 Hz).

EXAMPLE 44

8-Acetyloxy-2-butoxy-9-(6-chloro-3-pyridylmethyl)adenine

The title compound was obtained in the same manner as in Example 33 using the compound obtained in Example 17 and acetic anhydride.

$^1$H NMR (CDCl$_3$) δ 8.56 (1H, d, J=2.4 Hz), 7.80 (1H, dd, J=2.4, 8.4 Hz), 7.30 (1H, d, J=8.4 Hz), 7.28 (2H, brs), 5.00 (2H, s), 4.29 (2H, t, J=6.5 Hz), 2.72 (3H, s), 1.82–1.71 (2H, m), 1.52–1.42 (2H, m), 0.97 (3H, t, J=7.3 Hz).

EXAMPLE 45

8-Propionyloxy-2-butoxy-9-(6-chloro-3-pyridylmethyl)adenine

The title compound was obtained in the same manner as in Example 33 using the compound obtained in Example 17 and propionyl chloride.

$^1$H NMR (CDCl$_3$) δ 8.55 (1H, d, J=2.4 Hz), 7.80 (1H, dd, J=2.4, 8.1 Hz), 7.30 (1H, d, J=8.1 Hz), 7.28 (2H, brs), 5.00 (2H, s), 4.29 (2H, t, J=6.5 Hz), 3.14 (2H, q, J=7.4 Hz), 1.82–1.71 (2H, m), 1.55–1.42 (2H, m), 1.23 (3H, t, J=7.3 Hz), 0.97 (3H, t, J=7.3 Hz).

EXAMPLE 46

8-Benzoyloxy-2-butoxy-9-(6-methyl-3-pyridylmethyl)adenine

The title compound was obtained in the same manner as in Example 33 using the compound obtained in Example 25 and benzoyl chloride.

¹H NMR (CDCl₃) δ 8.64 (1H, d, J=2.4 Hz), 7.77 (2H, d, J=7.3 Hz), 7.69 (1H, dd, J=2.4, 8.1 Hz), 7.63 (1H, t, J=7.3 Hz), 7.49 (2H, t, J=7.3 Hz), 7.09 (1H, d, J=8.1 Hz), 5.76 (2H, brs), 4.95 (2H, s), 4.34 (2H, t, J=6.6 Hz), 2.52 (3H, s), 1.78 (2H, m), 1.52 (2H, m), 0.99 (3H, t, J=7.3 Hz).

EXAMPLE 47

8-Benzoyloxy-2-butylamino-9-(6-methyl-3-pyridyl-methyl)adenine

The title compound was obtained in the same manner as in Example 33 using the compound obtained in Example 27 and benzoyl chloride.

¹H NMR (CDCl₃) δ 8.63 (1H, d, J=2.0 Hz), 7.74 (2H, d, J=7.4 Hz), 7.69 (1H, dd, J=2.0, 7.9 Hz), 7.61 (1H, t, J=7.4 Hz), 7.47 (2H, t, J=7.4 Hz), 7.08 (1H, d, J=7.9 Hz), 5.57 (2H, brs), 4.88 (2H, s), 4.84 (1H, t, J=5.9 Hz), 3.40 (2H, m), 2.52 (3H, s), 1.58 (2H, m), 1.42 (2H, m), 0.97 (3H, t, J=7.3 Hz).

EXAMPLE 48

2-Butoxy-8-(4-methyl)benzoyloxy-9-(6-methyl-3-pyridylmethyl)adenine

The title compound was obtained in the same manner as in Example 33 using the compound obtained in Example 25 and p-toluoyl chloride.

¹H NMR (DMSO-d₆) δ 8.44 (1H, s), 7.73 (2H, d, J=8.2 Hz), 7.62 (1H, d, J=8.0 Hz), 7.30 (2H, d, J=8.2 Hz), 7.20 (1H, d, J=8.0 Hz), 6.84 (2H, brs), 4.84 (2H, s), 4.22 (2H, t, J=6.6 Hz), 2.42 (3H, s), 2.40(3H, s), 1.66 (2H, m), 1.41 (2H, m), 0.92 (3H, t, J=7.4 Hz).

EXAMPLE 49

2-Butylamino-8-(4-methyl)benzoyloxy-9-(6-methyl-3-pyridylmethyl)adenine

The title compound was obtained in the same manner as in Example 33 using the compound obtained in Example 27 and p-toluoyl chloride.

¹H NMR (DMSO-d₆) δ 8.43 (1H, s), 7.69 (2H, d, J=8.2 Hz), 7.62 (1H, d, J=8.0 Hz), 7.28 (2H, d, J=8.2 Hz), 7.19 (1H, d, J=8.0 Hz), 6.71 (1H, brs), 6.25 (2H, brs), 4.80 (2H, s), 3.22 (2H, t, J=6.6 Hz), 2.42 (3H, s), 2.39(3H, s), 1.46 (2H, m), 1.30 (2H, m), 0.89 (3H, t, J=7.4 Hz).

EXAMPLE 50

2-Butylamino-8-hydroxy-9-(1-naphthylmethyl)adenine

The title compound was obtained in the same manner as in Example 11 using the compound obtained in Reference Example 5.

¹H NMR (DMSO-d₆) δ 9.79 (1H, s), 8.39–8.41 (1H, m), 7.94–7.97 (1H, m), 7.83–7.86 (1H, m), 7.55–7.59 (2H, m), 7.40–7.46 (1H, m), 7.26 (1H, m), 6.17 (1H, t, J=5.8 Hz), 6.05 (2H, s), 5.28 (2H, s), 3.09–3.16 (2H, m), 1.36–1.44 (2H, m), 1.21–1.29 (2H, m), 0.83 (3H, t, J=7.4 Hz).

EXAMPLE 51

2-Butylamino-8-hydroxy-9-(2-naphthylmethyl)adenine

The title compound was obtained in the same manner as in Example 11 using the compound obtained in Reference Example 5.

¹H NMR (DMSO-d₆) δ 9.69 (1H, s), 7.84–7.89 (3H, m), 7.74 (1H, s), 7.47–7.25 (3H, m), 6.21 (1H, t, J=5.8 Hz), 6.03 (2H, s), 4.97 (2H, s), 3.12–3.20 (2H, m), 1.41–1.46 (2H, m), 1.22–1.31 (2H, m), 0.83 (3H, t, J=7.4 Hz)

EXAMPLE 52

2-Butoxy-8-hydroxy-9-(1-naphthylmethyl)adenine

The title compound was obtained in the same manner as in Example 1 using a corresponding starting material.

¹H NMR (DMSO-d₆) δ 10.21 (1H, s), 8.37–8.41 (1H, m), 7.85–7.98 (2H, m), 7.55–7.60 (2H, m), 7.41–7.47 (1H, m), 7.25–7.28 (1H, m), 6.52 (2H, s), 5.34 (2H, s), 4.10 (2H, d, J=6.6 Hz), 1.55–1.61 (2H, m), 1.29–1.38 (2H, m), 0.87 (3H, t, J=7.3 Hz).

EXAMPLE 53

2-Butoxy-8-hydroxy-9-(2-naphthylmethyl)adenine

The title compound was obtained in the same manner as in Example 1 using a corresponding starting material.

¹H NMR (DMSO-d₆) δ 10.12 (1H, s), 7.87–7.90 (3H, m), 7.76 (1H, s), 7.46–7.51 (3H, m), 6.45 (2H, s), 5.02 (2H, s), 4.14 (2H, d, J=6.6 Hz), 1.55–1.63 (2H, m), 1.31–1.39 (2H, m), 0.88 (3H, t, J=7.3 Hz).

EXAMPLE 54

2-Butylamino-8-hydroxy-9-(5-chloro-2-thienylmethyl)adenine

The title compound was obtained in the same manner as in Example 11 using the compound obtained in Reference Example 5.

¹H NMR (DMSO-d₆) δ 9.85 (1H, s), 6.96 (1H, d, J=3.8 Hz), 6.91 (1H, d, J=3.8 Hz), 6.23 (1H, t, J=5.4 Hz), 6.07 (2H, s), 4.87 (2H, s), 3.15–3.23 (2H, m), 1.43–1.53 (2H, m), 1.24–1.37 (2H, m), 0.89 (3H, t, J=7.3 Hz).

EXAMPLE 55

2-Butylamino-8-hydroxy-9-(6-methyl-3-pyridylmethyl)adenine monosulfate 0.5N sulfuric acid (30.8 ml) was added to a methanol solution (520 ml) of the compound of Example 27 (2.52 g, 7.70 mmol), and the precipitated crystal was collected by filtration. Thus, the title compound was obtained.

mp: 249–252° C.
Calc.: C, 45.17; H, 5.45; N, 23.04; S, 7.54.
Anal.: C, 44.96; H, 5.56; N, 22.90; S, 7.53.

EXAMPLE 56

Interferon-inducing Activity in Mouse Spleen Cell (in vitro)

Spleen was extirpated from a C3H/HeJ mouse strain (male, 8 to 10 weeks old), and $2\times10^6$ cells/ml of a splenic cell suspension was prepared using MEM medium containing 5% FBS. The resulting suspension was fractionated to each well of a 24-well microplate in amounts of 0.5 ml each. Thereafter, a test compound (comprising 0.2% DMSO) that was diluted in the same medium was added to each well in amounts of 0.5 ml each, and culture was conducted in an incubator in the presence of 5% $CO_2$ at 37° C. for 24 hours. The culture solution was aseptically filtered through a 0.2-μm filter to obtain a culture supernatant. The interferon titer in the culture supernatant was quantified by the bioassay described in J. A. Armstrong, Methods in Enzymology 78, 381-7. More specifically, $1\times10^4$ cells/50 μl of mouse fibroblasts, L929, were cultured in a 96-well culture plate for 24 hours, and 50 μl of diluted culture supernatant was added thereto, followed by culturing for an additional 24 hours. Subsequently, 100 μl each of vesicular stomatitis virus was added, and the cytopathogenic effect 44 hours after the virus infection was confirmed by crystal violet staining. Quantification was carried out by dissolving the dye with the aid of an aqueous solution of 2% sodium deoxycholate and assaying the absorbance at 595 nm. 9-Benzyl-2-butylamino-8-hydroxyadenine (a compound described in Example 24 of WO 99-28321) as Reference Compound 1, 9-benzyl-2-butoxy-8-hydroxyadenine (a compound described in Example 19 of WO 99-28321) as Reference Compound 2, R-837 (Imiquimod) as Comparative Example 1, and R-848 (1-(2-hydroxy-2-methylpropyl)-2-methoxyethyl-1H-imidazo[4,5-c]quinoline-4-amine) as Comparative Example 2 were used. Table 2 shows the minimum effective concentration of each compound.

TABLE 2

| Compound | Interferon-inducing activity Minimum effective concentration (nM) |
|---|---|
| Example 1 | 1 |
| Example 2 | 1 |
| Example 3 | 1 |
| Example 4 | 10 |
| Example 5 | 3 |
| Example 6 | 1 |
| Example 7 | 1 |
| Example 8 | 1 |
| Example 9 | 3 |
| Example 10 | 10 |
| Example 11 | 3 |
| Example 12 | 10 |
| Example 13 | 3 |
| Example 14 | 1 |
| Example 15 | 1 |
| Example 16 | 1 |
| Example 17 | 3 |
| Example 18 | 10 |
| Example 19 | 3 |
| Example 20 | 30 |
| Example 21 | 3 |
| Example 22 | 10 |
| Example 23 | 10 |
| Example 24 | 3 |
| Example 25 | 1 |
| Example 26 | 1 |
| Example 27 | 3 |
| Example 28 | 10 |
| Example 29 | 10 |
| Reference Compound 1 | 100 |
| Reference Compound 2 | 1 |
| Comparative Example 1 | 300 |
| Comparative Example 2 | 3 |

EXAMPLE 57

Interferon-inducing Activity in Mouse (in vivo)

A test compound was suspended in an aqueous solution of 0.5% carboxymethylcellulose, and the resulting suspension was orally administered to a Balb/c male mouse. Two hours later, blood was sampled from its heart, and the interferon titer in blood serum was assayed in the same manner as in Example 56. Table 3 shows the results.

TABLE 3

| | Interferon-inducing activity (U/ml) Dosage (mg/kg) | | | |
|---|---|---|---|---|
| | 0.01 | 0.03 | 0.1 | 0.3 |
| Example 1 | | 123 ± 87 | 322 ± 95 | 623 ± 32 |
| Example 2 | 25 ± 17 | 388 ± 87 | 1211 ± 263 | 2559 ± 495 |
| Example 3 | | | 353 ± 73 | 1966 ± 532 |
| Example 5 | | | 133 ± 33 | 473 ± 9 |
| Example 6 | | | 569 ± 42 | 1222 ± 248 |
| Example 7 | | | 347 ± 149 | 845 ± 22 |
| Example 8 | 13 ± 5 | 167 ± 97 | 725 ± 141 | 936 ± 438 |
| Example 9 | | | | 539 ± 107 |
| Example 10 | | 89 ± 22 | 409 ± 267 | 733 ± 256 |
| Example 11 | | | 279 ± 177 | 568 ± 160 |
| Example 12 | | | | 31 ± 5 |
| Example 13 | | | | 304 ± 138 |
| Example 14 | | | | 570 ± 63 |
| Example 15 | | | 52 ± 32 | 603 ± 147 |
| Example 16 | | | 251 ± 46 | 716 ± 155 |
| Example 17 | | 31 ± 23 | 183 ± 43 | 999 ± 379 |
| Example 18 | | | | 94 ± 49 |
| Example 19 | 14 ± 5 | 199 ± 84 | 383 ± 122 | 601 ± 187 |
| Example 21 | | 15 ± 8 | 290 ± 134 | 571 ± 164 |
| Example 22 | | | 21 ± 9 | 332 ± 83 |
| Example 23 | | | 42 ± 7 | 414 ± 118 |
| Example 24 | | | | 403 ± 146 |
| Example 25 | 65 ± 52 | 151 ± 29 | 753 ± 140 | 721 ± 299 |
| Example 26 | | 121 ± 11 | 433 ± 366 | 780 ± 190 |
| Example 27 | | 14 ± 3 | 324 ± 66 | 804 ± 274 |
| Example 28 | | | 186 ± 62 | 1462 ± 260 |
| Example 29 | | | | 619 ± 268 |
| Reference Compound 1 | | | 55 ± 25 | 275 ± 165 |
| Reference Compound 2 | | 60 ± 40 | 186 ± 42 | 317 ± 160 |
| Comparative Example 2 | | | 1638 ± 246 | 1961 ± 950 |

EXAMPLE 58

Interferon-inducing Activity in Cynomolgus Monkey (in vivo)

A test compound was suspended in an aqueous solution of 0.5% carboxymethylcellulose, and 10 mg/kg of the resulting suspension was orally administered to a group of five male cynomolgus monkeys. Blood was sampled with the elapse of time, and the interferon titer in blood serum was assayed in the same manner as in Example 56. The interferon titers in blood serum four hours after the administration (average±SE) were 13,876±825 U/ml in the compound of Example 17, 12,173±6619 U/ml in the compound of Example 19, 14,488±6365 U/ml in the compound of Example 27, and 18,305±5578 U/ml in the compound of Reference Example 2. These results indicate that interferon-inducing activity of each case was substantially the same. While vomition was observed in 4 out of 5 samples in the compound of Reference Example 2, no vomition was observed in any sample in the case of the compound according to the present invention.

EXAMPLE 59

Interferon-inducing Activity in Human Peripheral Blood Mononuclear Cells (PBMC)

Peripheral bloods were sampled from 5 healthy volunteers using a syringe containing heparin, and peripheral blood mononuclear cells (PBMC) were prepared by density gradient centrifugation utilizing the Lymphoprep™ (NYCOMED PHARMA AS). PBMCs were washed twice in serum-free RPMI 1640 medium and adjusted at $1\times10^6$ cells/ml in RPMI 1640 medium comprising 10% fetal bovine serum. The product was cultured in the presence of a test compound dissolved in dimethyl sulfoxide (final concentration: 0.1%) in an incubator in the presence of 5% $CO^2$ at 37° C. for 24 hours. As a control, 0.1% dimethyl sulfoxide containing no test compound was used. The culture supernatant was aseptically collected by filtration. Thereafter, the supernatant was cryopreserved at −20° C. or lower until it was subjected to the assay for IFN-inducing activity. Human IFN-α in the culture supernatant was quantified using a highly sensitive ELISA system (Amersham). Table 4 shows the results, wherein (−) indicates a detection limit (1.25 pg/ml) or lower and NT refers to "not tested."

TABLE 4

| | Interferon-inducing activity (pg/ml) | | | | |
|---|---|---|---|---|---|
| | Concentration (nM) | | | | |
| | 0.3 | 1 | 3 | 10 | 30 |
| Example 17 | NT | 5 ± 3 | 17 ± 17 | 50 ± 33 | 61 ± 38 |
| Example 19 | NT | 5 ± 1 | 12 ± 11 | 48 ± 34 | 60 ± 33 |
| Example 25 | 7 ± 3 | 28 ± 24 | 46 ± 34 | NT | NT |
| Example 27 | NT | 6 ± 3 | 26 ± 22 | 56 ± 37 | 59 ± 33 |
| Comparative Example 2 | — | — | 6 ± 5 | NT | NT |
| Reference Compound 2 | NT | — | 7 | 23 ± 22 | 64 ± 40 |

EXAMPLE 60

Inhibitory Activity Against Th2 Cytokine Produced from Sensitized Spleen Cells

A 7-week-old BALB/c mouse was immunized intraperitoneally with aluminum hydroxide gel (4 mg, 100 µl) having 10 µg of ovalbumin adsorbed thereon, and it was subjected to additional immunization with the same agent 14 days later. Seven days thereafter, spleen was taken out, and suspended in RPMI-1640 comprising inactivated fetal bovine serum (10%), 2-mercaptoethanol (50 µl), penicillin G (100 U/ml), and streptomycin (100 µg/ml). Thus, a splenic cell suspension was prepared. Ovalbumin (0.5 mg/ml) and a test compound were added to a splenic cell suspension ($5\times10^6$ cell/200 µl/well), and the resultant was cultured at 37° C. in the presence of 5% $CO_2$ for 3 days. The cytokine level in the culture supernatant was quantified by ELISA. IFN-γ and IL-4 were assayed using a kit available from Amersham, and IL-5 was assayed using a kit available from Endogen. Table 5 shows the results.

TABLE 5

| | Concentration (nM) | | | |
|---|---|---|---|---|
| | 0.1 | 1 | 10 | 100 |
| Inhibitory activity against IL-4 production (% of control) | | | | |
| Example 1 | 98 | 7 | 2 | <1 |
| Example 2 | 96 | 4 | <1 | <1 |
| Example 10 | — | 54 | 3 | <1 |
| Example 17 | — | 40 | <1 | <1 |
| Example 19 | — | 32 | <1 | <1 |
| Example 20 | — | 106 | 23 | 2 |
| Example 21 | — | 53 | 1 | <1 |
| Example 22 | — | 88 | 9 | 1 |
| Example 25 | 86 | 2 | <1 | <1 |
| Example 27 | — | 30 | 1 | <1 |
| Comparative Example 1 | — | 18 | 1 | <1 |
| Comparative Example 2 | 90 | 24 | 1 | <1 |
| Reference Compound 1 | — | — | 109 | 24 |
| Reference Compound 2 | 107 | 48 | 1 | <1 |
| Inhibitory activity against IL-5 production (% of control) | | | | |
| Example 1 | 116 | 41 | 16 | 15 |
| Example 2 | 98 | 37 | 14 | 12 |
| Example 10 | — | 91 | 32 | 15 |
| Example 17 | — | 77 | 24 | 10 |
| Example 19 | — | 83 | 16 | 13 |
| Example 20 | — | 106 | 71 | 19 |
| Example 21 | — | 97 | 23 | 15 |
| Example 22 | — | 115 | 50 | 18 |
| Example 25 | 102 | 31 | 13 | 13 |
| Example 27 | — | 68 | 20 | 12 |
| Comparative Example 1 | — | 54 | 15 | 10 |
| Comparative Example 2 | 106 | 73 | 18 | 10 |
| Reference Compound 1 | — | — | 92 | 69 |
| Reference Compound 2 | 99 | 79 | 16 | 11 |

EXAMPLE 61

Gastrointestinal Absorption in Rat

A test compound was suspended in an aqueous solution of 0.5% carboxymethylcellulose, and the resulting suspension was orally administered to an SD male rat. Blood was sampled with the elapse of time, and the level of the drug in blood was assayed by HPLC. The following table shows the Cmax and Tmax values.

TABLE 6

| | Cmax and Tmax | | |
|---|---|---|---|
| | Dose (mg/kg) | Cmax (ng/ml) | Tmax (hr) |
| Example 17 | 3 | 310 | 1 |
| Example 19 | 3 | 188 | 4 |
| Hydrochloride of Example 25 | 3 | 18 | 1 |
| | 10 | 150 | 0.25 |
| Example 27 | 3 | 565 | 0.5 |
| Comparative Example 1 | 3 | 90 | 0.5 |
| Comparative Example 2 | 3 | 19 | 1 |
| | 10 | 15 | 0.5 |

EXAMPLE 62

Solubility 5.53% citric acid (monohydrate) and 1.75% disodium phosphate (anhydrous) were mixed together to prepare buffers (pH 2.5, 5.5, 7.4). A compound was added thereto, the mixture was stirred in a vortex mixer and subjected to ultrasonication for 30 minutes. Thereafter, the resultant was stirred in a vortex mixer again and then centrifuged at 15,000 rpm for 20 minutes. The levels of the compounds in the supernatants were then quantified by HPLC. The following table shows these concentration levels.

TABLE 7

| | | | (µg/ml) |
|---|---|---|---|
| | pH 2.5 | pH 5.5 | pH 7.4 |
| Example 8 | 784 | 20 | 18 |
| Example 9 | 350 | 4 | 3 |
| Example 10 | 34 | 15 | 10 |
| Example 15 | 140 | 1 | <1 |
| Example 16 | 293 | NT | NT |
| Example 19 | 130 | 2 | 2 |
| Example 20 | 8,813 | NT | NT |
| Example 21 | 15,000 | 45 | 64 |
| Example 22 | >80,000 | 73 | 16 |
| Example 24 | 27,000 | 22 | 1 |
| Example 25 | >1,000 | 5 | 3 |
| Example 26 | >1,000 | 6 | 3 |
| Example 27 | 610 | 5 | 2 |
| Example 28 | >1,000 | 8 | 4 |
| Example 31 | >1,000 | 353 | 322 |
| Example 32 | >1,000 | 82 | 25 |
| Reference Compound 1 | 26 | <1 | <1 |
| Reference Compound 2 | 2 | <1 | <1 |

EXAMPLE 63

Medicinal Effect of the Compound of Example 27 in a Rat Model of Eosinophil Leukocytic Infiltration A rat was immunized intraperitoneally with 1 ml of a solution containing 1 mg of ovalbumin (OVA) and 100 mg of Al(OH)$_3$ on day 0 and day 7. On day 14, a 1% OVA solution was sprayed for 15 minutes using a ultrasonic nebulizer to induce reactions. A test compound was administered intratracheally 2.5 hours before the induction. Bronchoalveolar lavage was performed 24 hours after the induction, and eosinocytes in the wash was stained with Hinkelman to count the number of stained cells. Sensi.–/Challe.+, CMC-Na, and Fluticasone were used as controls. FIG. 1 and the following table show the results.

TABLE 8

| | ×10$^4$ cells | | |
|---|---|---|---|
| Compound (intratracheal administration) | Average | Standard deviation | Standard error |
| Sensi.–/Challe.+ | 26.22 | 15.60 | 6.37 |
| CMC-Na | 319.55 | 281.89 | 115.08 |
| Example 27 (0.001 mg/kg) | 383.85 | 392.01 | 160.04 |
| Example 27 (0.01 mg/kg) | 186.77 | 161.86 | 66.08 |
| Example 27 (0.1 mg/kg) | 46.84 | 51.84 | 21.16 |
| Fluticasone (0.01 mg/kg) | 300.07 | 231.84 | 94.65 |

EXAMPLE 64

Figure 2:
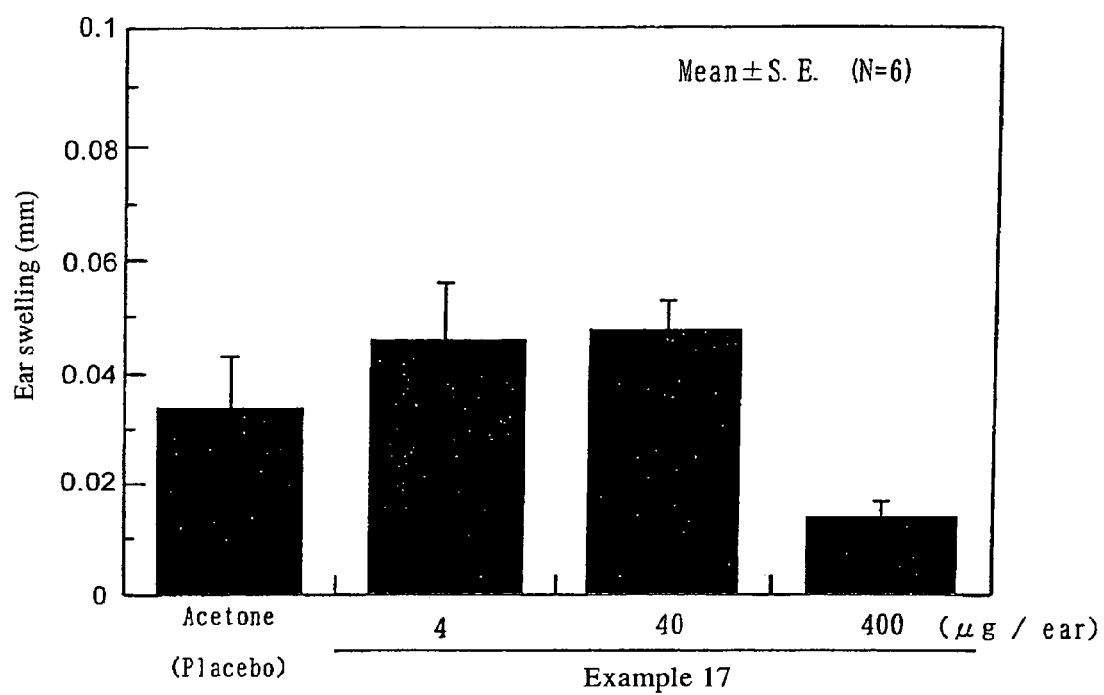
FIG. 2 is a diagram showing the result of evaluation for the medicinal effect of the compound according to the present invention in a mouse model of active cutaneous anaphylaxis.

Medicinal Effect of the Compound of Example 17 in a Mouse Model of Active Cutaneous Anaphylaxis A mouse was immunized intraperitoneally with 500 µl of a solution containing 2 µg of ovalbumin (OVA) and 5 mg of Al(OH)$_3$ on day 0. On day 14, 20 µl of 1 mg/ml OVA solution was intradermally injected in the left auricle under ether anesthesia to induce the reaction. A test compound was applied to both surfaces of the left auricle in amounts of 10 µl each 2 hours before the induction. The thickness of the auricle was measured using a micrometer 24 hours after the induction. Acetone was used as a control. FIG. 2 and the following table show the results.

TABLE 9

| | Ear swelling (mm) | | |
|---|---|---|---|
| Compound | Average | Standard deviation | Standard error |
| Acetone | 0.034 | 0.021 | 0.009 |
| Example 17 (4 µg/ear) | 0.046 | 0.024 | 0.010 |
| Example 17 (40 µg/ear) | 0.048 | 0.013 | 0.005 |
| Example 17 (400 µg/ear) | 0.014 | 0.008 | 0.003 |

EXAMPLE 65

Antitumor Effect of the Compound of Example 27 in Tumor-bearing Mouse Model

Murine renal adenocarcinoma-derived Renca cells (obtained from Iwate Medical University) were intradermally transplanted to the left ventral portions of 6-week-old BALB/c male mice (Charles River Japan, Inc.) at 5×10$^4$ cells/0.05 ml/mouse. Their body weights were measured on the next day, and they were divided into 5 groups (each group comprising 6 mice) in such a manner that the average body weights were substantially the same among groups. Vehicles (an aqueous solution of 0.5% carboxymethylcellulose (hereinafter referred to as "CMC-Na")) and the compound of Example 27 (1 mg/kg and 3 mg/kg) were forcibly administered orally using an oral Sonde (10 ml/kg). Mouse interferon α (hereinafter referred to as "mIFN-α") was intradermally administered to mice through their backs in amounts of 1×10$^4$ U/0.1 ml and 5×10$^4$ U/0.1 ml per mouse. Administration was carried out 5 times every 4 days. The longer diameter (L, mm) and the shorter diameter (W, mm) of the generated tumors were measured twice a week, and the tumor volumes (V, mm$^3$) were calculated (V=L×W$^2$). Also, significant difference was examined in accordance with Steel's multiple comparison. The SAS system for Windows Release 8.01 (SAS Institute Inc., Cary, N.C., U.S.A.) was used for the examination.

Figure 3:
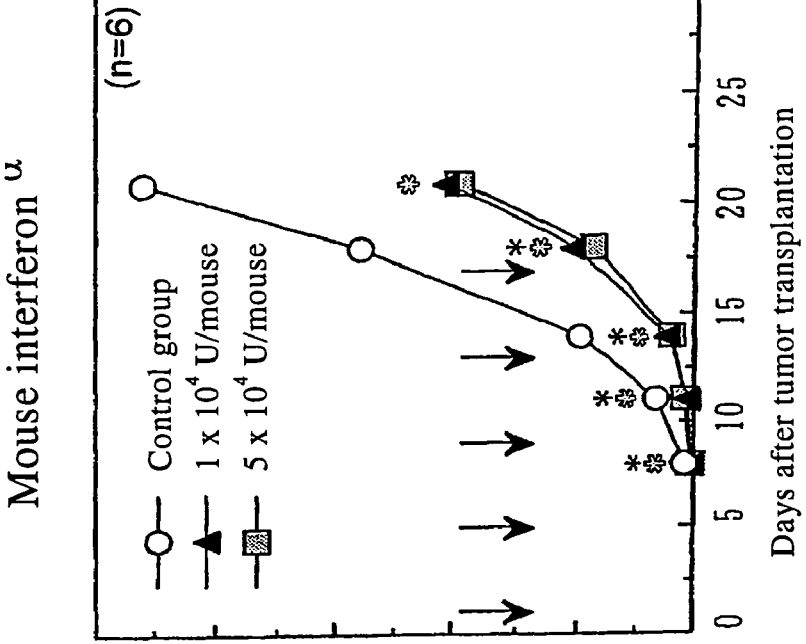
FIG. 3 is a diagram showing the result of evaluation for the antitumor effect described in Example 65, wherein the tumor volume of the compound of Example 27 and that of mouse interferon α were compared with that of the vehicle (a control group).
Figure 3:
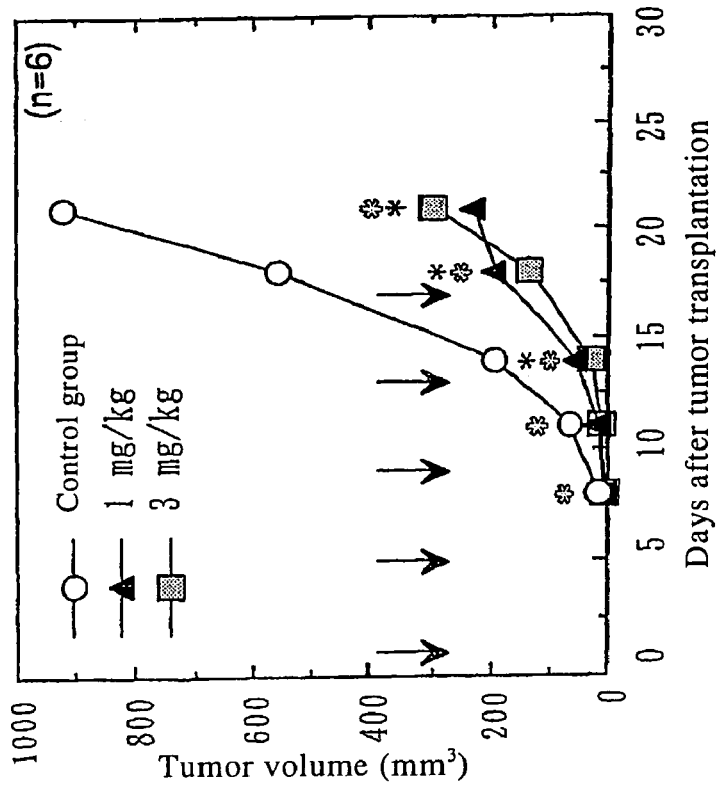

A surveillance period of about 30 days after the transplantation was provided, the tumor volume and the body weight were monitored, and an antitumor effect against the Renca cells was evaluated. The average tumor volume (n=6) of each agent was compared with those of cases involving vehicle administration. The results thereof are shown in FIG. 3. As a result, the tumor volume in the groups to which the compound of Example 27 and mIFN-α were administered was significantly smaller than that in the group to which vehicles had been administered (P<0.05). Administration of the compound of Example 27 was found to exhibit the antitumor effect equivalent to or higher than that attained by the administration of mIFN-α.

EXAMPLE 66

Antitumor Effect of the Compound of Example 27 in a Mouse Model of Spontaneous Metastasis (Inhibitory Effect Against Metastasis)

OV2944-HM-1 cells (obtained from Hiroshima University) derived from mouse ovarian cancer that is highly metastatic to the lymph nodes were intradermally transplanted to the buttocks of 6-week-old B6C3F1 female mice (Charles River Japan, Inc.) in amounts of $1 \times 10^6$ cells/0.05 ml/mouse. Ten days after the transplantation, the primary tumor was excised under Nembutal anaesthesia. Adhesives (Aron Alpha) were applied to the excised portions, and the stumps were sewed up with wound clips. The next day, body weights were measured, and they were divided into 3 groups (each group comprising 6 mice) in such a manner that the average body weights among groups were substantially the same. Vehicles (aqueous solutions of 0.5% CMC-Na) and the compound of Example 27 (3 mg/kg) were forcibly administered orally using an oral Sonde (10 ml/kg). Also, $5 \times 10^4$ U/0.1 ml/mouse of mIFN-α was intradermally administered through their backs. Administration was carried out 5 times every 4 days. Regional lymph nodes (mouse cervical, brachium, axillary cavity) were extirpated 35 days after the transplantation, and their wet weights were measured. Simultaneously, lungs were extirpated to visually inspect the metastasis. Also, significant difference was examined in accordance with Steel's multiple comparison. The SAS system for Windows Release 8.01 (SAS Institute Inc., Cary, N.C., U.S.A.) was used for the examination.

Figure 4:
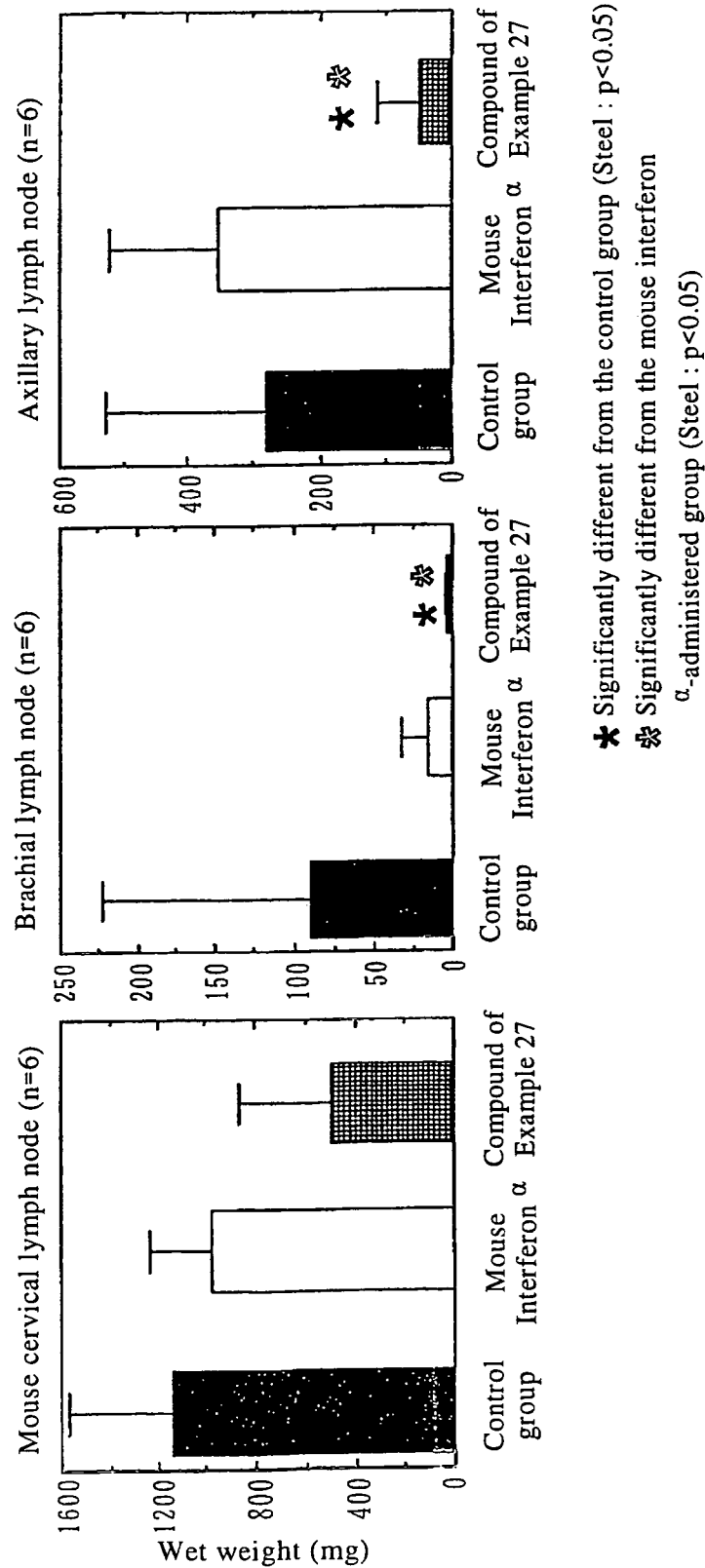
FIG. 4 is a diagram showing the result of evaluation for the antitumor effect described in Example 66 (the effect of inhibiting metastasis), wherein the wet weight of each lymph node was compared among the group to which the vehicle was administered (the control group), the group to which mouse interferon α was administered, and the group to which the compound of Example 27 was administered.

As shown in FIG. 4, the largest metastatic focus was the mouse cervical lymph node located close to the primary tumor, followed by the axillary cavity lymph node and brachium lymph node. The weight of each metastasis lymph node of the group to which the compound of Example 27 was administered was smaller than those attained from the group to which vehicles were administered. This indicates that the compound of Example 27 exhibits a metastasis-inhibiting effect. The HM-1 cells exhibit not only lymph node metastasis but also highly frequent pulmonary metastasis. Thus, pulmonary metastasis was examined. As shown in the table below, pulmonary metastasis was observed in 5 out of 6 mice in the group to which vehicles had been administered based on visual inspection; however, it was not observed at all with the administration of the compound of Example 27. This indicates that the compound of Example 27 can potently inhibit pulmonary metastasis in addition of its ability to inhibit lymph node metastasis. In contrast, mIFN-α did not inhibit lymph node metastasis, and the frequency of pulmonary metastasis was the same as that attained in the group to which vehicles had been administered.

TABLE 10

|  | The number of mice which exhibited pulmonary metastasis in 6 mice |
|---|---|
| Vehicle | 5 |
| Mouse interferon α | 5 |
| Compound of Example 27 | 0 |

EXAMPLE 67

Preparation Example

Tablets having the following composition were produced in accordance with a conventional technique.

| Compound of Example 25 | 10 mg |
|---|---|
| Lactose | 600 mg |
| Starch | 250 mg |
| Hydroxypropylcellulose | 30 mg |
| Calcium stearate | 5 mg |

EXAMPLE 68

Preparation Example

Solid dispersants having the following composition were produced in accordance with a conventional technique.

| Compound of Example 27 | 20 mg |
|---|---|
| Nikkol (surfactant) | 5 mg |
| Hydroxypropylcellulose | 200 mg |
| Methanol | 2 ml |
| Dichloromethane | 2 ml |

All publications cited herein are incorporated herein by reference in their entirety.

INDUSTRIAL APPLICABILITY

The adenine derivative according to the present invention has selective and significant interferon-inducing activity. The adenine derivative according to the present invention accelerates interferon secretion in living organisms, and thus, is useful for prevention or treatment of, for example, viral diseases such as hepatitis B, hepatitis C, or AIDS or cancerous diseases for which interferon is effective. The adenine derivative according to the present invention is of low molecular weight. Accordingly, it can be orally administered, unlike interferon preparations. In addition, the adenine derivative according to the present invention is a compound having excellent water solubility and high gastrointestinal absorption. Further, the adenine derivative according to the present invention selectively inhibits the production of inflammatory cytokines such as IL-4 or IL-5 that are discharged from Th2 cells. Accordingly, it is useful as a preventive or therapeutic agent for diseases such as asthma or atopic dermatitis with which Th2 cells are deeply involved.

What is claimed is:

1. An adenine derivative, a tautomer thereof, or a pharmaceutically acceptable salt thereof represented by formula (I):

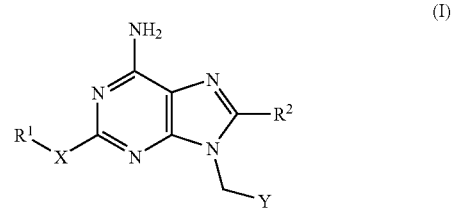

wherein X represents $NR^3$ (wherein $R^3$ represents a hydrogen atom or $C_{1-3}$ alkyl), an oxygen atom, or a sulfur atom; $R^1$ represents substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, or substituted or unsubstituted cycloalkenyl; $R^2$ represents hydroxyl, mercapto, $C_{1-8}$ acyloxy, or $C_{2-8}$ alkoxycarbonyloxy; and Y represents a substituted or unsubstituted naphthalene ring, a substituted or unsubstituted 5- or 6-membered monocyclic aromatic hetero ring containing 1 or 2 hetero atoms selected from the group consisting of nitrogen, oxygen, and sulfur atoms, or a substituted or unsubstituted fused bicyclic aromatic hetero ring containing 1 or 2 hetero atoms selected from the group consisting of nitrogen, oxygen, and sulfur atoms.

2. The compound according to claim 1, wherein, in formula (I), $R^1$ represents $C_{1-8}$ alkyl, $C_{2-8}$ alkenyl, $C_{2-8}$ alkynyl, $C_{2-8}$ alkoxyalkyl, $C_{1-8}$ hydroxyalkyl, aryl, heteroaryl, aralkyl, heteroarylalkyl, cycloalkyl or cycloalkenyl.

3. The compound according to claim 1, wherein, in formula (I), $R^1$ represents $C_{1-6}$ alkyl, cycloalkyl, or cycloalkenyl.

4. The compound according to claim 1, wherein, in formula (I), X represents NH.

5. The compound according to claim 1, wherein, in formula (I), X represents an oxygen atom.

6. The compound according to claim 1, wherein, in formula (I), Y represents a unsubstituted or substituted pyridine ring or a substituted or unsubstituted pyrazine ring.

7. The compound according to claim 1, wherein, in formula (I), Y represents a unsubstituted or substituted naphthalene ring or a substituted or unsubstituted thiophene ring.

8. The compound according to claim 1, wherein, in formula (I), Y has 1 to 4 substituents when Y is a pyridine ring, and 1 to 3 substituents when Y is a pyrazine ring at any positions, wherein the substituent is selected from the group consisting of $C_{1-4}$ alkyl, $C_{1-4}$ alkoxy, hydroxyl, mercapto, $C_{1-4}$ alkylthio, a halogen atom, amino, $C_{2-8}$ dialkylamino, $C_{1-4}$ monoalkylamino, pyrrolidinyl, piperidino, and morpholino.

9. The compound according to claim 1, wherein, in formula (I), Y represents a pyridine ring which may have a substituent selected from the group consisting of $C_{1-4}$ alkyl, $C_{1-4}$ alkoxy, hydroxyl, mercapto, $C_{1-4}$ alkylthio, a halogen atom, amino, $C_{2-8}$ dialkylamino, $C_{1-4}$ monoalkylamino, pyrrolidinyl, piperidino, and morpholino; $R^1$ represents $C_{1-6}$ alkyl; and $R^2$ represents hydroxyl.

10. The compound according to claim 9, wherein, in formula (I), X represents NH or an oxygen atom.

11. 2-Butylamino-8-hydroxy-9-(6-methyl-3-pyridylmethyl)adenine or a pharmaceutically acceptable salt thereof.

12. A pharmaceutical composition comprising the compound according to any one of claims 1 to 10 or 11 as an active ingredient, and a carrier.

* * * * *

UNITED STATES PATENT AND TRADEMARK OFFICE
CERTIFICATE OF CORRECTION

PATENT NO. : 7,157,465 B2 Page 1 of 1
APPLICATION NO. : 10/474199
DATED : January 2, 2007
INVENTOR(S) : Isobe et al.

It is certified that error appears in the above-identified patent and that said Letters Patent is hereby corrected as shown below:

On the title page, Item 73, the Assignee Information is incorrect. Item (73) should read:

-- (73) Assignee: Dainippon Sumitomo Pharma Co., Ltd., Osaka (JP) --

Signed and Sealed this

Twenty-seventh Day of March, 2007

JON W. DUDAS
*Director of the United States Patent and Trademark Office*